United States Patent
Alvarado et al.

(10) Patent No.: US 11,091,559 B2
(45) Date of Patent: Aug. 17, 2021

(54) ANTI-ALK ANTIBODIES AND METHODS FOR USE THEREOF

(71) Applicant: Celldex Therapeutics, Inc., Hampton, NJ (US)

(72) Inventors: Diego Alvarado, Madison, CT (US); Jay Lillquist, East Lyme, CT (US); Gwenda Ligon, Hamden, CT (US); Michael Feldhaus, Lebanon, NH (US)

(73) Assignee: Celldex Therapeutics, Inc., Hampton, NJ (US)

(*) Notice: Subject to any disclaimer, the term of this patent is extended or adjusted under 35 U.S.C. 154(b) by 583 days.

(21) Appl. No.: 15/755,421

(22) PCT Filed: Aug. 26, 2016

(86) PCT No.: PCT/US2016/048870
§ 371 (c)(1),
(2) Date: Feb. 26, 2018

(87) PCT Pub. No.: WO2017/035430
PCT Pub. Date: Mar. 2, 2017

(65) Prior Publication Data
US 2020/0157236 A1 May 21, 2020

Related U.S. Application Data

(60) Provisional application No. 62/210,705, filed on Aug. 27, 2015.

(51) Int. Cl.
*C07K 16/40* (2006.01)
*C07K 16/28* (2006.01)
*C07K 16/30* (2006.01)
*C12N 15/85* (2006.01)
*G01N 33/574* (2006.01)

(52) U.S. Cl.
CPC .......... *C07K 16/2896* (2013.01); *C07K 16/30* (2013.01); *C07K 16/40* (2013.01); *C12N 15/85* (2013.01); *G01N 33/57423* (2013.01); *C07K 2317/24* (2013.01); *C07K 2317/33* (2013.01); *C07K 2317/34* (2013.01); *C07K 2317/51* (2013.01); *C07K 2317/565* (2013.01); *C07K 2317/75* (2013.01); *C07K 2317/76* (2013.01); *C07K 2317/92* (2013.01); *C12N 2015/8518* (2013.01)

(58) Field of Classification Search
CPC .... C07K 16/2896; C07K 16/30; C07K 16/40; C07K 2317/24; C07K 2317/33; C07K 2317/34; C07K 2317/51; C07K 2317/52; C07K 2317/54; C07K 2317/55; C07K 2317/56; C07K 2317/565; C07K 2317/622; C07K 2317/624; C07K 2317/75; C07K 2317/76; C07K 2317/92; C07K 2317/90; C12N 15/85; C12N 2015/8518; G01N 33/57423
See application file for complete search history.

(56) References Cited

U.S. PATENT DOCUMENTS

| | | |
|---|---|---|
| 7,902,340 B2 | 3/2011 | Auf Der Maur et al. |
| 8,945,563 B2 | 2/2015 | Auf Der Maur et al. |
| 2002/0151682 A1 | 10/2002 | Athwal |
| 2005/0244409 A1 | 11/2005 | Erickson-Miller |
| 2010/0111964 A1 | 5/2010 | Wellstein et al. |
| 2010/0150940 A1 | 6/2010 | Adam |
| 2010/0260783 A1 | 10/2010 | Matsubara |
| 2011/0159008 A1 | 6/2011 | Auf Der Maur et al. |
| 2011/0217305 A1 | 9/2011 | Pedersen |
| 2012/0164153 A1 | 6/2012 | Dye |
| 2014/0154253 A1 | 6/2014 | Ng et al. |
| 2014/0302041 A1 | 10/2014 | Robert |

FOREIGN PATENT DOCUMENTS

| | | |
|---|---|---|
| EP | 1305337 B1 | 5/2003 |
| WO | WO 2007/059300 A2 | 5/2007 |
| WO | WO 2008/131575 A2 | 11/2008 |
| WO | WO 2015/069922 A2 | 5/2015 |

OTHER PUBLICATIONS

Rudikoff et al., Proc Natl Acad Sci USA 79: 1979-1983 (Year: 1982).*
Barrios et al., J Molecular Recognition 17: 332-338 (Year: 2004).*
Giusti et al., Proc. Natl. Acad. Sci USA.84 (9): 2926-2930 (Year: 1987).*
Winkler et al., J. Imm., 165:4505-4514 (Year: 2000).*
Chien et al., Proc. Natl. Acad. Sci USA. 86 (14): 5532-5536 (Year: 1989).*
Caldas et al., Mol ImmunoL 39 (15): 941-952 (Year: 2003).*
Wu et al., J. Mol. Biol. 294: 151-162 (Year: 1999).*
Stancoviski et al., PNAS; 88: 8691-8695 (Year: 1991).*
MacCallum et al (Mol. Biol 262: 732-745 (Year: 1996).*
Gruber et al., "A Novel, Highly Sensitive ALK Antibody 1A4 Facilitates Effective Screening for ALK Rearrangements in Lung Adenocarcinomas by Standard Immunohistochemistry." J Thorac Oncol. 10(4):713-716; Apr. 1, 2015.
Carpenter et al., "Antibody targeting of anaplastic lymphoma kinase induces cytotoxicity of human neuroblastoma." Oncogene 31(46): 4859-4867, Jan. 23, 2012.
Mazot et al., "Internalization and Down-Regulation of the ALK Receptor in Neuroblastoma Cell lines upon Monoclonal Antibody Treatment." PlosONE 7(3):e33581-1, Mar. 1, 2012.

(Continued)

*Primary Examiner* — Phuong Huynh
(74) *Attorney, Agent, or Firm* — Jones Day

(57) ABSTRACT

Provided herein are compositions, methods and uses involving antibodies that specifically bind to ALK, a receptor tyrosine kinase, and modulate the expression and/or activity of ALK. Also provided are uses and methods for treating, e.g., managing, disorders, such as cancer.

10 Claims, 11 Drawing Sheets
Specification includes a Sequence Listing.

(56) References Cited

OTHER PUBLICATIONS

Mazot et al., "The constitutive activity of the ALK mutated at positions F1174 or R1275 impairs receptor trafficking." Oncogene (2011) 30: 2017-2025, published online Jan. 17, 2011.
International Search Report and Written Opinion dated Feb. 17, 2017 of International application No. PCT/US16/48870 (11 pages).
Gouzi et al., "The Receptor Tyrosine Kinase Alk Controls Neurofibromin Functions in *Drosophila* Growth and Learning," PLoS Genetics 7(9):e1002281, Sep. 2011.
Lu et al., "The Binding Sites for Competitive Antagonistic, Allosteric Antagonistic, and Agonistic Antibodies to the I Domain of Integrin LFA-1," The Journal of Immunology 173(6):3972-8, Sep. 15, 2004.
Mikelis et al., "Integrin $\alpha_v\beta_3$ is a pleiotrophic receptor required for pleiotrophin-induced endothelial cell migration through receptor protein tyrosine phosphatase $\beta/\zeta$," The FASEB Journal 23:1459-1469, May 2009.
Robinson et al., "An anti-MET IgG2 monoclonal antibody degrades both wild-type and exon 14 mutant MET receptor tyrosine kinase through a novel exon 14-independent mechanism and inhibits tumor growth," Abstract No. 3835 for the American Association for Cancer Research 107th Annual Meeting, held Apr. 16-20, 2016 in New Orleans, LA, USA, published online Jul. 2016, 1 page.
Roell et al., Kinetic Approach to Pathway Attenuation Using XOMA 052, a Regulatory Therapeutic Antibody That Modulates Interleukin-1$\beta$ Activity, Journal of Biological Chemistry, 285(27):20607-20614, Jul. 2, 2010.
Sano "A Novel Antibody-Drug Conjugate Directed to the ALK Receptor Demonstrates Efficacy in Models of Neuroblastoma," slide presentation at the Advances in Neuroblastoma Research Congress, held Jun. 19-23, 2016 in Queensland, Australia, 13 pages.
Sano "A Novel Antibody-Drug Conjugate Directed to the ALK Receptor Demonstrates Efficacy in Models of Neuroblastoma," slide presentation at the American Association for Cancer Research 107th Annual Meeting, held Apr. 16-20, 2016 in New Orleans, LA, USA, 13 pages.
Sano et al., "A Novel Antibody-Drug Conjugate Directed to the ALK Receptor Demonstrates Efficacy in Models of Neuroblastoma," Abstract No. 2690 for the American Association for Cancer Research 107th Annual Meeting, 2016, held Apr. 16-20, in New Orleans, LA, USA, published online Jul. 2016, 1 page.
Stoica et al., "Identification of Anaplastic Lymphoma Kinase as a Receptor for the Growth Factor Pleiotrophin," Journal of Biological Chemistry 276(20):16772-16779, Feb. 8, 2001.
Weiss et al., "Anaplastic Lymphoma Kinase and Leukocyte Tyrosine Kinase Functions and genetic interactions in learning, memory and adult neurogenesis," Pharmacology, Biochemistry and Behavior 100 (2012) 566-574.

\* cited by examiner

```
   1 MGAIGLLWLL PLLLSTAAVG SGMGTGQRAG SPAAGPPLQP REPLSYSRLQ RKSLAVDFVV
  61 PSLFRVYARD LLLPPSSSEL KAGRPEARGS LALDCAPLLR LLGPAPGVSW TAGSPAPAEA
 121 RTLSRVLKGG SVRKLRRAKQ LVLELGEEAI LEGCVGPPGE AAVGLLQFNL SELFSWWIRQ
 181 GEGRLRIRLM PEKKASEVGR EGRLSAAIRA SQPRLLFQIF GTGHSSLESP TNMPSPSPDY
 241 FTWNLTWIMK DSFPFLSHRS RYGLECSFDF PCELEYSPPL HDLRNQSWSW RRIPSEEASQ
 301 MDLLDGPGAE RSKEMPRGSF LLLNTSADSK HTILSPWMRS SSEHCTLAVS VHRHLQPSGR
 361 YIAQLLPHNE AAREILLMPT PGKHGWTVLQ GRIGRPDNPF RVALEYISSG NRSLSAVDFF
 421 ALKNCSEGTS PGSKMALQSS FTCWNGTVLQ LGQACDFHQD CAQGEDESQM CRKLPVGFYC
 481 NFEDGFCGWT QGTLSPHTPQ WQVRTLKDAR FQDHQDHALL LSTTDVPASE SATVTSATFP
 541 APIKSSPCEL RMSWLIRGVL RGNVSLVLVE NKTGKEQGRM VWHVAAYEGL SLWQWMVLPL
 601 LDVSDRFWLQ MVAWWGQGSR AIVAFDNISI SLDCYLTISG EDKILQNTAP KSRNLFERNP
 661 NKELKPGENS PRQTPIFDPT VHWLFTTCGA SGPHGPTQAQ CNNAYQNSNL SVEVGSEGPL
 721 KGIQIWKVPA TDTYSISGYG AAGGKGGKNT MMRSHGVSVL GIFNLEKDDM LYILVGQQGE
 781 DACPSTNQLI QKVCIGENNV IEEEIRVNRS VHEWAGGGGG GGGATYVFKM KDGVPVPLII
 841 AAGGGGRAYG AKTDTFHPER LENNSSVLGL NGNSGAAGGG GGWNDNTSLL WAGKSLQEGA
 901 TGGHSCPQAM KKWGWETRGG FGGGGGGCSS GGGGGGYIGG NAASNNDPEM DGEDGVSFIS
 961 PLGILYTPAL KVMEGHGEVN IKHYLNCSHC EVDECHMDPE SHKVICFCDH GTVLAEDGVS
1021 CIVSPTPEPH LPLSLILSVV TSALVAALVL AFSGIMIVYR RKHQELQAMQ MELQSPEYKL
1081 SKLRTSTIMT DYNPNYCFAG KTSSISDLKE VPRKNITLIR GLGHGAFGEV YEGQVSGMPN
1141 DPSPLQVAVK TLPEVCSEQD ELDFLMEALI ISKFNHQNIV RCIGVSLQSL PRFILLELMA
1201 GGDLKSFLRE TRPRPSQPSS LAMLDLLHVA RDIACGCQYL EENHFIHRDI AARNCLLTCP
1261 GPGRVAKIGD FGMARDIYRA SYYRKGGCAM LPVKWMPPEA FMEGIFTSKT DTWSFGVLLW
1321 EIFSLGYMPY PSKSNQEVLE FVTSGGRMDP PKNCPGPVYR IMTQCWQHQP EDRPNFAIIL
1381 ERIEYCTQDP DVINTALPIE YGPLVEEEEK VPVRPKDPEG VPPLLVSQQA KREEERSPAA
1441 PPPLPTTSSG KAAKKPTAAE ISVRVPRGPA VEGGHVNMAF SQSNPPSELH KVHGSRNKPT
1501 SLWNPTYGSW FTEKPTKKNN PIAKKEPHDR GNLGLEGSCT VPPNVATGRL PGASLLLEPS
1561 SLTANMKEVP LFRLRHFPCG NVNYGYQQQG LPLEAATAPG AGHYEDTILK SKNSMNQPGP
```

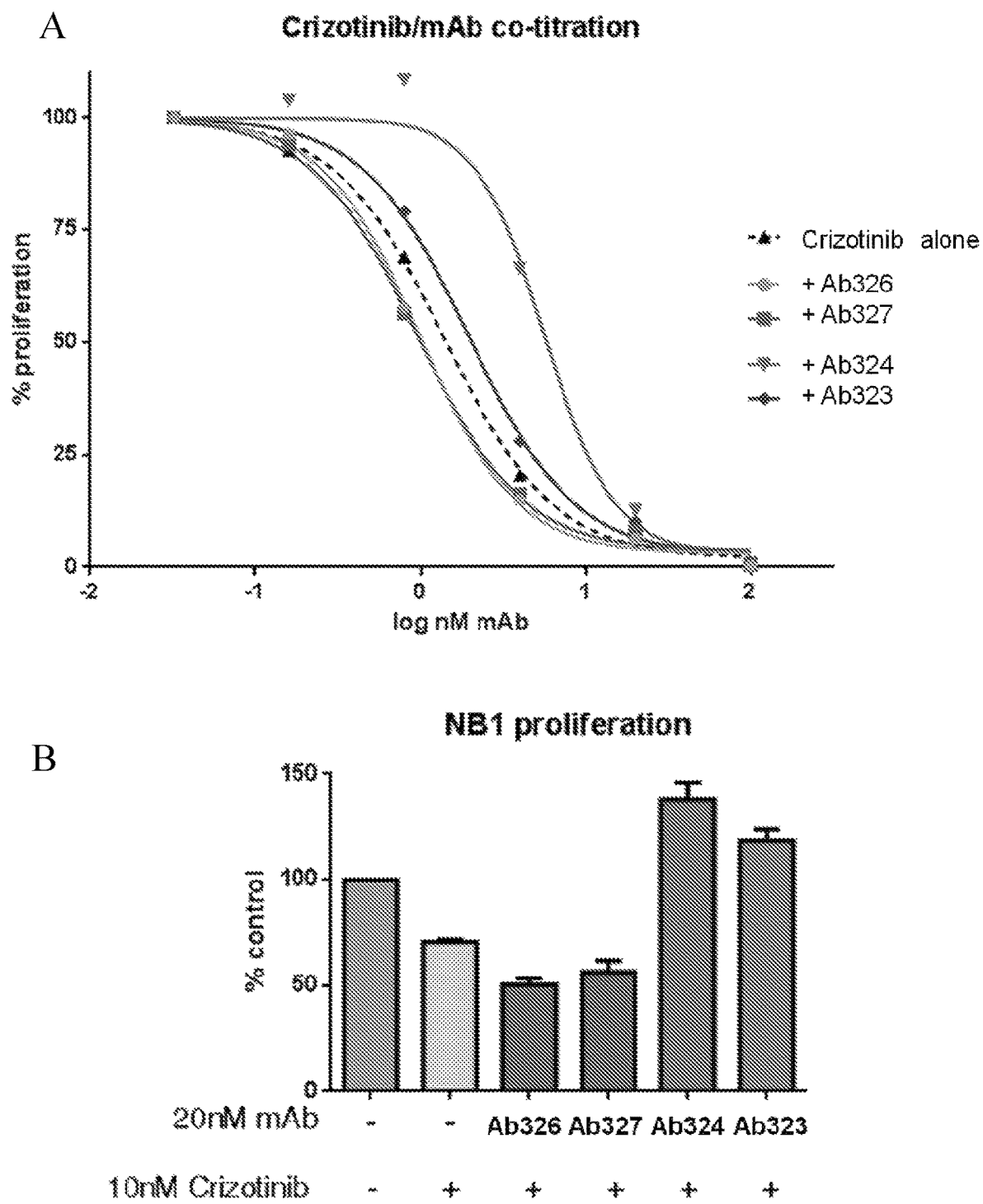
FIG. 7A-B

| | | |
|---|---|---|
| hALK | MGAIGLLWLLPLLLSTAAVGSGMGTGQRAGSPAAGPPLQPREPLSYSRLQRKSLAVDFVV | 60 |
| mALK | MGAAGFLWLLPPLLLAAASYSGAATDQRAGSPASGPPLQPREPLSYSRLQRKSLAVDFVV | 60 |
| rALK | MGALGFLWLLPPLLLTAASYSGAATDQRAGSPASGPPLQPREPLSYSRLQRKSLAVDFVV | 60 |
| | | |
| hALK | PSLFRVYARDLLLPP--SSSELKAGRPEARGSLALDCAPLLRLLGPAPGVSWTAG--SPA | 116 |
| mALK | PSLFRVYARDLLLPQPRSPSEPEAGGLEARGSLALDCEPLLRLLGPLPGISWADGASSPS | 120 |
| rALK | PSLFRVYARDLLLPQPPSPSEPGAGGLEARGSLALDCDPLLRLLGPSPGISWAEGASSPS | 120 |
| | | |
| hALK | PAEARTLSRVLKGGSVRKLRRAKQLVLELGEEAILEGCVGP-PGEAAVGLLQFNLSELFS | 175 |
| mALK | PEAGPTLSRVLKGGSVRKLRRAKQLVLELGEETILEGCIGPPEEVAAVGILQFNLSELFS | 180 |
| rALK | PEAAPTLSRVLKGGSVRKLRRAKQLVLELGEETILEGCIGPPEEAAAVGILQFNLSELFS | 180 |
| | | |
| hALK | WWIRQGEGRLRIRLMPEKKASEVGREGRLSAAIRASQPRLLFQIFGTGHSSLESPTNMPS | 235 |
| mALK | WWILHGEGRLRIRLMPEKKASEVGREGRLSSAIRASQPRLLFQIFGTGHSSMESPSETPS | 240 |
| rALK | WWILHGEGRLRIRLMPEKKASEVGREGRLSTAIRASQPRLLFQIFGTGHSSLESPSEMPS | 240 |
| | | |
| hALK | PSPDYFTWNLTWIMKDSFPFLSHRSRYGLECSFDFPCELEYSPPLHDLRNQSWSWRRIPS | 295 |
| mALK | P-PGTFMWNLTWTMKDSFPFLSHRSRYGLECSFDFPCELEYSPPLHNHGNQSWSWRHVPS | 299 |
| rALK | P-PGNFLWNLTWTMKDSFPFLSHRSRYGLECSFDFPCELEYSPPLHTHGNQSWSWRRVPS | 299 |
| | | |
| hALK | EEASQMDLLDGPGAERSKEMPRGSFLLLNTSADSKHTILSPWMRSSSEHCTLAVSVHRHL | 355 |
| mALK | EEASRMNLLDGPEAEHSQEMPRGSFLLLNTSADSKHTILSPWMRSSSDHCTLAVSVHRHL | 359 |
| rALK | EEASRMNLLDGPEAEHLKEMPRGSFLLLNTSADSKHTILSPWMRSSSEHCTLAVSVHRHL | 359 |
| | | |
| hALK | QPSGRYIAQLLPHNEAAREILLMPTPGKHGWTVLQGRIGRPDNPFRVALEYISSGNRSLS | 415 |
| mALK | QPSGRYVAQLLPHNEAGREILLVPTPGKHGWTVLQGRVGRPANPFRVALEYISSGNRSLS | 419 |
| rALK | QPSGRYVAQLLPHNEAGREILLVPTPGKHGWTVLHGRVGRPENPFRVALEYISSGNRSLS | 419 |
| | | |
| hALK | AVDFFALKNCSEGTSPGSKMALQSSFTCWNGTVLQLGQACDFHQDCAQGEDESQMCRKLP | 475 |
| mALK | AVDFFALKNCSEGTSPGSKMALQSSFTCWNGTVLQLGQACDFHQDCAQGEDEGQLCSKLP | 479 |
| rALK | AVDFFALKNCSEGTSPGSKMALQSSFTCWNGTVLQLGQACDFHQNCAQGEDEGQLCSKLP | 479 |
| | | |
| hALK | VGFYCNFEDGFCGWTQGTLSPHTPQWQVRTLKDARFQDHQDHALLLSTTDVPASESATVT | 535 |
| mALK | AGFYCNFENGFCGWTQSPLSPHMPRWQVRTLRDAHSQGHQGRALLLSTTDILASEGATVT | 539 |
| rALK | AGFYCNFEDGFCGWTQSPLSPRVPRWQVKTLKDTHSQGHQGHALLLSTTDDPTSESATVT | 539 |
| | | |
| hALK | SATFPAPIKSSPCELRMSWLIRGVLRGNVSLVLVENKTGKEQGRMVWHVAAYEGLSLWQW | 595 |
| mALK | SATFPAPMKNSPCELRMSWLIRGVLRGNVSLVLVENKTGKEQSRTVWHVATDEGLSLWQH | 599 |
| rALK | SATFPAPMKSSPCELRMSWLIRGVLKGNVSLVLVENKTGKEQSRTVWHVATNEGLSLWQW | 599 |
| | | |
| hALK | MVLPLLDVSDRFWLQMVAWWGQGSRAIVAFDNISISLDCYLTISGEDKILQNTAPKSRNL | 655 |
| mALK | TVLSLLDVTDRFWLQIVTWWGPGSRATVGFDNISISLDCYLTISGEEKMSLNSVPKSRNL | 659 |
| rALK | TVLSLLDVTDRFWLQIVTWWGPGSRATVAFDNISISLDCYLTISGEEKMSLNAVPKSRNL | 659 |
| | | |
| hALK | FERNPNKELKPGENSPRQTPIFDPTVHWLFTTCGASGPHGPTQAQCNNAYQNSNLSVEVG | 715 |
| mALK | FEKNPNKESKSWANISGPTPIFDPTVHWLFTTCGASGPHGPTQAQCNNAYQNSNLSVVVG | 719 |
| rALK | FEKNPNKEPKPWANISGPTPIFDPTVHWLFTTCGASGPHGPTQAQCNNAYQNSNLSVVVG | 719 |
| | | |
| hALK | SEGPLKGIQIWKVPATDTYSISGYGAAGGKGGKNTMMRSHGVSVLGIFNLEKDDMLYILV | 775 |
| mALK | SEGPLKGVQIWKVPATDTYSISGYGAAGGKGGKNTMMRSHGVSVLGIFNLEKGDTLYILV | 779 |
| rALK | SEGPLRGIQIWKVPATDTYSISGYGAAGGKGGKNTMMRSHGVSVLGIFNLEKDDTLYILV | 779 |
| | | |
| hALK | GQQGEDACPSTNQLIQKVCIGENNVIEEEIRVNRSVHEWAGGGGGGGGATYVFKMKDGVP | 835 |
| mALK | GQQGEDACPRANQLIQKVCVGENNVIEEEIRVNRSVHEWAGGGGGGGGATYVFKMKDGVP | 839 |
| rALK | GQQGEDACPRANQLIQKVCVGENNVIEEEIRVNRSVHEWAGGGGGGGGATYVFKMKDGVP | 839 |

FIG. 9

```
hALK    VPLIIAAGGGGRAYGAKTDTFHPERLENNSSVLGLNGNSGAAGGGGGWNDNTSLLWAGKS  895
mALK    VPLIIAAGGGGRAYGAKTETFHPERLESNSSVLGLNGNSGAAGGGGGWNDNTSLLWAGKS  899
rALK    VPLIIAAGGGGRAYGAKTETFHPERLENNSSVLGLNGNSGAAGGGGGWNDNTSLLWAGKS  899 hALK    LQEGATGGHSCPQAMKKWGWETRGGFGGGGGGCSSGGGGGGYIGGNAASNNDPEMDGEDG  955
mALK    LLEGAAGGHSCPQAMKKWGWETRGGFGGGGGGCSSGGGGGGYIGGNAASNNDPEMDGEDG  959
rALK    LLEGAAGGHSCPQAMKKWGWETRGGFGGGGGGCSSGGGGGGYIGGNAASNNDPEMDGEDG  959 hALK    VSFISPLGILYTPALKVMEGHGEVNIKHYLNCSHCEVDECHMDPESHKVICFCDHGTVLA  1015
mALK    VSFISPLGILYTPALKVMEGHGEVNIKHYLNCSHCEVDECHMDPESHKVICFCDHGTVLA  1019
rALK    VSFISPLGILYTPALKVMEGHGEVNIKHYLNCSHCEVDECHMDPESHKVICFCDHGTVLA  1019 hALK    EDGVSCIVSPTPEPHLPLSLILSLE  1040
mALK    DDGVSCIVSPTPEPHLPLSLILS--  1042
rALK    DDGVSCIVSPTPEPHLPLS-------  1038
```

FIG. 9 (continued)

SEQUENCE LISTING

```
<160> NUMBER OF SEQ ID NOS: 519

<210> SEQ ID NO 1
<211> LENGTH: 11
<212> TYPE: PRT
<213> ORGANISM: Artificial Sequence
<220> FEATURE:
<223> OTHER INFORMATION: VL CDR1 - AB320 (Kabat)

<400> SEQUENCE: 1

Arg Ala Ser Glu Asn Ile Tyr Tyr Ser Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: VL CDR2 - AB320 (Kabat)

<400> SEQUENCE: 2

Asn Ala Asn Ser Leu Glu Asp
```

```
1               5

<210> SEQ ID NO 3
<211> LENGTH: 9
<212> TYPE: PRT
<213> ORGANISM: Artificial Sequence
<220> FEATURE:
<223> OTHER INFORMATION: VL CDR3 - AB320 (Kabat)

<400> SEQUENCE: 3

Lys Gln Ala Tyr Asp Val Pro Phe Thr
1               5

<210> SEQ ID NO 4
<211> LENGTH: 5
<212> TYPE: PRT
<213> ORGANISM: Artificial Sequence
<220> FEATURE:
<223> OTHER INFORMATION: VH CDR1 - AB320 (Kabat)

<400> SEQUENCE: 4

Ser Tyr Trp Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: VH CDR2 - AB320 (Kabat)

<400> SEQUENCE: 5

Gln Ile Tyr Pro Gly Asp Gly Asp Thr Asn Tyr Asn Gly Lys Phe Lys
1               5                   10                  15

Gly

<210> SEQ ID NO 6
<211> LENGTH: 8
<212> TYPE: PRT
<213> ORGANISM: Artificial Sequence
<220> FEATURE:
<223> OTHER INFORMATION: VH CDR3 - AB320 (Kabat)

<400> SEQUENCE: 6

Tyr Tyr Tyr Gly Ser Lys Ala Tyr
1               5

<210> SEQ ID NO 7
<211> LENGTH: 11
<212> TYPE: PRT
<213> ORGANISM: Artificial Sequence
<220> FEATURE:
<223> OTHER INFORMATION: VL CDR1 - AB321 (Kabat)

<400> SEQUENCE: 7

Ser Val Ser Gln Gly Ile Ser Asn Ser Leu Asn
1               5                   10

<210> SEQ ID NO 8
<211> LENGTH: 7
<212> TYPE: PRT
<213> ORGANISM: Artificial Sequence
<220> FEATURE:
<223> OTHER INFORMATION: VL CDR2 - AB321 (Kabat)

<400> SEQUENCE: 8
```

Tyr Thr Ser Ser Leu His Ser
1               5

<210> SEQ ID NO 9
<211> LENGTH: 9
<212> TYPE: PRT
<213> ORGANISM: Artificial Sequence
<220> FEATURE:
<223> OTHER INFORMATION: VL CDR3 - AB321 (Kabat)

<400> SEQUENCE: 9

Gln Gln Tyr Ser Lys Leu Pro Leu Thr
1               5

<210> SEQ ID NO 10
<211> LENGTH: 5
<212> TYPE: PRT
<213> ORGANISM: Artificial Sequence
<220> FEATURE:
<223> OTHER INFORMATION: VH CDR1 - AB321 (Kabat)

<400> SEQUENCE: 10

Ser Tyr Trp Met His
1               5

<210> SEQ ID NO 11
<211> LENGTH: 17
<212> TYPE: PRT
<213> ORGANISM: Artificial Sequence
<220> FEATURE:
<223> OTHER INFORMATION: VH CDR2 - AB321 (Kabat)

<400> SEQUENCE: 11

Arg Ile Asp Pro Asn Ser Gly Gly Thr Lys Tyr Asn Glu Lys Phe Lys
1               5                   10                  15
Ser

<210> SEQ ID NO 12
<211> LENGTH: 11
<212> TYPE: PRT
<213> ORGANISM: Artificial Sequence
<220> FEATURE:
<223> OTHER INFORMATION: VH CDR3 - AB321 (Kabat)

<400> SEQUENCE: 12

Asp Tyr Tyr Gly Ser Ser Tyr Arg Phe Ala Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: VL CDR1 - AB322 (Kabat)

<400> SEQUENCE: 13

Lys Ala Ser Gln Asn Val Gly Thr Asn Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: VL CDR2 - AB322 (Kabat)

<400> SEQUENCE: 14

```
Ser Ala Ser Tyr Arg Tyr Ser
1               5

<210> SEQ ID NO 15
<211> LENGTH: 11
<212> TYPE: PRT
<213> ORGANISM: Artificial Sequence
<220> FEATURE:
<223> OTHER INFORMATION: VL CDR3 - AB322 (Kabat)

<400> SEQUENCE: 15

Gln Gln Tyr Asn Ser Tyr Pro Tyr Met Tyr Thr
1               5                   10

<210> SEQ ID NO 16
<211> LENGTH: 5
<212> TYPE: PRT
<213> ORGANISM: Artificial Sequence
<220> FEATURE:
<223> OTHER INFORMATION: VH CDR1 - AB322 (Kabat)

<400> SEQUENCE: 16

Asn Tyr Trp Met His
1               5

<210> SEQ ID NO 17
<211> LENGTH: 17
<212> TYPE: PRT
<213> ORGANISM: Artificial Sequence
<220> FEATURE:
<223> OTHER INFORMATION: VH CDR2 - AB322 (Kabat)

<400> SEQUENCE: 17

Tyr Ile Asn Pro Ser Ser Gly Tyr Thr Lys Tyr Asn Gln Lys Phe Lys
1               5                   10                  15

Asp

<210> SEQ ID NO 18
<211> LENGTH: 11
<212> TYPE: PRT
<213> ORGANISM: Artificial Sequence
<220> FEATURE:
<223> OTHER INFORMATION: VH CDR3 - AB322 (Kabat)

<400> SEQUENCE: 18

Asp Tyr Tyr Gly Ser Ser Ser Trp Phe Ala Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: VL CDR1 - AB323 (Kabat)

<400> SEQUENCE: 19

Lys Ala Ser Gln Asp Val Ser Thr Ala Val Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: VL CDR2 - AB323 (Kabat)
```

```
<400> SEQUENCE: 20

Trp Ala Ser Thr Arg His Thr
1               5

<210> SEQ ID NO 21
<211> LENGTH: 9
<212> TYPE: PRT
<213> ORGANISM: Artificial Sequence
<220> FEATURE:
<223> OTHER INFORMATION: VL CDR3 - AB323 (Kabat)

<400> SEQUENCE: 21

Gln Gln His Tyr Ser Thr Pro Arg Thr
1               5

<210> SEQ ID NO 22
<211> LENGTH: 5
<212> TYPE: PRT
<213> ORGANISM: Artificial Sequence
<220> FEATURE:
<223> OTHER INFORMATION: VH CDR1 - AB323 (Kabat)

<400> SEQUENCE: 22

Asn Tyr Trp Met Asn
1               5

<210> SEQ ID NO 23
<211> LENGTH: 17
<212> TYPE: PRT
<213> ORGANISM: Artificial Sequence
<220> FEATURE:
<223> OTHER INFORMATION: VH CDR2 - AB323 (Kabat)

<400> SEQUENCE: 23

Gln Ile Phe Pro Gly Asp Ala Asp Ala Asn Tyr Asn Gly Lys Phe Lys
1               5                   10                  15

Gly

<210> SEQ ID NO 24
<211> LENGTH: 9
<212> TYPE: PRT
<213> ORGANISM: Artificial Sequence
<220> FEATURE:
<223> OTHER INFORMATION: VH CDR3 - AB323 (Kabat)

<400> SEQUENCE: 24

Phe Ser Tyr Asp Gly Ala Phe Ala Tyr
1               5

<210> SEQ ID NO 25
<211> LENGTH: 15
<212> TYPE: PRT
<213> ORGANISM: Artificial Sequence
<220> FEATURE:
<223> OTHER INFORMATION: VL CDR1 - AB324 (Kabat)

<400> SEQUENCE: 25

Arg Ala Ser Glu Ser Val Asp Asn Tyr Gly Ile Ser Phe Met Asn
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: VL CDR2 - AB324 (Kabat)
```

```
<400> SEQUENCE: 26

Ala Ala Ser Asn Gln Gly Ser
1               5

<210> SEQ ID NO 27
<211> LENGTH: 9
<212> TYPE: PRT
<213> ORGANISM: Artificial Sequence
<220> FEATURE:
<223> OTHER INFORMATION: VL CDR3 - AB324 (Kabat)

<400> SEQUENCE: 27

Gln Gln Ser Lys Glu Val Pro Trp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: VH CDR1 - AB324 (Kabat)

<400> SEQUENCE: 28

Ser Tyr Trp Val Asn
1               5

<210> SEQ ID NO 29
<211> LENGTH: 12
<212> TYPE: PRT
<213> ORGANISM: Artificial Sequence
<220> FEATURE:
<223> OTHER INFORMATION: VH CDR3 - AB324 (Kabat)

<400> SEQUENCE: 29

Ser Arg Gly Tyr Phe Tyr Gly Ser Thr Tyr Asp Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: VL CDR1 - AB325 (Kabat)

<400> SEQUENCE: 30

Arg Ala Ser Gln Asp Ile Ser Asn Tyr Leu Asn
1               5                   10

<210> SEQ ID NO 31
<211> LENGTH: 7
<212> TYPE: PRT
<213> ORGANISM: Artificial Sequence
<220> FEATURE:
<223> OTHER INFORMATION: VL CDR2 - AB325 (Kabat)

<400> SEQUENCE: 31

Tyr Thr Ser Arg Leu His Ser
1               5

<210> SEQ ID NO 32
<211> LENGTH: 9
<212> TYPE: PRT
<213> ORGANISM: Artificial Sequence
<220> FEATURE:
<223> OTHER INFORMATION: VL CDR3 - AB325 (Kabat)
```

```
<400> SEQUENCE: 32

Gln Gln Gly Asn Thr Leu Pro Arg Thr
1               5

<210> SEQ ID NO 33
<211> LENGTH: 11
<212> TYPE: PRT
<213> ORGANISM: Artificial Sequence
<220> FEATURE:
<223> OTHER INFORMATION: VH CDR3 - AB325 (Kabat)

<400> SEQUENCE: 33

Trp Tyr Tyr Gly Ser Tyr Tyr Ala Met Asp Tyr
1               5                   10

<210> SEQ ID NO 34
<211> LENGTH: 17
<212> TYPE: PRT
<213> ORGANISM: Artificial Sequence
<220> FEATURE:
<223> OTHER INFORMATION: VH CDR2 - AB326 (Kabat)

<400> SEQUENCE: 34

Tyr Ile Lys Pro Ser Ser Gly Tyr Thr Lys Tyr Asn Gln Lys Phe Lys
1               5                   10                  15

Asp

<210> SEQ ID NO 35
<211> LENGTH: 11
<212> TYPE: PRT
<213> ORGANISM: Artificial Sequence
<220> FEATURE:
<223> OTHER INFORMATION: VL CDR1 - AB327 (Kabat)

<400> SEQUENCE: 35

Lys Ala Ser Gln Asn Val Gly Thr Ala Val Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: VL CDR2 - AB327 (Kabat)

<400> SEQUENCE: 36

Ser Ala Ser Asn Arg Phe Thr
1               5

<210> SEQ ID NO 37
<211> LENGTH: 9
<212> TYPE: PRT
<213> ORGANISM: Artificial Sequence
<220> FEATURE:
<223> OTHER INFORMATION: VL CDR3 - AB327 (Kabat)

<400> SEQUENCE: 37

Gln Gln Tyr Ser Ser Tyr Pro Leu Thr
1               5

<210> SEQ ID NO 38
<211> LENGTH: 5
<212> TYPE: PRT
<213> ORGANISM: Artificial Sequence
<220> FEATURE:
<223> OTHER INFORMATION: VH CDR1 - AB327 (Kabat)
```

```
<400> SEQUENCE: 38

Ser Tyr Ala Met Ser
1               5

<210> SEQ ID NO 39
<211> LENGTH: 17
<212> TYPE: PRT
<213> ORGANISM: Artificial Sequence
<220> FEATURE:
<223> OTHER INFORMATION: VH CDR2 - AB327 (Kabat)

<400> SEQUENCE: 39

Tyr Ile Ser Ser Gly Gly Asp Tyr Ile Tyr Tyr Ala Asp Thr Val Lys
1               5                   10                  15
Gly

<210> SEQ ID NO 40
<211> LENGTH: 11
<212> TYPE: PRT
<213> ORGANISM: Artificial Sequence
<220> FEATURE:
<223> OTHER INFORMATION: VH CDR3 - AB327 (Kabat)

<400> SEQUENCE: 40

Glu Arg Ile Trp Leu Arg Arg Phe Phe Asp Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: VL CDR3 - AB328 (Kabat)

<400> SEQUENCE: 41

Gln Arg Tyr Asn Ser Tyr Pro Tyr Met Phe Thr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: VL CDR1 - AB329 (Kabat)

<400> SEQUENCE: 42

Gln Ala Ser Gln Asp Ile Asp Asn Tyr Leu Ser
1               5                   10

<210> SEQ ID NO 43
<211> LENGTH: 7
<212> TYPE: PRT
<213> ORGANISM: Artificial Sequence
<220> FEATURE:
<223> OTHER INFORMATION: VL CDR2 - AB329 (Kabat)

<400> SEQUENCE: 43

Ser Ala Thr Ser Leu Ala Asp
1               5

<210> SEQ ID NO 44
<211> LENGTH: 8
<212> TYPE: PRT
<213> ORGANISM: Artificial Sequence
<220> FEATURE:
```

<223> OTHER INFORMATION: VL CDR3 - AB329 (Kabat)

<400> SEQUENCE: 44

Leu Gln His Tyr Ser Gly Trp Thr
1               5

<210> SEQ ID NO 45
<211> LENGTH: 5
<212> TYPE: PRT
<213> ORGANISM: Artificial Sequence
<220> FEATURE:
<223> OTHER INFORMATION: VH CDR1 - AB329 (Kabat)

<400> SEQUENCE: 45

Ser Tyr His Val Cys
1               5

<210> SEQ ID NO 46
<211> LENGTH: 16
<212> TYPE: PRT
<213> ORGANISM: Artificial Sequence
<220> FEATURE:
<223> OTHER INFORMATION: VH CDR2 - AB329 (Kabat)

<400> SEQUENCE: 46

Val Ile Trp Gly Asp Gly Arg Thr Thr Tyr Asn Pro Pro Leu Lys Ser
1               5                   10                  15

<210> SEQ ID NO 47
<211> LENGTH: 9
<212> TYPE: PRT
<213> ORGANISM: Artificial Sequence
<220> FEATURE:
<223> OTHER INFORMATION: VH CDR3 - AB329 (Kabat)

<400> SEQUENCE: 47

Ala Thr Met Thr Gly His Gly Asp Ala
1               5

<210> SEQ ID NO 48
<211> LENGTH: 11
<212> TYPE: PRT
<213> ORGANISM: Artificial Sequence
<220> FEATURE:
<223> OTHER INFORMATION: VL CDR1 - AB330 (Kabat)

<400> SEQUENCE: 48

Gln Ala Ser Gln Asp Ile Gly Asn Tyr Leu Ile
1               5                   10

<210> SEQ ID NO 49
<211> LENGTH: 7
<212> TYPE: PRT
<213> ORGANISM: Artificial Sequence
<220> FEATURE:
<223> OTHER INFORMATION: VL CDR2 - AB330 (Kabat)

<400> SEQUENCE: 49

Tyr Ala Thr Asn Leu Ala Asn
1               5

<210> SEQ ID NO 50
<211> LENGTH: 8
<212> TYPE: PRT
<213> ORGANISM: Artificial Sequence
<220> FEATURE:
<223> OTHER INFORMATION: VL CDR3 - AB330 (Kabat)

```
<400> SEQUENCE: 50

Leu Gln Tyr Lys Gln His Leu Thr
1               5

<210> SEQ ID NO 51
<211> LENGTH: 5
<212> TYPE: PRT
<213> ORGANISM: Artificial Sequence
<220> FEATURE:
<223> OTHER INFORMATION: VH CDR1 - AB330 (Kabat)

<400> SEQUENCE: 51

Thr Ala Trp Met Tyr
1               5

<210> SEQ ID NO 52
<211> LENGTH: 19
<212> TYPE: PRT
<213> ORGANISM: Artificial Sequence
<220> FEATURE:
<223> OTHER INFORMATION: VH CDR2 - AB330 (Kabat)

<400> SEQUENCE: 52

Arg Ile Lys Asp Lys Ser Asn Lys Phe Ala Ser Asp Tyr Val Glu Ser
1               5                   10                  15

Val Arg Gly

<210> SEQ ID NO 53
<211> LENGTH: 5
<212> TYPE: PRT
<213> ORGANISM: Artificial Sequence
<220> FEATURE:
<223> OTHER INFORMATION: VH CDR3 - AB330 (Kabat)

<400> SEQUENCE: 53

Ser Tyr Gly Tyr Ala
1               5

<210> SEQ ID NO 54
<211> LENGTH: 19
<212> TYPE: PRT
<213> ORGANISM: Artificial Sequence
<220> FEATURE:
<223> OTHER INFORMATION: VH CDR2 - AB331 (Kabat)

<400> SEQUENCE: 54

Arg Ile Lys Asp Lys Ser Asn Asn Phe Ala Ser Asp Tyr Val Glu Ser
1               5                   10                  15

Val Arg Gly

<210> SEQ ID NO 55
<211> LENGTH: 15
<212> TYPE: PRT
<213> ORGANISM: Artificial Sequence
<220> FEATURE:
<223> OTHER INFORMATION: VL CDR1 - AB332 (Kabat)

<400> SEQUENCE: 55

Lys Ala Ser Gln Ser Val Asp Tyr Asp Gly Asp Ser Tyr Met Asn
1               5                   10                  15

<210> SEQ ID NO 56
<211> LENGTH: 7
<212> TYPE: PRT
```

```
<213> ORGANISM: Artificial Sequence
<220> FEATURE:
<223> OTHER INFORMATION: VL CDR2 - AB332 (Kabat)

<400> SEQUENCE: 56

Ala Ala Ser Asn Leu Glu Ser
1               5

<210> SEQ ID NO 57
<211> LENGTH: 9
<212> TYPE: PRT
<213> ORGANISM: Artificial Sequence
<220> FEATURE:
<223> OTHER INFORMATION: VL CDR3 - AB332 (Kabat)

<400> SEQUENCE: 57

Gln Gln Ser Asn Glu Asp Pro Pro Thr
1               5

<210> SEQ ID NO 58
<211> LENGTH: 5
<212> TYPE: PRT
<213> ORGANISM: Artificial Sequence
<220> FEATURE:
<223> OTHER INFORMATION: VH CDR1 - AB332 (Kabat)

<400> SEQUENCE: 58

Asp Tyr Tyr Met Asn
1               5

<210> SEQ ID NO 59
<211> LENGTH: 16
<212> TYPE: PRT
<213> ORGANISM: Artificial Sequence
<220> FEATURE:
<223> OTHER INFORMATION: VH CDR2 - AB332 (Kabat)

<400> SEQUENCE: 59

Asp Ile Asn Pro Asn Asn Gly Val Thr Ser Tyr Asn Gln Lys Phe Lys
1               5                   10                  15

<210> SEQ ID NO 60
<211> LENGTH: 10
<212> TYPE: PRT
<213> ORGANISM: Artificial Sequence
<220> FEATURE:
<223> OTHER INFORMATION: VH CDR3 - AB332 (Kabat)

<400> SEQUENCE: 60

Glu Asp Tyr Gly Ser Asn Tyr Phe Asp Tyr
1               5                   10

<210> SEQ ID NO 61
<211> LENGTH: 23
<212> TYPE: PRT
<213> ORGANISM: Artificial Sequence
<220> FEATURE:
<223> OTHER INFORMATION: VL FR1 - AB320 (Kabat)

<400> SEQUENCE: 61

Asp Ile Gln Met Thr Gln Ser Pro Ala Ser Leu Ala Ala Ser Val Gly
1               5                   10                  15

Glu Thr Val Thr Ile Thr Cys
            20

<210> SEQ ID NO 62
```

```
<211> LENGTH: 15
<212> TYPE: PRT
<213> ORGANISM: Artificial Sequence
<220> FEATURE:
<223> OTHER INFORMATION: VL FR2 - AB320 (Kabat)

<400> SEQUENCE: 62

Trp Tyr Gln Gln Lys Gln Gly Lys Ser Pro Gln Leu Leu Ile Tyr
1               5                   10                  15

<210> SEQ ID NO 63
<211> LENGTH: 32
<212> TYPE: PRT
<213> ORGANISM: Artificial Sequence
<220> FEATURE:
<223> OTHER INFORMATION: VL FR3 - AB320 (Kabat)

<400> SEQUENCE: 63

Gly Val Pro Ser Arg Phe Ser Gly Ser Gly Ser Gly Thr Gln Tyr Ser
1               5                   10                  15

Met Lys Ile Asn Ser Met Gln Pro Glu Asp Thr Ala Thr Tyr Phe Cys
            20                  25                  30

<210> SEQ ID NO 64
<211> LENGTH: 11
<212> TYPE: PRT
<213> ORGANISM: Artificial Sequence
<220> FEATURE:
<223> OTHER INFORMATION: VL FR4 - AB320 (Kabat)

<400> SEQUENCE: 64

Phe Gly Ser Gly Thr Lys Leu Glu Ile Lys Arg
1               5                   10

<210> SEQ ID NO 65
<211> LENGTH: 30
<212> TYPE: PRT
<213> ORGANISM: Artificial Sequence
<220> FEATURE:
<223> OTHER INFORMATION: VH FR1 - AB320 (Kabat)

<400> SEQUENCE: 65

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser
            20                  25                  30

<210> SEQ ID NO 66
<211> LENGTH: 14
<212> TYPE: PRT
<213> ORGANISM: Artificial Sequence
<220> FEATURE:
<223> OTHER INFORMATION: VH FR2 - AB320 (Kabat)

<400> SEQUENCE: 66

Trp Val Lys Gln Arg Pro Gly Lys Gly Leu Glu Trp Ile Gly
1               5                   10

<210> SEQ ID NO 67
<211> LENGTH: 32
<212> TYPE: PRT
<213> ORGANISM: Artificial Sequence
<220> FEATURE:
<223> OTHER INFORMATION: VH FR3 - AB320 (Kabat)

<400> SEQUENCE: 67
```

```
Lys Ala Thr Leu Thr Ala Asp Lys Ser Ser Thr Ala Tyr Met Gln
1               5                   10                  15

Leu Ser Ser Leu Thr Ser Glu Asp Ser Ala Val Tyr Phe Cys Ala Ser
                20                  25                  30
```

<210> SEQ ID NO 68
<211> LENGTH: 11
<212> TYPE: PRT
<213> ORGANISM: Artificial Sequence
<220> FEATURE:
<223> OTHER INFORMATION: VH FR4 - AB320 (Kabat)

<400> SEQUENCE: 68

```
Trp Gly Gln Gly Thr Leu Val Thr Val Ser Ala
1               5                   10
```

<210> SEQ ID NO 69
<211> LENGTH: 23
<212> TYPE: PRT
<213> ORGANISM: Artificial Sequence
<220> FEATURE:
<223> OTHER INFORMATION: VL FR1 - AB321 (Kabat)

<400> SEQUENCE: 69

```
Ala Ile Gln Met Thr Gln Thr Thr Ser Ser Leu Ser Ala Ser Leu Gly
1               5                   10                  15

Asp Arg Val Thr Ile Ser Cys
                20
```

<210> SEQ ID NO 70
<211> LENGTH: 15
<212> TYPE: PRT
<213> ORGANISM: Artificial Sequence
<220> FEATURE:
<223> OTHER INFORMATION: VL FR2 - AB321 (Kabat)

<400> SEQUENCE: 70

```
Trp Tyr Gln Gln Lys Pro Asp Gly Thr Val Lys Leu Leu Ile Tyr
1               5                   10                  15
```

<210> SEQ ID NO 71
<211> LENGTH: 32
<212> TYPE: PRT
<213> ORGANISM: Artificial Sequence
<220> FEATURE:
<223> OTHER INFORMATION: VL FR3 - AB321 (Kabat)

<400> SEQUENCE: 71

```
Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Thr Tyr Tyr Cys
                20                  25                  30
```

<210> SEQ ID NO 72
<211> LENGTH: 11
<212> TYPE: PRT
<213> ORGANISM: Artificial Sequence
<220> FEATURE:
<223> OTHER INFORMATION: VL FR4 - AB321 (Kabat)

<400> SEQUENCE: 72

```
Phe Gly Ala Gly Thr Lys Leu Glu Leu Lys Arg
1               5                   10
```

<210> SEQ ID NO 73

<211> LENGTH: 30
<212> TYPE: PRT
<213> ORGANISM: Artificial Sequence
<220> FEATURE:
<223> OTHER INFORMATION: VH FR1 - AB321 (Kabat)

<400> SEQUENCE: 73

Gln Val Gln Leu Gln Gln Pro Gly Ala Glu Phe Val Lys Pro Gly Ala
1               5                   10                  15
Ser Val Lys Leu Ser Cys Lys Ala Ser Gly Tyr Thr Phe Thr
            20                  25                  30

<210> SEQ ID NO 74
<211> LENGTH: 14
<212> TYPE: PRT
<213> ORGANISM: Artificial Sequence
<220> FEATURE:
<223> OTHER INFORMATION: VH FR2 - AB321 (Kabat)

<400> SEQUENCE: 74

Trp Val Lys Gln Arg Pro Gly Arg Gly Leu Glu Trp Ile Gly
1               5                   10

<210> SEQ ID NO 75
<211> LENGTH: 32
<212> TYPE: PRT
<213> ORGANISM: Artificial Sequence
<220> FEATURE:
<223> OTHER INFORMATION: VH FR3 - AB321 (Kabat)

<400> SEQUENCE: 75

Lys Ala Thr Leu Thr Val Asp Lys Pro Ser Ser Thr Ala Tyr Met Gln
1               5                   10                  15
Leu Ser Ser Leu Thr Ser Glu Asp Ser Ala Val Tyr Tyr Cys Ala Arg
            20                  25                  30

<210> SEQ ID NO 76
<211> LENGTH: 23
<212> TYPE: PRT
<213> ORGANISM: Artificial Sequence
<220> FEATURE:
<223> OTHER INFORMATION: VL FR1 - AB322 (Kabat)

<400> SEQUENCE: 76

Asp Ile Val Met Thr Gln Ser Gln Arg Phe Met Ser Thr Ser Val Gly
1               5                   10                  15
Asp Arg Val Ser Val Thr Cys
            20

<210> SEQ ID NO 77
<211> LENGTH: 15
<212> TYPE: PRT
<213> ORGANISM: Artificial Sequence
<220> FEATURE:
<223> OTHER INFORMATION: VL FR2 - AB322 (Kabat)

<400> SEQUENCE: 77

Trp Tyr Gln Gln Lys Pro Gly Gln Ser Pro Lys Ala Leu Ile Tyr
1               5                   10                  15

<210> SEQ ID NO 78
<211> LENGTH: 32
<212> TYPE: PRT
<213> ORGANISM: Artificial Sequence
<220> FEATURE:
<223> OTHER INFORMATION: VL FR3 - AB322 (Kabat)

<400> SEQUENCE: 78

Gly Val Pro Asp Arg Phe Thr Gly Ser Gly Ser Gly Thr Asp Phe Thr
1               5                   10                  15

Leu Thr Val Ser Asn Val Gln Ser Glu Asp Leu Ala Glu Tyr Phe Cys
            20                  25                  30

<210> SEQ ID NO 79
<211> LENGTH: 11
<212> TYPE: PRT
<213> ORGANISM: Artificial Sequence
<220> FEATURE:
<223> OTHER INFORMATION: VL FR4 - AB322 (Kabat)

<400> SEQUENCE: 79

Phe Gly Gly Gly Thr Lys Leu Glu Ile Lys Arg
1               5                   10

<210> SEQ ID NO 80
<211> LENGTH: 30
<212> TYPE: PRT
<213> ORGANISM: Artificial Sequence
<220> FEATURE:
<223> OTHER INFORMATION: VH FR1 - AB326 (Kabat)

<400> SEQUENCE: 80

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr
            20                  25                  30

<210> SEQ ID NO 81
<211> LENGTH: 14
<212> TYPE: PRT
<213> ORGANISM: Artificial Sequence
<220> FEATURE:
<223> OTHER INFORMATION: VH FR2 - AB326 (Kabat)

<400> SEQUENCE: 81

Trp Val Lys Gln Arg Pro Gly Gln Gly Leu Glu Trp Ile Gly
1               5                   10

<210> SEQ ID NO 82
<211> LENGTH: 32
<212> TYPE: PRT
<213> ORGANISM: Artificial Sequence
<220> FEATURE:
<223> OTHER INFORMATION: VH FR3 - AB326 (Kabat)

<400> SEQUENCE: 82

Lys Ala Thr Leu Thr Ala Asp Lys Ser Ser Thr Ala Tyr Met Gln
1               5                   10                  15

Leu Ser Ser Leu Thr Tyr Glu Asp Ser Ala Val Tyr Tyr Cys Ala Arg
            20                  25                  30

<210> SEQ ID NO 83
<211> LENGTH: 23
<212> TYPE: PRT
<213> ORGANISM: Artificial Sequence
<220> FEATURE:
<223> OTHER INFORMATION: VL FR1 - AB323 (Kabat)

<400> SEQUENCE: 83

Asp Ile Val Met Thr Gln Ser His Lys Phe Met Ser Thr Ser Val Gly
1               5                   10                  15

Asp Arg Val Ser Ile Thr Cys
            20

<210> SEQ ID NO 84
<211> LENGTH: 15
<212> TYPE: PRT
<213> ORGANISM: Artificial Sequence
<220> FEATURE:
<223> OTHER INFORMATION: VL FR2 - AB323 (Kabat)

<400> SEQUENCE: 84

Trp Tyr Gln Gln Lys Pro Gly Gln Ser Pro Lys Pro Leu Ile Tyr
1               5                   10                  15

<210> SEQ ID NO 85
<211> LENGTH: 32
<212> TYPE: PRT
<213> ORGANISM: Artificial Sequence
<220> FEATURE:
<223> OTHER INFORMATION: VL FR3 - AB323 (Kabat)

<400> SEQUENCE: 85

Gly Val Pro Asp Arg Phe Thr Gly Ser Gly Ser Gly Thr Asp Tyr Thr
1               5                   10                  15

Leu Thr Ile Ser Ser Val Gln Thr Glu Asp Leu Ala Leu Tyr Tyr Cys
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: VH FR1 - AB323 (Kabat)

<400> SEQUENCE: 86

Gln Val Gln Leu Gln Gln Ser Gly Ala Glu Leu Val Lys Pro Gly Ala
1               5                   10                  15

Ser Val Lys Ile Ser Cys Lys Thr Ser Gly Tyr Thr Phe Ser
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: VH FR3 - AB323 (Kabat)

<400> SEQUENCE: 87

Lys Ala Thr Leu Thr Ala Asp Lys Ser Ser Ser Ala Ala Phe Met Gln
1               5                   10                  15

Leu Ser Ser Leu Thr Ser Glu Asp Ser Ala Val Tyr Phe Cys Ala Arg
            20                  25                  30

<210> SEQ ID NO 88
<211> LENGTH: 23
<212> TYPE: PRT
<213> ORGANISM: Artificial Sequence
<220> FEATURE:
<223> OTHER INFORMATION: VL FR1 - AB324 (Kabat)

<400> SEQUENCE: 88

Asp Ile Val Leu Thr Gln Ser Pro Ala Ser Leu Ala Val Ser Leu Gly
1               5                   10                  15

Gln Arg Ala Thr Ile Ser Cys
            20

20

<210> SEQ ID NO 89
<211> LENGTH: 15
<212> TYPE: PRT
<213> ORGANISM: Artificial Sequence
<220> FEATURE:
<223> OTHER INFORMATION: VL FR2 - AB324 (Kabat)

<400> SEQUENCE: 89

Trp Tyr Gln Gln Lys Pro Gly Gln Pro Pro Lys Leu Leu Ile Tyr
1               5                   10                  15

<210> SEQ ID NO 90
<211> LENGTH: 32
<212> TYPE: PRT
<213> ORGANISM: Artificial Sequence
<220> FEATURE:
<223> OTHER INFORMATION: VL FR3 - AB324 (Kabat)

<400> SEQUENCE: 90

Gly Val Pro Ala Arg Phe Ser Gly Ser Gly Ser Gly Thr Asp Phe Ser
1               5                   10                  15

Leu Asn Ile His Pro Met Glu Glu Asp Asp Thr Ala Met Tyr Phe Cys
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: VH FR3 - AB324 (Kabat)

<400> SEQUENCE: 91

Lys Ala Thr Leu Thr Ala Asp Lys Ser Ser Ser Thr Ala Tyr Met Gln
1               5                   10                  15

Leu Ser Ser Leu Thr Ser Glu Asp Ser Ala Val Tyr Phe Cys Ala Arg
            20                  25                  30

<210> SEQ ID NO 92
<211> LENGTH: 11
<212> TYPE: PRT
<213> ORGANISM: Artificial Sequence
<220> FEATURE:
<223> OTHER INFORMATION: VH FR4 - AB324 (Kabat)

<400> SEQUENCE: 92

Trp Gly Gln Gly Thr Thr Leu Thr Val Ser Ser
1               5                   10

<210> SEQ ID NO 93
<211> LENGTH: 23
<212> TYPE: PRT
<213> ORGANISM: Artificial Sequence
<220> FEATURE:
<223> OTHER INFORMATION: VL FR1 - AB325 (Kabat)

<400> SEQUENCE: 93

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 94
<211> LENGTH: 32

<212> TYPE: PRT
<213> ORGANISM: Artificial Sequence
<220> FEATURE:
<223> OTHER INFORMATION: VL FR3 - AB325 (Kabat)

<400> SEQUENCE: 94

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30

<210> SEQ ID NO 95
<211> LENGTH: 11
<212> TYPE: PRT
<213> ORGANISM: Artificial Sequence
<220> FEATURE:
<223> OTHER INFORMATION: VH FR4 - AB325 (Kabat)

<400> SEQUENCE: 95

Trp Gly Gln Gly Thr Ser Val Thr Val Ser Ser
1               5                   10

<210> SEQ ID NO 96
<211> LENGTH: 32
<212> TYPE: PRT
<213> ORGANISM: Artificial Sequence
<220> FEATURE:
<223> OTHER INFORMATION: VL FR3 - AB326 (Kabat)

<400> SEQUENCE: 96

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Glu Tyr Phe Cys
            20                  25                  30

<210> SEQ ID NO 97
<211> LENGTH: 23
<212> TYPE: PRT
<213> ORGANISM: Artificial Sequence
<220> FEATURE:
<223> OTHER INFORMATION: VL FR1 - AB327 (Kabat)

<400> SEQUENCE: 97

Asp Ile Val Met Thr Gln Ser Gln Lys Phe Met Ser Thr Ser Val Gly
1               5                   10                  15

Asp Arg Val Ser Ile Thr Cys
            20

<210> SEQ ID NO 98
<211> LENGTH: 15
<212> TYPE: PRT
<213> ORGANISM: Artificial Sequence
<220> FEATURE:
<223> OTHER INFORMATION: VL FR2 - AB327 (Kabat)

<400> SEQUENCE: 98

Trp Tyr Gln Leu Lys Pro Gly Gln Ser Pro Lys Leu Leu Ile Tyr
1               5                   10                  15

<210> SEQ ID NO 99
<211> LENGTH: 32
<212> TYPE: PRT
<213> ORGANISM: Artificial Sequence
<220> FEATURE:
<223> OTHER INFORMATION: VL FR3 - AB327 (Kabat)

```
<400> SEQUENCE: 99

Gly Val Pro Asp Arg Phe Thr Gly Ser Gly Ser Gly Thr Asp Phe Thr
1               5                   10                  15

Leu Thr Ile Ser Asn Met Gln Ser Glu Asp Leu Ala Asp Tyr Phe Cys
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: VH FR1 - AB327 (Kabat)

<400> SEQUENCE: 100

Asp Val Lys Leu Val Glu Ser Gly Glu Gly Leu Val Lys Pro Gly Gly
1               5                   10                  15

Ser Leu Lys Leu Ser Cys Ala Ala Ser Gly Phe Thr Phe Ser
            20                  25                  30

<210> SEQ ID NO 101
<211> LENGTH: 14
<212> TYPE: PRT
<213> ORGANISM: Artificial Sequence
<220> FEATURE:
<223> OTHER INFORMATION: VH FR2 - AB327 (Kabat)

<400> SEQUENCE: 101

Trp Val Arg Gln Thr Pro Glu Lys Arg Leu Glu Trp Val Thr
1               5                   10

<210> SEQ ID NO 102
<211> LENGTH: 32
<212> TYPE: PRT
<213> ORGANISM: Artificial Sequence
<220> FEATURE:
<223> OTHER INFORMATION: VH FR3 - AB327 (Kabat)

<400> SEQUENCE: 102

Arg Phe Thr Ile Ser Arg Asp Asn Ala Arg Asn Thr Leu Tyr Leu Gln
1               5                   10                  15

Met Ser Ser Leu Lys Ser Glu Asp Thr Ala Met Tyr Tyr Cys Thr Arg
            20                  25                  30

<210> SEQ ID NO 103
<211> LENGTH: 11
<212> TYPE: PRT
<213> ORGANISM: Artificial Sequence
<220> FEATURE:
<223> OTHER INFORMATION: VH FR4 - AB327 (Kabat)

<400> SEQUENCE: 103

Trp Gly Thr Gly Thr Thr Val Thr Val Ser Ser
1               5                   10

<210> SEQ ID NO 104
<211> LENGTH: 23
<212> TYPE: PRT
<213> ORGANISM: Artificial Sequence
<220> FEATURE:
<223> OTHER INFORMATION: VL FR1 - AB328 (Kabat)

<400> SEQUENCE: 104

Asp Ile Val Met Thr Gln Ser Gln Lys Phe Met Ser Thr Ser Val Gly
1               5                   10                  15
```

Asp Arg Val Ser Val Thr Cys
            20

<210> SEQ ID NO 105
<211> LENGTH: 15
<212> TYPE: PRT
<213> ORGANISM: Artificial Sequence
<220> FEATURE:
<223> OTHER INFORMATION: VL FR2 - AB328 (Kabat)

<400> SEQUENCE: 105

Trp Tyr Gln Gln Lys Pro Gly His Ser Pro Lys Ala Leu Ile Tyr
1               5                   10                  15

<210> SEQ ID NO 106
<211> LENGTH: 32
<212> TYPE: PRT
<213> ORGANISM: Artificial Sequence
<220> FEATURE:
<223> OTHER INFORMATION: VH FR3 - AB328 (Kabat)

<400> SEQUENCE: 106

Lys Ala Thr Leu Thr Ala Asp Lys Ser Ser Thr Ala Tyr Met Gln
1               5                   10                  15

Leu Ser Ser Leu Thr Phe Glu Asp Ser Ala Val Tyr Tyr Cys Ala Arg
            20                  25                  30

<210> SEQ ID NO 107
<211> LENGTH: 23
<212> TYPE: PRT
<213> ORGANISM: Artificial Sequence
<220> FEATURE:
<223> OTHER INFORMATION: VL FR1 - AB329 (Kabat)

<400> SEQUENCE: 107

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 108
<211> LENGTH: 15
<212> TYPE: PRT
<213> ORGANISM: Artificial Sequence
<220> FEATURE:
<223> OTHER INFORMATION: VL FR2 - AB329 (Kabat)

<400> SEQUENCE: 108

Trp Tyr Gln Gln Lys Pro Gly Lys Ser Pro His Leu Leu Ile His
1               5                   10                  15

<210> SEQ ID NO 109
<211> LENGTH: 32
<212> TYPE: PRT
<213> ORGANISM: Artificial Sequence
<220> FEATURE:
<223> OTHER INFORMATION: VL FR3 - AB329 (Kabat)

<400> SEQUENCE: 109

Gly Val Pro Ser Arg Phe Ser Gly Gly Arg Ser Gly Thr Gln Phe Ser
1               5                   10                  15

Leu Lys Ile Asn Arg Leu Gln Val Glu Asp Thr Gly Ile Tyr Tyr Cys
            20                  25                  30

<210> SEQ ID NO 110

```
<211> LENGTH: 11
<212> TYPE: PRT
<213> ORGANISM: Artificial Sequence
<220> FEATURE:
<223> OTHER INFORMATION: VL FR4 - AB329 (Kabat)

<400> SEQUENCE: 110

Phe Gly Gly Gly Thr Lys Leu Glu Leu Lys Arg
1               5                   10

<210> SEQ ID NO 111
<211> LENGTH: 30
<212> TYPE: PRT
<213> ORGANISM: Artificial Sequence
<220> FEATURE:
<223> OTHER INFORMATION: VH FR1 - AB329 (Kabat)

<400> SEQUENCE: 111

Gln Val Gln Leu Lys Glu Ser Gly Pro Gly Leu Val Lys Pro Ser Ala
1               5                   10                  15

Thr Leu Ser Leu Thr Cys Thr Val Ser Gly Phe Ser Leu Thr
            20                  25                  30

<210> SEQ ID NO 112
<211> LENGTH: 14
<212> TYPE: PRT
<213> ORGANISM: Artificial Sequence
<220> FEATURE:
<223> OTHER INFORMATION: VH FR2 - AB329 (Kabat)

<400> SEQUENCE: 112

Trp Ile Arg Gln Thr Pro Gly Lys Gly Leu Glu Trp Met Gly
1               5                   10

<210> SEQ ID NO 113
<211> LENGTH: 32
<212> TYPE: PRT
<213> ORGANISM: Artificial Sequence
<220> FEATURE:
<223> OTHER INFORMATION: VH FR3 - AB329 (Kabat)

<400> SEQUENCE: 113

Arg Leu Ser Ile Ser Arg Asp Thr Ser Lys Ser Gln Val Phe Leu Lys
1               5                   10                  15

Met Ser Ser Leu Lys Thr Glu Asp Thr Ala Thr Tyr Tyr Cys Ala Arg
            20                  25                  30

<210> SEQ ID NO 114
<211> LENGTH: 11
<212> TYPE: PRT
<213> ORGANISM: Artificial Sequence
<220> FEATURE:
<223> OTHER INFORMATION: VH FR4 - AB329 (Kabat)

<400> SEQUENCE: 114

Trp Gly Gln Gly Ala Ser Val Thr Val Ser Ser
1               5                   10

<210> SEQ ID NO 115
<211> LENGTH: 23
<212> TYPE: PRT
<213> ORGANISM: Artificial Sequence
<220> FEATURE:
<223> OTHER INFORMATION: VL FR1 - AB330 (Kabat)

<400> SEQUENCE: 115
```

```
Asp Ile Gln Met Thr Gln Ser Pro Ser Ser Met Ser Ala Ser Leu Gly
1               5                   10                  15

Asp Arg Val Thr Ile Thr Cys
            20
```

<210> SEQ ID NO 116
<211> LENGTH: 15
<212> TYPE: PRT
<213> ORGANISM: Artificial Sequence
<220> FEATURE:
<223> OTHER INFORMATION: VL FR2 - AB330 (Kabat)

<400> SEQUENCE: 116

```
Trp Phe Gln Gln Lys Pro Gly Lys Ser Pro Arg Pro Leu Ile Tyr
1               5                   10                  15
```

<210> SEQ ID NO 117
<211> LENGTH: 32
<212> TYPE: PRT
<213> ORGANISM: Artificial Sequence
<220> FEATURE:
<223> OTHER INFORMATION: VL FR3 - AB330 (Kabat)

<400> SEQUENCE: 117

```
Gly Val Pro Ser Arg Phe Ser Gly Ser Arg Ser Gly Ser Glu Tyr Ser
1               5                   10                  15

Leu Thr Ile Thr Ser Leu Glu Ser Glu Asp Met Ala Asp Tyr His Cys
            20                  25                  30
```

<210> SEQ ID NO 118
<211> LENGTH: 11
<212> TYPE: PRT
<213> ORGANISM: Artificial Sequence
<220> FEATURE:
<223> OTHER INFORMATION: VL FR4 - AB330 (Kabat)

<400> SEQUENCE: 118

```
Phe Gly Ser Gly Thr Lys Leu Glu Ile Glu Arg
1               5                   10
```

<210> SEQ ID NO 119
<211> LENGTH: 30
<212> TYPE: PRT
<213> ORGANISM: Artificial Sequence
<220> FEATURE:
<223> OTHER INFORMATION: VH FR1 - AB330 (Kabat)

<400> SEQUENCE: 119

```
Glu Val Gln Val Val Glu Thr Gly Gly Gly Val Val Gln Pro Gly Lys
1               5                   10                  15

Ser Leu Glu Ile Thr Cys Ala Thr Ser Gly Leu Thr Phe Ser
            20                  25                  30
```

<210> SEQ ID NO 120
<211> LENGTH: 14
<212> TYPE: PRT
<213> ORGANISM: Artificial Sequence
<220> FEATURE:
<223> OTHER INFORMATION: VH FR2 - AB330 (Kabat)

<400> SEQUENCE: 120

```
Trp Val Arg Gln Ser Ser Asp Arg Arg Leu Glu Trp Ile Ala
1               5                   10
```

<210> SEQ ID NO 121

```
<211> LENGTH: 32
<212> TYPE: PRT
<213> ORGANISM: Artificial Sequence
<220> FEATURE:
<223> OTHER INFORMATION: VH FR3 - AB330 (Kabat)

<400> SEQUENCE: 121

Arg Phe Thr Ile Ser Arg Asp Asp Ser Arg Ser Ser Val Tyr Leu Gln
1               5                   10                  15
Met Asn Asn Leu Lys Glu Glu Asp Thr Ala Thr Tyr Tyr Cys Thr Thr
            20                  25                  30

<210> SEQ ID NO 122
<211> LENGTH: 11
<212> TYPE: PRT
<213> ORGANISM: Artificial Sequence
<220> FEATURE:
<223> OTHER INFORMATION: VH FR4 - AB330 (Kabat)

<400> SEQUENCE: 122

Trp Gly Gln Gly Val Met Val Thr Val Ser Ser
1               5                   10

<210> SEQ ID NO 123
<211> LENGTH: 23
<212> TYPE: PRT
<213> ORGANISM: Artificial Sequence
<220> FEATURE:
<223> OTHER INFORMATION: VL FR1 - AB331 (Kabat)

<400> SEQUENCE: 123

Asp Ile Gln Met Thr Gln Ser Pro Ser Ser Met Ser Ala Ser Leu Gly
1               5                   10                  15
Asp Arg Ile Thr Ile Thr Cys
            20

<210> SEQ ID NO 124
<211> LENGTH: 32
<212> TYPE: PRT
<213> ORGANISM: Artificial Sequence
<220> FEATURE:
<223> OTHER INFORMATION: VL FR3 - AB332 (Kabat)

<400> SEQUENCE: 124

Gly Ile Pro Ala Arg Leu Ser Gly Ser Gly Ser Gly Thr Asp Phe Thr
1               5                   10                  15
Leu Asn Ile His Pro Val Glu Glu Asp Ala Ala Thr Tyr Tyr Cys
            20                  25                  30

<210> SEQ ID NO 125
<211> LENGTH: 11
<212> TYPE: PRT
<213> ORGANISM: Artificial Sequence
<220> FEATURE:
<223> OTHER INFORMATION: VL FR4 - AB332 (Kabat)

<400> SEQUENCE: 125

Phe Gly Gly Gly Thr Lys Leu Glu Ile Arg Arg
1               5                   10

<210> SEQ ID NO 126
<211> LENGTH: 30
<212> TYPE: PRT
<213> ORGANISM: Artificial Sequence
<220> FEATURE:
<223> OTHER INFORMATION: VH FR1 - AB332 (Kabat)
```

```
<400> SEQUENCE: 126

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Thr Phe Thr
            20                  25                  30

<210> SEQ ID NO 127
<211> LENGTH: 14
<212> TYPE: PRT
<213> ORGANISM: Artificial Sequence
<220> FEATURE:
<223> OTHER INFORMATION: VH FR2 - AB332 (Kabat)

<400> SEQUENCE: 127

Trp Met Lys Gln Ser His Gly Lys Ser Leu Glu Trp Ile Gly
1               5                   10

<210> SEQ ID NO 128
<211> LENGTH: 33
<212> TYPE: PRT
<213> ORGANISM: Artificial Sequence
<220> FEATURE:
<223> OTHER INFORMATION: VH FR3 - AB332 (Kabat)

<400> SEQUENCE: 128

Gly Lys Ala Thr Leu Thr Val Asp Lys Ser Ser Thr Ala Tyr Met
1               5                   10                  15

Glu Leu Arg Ser Leu Thr Ser Glu Asp Ser Ala Val Tyr Tyr Cys Ala
            20                  25                  30

Arg

<210> SEQ ID NO 129
<211> LENGTH: 6
<212> TYPE: PRT
<213> ORGANISM: Artificial Sequence
<220> FEATURE:
<223> OTHER INFORMATION: VL CDR1 - AB320 (IMGT)

<400> SEQUENCE: 129

Glu Asn Ile Tyr Tyr Ser
1               5

<210> SEQ ID NO 130
<211> LENGTH: 3
<212> TYPE: PRT
<213> ORGANISM: Artificial Sequence
<220> FEATURE:
<223> OTHER INFORMATION: VL CDR2 - AB320 (IMGT)

<400> SEQUENCE: 130

Asn Ala Asn
1

<210> SEQ ID NO 131
<211> LENGTH: 7
<212> TYPE: PRT
<213> ORGANISM: Artificial Sequence
<220> FEATURE:
<223> OTHER INFORMATION: VL CDR3 - AB320 (IMGT)

<400> SEQUENCE: 131

Lys Gln Ala Tyr Asp Val Pro
1               5
```

<210> SEQ ID NO 132
<211> LENGTH: 8
<212> TYPE: PRT
<213> ORGANISM: Artificial Sequence
<220> FEATURE:
<223> OTHER INFORMATION: VH CDR1 - AB320 (IMGT)

<400> SEQUENCE: 132

Gly Tyr Ala Phe Ser Ser Tyr Trp
1               5

<210> SEQ ID NO 133
<211> LENGTH: 8
<212> TYPE: PRT
<213> ORGANISM: Artificial Sequence
<220> FEATURE:
<223> OTHER INFORMATION: VH CDR2 - AB320 (IMGT)

<400> SEQUENCE: 133

Ile Tyr Pro Gly Asp Gly Asp Thr
1               5

<210> SEQ ID NO 134
<211> LENGTH: 10
<212> TYPE: PRT
<213> ORGANISM: Artificial Sequence
<220> FEATURE:
<223> OTHER INFORMATION: VH CDR3 - AB320 (IMGT)

<400> SEQUENCE: 134

Ala Ser Tyr Tyr Tyr Gly Ser Lys Ala Tyr
1               5                   10

<210> SEQ ID NO 135
<211> LENGTH: 6
<212> TYPE: PRT
<213> ORGANISM: Artificial Sequence
<220> FEATURE:
<223> OTHER INFORMATION: VL CDR1 - AB321 (IMGT)

<400> SEQUENCE: 135

Gln Gly Ile Ser Asn Ser
1               5

<210> SEQ ID NO 136
<211> LENGTH: 3
<212> TYPE: PRT
<213> ORGANISM: Artificial Sequence
<220> FEATURE:
<223> OTHER INFORMATION: VL CDR2 - AB321 (IMGT)

<400> SEQUENCE: 136

Tyr Thr Ser
1

<210> SEQ ID NO 137
<211> LENGTH: 7
<212> TYPE: PRT
<213> ORGANISM: Artificial Sequence
<220> FEATURE:
<223> OTHER INFORMATION: VL CDR3 - AB321 (IMGT)

<400> SEQUENCE: 137

Gln Gln Tyr Ser Lys Leu Pro
1               5

```
<210> SEQ ID NO 138
<211> LENGTH: 8
<212> TYPE: PRT
<213> ORGANISM: Artificial Sequence
<220> FEATURE:
<223> OTHER INFORMATION: VH CDR1 - AB321 (IMGT)

<400> SEQUENCE: 138

Gly Tyr Thr Phe Thr Ser Tyr Trp
1               5

<210> SEQ ID NO 139
<211> LENGTH: 8
<212> TYPE: PRT
<213> ORGANISM: Artificial Sequence
<220> FEATURE:
<223> OTHER INFORMATION: VH CDR2 - AB321 (IMGT)

<400> SEQUENCE: 139

Ile Asp Pro Asn Ser Gly Gly Thr
1               5

<210> SEQ ID NO 140
<211> LENGTH: 13
<212> TYPE: PRT
<213> ORGANISM: Artificial Sequence
<220> FEATURE:
<223> OTHER INFORMATION: VH CDR3 - AB321 (IMGT)

<400> SEQUENCE: 140

Ala Arg Asp Tyr Tyr Gly Ser Ser Tyr Arg Phe Ala Tyr
1               5                   10

<210> SEQ ID NO 141
<211> LENGTH: 6
<212> TYPE: PRT
<213> ORGANISM: Artificial Sequence
<220> FEATURE:
<223> OTHER INFORMATION: VL CDR1 - AB322 (IMGT)

<400> SEQUENCE: 141

Gln Asn Val Gly Thr Asn
1               5

<210> SEQ ID NO 142
<211> LENGTH: 3
<212> TYPE: PRT
<213> ORGANISM: Artificial Sequence
<220> FEATURE:
<223> OTHER INFORMATION: VL CDR2 - AB322 (IMGT)

<400> SEQUENCE: 142

Ser Ala Ser
1

<210> SEQ ID NO 143
<211> LENGTH: 7
<212> TYPE: PRT
<213> ORGANISM: Artificial Sequence
<220> FEATURE:
<223> OTHER INFORMATION: VL CDR3 - AB322 (IMGT)

<400> SEQUENCE: 143

Gln Gln Tyr Asn Ser Tyr Pro
1               5

<210> SEQ ID NO 144
```

```
<211> LENGTH: 8
<212> TYPE: PRT
<213> ORGANISM: Artificial Sequence
<220> FEATURE:
<223> OTHER INFORMATION: VH CDR1 - AB322 (IMGT)

<400> SEQUENCE: 144

Gly Tyr Thr Phe Thr Asn Tyr Trp
1               5

<210> SEQ ID NO 145
<211> LENGTH: 8
<212> TYPE: PRT
<213> ORGANISM: Artificial Sequence
<220> FEATURE:
<223> OTHER INFORMATION: VH CDR2 - AB322 (IMGT)

<400> SEQUENCE: 145

Ile Asn Pro Ser Ser Gly Tyr Thr
1               5

<210> SEQ ID NO 146
<211> LENGTH: 13
<212> TYPE: PRT
<213> ORGANISM: Artificial Sequence
<220> FEATURE:
<223> OTHER INFORMATION: VH CDR3 - AB322 (IMGT)

<400> SEQUENCE: 146

Ala Arg Asp Tyr Tyr Gly Ser Ser Trp Phe Ala Tyr
1               5                   10

<210> SEQ ID NO 147
<211> LENGTH: 6
<212> TYPE: PRT
<213> ORGANISM: Artificial Sequence
<220> FEATURE:
<223> OTHER INFORMATION: VL CDR1 - AB323 (IMGT)

<400> SEQUENCE: 147

Gln Asp Val Ser Thr Ala
1               5

<210> SEQ ID NO 148
<211> LENGTH: 3
<212> TYPE: PRT
<213> ORGANISM: Artificial Sequence
<220> FEATURE:
<223> OTHER INFORMATION: VL CDR2 - AB323 (IMGT)

<400> SEQUENCE: 148

Trp Ala Ser
1

<210> SEQ ID NO 149
<211> LENGTH: 7
<212> TYPE: PRT
<213> ORGANISM: Artificial Sequence
<220> FEATURE:
<223> OTHER INFORMATION: VL CDR3 - AB323 (IMGT)

<400> SEQUENCE: 149

Gln Gln His Tyr Ser Thr Pro
1               5

<210> SEQ ID NO 150
<211> LENGTH: 8
```

```
<212> TYPE: PRT
<213> ORGANISM: Artificial Sequence
<220> FEATURE:
<223> OTHER INFORMATION: VH CDR1 - AB323 (IMGT)

<400> SEQUENCE: 150

Gly Tyr Thr Phe Ser Asn Tyr Trp
1               5

<210> SEQ ID NO 151
<211> LENGTH: 8
<212> TYPE: PRT
<213> ORGANISM: Artificial Sequence
<220> FEATURE:
<223> OTHER INFORMATION: VH CDR2 - AB323 (IMGT)

<400> SEQUENCE: 151

Ile Phe Pro Gly Asp Ala Asp Ala
1               5

<210> SEQ ID NO 152
<211> LENGTH: 11
<212> TYPE: PRT
<213> ORGANISM: Artificial Sequence
<220> FEATURE:
<223> OTHER INFORMATION: VH CDR3 - AB323 (IMGT)

<400> SEQUENCE: 152

Ala Arg Phe Ser Tyr Asp Gly Ala Phe Ala Tyr
1               5                   10

<210> SEQ ID NO 153
<211> LENGTH: 10
<212> TYPE: PRT
<213> ORGANISM: Artificial Sequence
<220> FEATURE:
<223> OTHER INFORMATION: VL CDR1 - AB324 (IMGT)

<400> SEQUENCE: 153

Glu Ser Val Asp Asn Tyr Gly Ile Ser Phe
1               5                   10

<210> SEQ ID NO 154
<211> LENGTH: 3
<212> TYPE: PRT
<213> ORGANISM: Artificial Sequence
<220> FEATURE:
<223> OTHER INFORMATION: VL CDR2 - AB324 (IMGT)

<400> SEQUENCE: 154

Ala Ala Ser
1

<210> SEQ ID NO 155
<211> LENGTH: 7
<212> TYPE: PRT
<213> ORGANISM: Artificial Sequence
<220> FEATURE:
<223> OTHER INFORMATION: VL CDR3 - AB324 (IMGT)

<400> SEQUENCE: 155

Gln Gln Ser Lys Glu Val Pro
1               5

<210> SEQ ID NO 156
<211> LENGTH: 14
<212> TYPE: PRT
```

```
<213> ORGANISM: Artificial Sequence
<220> FEATURE:
<223> OTHER INFORMATION: VH CDR3 - AB324 (IMGT)

<400> SEQUENCE: 156

Ala Arg Ser Arg Gly Tyr Phe Tyr Gly Ser Thr Tyr Asp Ser
1               5                   10

<210> SEQ ID NO 157
<211> LENGTH: 6
<212> TYPE: PRT
<213> ORGANISM: Artificial Sequence
<220> FEATURE:
<223> OTHER INFORMATION: VL CDR1 - AB325 (IMGT)

<400> SEQUENCE: 157

Gln Asp Ile Ser Asn Tyr
1               5

<210> SEQ ID NO 158
<211> LENGTH: 7
<212> TYPE: PRT
<213> ORGANISM: Artificial Sequence
<220> FEATURE:
<223> OTHER INFORMATION: VL CDR3 - AB325 (IMGT)

<400> SEQUENCE: 158

Gln Gln Gly Asn Thr Leu Pro
1               5

<210> SEQ ID NO 159
<211> LENGTH: 13
<212> TYPE: PRT
<213> ORGANISM: Artificial Sequence
<220> FEATURE:
<223> OTHER INFORMATION: VH CDR3 - AB325 (IMGT)

<400> SEQUENCE: 159

Ala Arg Trp Tyr Tyr Gly Ser Tyr Tyr Ala Met Asp Tyr
1               5                   10

<210> SEQ ID NO 160
<211> LENGTH: 8
<212> TYPE: PRT
<213> ORGANISM: Artificial Sequence
<220> FEATURE:
<223> OTHER INFORMATION: VH CDR2 - AB326 (IMGT)

<400> SEQUENCE: 160

Ile Lys Pro Ser Ser Gly Tyr Thr
1               5

<210> SEQ ID NO 161
<211> LENGTH: 8
<212> TYPE: PRT
<213> ORGANISM: Artificial Sequence
<220> FEATURE:
<223> OTHER INFORMATION: VL CDR1 - AB327 (IMGT)

<400> SEQUENCE: 161

Gln Asn Val Gly Thr Ala Val Ala
1               5

<210> SEQ ID NO 162
<211> LENGTH: 7
<212> TYPE: PRT
<213> ORGANISM: Artificial Sequence
```

```
<220> FEATURE:
<223> OTHER INFORMATION: VL CDR3 - AB327 (IMGT)

<400> SEQUENCE: 162

Gln Gln Tyr Ser Ser Tyr Pro
1               5

<210> SEQ ID NO 163
<211> LENGTH: 8
<212> TYPE: PRT
<213> ORGANISM: Artificial Sequence
<220> FEATURE:
<223> OTHER INFORMATION: VH CDR1 - AB327 (IMGT)

<400> SEQUENCE: 163

Gly Phe Thr Phe Ser Ser Tyr Ala
1               5

<210> SEQ ID NO 164
<211> LENGTH: 8
<212> TYPE: PRT
<213> ORGANISM: Artificial Sequence
<220> FEATURE:
<223> OTHER INFORMATION: VH CDR2 - AB327 (IMGT)

<400> SEQUENCE: 164

Ile Ser Ser Gly Gly Asp Tyr Ile
1               5

<210> SEQ ID NO 165
<211> LENGTH: 13
<212> TYPE: PRT
<213> ORGANISM: Artificial Sequence
<220> FEATURE:
<223> OTHER INFORMATION: VH CDR3 - AB327 (IMGT)

<400> SEQUENCE: 165

Thr Arg Glu Arg Ile Trp Leu Arg Arg Phe Phe Asp Val
1               5                   10

<210> SEQ ID NO 166
<211> LENGTH: 8
<212> TYPE: PRT
<213> ORGANISM: Artificial Sequence
<220> FEATURE:
<223> OTHER INFORMATION: VL CDR1 - AB328 (IMGT)

<400> SEQUENCE: 166

Gln Asn Val Gly Thr Asn Val Ala
1               5

<210> SEQ ID NO 167
<211> LENGTH: 7
<212> TYPE: PRT
<213> ORGANISM: Artificial Sequence
<220> FEATURE:
<223> OTHER INFORMATION: VL CDR3 - AB328 (IMGT)

<400> SEQUENCE: 167

Gln Arg Tyr Asn Ser Tyr Pro
1               5

<210> SEQ ID NO 168
<211> LENGTH: 6
<212> TYPE: PRT
<213> ORGANISM: Artificial Sequence
<220> FEATURE:
```

```
<223> OTHER INFORMATION: VL CDR1 - AB329 (IMGT)

<400> SEQUENCE: 168

Gln Asp Ile Asp Asn Tyr
1               5

<210> SEQ ID NO 169
<211> LENGTH: 3
<212> TYPE: PRT
<213> ORGANISM: Artificial Sequence
<220> FEATURE:
<223> OTHER INFORMATION: VL CDR2 - AB329 (IMGT)

<400> SEQUENCE: 169

Ser Ala Thr
1

<210> SEQ ID NO 170
<211> LENGTH: 4
<212> TYPE: PRT
<213> ORGANISM: Artificial Sequence
<220> FEATURE:
<223> OTHER INFORMATION: VL CDR3 - AB329 (IMGT)

<400> SEQUENCE: 170

Leu Gln His Tyr
1

<210> SEQ ID NO 171
<211> LENGTH: 8
<212> TYPE: PRT
<213> ORGANISM: Artificial Sequence
<220> FEATURE:
<223> OTHER INFORMATION: VH CDR1 - AB329 (IMGT)

<400> SEQUENCE: 171

Gly Phe Ser Leu Thr Ser Tyr His
1               5

<210> SEQ ID NO 172
<211> LENGTH: 8
<212> TYPE: PRT
<213> ORGANISM: Artificial Sequence
<220> FEATURE:
<223> OTHER INFORMATION: VH CDR2 - AB329 (IMGT)

<400> SEQUENCE: 172

Ile Trp Gly Asp Gly Arg Thr Thr
1               5

<210> SEQ ID NO 173
<211> LENGTH: 11
<212> TYPE: PRT
<213> ORGANISM: Artificial Sequence
<220> FEATURE:
<223> OTHER INFORMATION: VH CDR3 - AB329 (IMGT)

<400> SEQUENCE: 173

Ala Arg Ala Thr Met Thr Gly His Gly Asp Ala
1               5                   10

<210> SEQ ID NO 174
<211> LENGTH: 6
<212> TYPE: PRT
<213> ORGANISM: Artificial Sequence
<220> FEATURE:
<223> OTHER INFORMATION: VL CDR1 - AB330 (IMGT)
```

```
<400> SEQUENCE: 174

Gln Asp Ile Gly Asn Tyr
1               5

<210> SEQ ID NO 175
<211> LENGTH: 3
<212> TYPE: PRT
<213> ORGANISM: Artificial Sequence
<220> FEATURE:
<223> OTHER INFORMATION: VL CDR2 - AB330 (IMGT)

<400> SEQUENCE: 175

Tyr Ala Thr
1

<210> SEQ ID NO 176
<211> LENGTH: 5
<212> TYPE: PRT
<213> ORGANISM: Artificial Sequence
<220> FEATURE:
<223> OTHER INFORMATION: VL CDR3 - AB330 (IMGT)

<400> SEQUENCE: 176

Leu Gln Tyr Lys Gln
1               5

<210> SEQ ID NO 177
<211> LENGTH: 8
<212> TYPE: PRT
<213> ORGANISM: Artificial Sequence
<220> FEATURE:
<223> OTHER INFORMATION: VH CDR1 - AB330 (IMGT)

<400> SEQUENCE: 177

Gly Leu Thr Phe Ser Thr Ala Trp
1               5

<210> SEQ ID NO 178
<211> LENGTH: 8
<212> TYPE: PRT
<213> ORGANISM: Artificial Sequence
<220> FEATURE:
<223> OTHER INFORMATION: VH CDR2 - AB330 (IMGT)

<400> SEQUENCE: 178

Ile Lys Asp Lys Ser Asn Lys Phe
1               5

<210> SEQ ID NO 179
<211> LENGTH: 7
<212> TYPE: PRT
<213> ORGANISM: Artificial Sequence
<220> FEATURE:
<223> OTHER INFORMATION: VH CDR3 - AB330 (IMGT)

<400> SEQUENCE: 179

Thr Thr Ser Tyr Gly Tyr Ala
1               5

<210> SEQ ID NO 180
<211> LENGTH: 8
<212> TYPE: PRT
<213> ORGANISM: Artificial Sequence
<220> FEATURE:
<223> OTHER INFORMATION: VH CDR2 - AB331 (IMGT)
```

```
<400> SEQUENCE: 180

Ile Lys Asp Lys Ser Asn Asn Phe
1               5

<210> SEQ ID NO 181
<211> LENGTH: 10
<212> TYPE: PRT
<213> ORGANISM: Artificial Sequence
<220> FEATURE:
<223> OTHER INFORMATION: VL CDR1 - AB332 (IMGT)

<400> SEQUENCE: 181

Gln Ser Val Asp Tyr Asp Gly Asp Ser Tyr
1               5                   10

<210> SEQ ID NO 182
<211> LENGTH: 7
<212> TYPE: PRT
<213> ORGANISM: Artificial Sequence
<220> FEATURE:
<223> OTHER INFORMATION: VL CDR3 - AB332 (IMGT)

<400> SEQUENCE: 182

Gln Gln Ser Asn Glu Asp Pro
1               5

<210> SEQ ID NO 183
<211> LENGTH: 8
<212> TYPE: PRT
<213> ORGANISM: Artificial Sequence
<220> FEATURE:
<223> OTHER INFORMATION: VH CDR1 - AB332 (IMGT)

<400> SEQUENCE: 183

Gly Tyr Thr Phe Thr Asp Tyr Tyr
1               5

<210> SEQ ID NO 184
<211> LENGTH: 8
<212> TYPE: PRT
<213> ORGANISM: Artificial Sequence
<220> FEATURE:
<223> OTHER INFORMATION: VH CDR2 - AB332 (IMGT)

<400> SEQUENCE: 184

Ile Asn Pro Asn Asn Gly Val Thr
1               5

<210> SEQ ID NO 185
<211> LENGTH: 12
<212> TYPE: PRT
<213> ORGANISM: Artificial Sequence
<220> FEATURE:
<223> OTHER INFORMATION: VH CDR3 - AB332 (IMGT)

<400> SEQUENCE: 185

Ala Arg Glu Asp Tyr Gly Ser Asn Tyr Phe Asp Tyr
1               5                   10

<210> SEQ ID NO 186
<211> LENGTH: 26
<212> TYPE: PRT
<213> ORGANISM: Artificial Sequence
<220> FEATURE:
<223> OTHER INFORMATION: VL FR1 - AB320 (IMGT)

<400> SEQUENCE: 186
```

Asp Ile Gln Met Thr Gln Ser Pro Ala Ser Leu Ala Ala Ser Val Gly
1               5                   10                  15

Glu Thr Val Thr Ile Thr Cys Arg Ala Ser
            20                  25

<210> SEQ ID NO 187
<211> LENGTH: 17
<212> TYPE: PRT
<213> ORGANISM: Artificial Sequence
<220> FEATURE:
<223> OTHER INFORMATION: VL FR2 - AB320 (IMGT)

<400> SEQUENCE: 187

Leu Ala Trp Tyr Gln Gln Lys Gln Gly Lys Ser Pro Gln Leu Leu Ile
1               5                   10                  15

Tyr

<210> SEQ ID NO 188
<211> LENGTH: 36
<212> TYPE: PRT
<213> ORGANISM: Artificial Sequence
<220> FEATURE:
<223> OTHER INFORMATION: VL FR3 - AB320 (IMGT)

<400> SEQUENCE: 188

Ser Leu Glu Asp Gly Val Pro Ser Arg Phe Ser Gly Ser Gly Ser Gly
1               5                   10                  15

Thr Gln Tyr Ser Met Lys Ile Asn Ser Met Gln Pro Glu Asp Thr Ala
            20                  25                  30

Thr Tyr Phe Cys
        35

<210> SEQ ID NO 189
<211> LENGTH: 13
<212> TYPE: PRT
<213> ORGANISM: Artificial Sequence
<220> FEATURE:
<223> OTHER INFORMATION: VL FR4 - AB320 (IMGT)

<400> SEQUENCE: 189

Phe Thr Phe Gly Ser Gly Thr Lys Leu Glu Ile Lys Arg
1               5                   10

<210> SEQ ID NO 190
<211> LENGTH: 25
<212> TYPE: PRT
<213> ORGANISM: Artificial Sequence
<220> FEATURE:
<223> OTHER INFORMATION: VH FR1 - AB320 (IMGT)

<400> SEQUENCE: 190

Gln Val Gln Leu Gln Gln Ser Gly Ala Glu Leu Val Lys Pro Gly Ala
1               5                   10                  15

Ser Val Lys Ile Ser Cys Lys Ala Ser
            20                  25

<210> SEQ ID NO 191
<211> LENGTH: 17
<212> TYPE: PRT
<213> ORGANISM: Artificial Sequence
<220> FEATURE:
<223> OTHER INFORMATION: VH FR2 - AB320 (IMGT)

<400> SEQUENCE: 191

```
Met Asn Trp Val Lys Gln Arg Pro Gly Lys Gly Leu Glu Trp Ile Gly
1               5                   10                  15

Gln

<210> SEQ ID NO 192
<211> LENGTH: 38
<212> TYPE: PRT
<213> ORGANISM: Artificial Sequence
<220> FEATURE:
<223> OTHER INFORMATION: VH FR3 - AB320 (IMGT)

<400> SEQUENCE: 192

Asn Tyr Asn Gly Lys Phe Lys Gly Lys Ala Thr Leu Thr Ala Asp Lys
1               5                   10                  15

Ser Ser Ser Thr Ala Tyr Met Gln Leu Ser Ser Leu Thr Ser Glu Asp
                20                  25                  30

Ser Ala Val Tyr Phe Cys
        35

<210> SEQ ID NO 193
<211> LENGTH: 11
<212> TYPE: PRT
<213> ORGANISM: Artificial Sequence
<220> FEATURE:
<223> OTHER INFORMATION: VH FR4 - AB320 (IMGT)

<400> SEQUENCE: 193

Trp Gly Gln Gly Thr Leu Val Thr Val Ser Ala
1               5                   10

<210> SEQ ID NO 194
<211> LENGTH: 26
<212> TYPE: PRT
<213> ORGANISM: Artificial Sequence
<220> FEATURE:
<223> OTHER INFORMATION: VL FR1 - AB321 (IMGT)

<400> SEQUENCE: 194

Ala Ile Gln Met Thr Gln Thr Thr Ser Ser Leu Ser Ala Ser Leu Gly
1               5                   10                  15

Asp Arg Val Thr Ile Ser Cys Ser Val Ser
                20                  25

<210> SEQ ID NO 195
<211> LENGTH: 17
<212> TYPE: PRT
<213> ORGANISM: Artificial Sequence
<220> FEATURE:
<223> OTHER INFORMATION: VL FR2 - AB321 (IMGT)

<400> SEQUENCE: 195

Leu Asn Trp Tyr Gln Gln Lys Pro Asp Gly Thr Val Lys Leu Leu Ile
1               5                   10                  15

Tyr

<210> SEQ ID NO 196
<211> LENGTH: 36
<212> TYPE: PRT
<213> ORGANISM: Artificial Sequence
<220> FEATURE:
<223> OTHER INFORMATION: VL FR3 - AB321 (IMGT)

<400> SEQUENCE: 196
```

```
Ser Leu His Ser Gly Val Pro Ser Arg Phe Ser Gly Ser Gly Ser Gly
1               5                   10                  15

Thr Asp Tyr Ser Leu Thr Ile Ser Asn Leu Glu Pro Glu Asp Ile Ala
                20                  25              30

Thr Tyr Tyr Cys
        35

<210> SEQ ID NO 197
<211> LENGTH: 13
<212> TYPE: PRT
<213> ORGANISM: Artificial Sequence
<220> FEATURE:
<223> OTHER INFORMATION: VL FR4 - AB321 (IMGT)

<400> SEQUENCE: 197

Leu Thr Phe Gly Ala Gly Thr Lys Leu Glu Leu Lys Arg
1               5                   10

<210> SEQ ID NO 198
<211> LENGTH: 25
<212> TYPE: PRT
<213> ORGANISM: Artificial Sequence
<220> FEATURE:
<223> OTHER INFORMATION: VH FR1 - AB321 (IMGT)

<400> SEQUENCE: 198

Gln Val Gln Leu Gln Gln Pro Gly Ala Glu Phe Val Lys Pro Gly Ala
1               5                   10                  15

Ser Val Lys Leu Ser Cys Lys Ala Ser
            20                  25

<210> SEQ ID NO 199
<211> LENGTH: 17
<212> TYPE: PRT
<213> ORGANISM: Artificial Sequence
<220> FEATURE:
<223> OTHER INFORMATION: VH FR2 - AB321 (IMGT)

<400> SEQUENCE: 199

Met His Trp Val Lys Gln Arg Pro Gly Arg Gly Leu Glu Trp Ile Gly
1               5                   10                  15

Arg

<210> SEQ ID NO 200
<211> LENGTH: 38
<212> TYPE: PRT
<213> ORGANISM: Artificial Sequence
<220> FEATURE:
<223> OTHER INFORMATION: VH FR3 - AB321 (IMGT)

<400> SEQUENCE: 200

Lys Tyr Asn Glu Lys Phe Lys Ser Lys Ala Thr Leu Thr Val Asp Lys
1               5                   10                  15

Pro Ser Thr Ala Tyr Met Gln Leu Ser Ser Leu Thr Ser Glu Asp
            20                  25              30

Ser Ala Val Tyr Tyr Cys
        35

<210> SEQ ID NO 201
<211> LENGTH: 26
<212> TYPE: PRT
<213> ORGANISM: Artificial Sequence
<220> FEATURE:
<223> OTHER INFORMATION: VL FR1 - AB322 (IMGT)
```

<400> SEQUENCE: 201

Asp Ile Val Met Thr Gln Ser Gln Arg Phe Met Ser Thr Ser Val Gly
1               5                   10                  15

Asp Arg Val Ser Val Thr Cys Lys Ala Ser
            20                  25

<210> SEQ ID NO 202
<211> LENGTH: 17
<212> TYPE: PRT
<213> ORGANISM: Artificial Sequence
<220> FEATURE:
<223> OTHER INFORMATION: VL FR2 - AB322 (IMGT)

<400> SEQUENCE: 202

Val Ala Trp Tyr Gln Gln Lys Pro Gly Gln Ser Pro Lys Ala Leu Ile
1               5                   10                  15

Tyr

<210> SEQ ID NO 203
<211> LENGTH: 36
<212> TYPE: PRT
<213> ORGANISM: Artificial Sequence
<220> FEATURE:
<223> OTHER INFORMATION: VL FR3 - AB322 (IMGT)

<400> SEQUENCE: 203

Tyr Arg Tyr Ser Gly Val Pro Asp Arg Phe Thr Gly Ser Gly Ser Gly
1               5                   10                  15

Thr Asp Phe Thr Leu Thr Val Ser Asn Val Gln Ser Glu Asp Leu Ala
            20                  25                  30

Glu Tyr Phe Cys
        35

<210> SEQ ID NO 204
<211> LENGTH: 15
<212> TYPE: PRT
<213> ORGANISM: Artificial Sequence
<220> FEATURE:
<223> OTHER INFORMATION: VL FR4 - AB322 (IMGT)

<400> SEQUENCE: 204

Tyr Met Tyr Thr Phe Gly Gly Gly Thr Lys Leu Glu Ile Lys Arg
1               5                   10                  15

<210> SEQ ID NO 205
<211> LENGTH: 25
<212> TYPE: PRT
<213> ORGANISM: Artificial Sequence
<220> FEATURE:
<223> OTHER INFORMATION: VH FR1 - AB322 (IMGT)

<400> SEQUENCE: 205

Gln Val Gln Leu Gln Gln Ser Gly Ala Glu Leu Ala Lys Pro Gly Ala
1               5                   10                  15

Ser Val Lys Leu Ser Cys Lys Ala Ser
            20                  25

<210> SEQ ID NO 206
<211> LENGTH: 17
<212> TYPE: PRT
<213> ORGANISM: Artificial Sequence
<220> FEATURE:
<223> OTHER INFORMATION: VH FR2 - AB322 (IMGT)

<400> SEQUENCE: 206

Met His Trp Val Lys Gln Arg Pro Gly Gln Gly Leu Glu Trp Ile Gly
1               5                   10                  15

Tyr

<210> SEQ ID NO 207
<211> LENGTH: 38
<212> TYPE: PRT
<213> ORGANISM: Artificial Sequence
<220> FEATURE:
<223> OTHER INFORMATION: VH FR3 - AB322 (IMGT)

<400> SEQUENCE: 207

Lys Tyr Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Thr Tyr Glu Asp
            20                  25                  30

Ser Ala Val Tyr Tyr Cys
        35

<210> SEQ ID NO 208
<211> LENGTH: 26
<212> TYPE: PRT
<213> ORGANISM: Artificial Sequence
<220> FEATURE:
<223> OTHER INFORMATION: VL FR1 - AB323 (IMGT)

<400> SEQUENCE: 208

Asp Ile Val Met Thr Gln Ser His Lys Phe Met Ser Thr Ser Val Gly
1               5                   10                  15

Asp Arg Val Ser Ile Thr Cys Lys Ala Ser
            20                  25

<210> SEQ ID NO 209
<211> LENGTH: 17
<212> TYPE: PRT
<213> ORGANISM: Artificial Sequence
<220> FEATURE:
<223> OTHER INFORMATION: VL FR2 - AB323 (IMGT)

<400> SEQUENCE: 209

Val Ala Trp Tyr Gln Gln Lys Pro Gly Gln Ser Pro Lys Pro Leu Ile
1               5                   10                  15

Tyr

<210> SEQ ID NO 210
<211> LENGTH: 36
<212> TYPE: PRT
<213> ORGANISM: Artificial Sequence
<220> FEATURE:
<223> OTHER INFORMATION: VL FR3 - AB323 (IMGT)

<400> SEQUENCE: 210

Thr Arg His Thr Gly Val Pro Asp Arg Phe Thr Gly Ser Gly Ser Gly
1               5                   10                  15

Thr Asp Tyr Thr Leu Thr Ile Ser Ser Val Gln Thr Glu Asp Leu Ala
            20                  25                  30

Leu Tyr Tyr Cys
        35

<210> SEQ ID NO 211

```
<211> LENGTH: 13
<212> TYPE: PRT
<213> ORGANISM: Artificial Sequence
<220> FEATURE:
<223> OTHER INFORMATION: VL FR4 - AB323 (IMGT)

<400> SEQUENCE: 211

Arg Thr Phe Gly Gly Gly Thr Lys Leu Glu Ile Lys Arg
1               5                   10

<210> SEQ ID NO 212
<211> LENGTH: 25
<212> TYPE: PRT
<213> ORGANISM: Artificial Sequence
<220> FEATURE:
<223> OTHER INFORMATION: VH FR1 - AB323 (IMGT)

<400> SEQUENCE: 212

Gln Val Gln Leu Gln Gln Ser Gly Ala Glu Leu Val Lys Pro Gly Ala
1               5                   10                  15

Ser Val Lys Ile Ser Cys Lys Thr Ser
            20                  25

<210> SEQ ID NO 213
<211> LENGTH: 38
<212> TYPE: PRT
<213> ORGANISM: Artificial Sequence
<220> FEATURE:
<223> OTHER INFORMATION: VH FR3 - AB323 (IMGT)

<400> SEQUENCE: 213

Asn Tyr Asn Gly Lys Phe Lys Gly Lys Ala Thr Leu Thr Ala Asp Lys
1               5                   10                  15

Ser Ser Ser Ala Ala Phe Met Gln Leu Ser Ser Leu Thr Ser Glu Asp
            20                  25                  30

Ser Ala Val Tyr Phe Cys
        35

<210> SEQ ID NO 214
<211> LENGTH: 26
<212> TYPE: PRT
<213> ORGANISM: Artificial Sequence
<220> FEATURE:
<223> OTHER INFORMATION: VL FR1 - AB324 (IMGT)

<400> SEQUENCE: 214

Asp Ile Val Leu Thr Gln Ser Pro Ala Ser Leu Ala Val Ser Leu Gly
1               5                   10                  15

Gln Arg Ala Thr Ile Ser Cys Arg Ala Ser
            20                  25

<210> SEQ ID NO 215
<211> LENGTH: 17
<212> TYPE: PRT
<213> ORGANISM: Artificial Sequence
<220> FEATURE:
<223> OTHER INFORMATION: VL FR2 - AB324 (IMGT)

<400> SEQUENCE: 215

Met Asn Trp Phe Gln Gln Lys Pro Gly Gln Pro Pro Lys Leu Leu Ile
1               5                   10                  15

Tyr

<210> SEQ ID NO 216
```

```
<211> LENGTH: 36
<212> TYPE: PRT
<213> ORGANISM: Artificial Sequence
<220> FEATURE:
<223> OTHER INFORMATION: VL FR3 - AB324 (IMGT)

<400> SEQUENCE: 216

Asn Gln Gly Ser Gly Val Pro Ala Arg Phe Ser Gly Ser Gly Ser Gly
1               5                   10                  15

Thr Asp Phe Ser Leu Asn Ile His Pro Met Glu Glu Asp Asp Thr Ala
            20                  25                  30

Met Tyr Phe Cys
        35

<210> SEQ ID NO 217
<211> LENGTH: 13
<212> TYPE: PRT
<213> ORGANISM: Artificial Sequence
<220> FEATURE:
<223> OTHER INFORMATION: VL FR4 - AB324 (IMGT)

<400> SEQUENCE: 217

Trp Thr Phe Gly Gly Gly Thr Lys Leu Glu Ile Lys Arg
1               5                   10

<210> SEQ ID NO 218
<211> LENGTH: 17
<212> TYPE: PRT
<213> ORGANISM: Artificial Sequence
<220> FEATURE:
<223> OTHER INFORMATION: VH FR2 - AB324 (IMGT)

<400> SEQUENCE: 218

Val Asn Trp Val Lys Gln Arg Pro Gly Lys Gly Leu Glu Trp Ile Gly
1               5                   10                  15

Gln

<210> SEQ ID NO 219
<211> LENGTH: 11
<212> TYPE: PRT
<213> ORGANISM: Artificial Sequence
<220> FEATURE:
<223> OTHER INFORMATION: VH FR4 - AB324 (IMGT)

<400> SEQUENCE: 219

Trp Gly Gln Gly Thr Thr Leu Thr Val Ser Ser
1               5                   10

<210> SEQ ID NO 220
<211> LENGTH: 26
<212> TYPE: PRT
<213> ORGANISM: Artificial Sequence
<220> FEATURE:
<223> OTHER INFORMATION: VL FR1 - AB325 (IMGT)

<400> SEQUENCE: 220

Asp Ile Gln Met Thr Gln Thr Thr Ser Ser Leu Ser Ala Ser Leu Gly
1               5                   10                  15

Asp Arg Val Thr Ile Ser Cys Arg Ala Ser
            20                  25

<210> SEQ ID NO 221
<211> LENGTH: 36
<212> TYPE: PRT
<213> ORGANISM: Artificial Sequence
```

-continued

```
<220> FEATURE:
<223> OTHER INFORMATION: VL FR3 - AB325 (IMGT)

<400> SEQUENCE: 221

Arg Leu His Ser Gly Val Pro Ser Arg Phe Ser Gly Ser Gly Ser Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 222
<211> LENGTH: 11
<212> TYPE: PRT
<213> ORGANISM: Artificial Sequence
<220> FEATURE:
<223> OTHER INFORMATION: VH FR4 - AB325 (IMGT)

<400> SEQUENCE: 222

Trp Gly Gln Gly Thr Ser Val Thr Val Ser Ser
1               5                   10

<210> SEQ ID NO 223
<211> LENGTH: 26
<212> TYPE: PRT
<213> ORGANISM: Artificial Sequence
<220> FEATURE:
<223> OTHER INFORMATION: VL FR1 - AB327 (IMGT)

<400> SEQUENCE: 223

Asp Ile Val Met Thr Gln Ser Gln Lys Phe Met Ser Thr Ser Val Gly
1               5                   10                  15

Asp Arg Val Ser Ile Thr Cys Lys Ala Ser
            20                  25

<210> SEQ ID NO 224
<211> LENGTH: 15
<212> TYPE: PRT
<213> ORGANISM: Artificial Sequence
<220> FEATURE:
<223> OTHER INFORMATION: VL FR2 - AB327 (IMGT)

<400> SEQUENCE: 224

Trp Tyr Gln Leu Lys Pro Gly Gln Ser Pro Lys Leu Leu Ile Tyr
1               5                   10                  15

<210> SEQ ID NO 225
<211> LENGTH: 36
<212> TYPE: PRT
<213> ORGANISM: Artificial Sequence
<220> FEATURE:
<223> OTHER INFORMATION: VL FR3 - AB327 (IMGT)

<400> SEQUENCE: 225

Asn Arg Phe Thr Gly Val Pro Asp Arg Phe Thr Gly Ser Gly Ser Gly
1               5                   10                  15

Thr Asp Phe Thr Leu Thr Ile Ser Asn Met Gln Ser Glu Asp Leu Ala
            20                  25                  30

Asp Tyr Phe Cys
        35

<210> SEQ ID NO 226
<211> LENGTH: 13
<212> TYPE: PRT
```

<213> ORGANISM: Artificial Sequence
<220> FEATURE:
<223> OTHER INFORMATION: VL FR4 - AB327 (IMGT)

<400> SEQUENCE: 226

Leu Thr Phe Gly Ser Gly Thr Lys Leu Glu Ile Lys Arg
1               5                   10

<210> SEQ ID NO 227
<211> LENGTH: 25
<212> TYPE: PRT
<213> ORGANISM: Artificial Sequence
<220> FEATURE:
<223> OTHER INFORMATION: VH FR1 - AB327 (IMGT)

<400> SEQUENCE: 227

Asp Val Lys Leu Val Glu Ser Gly Glu Gly Leu Val Lys Pro Gly Gly
1               5                   10                  15

Ser Leu Lys Leu Ser Cys Ala Ala Ser
            20                  25

<210> SEQ ID NO 228
<211> LENGTH: 17
<212> TYPE: PRT
<213> ORGANISM: Artificial Sequence
<220> FEATURE:
<223> OTHER INFORMATION: VH FR2 - AB327 (IMGT)

<400> SEQUENCE: 228

Met Ser Trp Val Arg Gln Thr Pro Glu Lys Arg Leu Glu Trp Val Thr
1               5                   10                  15

Tyr

<210> SEQ ID NO 229
<211> LENGTH: 38
<212> TYPE: PRT
<213> ORGANISM: Artificial Sequence
<220> FEATURE:
<223> OTHER INFORMATION: VH FR3 - AB327 (IMGT)

<400> SEQUENCE: 229

Tyr Tyr Ala Asp Thr Val Lys Gly Arg Phe Thr Ile Ser Arg Asp Asn
1               5                   10                  15

Ala Arg Asn Thr Leu Tyr Leu Gln Met Ser Ser Leu Lys Ser Glu Asp
            20                  25                  30

Thr Ala Met Tyr Tyr Cys
        35

<210> SEQ ID NO 230
<211> LENGTH: 11
<212> TYPE: PRT
<213> ORGANISM: Artificial Sequence
<220> FEATURE:
<223> OTHER INFORMATION: VH FR4 - AB327 (IMGT)

<400> SEQUENCE: 230

Trp Gly Thr Gly Thr Thr Val Thr Val Ser Ser
1               5                   10

<210> SEQ ID NO 231
<211> LENGTH: 26
<212> TYPE: PRT
<213> ORGANISM: Artificial Sequence
<220> FEATURE:
<223> OTHER INFORMATION: VL FR1 - AB328 (IMGT)

<400> SEQUENCE: 231

Asp Ile Val Met Thr Gln Ser Gln Lys Phe Met Ser Thr Ser Val Gly
1               5                   10                  15

Asp Arg Val Ser Val Thr Cys Lys Ala Ser
            20                  25

<210> SEQ ID NO 232
<211> LENGTH: 15
<212> TYPE: PRT
<213> ORGANISM: Artificial Sequence
<220> FEATURE:
<223> OTHER INFORMATION: VL FR2 - AB328 (IMGT)

<400> SEQUENCE: 232

Trp Tyr Gln Gln Lys Pro Gly His Ser Pro Lys Ala Leu Ile Tyr
1               5                   10                  15

<210> SEQ ID NO 233
<211> LENGTH: 36
<212> TYPE: PRT
<213> ORGANISM: Artificial Sequence
<220> FEATURE:
<223> OTHER INFORMATION: VL FR3 - AB328 (IMGT)

<400> SEQUENCE: 233

Tyr Arg Tyr Ser Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Glu Tyr Phe Cys
        35

<210> SEQ ID NO 234
<211> LENGTH: 15
<212> TYPE: PRT
<213> ORGANISM: Artificial Sequence
<220> FEATURE:
<223> OTHER INFORMATION: VL FR4 - AB328 (IMGT)

<400> SEQUENCE: 234

Tyr Met Phe Thr Phe Gly Gly Gly Thr Lys Leu Glu Ile Lys Arg
1               5                   10                  15

<210> SEQ ID NO 235
<211> LENGTH: 17
<212> TYPE: PRT
<213> ORGANISM: Artificial Sequence
<220> FEATURE:
<223> OTHER INFORMATION: VH FR2 - AB328 (IMGT)

<400> SEQUENCE: 235

Met His Trp Val Lys Gln Arg Pro Gly Gln Gly Leu Glu Trp Ile Gly
1               5                   10                  15

Tyr

<210> SEQ ID NO 236
<211> LENGTH: 38
<212> TYPE: PRT
<213> ORGANISM: Artificial Sequence
<220> FEATURE:
<223> OTHER INFORMATION: VH FR3 - AB328 (IMGT)

<400> SEQUENCE: 236

-continued

Lys Tyr Asn Gln Lys Phe Lys Asp Lys Ala Thr Leu Thr Ala Asp Lys
1               5                   10                  15

Ser Ser Ser Thr Ala Tyr Met Gln Leu Ser Ser Leu Thr Phe Glu Asp
            20                  25                  30

Ser Ala Val Tyr Tyr Cys
        35

<210> SEQ ID NO 237
<211> LENGTH: 26
<212> TYPE: PRT
<213> ORGANISM: Artificial Sequence
<220> FEATURE:
<223> OTHER INFORMATION: VL FR1 - AB329 (IMGT)

<400> SEQUENCE: 237

Asp Ile Gln Met Thr Gln Ser Pro Ala Ser Leu Ser Ala Ser Leu Glu
1               5                   10                  15

Glu Ile Val Thr Ile Thr Cys Gln Ala Ser
            20                  25

<210> SEQ ID NO 238
<211> LENGTH: 17
<212> TYPE: PRT
<213> ORGANISM: Artificial Sequence
<220> FEATURE:
<223> OTHER INFORMATION: VL FR2 - AB329 (IMGT)

<400> SEQUENCE: 238

Leu Ser Trp Tyr Gln Gln Lys Pro Gly Lys Ser Pro His Leu Leu Ile
1               5                   10                  15

His

<210> SEQ ID NO 239
<211> LENGTH: 36
<212> TYPE: PRT
<213> ORGANISM: Artificial Sequence
<220> FEATURE:
<223> OTHER INFORMATION: VL FR3 - AB329 (IMGT)

<400> SEQUENCE: 239

Ser Leu Ala Asp Gly Val Pro Ser Arg Phe Ser Gly Gly Arg Ser Gly
1               5                   10                  15

Thr Gln Phe Ser Leu Lys Ile Asn Arg Leu Gln Val Glu Asp Thr Gly
            20                  25                  30

Ile Tyr Tyr Cys
        35

<210> SEQ ID NO 240
<211> LENGTH: 15
<212> TYPE: PRT
<213> ORGANISM: Artificial Sequence
<220> FEATURE:
<223> OTHER INFORMATION: VL FR4 - AB329 (IMGT)

<400> SEQUENCE: 240

Ser Gly Trp Thr Phe Gly Gly Gly Thr Lys Leu Glu Leu Lys Arg
1               5                   10                  15

<210> SEQ ID NO 241
<211> LENGTH: 25
<212> TYPE: PRT
<213> ORGANISM: Artificial Sequence
<220> FEATURE:
<223> OTHER INFORMATION: VH FR1 - AB329 (IMGT)

<400> SEQUENCE: 241

Gln Val Gln Leu Lys Glu Ser Gly Pro Gly Leu Val Lys Pro Ser Ala
1               5                   10                  15

Thr Leu Ser Leu Thr Cys Thr Val Ser
            20                  25

<210> SEQ ID NO 242
<211> LENGTH: 17
<212> TYPE: PRT
<213> ORGANISM: Artificial Sequence
<220> FEATURE:
<223> OTHER INFORMATION: VH FR2 - AB329 (IMGT)

<400> SEQUENCE: 242

Val Cys Trp Ile Arg Gln Thr Pro Gly Lys Gly Leu Glu Trp Met Gly
1               5                   10                  15

Val

<210> SEQ ID NO 243
<211> LENGTH: 37
<212> TYPE: PRT
<213> ORGANISM: Artificial Sequence
<220> FEATURE:
<223> OTHER INFORMATION: VH FR3 - AB329 (IMGT)

<400> SEQUENCE: 243

Tyr Asn Pro Pro Leu Lys Ser Arg Leu Ser Ile Ser Arg Asp Thr Ser
1               5                   10                  15

Lys Ser Gln Val Phe Leu Lys Met Ser Ser Leu Lys Thr Glu Asp Thr
            20                  25                  30

Ala Thr Tyr Tyr Cys
        35

<210> SEQ ID NO 244
<211> LENGTH: 11
<212> TYPE: PRT
<213> ORGANISM: Artificial Sequence
<220> FEATURE:
<223> OTHER INFORMATION: VH FR4 - AB329 (IMGT)

<400> SEQUENCE: 244

Trp Gly Gln Gly Ala Ser Val Thr Val Ser Ser
1               5                   10

<210> SEQ ID NO 245
<211> LENGTH: 26
<212> TYPE: PRT
<213> ORGANISM: Artificial Sequence
<220> FEATURE:
<223> OTHER INFORMATION: VL FR1 - AB330 (IMGT)

<400> SEQUENCE: 245

Asp Ile Gln Met Thr Gln Ser Pro Ser Ser Met Ser Ala Ser Leu Gly
1               5                   10                  15

Asp Arg Val Thr Ile Thr Cys Gln Ala Ser
            20                  25

<210> SEQ ID NO 246
<211> LENGTH: 17
<212> TYPE: PRT
<213> ORGANISM: Artificial Sequence
<220> FEATURE:
<223> OTHER INFORMATION: VL FR2 - AB330 (IMGT)

```
<400> SEQUENCE: 246

Leu Ile Trp Phe Gln Gln Lys Pro Gly Lys Ser Pro Arg Pro Leu Ile
1               5                   10                  15

Tyr

<210> SEQ ID NO 247
<211> LENGTH: 36
<212> TYPE: PRT
<213> ORGANISM: Artificial Sequence
<220> FEATURE:
<223> OTHER INFORMATION: VL FR3 - AB330 (IMGT)

<400> SEQUENCE: 247

Asn Leu Ala Asn Gly Val Pro Ser Arg Phe Ser Gly Ser Arg Ser Gly
1               5                   10                  15

Ser Glu Tyr Ser Leu Thr Ile Thr Ser Leu Glu Ser Glu Asp Met Ala
            20                  25                  30

Asp Tyr His Cys
        35

<210> SEQ ID NO 248
<211> LENGTH: 14
<212> TYPE: PRT
<213> ORGANISM: Artificial Sequence
<220> FEATURE:
<223> OTHER INFORMATION: VL FR4 - AB330 (IMGT)

<400> SEQUENCE: 248

His Leu Thr Phe Gly Ser Gly Thr Lys Leu Glu Ile Glu Arg
1               5                   10

<210> SEQ ID NO 249
<211> LENGTH: 25
<212> TYPE: PRT
<213> ORGANISM: Artificial Sequence
<220> FEATURE:
<223> OTHER INFORMATION: VH FR1 - AB330 (IMGT)

<400> SEQUENCE: 249

Glu Val Gln Val Val Glu Thr Gly Gly Gly Val Val Gln Pro Gly Lys
1               5                   10                  15

Ser Leu Glu Ile Thr Cys Ala Thr Ser
            20                  25

<210> SEQ ID NO 250
<211> LENGTH: 17
<212> TYPE: PRT
<213> ORGANISM: Artificial Sequence
<220> FEATURE:
<223> OTHER INFORMATION: VH FR2 - AB330 (IMGT)

<400> SEQUENCE: 250

Met Tyr Trp Val Arg Gln Ser Ser Asp Arg Arg Leu Glu Trp Ile Ala
1               5                   10                  15

Arg

<210> SEQ ID NO 251
<211> LENGTH: 40
<212> TYPE: PRT
<213> ORGANISM: Artificial Sequence
<220> FEATURE:
<223> OTHER INFORMATION: VH FR3 - AB330 (IMGT)
```

```
<400> SEQUENCE: 251

Ala Ser Asp Tyr Val Glu Ser Val Arg Gly Arg Phe Thr Ile Ser Arg
1               5                   10                  15

Asp Asp Ser Arg Ser Ser Val Tyr Leu Gln Met Asn Asn Leu Lys Glu
            20                  25                  30

Glu Asp Thr Ala Thr Tyr Tyr Cys
            35                  40

<210> SEQ ID NO 252
<211> LENGTH: 11
<212> TYPE: PRT
<213> ORGANISM: Artificial Sequence
<220> FEATURE:
<223> OTHER INFORMATION: VH FR4 - AB330 (IMGT)

<400> SEQUENCE: 252

Trp Gly Gln Gly Val Met Val Thr Val Ser Ser
1               5                   10

<210> SEQ ID NO 253
<211> LENGTH: 26
<212> TYPE: PRT
<213> ORGANISM: Artificial Sequence
<220> FEATURE:
<223> OTHER INFORMATION: VL FR1 - AB331 (IMGT)

<400> SEQUENCE: 253

Asp Ile Gln Met Thr Gln Ser Pro Ser Ser Met Ser Ala Ser Leu Gly
1               5                   10                  15

Asp Arg Ile Thr Ile Thr Cys Gln Ala Ser
            20                  25

<210> SEQ ID NO 254
<211> LENGTH: 26
<212> TYPE: PRT
<213> ORGANISM: Artificial Sequence
<220> FEATURE:
<223> OTHER INFORMATION: VL FR1 - AB332 (IMGT)

<400> SEQUENCE: 254

Asp Ile Val Leu Thr Gln Ser Pro Ala Ser Leu Ala Val Ser Leu Gly
1               5                   10                  15

Gln Arg Ala Thr Ile Ser Cys Lys Ala Ser
            20                  25

<210> SEQ ID NO 255
<211> LENGTH: 17
<212> TYPE: PRT
<213> ORGANISM: Artificial Sequence
<220> FEATURE:
<223> OTHER INFORMATION: VL FR2 - AB332 (IMGT)

<400> SEQUENCE: 255

Met Asn Trp Tyr Gln Gln Lys Pro Gly Gln Pro Pro Lys Leu Leu Ile
1               5                   10                  15

Tyr

<210> SEQ ID NO 256
<211> LENGTH: 36
<212> TYPE: PRT
<213> ORGANISM: Artificial Sequence
<220> FEATURE:
<223> OTHER INFORMATION: VL FR3 - AB332 (IMGT)
```

```
<400> SEQUENCE: 256

Asn Leu Glu Ser Gly Ile Pro Ala Arg Leu Ser Gly Ser Gly Ser Gly
1               5                   10                  15

Thr Asp Phe Thr Leu Asn Ile His Pro Val Glu Glu Glu Asp Ala Ala
                20                  25                  30

Thr Tyr Tyr Cys
            35

<210> SEQ ID NO 257
<211> LENGTH: 13
<212> TYPE: PRT
<213> ORGANISM: Artificial Sequence
<220> FEATURE:
<223> OTHER INFORMATION: VL FR4 - AB332 (IMGT)

<400> SEQUENCE: 257

Pro Thr Phe Gly Gly Gly Thr Lys Leu Glu Ile Arg Arg
1               5                   10

<210> SEQ ID NO 258
<211> LENGTH: 25
<212> TYPE: PRT
<213> ORGANISM: Artificial Sequence
<220> FEATURE:
<223> OTHER INFORMATION: VH FR1 - AB332 (IMGT)

<400> SEQUENCE: 258

Glu Val Gln Leu Gln Gln Ser Gly Pro Glu Leu Val Lys Pro Gly Thr
1               5                   10                  15

Ser Val Lys Ile Ser Cys Lys Ala Ser
                20                  25

<210> SEQ ID NO 259
<211> LENGTH: 17
<212> TYPE: PRT
<213> ORGANISM: Artificial Sequence
<220> FEATURE:
<223> OTHER INFORMATION: VH FR2 - AB332 (IMGT)

<400> SEQUENCE: 259

Met Asn Trp Met Lys Gln Ser His Gly Lys Ser Leu Glu Trp Ile Gly
1               5                   10                  15

Asp

<210> SEQ ID NO 260
<211> LENGTH: 38
<212> TYPE: PRT
<213> ORGANISM: Artificial Sequence
<220> FEATURE:
<223> OTHER INFORMATION: VH FR3 - AB332 (IMGT)

<400> SEQUENCE: 260

Ser Tyr Asn Gln Lys Phe Lys Gly Lys Ala Thr Leu Thr Val Asp Lys
1               5                   10                  15

Ser Ser Ser Thr Ala Tyr Met Glu Leu Arg Ser Leu Thr Ser Glu Asp
                20                  25                  30

Ser Ala Val Tyr Tyr Cys
            35

<210> SEQ ID NO 261
<211> LENGTH: 11
<212> TYPE: PRT
<213> ORGANISM: Artificial Sequence
```

```
<220> FEATURE:
<223> OTHER INFORMATION: VH FR4 - AB332 (IMGT)

<400> SEQUENCE: 261

Trp Gly Gln Gly Thr Thr Leu Thr Val Ser Ser
1               5                   10

<210> SEQ ID NO 262
<211> LENGTH: 11
<212> TYPE: PRT
<213> ORGANISM: Artificial Sequence
<220> FEATURE:
<223> OTHER INFORMATION: VL CDR1 - AB320 (Chothia)

<400> SEQUENCE: 262

Arg Ala Ser Glu Asn Ile Tyr Tyr Ser Leu Ala
1               5                   10

<210> SEQ ID NO 263
<211> LENGTH: 7
<212> TYPE: PRT
<213> ORGANISM: Artificial Sequence
<220> FEATURE:
<223> OTHER INFORMATION: VL CDR2 - AB320 (Chothia)

<400> SEQUENCE: 263

Asn Ala Asn Ser Leu Glu Asp
1               5

<210> SEQ ID NO 264
<211> LENGTH: 8
<212> TYPE: PRT
<213> ORGANISM: Artificial Sequence
<220> FEATURE:
<223> OTHER INFORMATION: VL CDR3 - AB320 (Chothia)

<400> SEQUENCE: 264

Lys Gln Ala Tyr Asp Val Pro Phe
1               5

<210> SEQ ID NO 265
<211> LENGTH: 7
<212> TYPE: PRT
<213> ORGANISM: Artificial Sequence
<220> FEATURE:
<223> OTHER INFORMATION: VH CDR1 - AB320 (Chothia)

<400> SEQUENCE: 265

Gly Tyr Ala Phe Ser Ser Tyr
1               5

<210> SEQ ID NO 266
<211> LENGTH: 6
<212> TYPE: PRT
<213> ORGANISM: Artificial Sequence
<220> FEATURE:
<223> OTHER INFORMATION: VH CDR2 - AB320 (Chothia)

<400> SEQUENCE: 266

Tyr Pro Gly Asp Gly Asp
1               5

<210> SEQ ID NO 267
<211> LENGTH: 8
<212> TYPE: PRT
<213> ORGANISM: Artificial Sequence
<220> FEATURE:
```

```
<223> OTHER INFORMATION: VH CDR3 - AB320 (Chothia)

<400> SEQUENCE: 267

Tyr Tyr Tyr Gly Ser Lys Ala Tyr
1               5

<210> SEQ ID NO 268
<211> LENGTH: 11
<212> TYPE: PRT
<213> ORGANISM: Artificial Sequence
<220> FEATURE:
<223> OTHER INFORMATION: VL CDR1 - AB321 (Chothia)

<400> SEQUENCE: 268

Ser Val Ser Gln Gly Ile Ser Asn Ser Leu Asn
1               5                   10

<210> SEQ ID NO 269
<211> LENGTH: 7
<212> TYPE: PRT
<213> ORGANISM: Artificial Sequence
<220> FEATURE:
<223> OTHER INFORMATION: VL CDR2 - AB321 (Chothia)

<400> SEQUENCE: 269

Tyr Thr Ser Ser Leu His Ser
1               5

<210> SEQ ID NO 270
<211> LENGTH: 8
<212> TYPE: PRT
<213> ORGANISM: Artificial Sequence
<220> FEATURE:
<223> OTHER INFORMATION: VL CDR3 - AB321 (Chothia)

<400> SEQUENCE: 270

Gln Gln Tyr Ser Lys Leu Pro Leu
1               5

<210> SEQ ID NO 271
<211> LENGTH: 7
<212> TYPE: PRT
<213> ORGANISM: Artificial Sequence
<220> FEATURE:
<223> OTHER INFORMATION: VH CDR1 - AB321 (Chothia)

<400> SEQUENCE: 271

Gly Tyr Thr Phe Thr Ser Tyr
1               5

<210> SEQ ID NO 272
<211> LENGTH: 6
<212> TYPE: PRT
<213> ORGANISM: Artificial Sequence
<220> FEATURE:
<223> OTHER INFORMATION: VH CDR2 - AB321 (Chothia)

<400> SEQUENCE: 272

Asp Pro Asn Ser Gly Gly
1               5

<210> SEQ ID NO 273
<211> LENGTH: 11
<212> TYPE: PRT
<213> ORGANISM: Artificial Sequence
<220> FEATURE:
<223> OTHER INFORMATION: VH CDR3 - AB321 (Chothia)
```

```
<400> SEQUENCE: 273

Asp Tyr Tyr Gly Ser Ser Tyr Arg Phe Ala Tyr
1               5                   10

<210> SEQ ID NO 274
<211> LENGTH: 11
<212> TYPE: PRT
<213> ORGANISM: Artificial Sequence
<220> FEATURE:
<223> OTHER INFORMATION: VL CDR1 - AB322 (Chothia)

<400> SEQUENCE: 274

Lys Ala Ser Gln Asn Val Gly Thr Asn Val Ala
1               5                   10

<210> SEQ ID NO 275
<211> LENGTH: 7
<212> TYPE: PRT
<213> ORGANISM: Artificial Sequence
<220> FEATURE:
<223> OTHER INFORMATION: VL CDR2 - AB322 (Chothia)

<400> SEQUENCE: 275

Ser Ala Ser Tyr Arg Tyr Ser
1               5

<210> SEQ ID NO 276
<211> LENGTH: 11
<212> TYPE: PRT
<213> ORGANISM: Artificial Sequence
<220> FEATURE:
<223> OTHER INFORMATION: VL CDR3 - AB322 (Chothia)

<400> SEQUENCE: 276

Gln Gln Tyr Asn Ser Tyr Pro Tyr Met Tyr Thr
1               5                   10

<210> SEQ ID NO 277
<211> LENGTH: 7
<212> TYPE: PRT
<213> ORGANISM: Artificial Sequence
<220> FEATURE:
<223> OTHER INFORMATION: VH CDR1 - AB322 (Chothia)

<400> SEQUENCE: 277

Gly Tyr Thr Phe Thr Asn Tyr
1               5

<210> SEQ ID NO 278
<211> LENGTH: 6
<212> TYPE: PRT
<213> ORGANISM: Artificial Sequence
<220> FEATURE:
<223> OTHER INFORMATION: VH CDR2 - AB322 (Chothia)

<400> SEQUENCE: 278

Asn Pro Ser Ser Gly Tyr
1               5

<210> SEQ ID NO 279
<211> LENGTH: 11
<212> TYPE: PRT
<213> ORGANISM: Artificial Sequence
<220> FEATURE:
<223> OTHER INFORMATION: VH CDR3 - AB322 (Chothia)
```

<400> SEQUENCE: 279

Asp Tyr Tyr Gly Ser Ser Ser Trp Phe Ala Tyr
1               5                   10

<210> SEQ ID NO 280
<211> LENGTH: 11
<212> TYPE: PRT
<213> ORGANISM: Artificial Sequence
<220> FEATURE:
<223> OTHER INFORMATION: VL CDR1 - AB323 (Chothia)

<400> SEQUENCE: 280

Lys Ala Ser Gln Asp Val Ser Thr Ala Val Ala
1               5                   10

<210> SEQ ID NO 281
<211> LENGTH: 7
<212> TYPE: PRT
<213> ORGANISM: Artificial Sequence
<220> FEATURE:
<223> OTHER INFORMATION: VL CDR2 - AB323 (Chothia)

<400> SEQUENCE: 281

Trp Ala Ser Thr Arg His Thr
1               5

<210> SEQ ID NO 282
<211> LENGTH: 9
<212> TYPE: PRT
<213> ORGANISM: Artificial Sequence
<220> FEATURE:
<223> OTHER INFORMATION: VL CDR3 - AB323 (Chothia)

<400> SEQUENCE: 282

Gln Gln His Tyr Ser Thr Pro Arg Thr
1               5

<210> SEQ ID NO 283
<211> LENGTH: 7
<212> TYPE: PRT
<213> ORGANISM: Artificial Sequence
<220> FEATURE:
<223> OTHER INFORMATION: VH CDR1 - AB323 (Chothia)

<400> SEQUENCE: 283

Gly Tyr Thr Phe Ser Asn Tyr
1               5

<210> SEQ ID NO 284
<211> LENGTH: 6
<212> TYPE: PRT
<213> ORGANISM: Artificial Sequence
<220> FEATURE:
<223> OTHER INFORMATION: VH CDR2 - AB323 (Chothia)

<400> SEQUENCE: 284

Phe Pro Gly Asp Ala Asp
1               5

<210> SEQ ID NO 285
<211> LENGTH: 9
<212> TYPE: PRT
<213> ORGANISM: Artificial Sequence
<220> FEATURE:
<223> OTHER INFORMATION: VH CDR3 - AB323 (Chothia)

<400> SEQUENCE: 285

```
Phe Ser Tyr Asp Gly Ala Phe Ala Tyr
1               5

<210> SEQ ID NO 286
<211> LENGTH: 15
<212> TYPE: PRT
<213> ORGANISM: Artificial Sequence
<220> FEATURE:
<223> OTHER INFORMATION: VL CDR1 - AB324 (Chothia)

<400> SEQUENCE: 286

Arg Ala Ser Glu Ser Val Asp Asn Tyr Gly Ile Ser Phe Met Asn
1               5                   10                  15

<210> SEQ ID NO 287
<211> LENGTH: 7
<212> TYPE: PRT
<213> ORGANISM: Artificial Sequence
<220> FEATURE:
<223> OTHER INFORMATION: VL CDR2 - AB324 (Chothia)

<400> SEQUENCE: 287

Ala Ala Ser Asn Gln Gly Ser
1               5

<210> SEQ ID NO 288
<211> LENGTH: 9
<212> TYPE: PRT
<213> ORGANISM: Artificial Sequence
<220> FEATURE:
<223> OTHER INFORMATION: VL CDR3 - AB324 (Chothia)

<400> SEQUENCE: 288

Gln Gln Ser Lys Glu Val Pro Trp Thr
1               5

<210> SEQ ID NO 289
<211> LENGTH: 12
<212> TYPE: PRT
<213> ORGANISM: Artificial Sequence
<220> FEATURE:
<223> OTHER INFORMATION: VH CDR3 - AB324 (Chothia)

<400> SEQUENCE: 289

Ser Arg Gly Tyr Phe Tyr Gly Ser Thr Tyr Asp Ser
1               5                   10

<210> SEQ ID NO 290
<211> LENGTH: 11
<212> TYPE: PRT
<213> ORGANISM: Artificial Sequence
<220> FEATURE:
<223> OTHER INFORMATION: VL CDR1 - AB325 (Chothia)

<400> SEQUENCE: 290

Arg Ala Ser Gln Asp Ile Ser Asn Tyr Leu Asn
1               5                   10

<210> SEQ ID NO 291
<211> LENGTH: 7
<212> TYPE: PRT
<213> ORGANISM: Artificial Sequence
<220> FEATURE:
<223> OTHER INFORMATION: VL CDR2 - AB325 (Chothia)

<400> SEQUENCE: 291
```

```
Tyr Thr Ser Arg Leu His Ser
1               5

<210> SEQ ID NO 292
<211> LENGTH: 9
<212> TYPE: PRT
<213> ORGANISM: Artificial Sequence
<220> FEATURE:
<223> OTHER INFORMATION: VL CDR3 - AB325 (Chothia)

<400> SEQUENCE: 292

Gln Gln Gly Asn Thr Leu Pro Arg Thr
1               5

<210> SEQ ID NO 293
<211> LENGTH: 6
<212> TYPE: PRT
<213> ORGANISM: Artificial Sequence
<220> FEATURE:
<223> OTHER INFORMATION: VH CDR1 - AB325 (Chothia)

<400> SEQUENCE: 293

Tyr Ala Phe Ser Ser Tyr
1               5

<210> SEQ ID NO 294
<211> LENGTH: 11
<212> TYPE: PRT
<213> ORGANISM: Artificial Sequence
<220> FEATURE:
<223> OTHER INFORMATION: VH CDR3 - AB325 (Chothia)

<400> SEQUENCE: 294

Trp Tyr Tyr Gly Ser Tyr Tyr Ala Met Asp Tyr
1               5                   10

<210> SEQ ID NO 295
<211> LENGTH: 6
<212> TYPE: PRT
<213> ORGANISM: Artificial Sequence
<220> FEATURE:
<223> OTHER INFORMATION: VH CDR2 - AB326 (Chothia)

<400> SEQUENCE: 295

Lys Pro Ser Ser Gly Tyr
1               5

<210> SEQ ID NO 296
<211> LENGTH: 11
<212> TYPE: PRT
<213> ORGANISM: Artificial Sequence
<220> FEATURE:
<223> OTHER INFORMATION: VL CDR1 - AB327 (Chothia)

<400> SEQUENCE: 296

Lys Ala Ser Gln Asn Val Gly Thr Ala Val Ala
1               5                   10

<210> SEQ ID NO 297
<211> LENGTH: 7
<212> TYPE: PRT
<213> ORGANISM: Artificial Sequence
<220> FEATURE:
<223> OTHER INFORMATION: VL CDR2 - AB327 (Chothia)

<400> SEQUENCE: 297

Ser Ala Ser Asn Arg Phe Thr
```

```
1               5

<210> SEQ ID NO 298
<211> LENGTH: 9
<212> TYPE: PRT
<213> ORGANISM: Artificial Sequence
<220> FEATURE:
<223> OTHER INFORMATION: VL CDR3 - AB327 (Chothia)

<400> SEQUENCE: 298

Gln Gln Tyr Ser Ser Tyr Pro Leu Thr
1               5

<210> SEQ ID NO 299
<211> LENGTH: 7
<212> TYPE: PRT
<213> ORGANISM: Artificial Sequence
<220> FEATURE:
<223> OTHER INFORMATION: VH CDR1 - AB327 (Chothia)

<400> SEQUENCE: 299

Gly Phe Thr Phe Ser Ser Tyr
1               5

<210> SEQ ID NO 300
<211> LENGTH: 6
<212> TYPE: PRT
<213> ORGANISM: Artificial Sequence
<220> FEATURE:
<223> OTHER INFORMATION: VH CDR2 - AB327 (Chothia)

<400> SEQUENCE: 300

Ser Ser Gly Gly Asp Tyr
1               5

<210> SEQ ID NO 301
<211> LENGTH: 11
<212> TYPE: PRT
<213> ORGANISM: Artificial Sequence
<220> FEATURE:
<223> OTHER INFORMATION: VH CDR3 - AB327 (Chothia)

<400> SEQUENCE: 301

Glu Arg Ile Trp Leu Arg Arg Phe Phe Asp Val
1               5                   10

<210> SEQ ID NO 302
<211> LENGTH: 11
<212> TYPE: PRT
<213> ORGANISM: Artificial Sequence
<220> FEATURE:
<223> OTHER INFORMATION: VL CDR3 - AB328 (Chothia)

<400> SEQUENCE: 302

Gln Arg Tyr Asn Ser Tyr Pro Tyr Met Phe Thr
1               5                   10

<210> SEQ ID NO 303
<211> LENGTH: 11
<212> TYPE: PRT
<213> ORGANISM: Artificial Sequence
<220> FEATURE:
<223> OTHER INFORMATION: VL CDR1 - AB329 (Chothia)

<400> SEQUENCE: 303

Gln Ala Ser Gln Asp Ile Asp Asn Tyr Leu Ser
1               5                   10
```

<210> SEQ ID NO 304
<211> LENGTH: 7
<212> TYPE: PRT
<213> ORGANISM: Artificial Sequence
<220> FEATURE:
<223> OTHER INFORMATION: VL CDR2 - AB329 (Chothia)

<400> SEQUENCE: 304

Ser Ala Thr Ser Leu Ala Asp
1               5

<210> SEQ ID NO 305
<211> LENGTH: 8
<212> TYPE: PRT
<213> ORGANISM: Artificial Sequence
<220> FEATURE:
<223> OTHER INFORMATION: VL CDR5 - AB329 (Chothia)

<400> SEQUENCE: 305

Leu Gln His Tyr Ser Gly Trp Thr
1               5

<210> SEQ ID NO 306
<211> LENGTH: 7
<212> TYPE: PRT
<213> ORGANISM: Artificial Sequence
<220> FEATURE:
<223> OTHER INFORMATION: VH CDR1 - AB329 (Chothia)

<400> SEQUENCE: 306

Gly Phe Ser Leu Thr Ser Tyr
1               5

<210> SEQ ID NO 307
<211> LENGTH: 5
<212> TYPE: PRT
<213> ORGANISM: Artificial Sequence
<220> FEATURE:
<223> OTHER INFORMATION: VH CDR2 - AB329 (Chothia)

<400> SEQUENCE: 307

Trp Gly Asp Gly Arg
1               5

<210> SEQ ID NO 308
<211> LENGTH: 9
<212> TYPE: PRT
<213> ORGANISM: Artificial Sequence
<220> FEATURE:
<223> OTHER INFORMATION: VH CDR3 - AB329 (Chothia)

<400> SEQUENCE: 308

Ala Thr Met Thr Gly His Gly Asp Ala
1               5

<210> SEQ ID NO 309
<211> LENGTH: 11
<212> TYPE: PRT
<213> ORGANISM: Artificial Sequence
<220> FEATURE:
<223> OTHER INFORMATION: VL CDR1 - AB330 (Chothia)

<400> SEQUENCE: 309

Gln Ala Ser Gln Asp Ile Gly Asn Tyr Leu Ile
1               5                   10

<210> SEQ ID NO 310
<211> LENGTH: 7
<212> TYPE: PRT
<213> ORGANISM: Artificial Sequence
<220> FEATURE:
<223> OTHER INFORMATION: VL CDR2 - AB330 (Chothia)

<400> SEQUENCE: 310

Tyr Ala Thr Asn Leu Ala Asn
1               5

<210> SEQ ID NO 311
<211> LENGTH: 8
<212> TYPE: PRT
<213> ORGANISM: Artificial Sequence
<220> FEATURE:
<223> OTHER INFORMATION: VL CDR3 - AB330 (Chothia)

<400> SEQUENCE: 311

Leu Gln Tyr Lys Gln His Leu Thr
1               5

<210> SEQ ID NO 312
<211> LENGTH: 7
<212> TYPE: PRT
<213> ORGANISM: Artificial Sequence
<220> FEATURE:
<223> OTHER INFORMATION: VH CDR1 - AB330 (Chothia)

<400> SEQUENCE: 312

Gly Leu Thr Phe Ser Thr Ala
1               5

<210> SEQ ID NO 313
<211> LENGTH: 8
<212> TYPE: PRT
<213> ORGANISM: Artificial Sequence
<220> FEATURE:
<223> OTHER INFORMATION: VH CDR2 - AB330 (Chothia)

<400> SEQUENCE: 313

Lys Asp Lys Ser Asn Lys Phe Ala
1               5

<210> SEQ ID NO 314
<211> LENGTH: 5
<212> TYPE: PRT
<213> ORGANISM: Artificial Sequence
<220> FEATURE:
<223> OTHER INFORMATION: VH CDR3 - AB330 (Chothia)

<400> SEQUENCE: 314

Ser Tyr Gly Tyr Ala
1               5

<210> SEQ ID NO 315
<211> LENGTH: 8
<212> TYPE: PRT
<213> ORGANISM: Artificial Sequence
<220> FEATURE:
<223> OTHER INFORMATION: VH CDR2 - AB331 (Chothia)

<400> SEQUENCE: 315

Lys Asp Lys Ser Asn Asn Phe Ala
1               5

```
<210> SEQ ID NO 316
<211> LENGTH: 15
<212> TYPE: PRT
<213> ORGANISM: Artificial Sequence
<220> FEATURE:
<223> OTHER INFORMATION: VL CDR1 - AB332 (Chothia)

<400> SEQUENCE: 316

Lys Ala Ser Gln Ser Val Asp Tyr Asp Gly Asp Ser Tyr Met Asn
1               5                   10                  15

<210> SEQ ID NO 317
<211> LENGTH: 7
<212> TYPE: PRT
<213> ORGANISM: Artificial Sequence
<220> FEATURE:
<223> OTHER INFORMATION: VL CDR2 - AB332 (Chothia)

<400> SEQUENCE: 317

Ala Ala Ser Asn Leu Glu Ser
1               5

<210> SEQ ID NO 318
<211> LENGTH: 9
<212> TYPE: PRT
<213> ORGANISM: Artificial Sequence
<220> FEATURE:
<223> OTHER INFORMATION: VL CDR3 - AB332 (Chothia)

<400> SEQUENCE: 318

Gln Gln Ser Asn Glu Asp Pro Pro Thr
1               5

<210> SEQ ID NO 319
<211> LENGTH: 7
<212> TYPE: PRT
<213> ORGANISM: Artificial Sequence
<220> FEATURE:
<223> OTHER INFORMATION: VH CDR1 - AB332 (Chothia)

<400> SEQUENCE: 319

Gly Tyr Thr Phe Thr Asp Tyr
1               5

<210> SEQ ID NO 320
<211> LENGTH: 6
<212> TYPE: PRT
<213> ORGANISM: Artificial Sequence
<220> FEATURE:
<223> OTHER INFORMATION: VH CDR2 - AB332 (Chothia)

<400> SEQUENCE: 320

Asn Pro Asn Asn Gly Val
1               5

<210> SEQ ID NO 321
<211> LENGTH: 9
<212> TYPE: PRT
<213> ORGANISM: Artificial Sequence
<220> FEATURE:
<223> OTHER INFORMATION: VH CDR3 - AB332 (Chothia)

<400> SEQUENCE: 321

Asp Tyr Gly Ser Asn Tyr Phe Asp Tyr
1               5

<210> SEQ ID NO 322
```

```
<211> LENGTH: 23
<212> TYPE: PRT
<213> ORGANISM: Artificial Sequence
<220> FEATURE:
<223> OTHER INFORMATION: VL FR1 - AB320 (Chothia)

<400> SEQUENCE: 322

Asp Ile Gln Met Thr Gln Ser Pro Ala Ser Leu Ala Ala Ser Val Gly
1               5                   10                  15

Glu Thr Val Thr Ile Thr Cys
            20

<210> SEQ ID NO 323
<211> LENGTH: 15
<212> TYPE: PRT
<213> ORGANISM: Artificial Sequence
<220> FEATURE:
<223> OTHER INFORMATION: VL FR2 - AB320 (Chothia)

<400> SEQUENCE: 323

Trp Tyr Gln Gln Lys Gln Gly Lys Ser Pro Gln Leu Leu Ile Tyr
1               5                   10                  15

<210> SEQ ID NO 324
<211> LENGTH: 32
<212> TYPE: PRT
<213> ORGANISM: Artificial Sequence
<220> FEATURE:
<223> OTHER INFORMATION: VL FR3 - AB320 (Chothia)

<400> SEQUENCE: 324

Gly Val Pro Ser Arg Phe Ser Gly Ser Gly Ser Gly Thr Gln Tyr Ser
1               5                   10                  15

Met Lys Ile Asn Ser Met Gln Pro Glu Asp Thr Ala Thr Tyr Phe Cys
            20                  25                  30

<210> SEQ ID NO 325
<211> LENGTH: 12
<212> TYPE: PRT
<213> ORGANISM: Artificial Sequence
<220> FEATURE:
<223> OTHER INFORMATION: VL FR4 - AB320 (Chothia)

<400> SEQUENCE: 325

Thr Phe Gly Ser Gly Thr Lys Leu Glu Ile Lys Arg
1               5                   10

<210> SEQ ID NO 326
<211> LENGTH: 25
<212> TYPE: PRT
<213> ORGANISM: Artificial Sequence
<220> FEATURE:
<223> OTHER INFORMATION: VH FR1 - AB320 (Chothia)

<400> SEQUENCE: 326

Gln Val Gln Leu Gln Gln Ser Gly Ala Glu Leu Val Lys Pro Gly Ala
1               5                   10                  15

Ser Val Lys Ile Ser Cys Lys Ala Ser
            20                  25

<210> SEQ ID NO 327
<211> LENGTH: 19
<212> TYPE: PRT
<213> ORGANISM: Artificial Sequence
<220> FEATURE:
<223> OTHER INFORMATION: VH FR2 - AB320 (Chothia)
```

<400> SEQUENCE: 327

Trp Met Asn Trp Val Lys Gln Arg Pro Gly Lys Gly Leu Glu Trp Ile
1               5                   10                  15

Gly Gln Ile

<210> SEQ ID NO 328
<211> LENGTH: 41
<212> TYPE: PRT
<213> ORGANISM: Artificial Sequence
<220> FEATURE:
<223> OTHER INFORMATION: VH FR3 - AB320 (Chothia)

<400> SEQUENCE: 328

Thr Asn Tyr Asn Gly Lys Phe Lys Gly Lys Ala Thr Leu Thr Ala Asp
1               5                   10                  15

Lys Ser Ser Ser Thr Ala Tyr Met Gln Leu Ser Ser Leu Thr Ser Glu
                20                  25                  30

Asp Ser Ala Val Tyr Phe Cys Ala Ser
        35                  40

<210> SEQ ID NO 329
<211> LENGTH: 11
<212> TYPE: PRT
<213> ORGANISM: Artificial Sequence
<220> FEATURE:
<223> OTHER INFORMATION: VH FR4 - AB320 (Chothia)

<400> SEQUENCE: 329

Trp Gly Gln Gly Thr Leu Val Thr Val Ser Ala
1               5                   10

<210> SEQ ID NO 330
<211> LENGTH: 23
<212> TYPE: PRT
<213> ORGANISM: Artificial Sequence
<220> FEATURE:
<223> OTHER INFORMATION: VL FR1 - AB321 (Chothia)

<400> SEQUENCE: 330

Ala Ile Gln Met Thr Gln Thr Thr Ser Ser Leu Ser Ala Ser Leu Gly
1               5                   10                  15

Asp Arg Val Thr Ile Ser Cys
                20

<210> SEQ ID NO 331
<211> LENGTH: 15
<212> TYPE: PRT
<213> ORGANISM: Artificial Sequence
<220> FEATURE:
<223> OTHER INFORMATION: VL FR2 - AB321 (Chothia)

<400> SEQUENCE: 331

Trp Tyr Gln Gln Lys Pro Asp Gly Thr Val Lys Leu Leu Ile Tyr
1               5                   10                  15

<210> SEQ ID NO 332
<211> LENGTH: 32
<212> TYPE: PRT
<213> ORGANISM: Artificial Sequence
<220> FEATURE:
<223> OTHER INFORMATION: VL FR3 - AB321 (Chothia)

<400> SEQUENCE: 332

Gly Val Pro Ser Arg Phe Ser Gly Ser Gly Thr Asp Tyr Ser
1               5                   10                  15

Leu Thr Ile Ser Asn Leu Glu Pro Glu Asp Ile Ala Thr Tyr Tyr Cys
            20                  25                  30

<210> SEQ ID NO 333
<211> LENGTH: 12
<212> TYPE: PRT
<213> ORGANISM: Artificial Sequence
<220> FEATURE:
<223> OTHER INFORMATION: VL FR4 - AB321 (Chothia)

<400> SEQUENCE: 333

Thr Phe Gly Ala Gly Thr Lys Leu Glu Leu Lys Arg
1               5                   10

<210> SEQ ID NO 334
<211> LENGTH: 25
<212> TYPE: PRT
<213> ORGANISM: Artificial Sequence
<220> FEATURE:
<223> OTHER INFORMATION: VH FR1 - AB321 (Chothia)

<400> SEQUENCE: 334

Gln Val Gln Leu Gln Gln Pro Gly Ala Glu Phe Val Lys Pro Gly Ala
1               5                   10                  15

Ser Val Lys Leu Ser Cys Lys Ala Ser
            20                  25

<210> SEQ ID NO 335
<211> LENGTH: 19
<212> TYPE: PRT
<213> ORGANISM: Artificial Sequence
<220> FEATURE:
<223> OTHER INFORMATION: VH FR2 - AB321 (Chothia)

<400> SEQUENCE: 335

Trp Met His Trp Val Lys Gln Arg Pro Gly Arg Gly Leu Glu Trp Ile
1               5                   10                  15

Gly Arg Ile

<210> SEQ ID NO 336
<211> LENGTH: 41
<212> TYPE: PRT
<213> ORGANISM: Artificial Sequence
<220> FEATURE:
<223> OTHER INFORMATION: VH FR3 - AB321 (Chothia)

<400> SEQUENCE: 336

Thr Lys Tyr Asn Glu Lys Phe Lys Ser Lys Ala Thr Leu Thr Val Asp
1               5                   10                  15

Lys Pro Ser Ser Thr Ala Tyr Met Gln Leu Ser Ser Leu Thr Ser Glu
            20                  25                  30

Asp Ser Ala Val Tyr Tyr Cys Ala Arg
            35                  40

<210> SEQ ID NO 337
<211> LENGTH: 23
<212> TYPE: PRT
<213> ORGANISM: Artificial Sequence
<220> FEATURE:
<223> OTHER INFORMATION: VL FR1 - AB322 (Chothia)

<400> SEQUENCE: 337

```
Asp Ile Val Met Thr Gln Ser Gln Arg Phe Met Ser Thr Ser Val Gly
1               5                   10                  15

Asp Arg Val Ser Val Thr Cys
            20
```

<210> SEQ ID NO 338
<211> LENGTH: 15
<212> TYPE: PRT
<213> ORGANISM: Artificial Sequence
<220> FEATURE:
<223> OTHER INFORMATION: VL FR2 - AB322 (Chothia)

<400> SEQUENCE: 338

```
Trp Tyr Gln Gln Lys Pro Gly Gln Ser Pro Lys Ala Leu Ile Tyr
1               5                   10                  15
```

<210> SEQ ID NO 339
<211> LENGTH: 32
<212> TYPE: PRT
<213> ORGANISM: Artificial Sequence
<220> FEATURE:
<223> OTHER INFORMATION: VL FR3 - AB322 (Chothia)

<400> SEQUENCE: 339

```
Gly Val Pro Asp Arg Phe Thr Gly Ser Gly Ser Gly Thr Asp Phe Thr
1               5                   10                  15

Leu Thr Val Ser Asn Val Gln Ser Glu Asp Leu Ala Glu Tyr Phe Cys
            20                  25                  30
```

<210> SEQ ID NO 340
<211> LENGTH: 11
<212> TYPE: PRT
<213> ORGANISM: Artificial Sequence
<220> FEATURE:
<223> OTHER INFORMATION: VL FR4 - AB322 (Chothia)

<400> SEQUENCE: 340

```
Phe Gly Gly Gly Thr Lys Leu Glu Ile Lys Arg
1               5                   10
```

<210> SEQ ID NO 341
<211> LENGTH: 25
<212> TYPE: PRT
<213> ORGANISM: Artificial Sequence
<220> FEATURE:
<223> OTHER INFORMATION: VH FR1 - AB322 (Chothia)

<400> SEQUENCE: 341

```
Gln Val Gln Leu Gln Gln Ser Gly Ala Glu Leu Ala Lys Pro Gly Ala
1               5                   10                  15

Ser Val Lys Leu Ser Cys Lys Ala Ser
            20                  25
```

<210> SEQ ID NO 342
<211> LENGTH: 19
<212> TYPE: PRT
<213> ORGANISM: Artificial Sequence
<220> FEATURE:
<223> OTHER INFORMATION: VH FR2 - AB322 (Chothia)

<400> SEQUENCE: 342

```
Trp Met His Trp Val Lys Gln Arg Pro Gly Gln Gly Leu Glu Trp Ile
1               5                   10                  15

Gly Tyr Ile
```

<210> SEQ ID NO 343
<211> LENGTH: 41
<212> TYPE: PRT
<213> ORGANISM: Artificial Sequence
<220> FEATURE:
<223> OTHER INFORMATION: VH FR3 - AB322 (Chothia)

<400> SEQUENCE: 343

Thr Lys Tyr Asn Gln Lys Phe Lys Asp Lys Ala Thr Leu Thr Ala Asp
1               5                   10                  15

Lys Ser Ser Ser Thr Ala Tyr Met Gln Leu Ser Ser Leu Thr Tyr Glu
            20                  25                  30

Asp Ser Ala Val Tyr Tyr Cys Ala Arg
        35                  40

<210> SEQ ID NO 344
<211> LENGTH: 23
<212> TYPE: PRT
<213> ORGANISM: Artificial Sequence
<220> FEATURE:
<223> OTHER INFORMATION: VL FR1 - AB323 (Chothia)

<400> SEQUENCE: 344

Asp Ile Val Met Thr Gln Ser His Lys Phe Met Ser Thr Ser Val Gly
1               5                   10                  15

Asp Arg Val Ser Ile Thr Cys
            20

<210> SEQ ID NO 345
<211> LENGTH: 15
<212> TYPE: PRT
<213> ORGANISM: Artificial Sequence
<220> FEATURE:
<223> OTHER INFORMATION: VL FR2 - AB323 (Chothia)

<400> SEQUENCE: 345

Trp Tyr Gln Gln Lys Pro Gly Gln Ser Pro Lys Pro Leu Ile Tyr
1               5                   10                  15

<210> SEQ ID NO 346
<211> LENGTH: 32
<212> TYPE: PRT
<213> ORGANISM: Artificial Sequence
<220> FEATURE:
<223> OTHER INFORMATION: VL FR3 - AB323 (Chothia)

<400> SEQUENCE: 346

Gly Val Pro Asp Arg Phe Thr Gly Ser Gly Ser Gly Thr Asp Tyr Thr
1               5                   10                  15

Leu Thr Ile Ser Ser Val Gln Thr Glu Asp Leu Ala Leu Tyr Tyr Cys
            20                  25                  30

<210> SEQ ID NO 347
<211> LENGTH: 25
<212> TYPE: PRT
<213> ORGANISM: Artificial Sequence
<220> FEATURE:
<223> OTHER INFORMATION: VH FR1 - AB323 (Chothia)

<400> SEQUENCE: 347

Gln Val Gln Leu Gln Gln Ser Gly Ala Glu Leu Val Lys Pro Gly Ala
1               5                   10                  15

Ser Val Lys Ile Ser Cys Lys Thr Ser
            20                  25

<210> SEQ ID NO 348
<211> LENGTH: 41
<212> TYPE: PRT
<213> ORGANISM: Artificial Sequence
<220> FEATURE:
<223> OTHER INFORMATION: VH FR3 - AB323 (Chothia)

<400> SEQUENCE: 348

Ala Asn Tyr Asn Gly Lys Phe Lys Gly Lys Ala Thr Leu Thr Ala Asp
1               5                   10                  15

Lys Ser Ser Ser Ala Ala Phe Met Gln Leu Ser Ser Leu Thr Ser Glu
            20                  25                  30

Asp Ser Ala Val Tyr Phe Cys Ala Arg
            35                  40

<210> SEQ ID NO 349
<211> LENGTH: 23
<212> TYPE: PRT
<213> ORGANISM: Artificial Sequence
<220> FEATURE:
<223> OTHER INFORMATION: VL FR1 - AB324 (Chothia)

<400> SEQUENCE: 349

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 350
<211> LENGTH: 15
<212> TYPE: PRT
<213> ORGANISM: Artificial Sequence
<220> FEATURE:
<223> OTHER INFORMATION: VL FR2 - AB324 (Chothia)

<400> SEQUENCE: 350

Trp Phe Gln Gln Lys Pro Gly Gln Pro Pro Lys Leu Leu Ile Tyr
1               5                   10                  15

<210> SEQ ID NO 351
<211> LENGTH: 32
<212> TYPE: PRT
<213> ORGANISM: Artificial Sequence
<220> FEATURE:
<223> OTHER INFORMATION: VL FR3 - AB324 (Chothia)

<400> SEQUENCE: 351

Gly Val Pro Ala Arg Phe Ser Gly Ser Gly Ser Gly Thr Asp Phe Ser
1               5                   10                  15

Leu Asn Ile His Pro Met Glu Glu Asp Asp Thr Ala Met Tyr Phe Cys
            20                  25                  30

<210> SEQ ID NO 352
<211> LENGTH: 19
<212> TYPE: PRT
<213> ORGANISM: Artificial Sequence
<220> FEATURE:
<223> OTHER INFORMATION: VH FR2 - AB324 (Chothia)

<400> SEQUENCE: 352

Trp Val Asn Trp Val Lys Gln Arg Pro Gly Lys Gly Leu Glu Trp Ile
1               5                   10                  15

Gly Gln Ile

<210> SEQ ID NO 353
<211> LENGTH: 41
<212> TYPE: PRT
<213> ORGANISM: Artificial Sequence
<220> FEATURE:
<223> OTHER INFORMATION: VH FR3 - AB324 (Chothia)

<400> SEQUENCE: 353

Thr Asn Tyr Asn Gly Lys Phe Lys Gly Lys Ala Thr Leu Thr Ala Asp
1               5                   10                  15

Lys Ser Ser Ser Thr Ala Tyr Met Gln Leu Ser Ser Leu Thr Ser Glu
            20                  25                  30

Asp Ser Ala Val Tyr Phe Cys Ala Arg
        35                  40

<210> SEQ ID NO 354
<211> LENGTH: 11
<212> TYPE: PRT
<213> ORGANISM: Artificial Sequence
<220> FEATURE:
<223> OTHER INFORMATION: VH FR4 - AB324 (Chothia)

<400> SEQUENCE: 354

Trp Gly Gln Gly Thr Thr Leu Thr Val Ser Ser
1               5                   10

<210> SEQ ID NO 355
<211> LENGTH: 23
<212> TYPE: PRT
<213> ORGANISM: Artificial Sequence
<220> FEATURE:
<223> OTHER INFORMATION: VL FR1 - AB325 (Chothia)

<400> SEQUENCE: 355

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 356
<211> LENGTH: 32
<212> TYPE: PRT
<213> ORGANISM: Artificial Sequence
<220> FEATURE:
<223> OTHER INFORMATION: VL FR3 - AB325 (Chothia)

<400> SEQUENCE: 356

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30

<210> SEQ ID NO 357
<211> LENGTH: 26
<212> TYPE: PRT
<213> ORGANISM: Artificial Sequence
<220> FEATURE:
<223> OTHER INFORMATION: VH FR1 - AB325 (Chothia)

<400> SEQUENCE: 357

Gln Val Gln Leu Gln Gln Ser Gly Ala Glu Leu Val Lys Pro Gly Ala
1               5                   10                  15

Ser Val Lys Ile Ser Cys Lys Ala Ser Gly

```
                    20                  25

<210> SEQ ID NO 358
<211> LENGTH: 11
<212> TYPE: PRT
<213> ORGANISM: Artificial Sequence
<220> FEATURE:
<223> OTHER INFORMATION: VH FR4 - AB325 (Chothia)

<400> SEQUENCE: 358

Trp Gly Gln Gly Thr Ser Val Thr Val Ser Ser
1               5                   10

<210> SEQ ID NO 359
<211> LENGTH: 32
<212> TYPE: PRT
<213> ORGANISM: Artificial Sequence
<220> FEATURE:
<223> OTHER INFORMATION: VL FR3 - AB326 (Chothia)

<400> SEQUENCE: 359

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Glu Tyr Phe Cys
            20                  25                  30

<210> SEQ ID NO 360
<211> LENGTH: 23
<212> TYPE: PRT
<213> ORGANISM: Artificial Sequence
<220> FEATURE:
<223> OTHER INFORMATION: VL FR1 - AB327 (Chothia)

<400> SEQUENCE: 360

Asp Ile Val Met Thr Gln Ser Gln Lys Phe Met Ser Thr Ser Val Gly
1               5                   10                  15

Asp Arg Val Ser Ile Thr Cys
            20

<210> SEQ ID NO 361
<211> LENGTH: 15
<212> TYPE: PRT
<213> ORGANISM: Artificial Sequence
<220> FEATURE:
<223> OTHER INFORMATION: VL FR2 - AB327 (Chothia)

<400> SEQUENCE: 361

Trp Tyr Gln Leu Lys Pro Gly Gln Ser Pro Lys Leu Leu Ile Tyr
1               5                   10                  15

<210> SEQ ID NO 362
<211> LENGTH: 32
<212> TYPE: PRT
<213> ORGANISM: Artificial Sequence
<220> FEATURE:
<223> OTHER INFORMATION: VL FR3 - AB327 (Chothia)

<400> SEQUENCE: 362

Gly Val Pro Asp Arg Phe Thr Gly Ser Gly Ser Gly Thr Asp Phe Thr
1               5                   10                  15

Leu Thr Ile Ser Asn Met Gln Ser Glu Asp Leu Ala Asp Tyr Phe Cys
            20                  25                  30

<210> SEQ ID NO 363
<211> LENGTH: 11
```

```
<212> TYPE: PRT
<213> ORGANISM: Artificial Sequence
<220> FEATURE:
<223> OTHER INFORMATION: VL FR4 - AB327 (Chothia)

<400> SEQUENCE: 363

Phe Gly Ser Gly Thr Lys Leu Glu Ile Lys Arg
1               5                   10

<210> SEQ ID NO 364
<211> LENGTH: 25
<212> TYPE: PRT
<213> ORGANISM: Artificial Sequence
<220> FEATURE:
<223> OTHER INFORMATION: VH FR1 - AB327 (Chothia)

<400> SEQUENCE: 364

Asp Val Lys Leu Val Glu Ser Gly Glu Gly Leu Val Lys Pro Gly Gly
1               5                   10                  15

Ser Leu Lys Leu Ser Cys Ala Ala Ser
            20                  25

<210> SEQ ID NO 365
<211> LENGTH: 19
<212> TYPE: PRT
<213> ORGANISM: Artificial Sequence
<220> FEATURE:
<223> OTHER INFORMATION: VH FR2 - AB327 (Chothia)

<400> SEQUENCE: 365

Ala Met Ser Trp Val Arg Gln Thr Pro Glu Lys Arg Leu Glu Trp Val
1               5                   10                  15

Thr Tyr Ile

<210> SEQ ID NO 366
<211> LENGTH: 41
<212> TYPE: PRT
<213> ORGANISM: Artificial Sequence
<220> FEATURE:
<223> OTHER INFORMATION: VH FR3 - AB327 (Chothia)

<400> SEQUENCE: 366

Ile Tyr Tyr Ala Asp Thr Val Lys Gly Arg Phe Thr Ile Ser Arg Asp
1               5                   10                  15

Asn Ala Arg Asn Thr Leu Tyr Leu Gln Met Ser Ser Leu Lys Ser Glu
            20                  25                  30

Asp Thr Ala Met Tyr Tyr Cys Thr Arg
        35                  40

<210> SEQ ID NO 367
<211> LENGTH: 11
<212> TYPE: PRT
<213> ORGANISM: Artificial Sequence
<220> FEATURE:
<223> OTHER INFORMATION: VH FR4 - AB327 (Chothia)

<400> SEQUENCE: 367

Trp Gly Thr Gly Thr Thr Val Thr Val Ser Ser
1               5                   10

<210> SEQ ID NO 368
<211> LENGTH: 23
<212> TYPE: PRT
<213> ORGANISM: Artificial Sequence
<220> FEATURE:
```

<223> OTHER INFORMATION: VL FR1 - AB328 (Chothia)

<400> SEQUENCE: 368

Asp Ile Val Met Thr Gln Ser Gln Lys Phe Met Ser Thr Ser Val Gly
1               5                   10                  15

Asp Arg Val Ser Val Thr Cys
            20

<210> SEQ ID NO 369
<211> LENGTH: 15
<212> TYPE: PRT
<213> ORGANISM: Artificial Sequence
<220> FEATURE:
<223> OTHER INFORMATION: VL FR2 - AB328 (Chothia)

<400> SEQUENCE: 369

Trp Tyr Gln Gln Lys Pro Gly His Ser Pro Lys Ala Leu Ile Tyr
1               5                   10                  15

<210> SEQ ID NO 370
<211> LENGTH: 19
<212> TYPE: PRT
<213> ORGANISM: Artificial Sequence
<220> FEATURE:
<223> OTHER INFORMATION: VH FR2 - AB328 (Chothia)

<400> SEQUENCE: 370

Trp Met His Trp Val Lys Gln Arg Pro Gly Gln Gly Leu Glu Trp Ile
1               5                   10                  15

Gly Tyr Ile

<210> SEQ ID NO 371
<211> LENGTH: 41
<212> TYPE: PRT
<213> ORGANISM: Artificial Sequence
<220> FEATURE:
<223> OTHER INFORMATION: VH FR3 - AB328 (Chothia)

<400> SEQUENCE: 371

Thr Lys Tyr Asn Gln Lys Phe Lys Asp Lys Ala Thr Leu Thr Ala Asp
1               5                   10                  15

Lys Ser Ser Ser Thr Ala Tyr Met Gln Leu Ser Ser Leu Thr Phe Glu
            20                  25                  30

Asp Ser Ala Val Tyr Tyr Cys Ala Arg
        35                  40

<210> SEQ ID NO 372
<211> LENGTH: 23
<212> TYPE: PRT
<213> ORGANISM: Artificial Sequence
<220> FEATURE:
<223> OTHER INFORMATION: VL FR1 - AB329 (Chothia)

<400> SEQUENCE: 372

Asp Ile Gln Met Thr Gln Ser Pro Ala Ser Leu Ser Ala Ser Leu Glu
1               5                   10                  15

Glu Ile Val Thr Ile Thr Cys
            20

<210> SEQ ID NO 373
<211> LENGTH: 15
<212> TYPE: PRT
<213> ORGANISM: Artificial Sequence
<220> FEATURE:

```
<223> OTHER INFORMATION: VL FR2 - AB329 (Chothia)

<400> SEQUENCE: 373

Trp Tyr Gln Gln Lys Pro Gly Lys Ser Pro His Leu Leu Ile His
1               5                   10                  15

<210> SEQ ID NO 374
<211> LENGTH: 32
<212> TYPE: PRT
<213> ORGANISM: Artificial Sequence
<220> FEATURE:
<223> OTHER INFORMATION: VL FR3 - AB329 (Chothia)

<400> SEQUENCE: 374

Gly Val Pro Ser Arg Phe Ser Gly Gly Arg Ser Gly Thr Gln Phe Ser
1               5                   10                  15

Leu Lys Ile Asn Arg Leu Gln Val Glu Asp Thr Gly Ile Tyr Tyr Cys
            20                  25                  30

<210> SEQ ID NO 375
<211> LENGTH: 11
<212> TYPE: PRT
<213> ORGANISM: Artificial Sequence
<220> FEATURE:
<223> OTHER INFORMATION: VL FR4 - AB329 (Chothia)

<400> SEQUENCE: 375

Phe Gly Gly Gly Thr Lys Leu Glu Leu Lys Arg
1               5                   10

<210> SEQ ID NO 376
<211> LENGTH: 25
<212> TYPE: PRT
<213> ORGANISM: Artificial Sequence
<220> FEATURE:
<223> OTHER INFORMATION: VH FR1 - AB329 (Chothia)

<400> SEQUENCE: 376

Gln Val Gln Leu Lys Glu Ser Gly Pro Gly Leu Val Lys Pro Ser Ala
1               5                   10                  15

Thr Leu Ser Leu Thr Cys Thr Val Ser
            20                  25

<210> SEQ ID NO 377
<211> LENGTH: 19
<212> TYPE: PRT
<213> ORGANISM: Artificial Sequence
<220> FEATURE:
<223> OTHER INFORMATION: VH FR2 - AB329 (Chothia)

<400> SEQUENCE: 377

His Val Cys Trp Ile Arg Gln Thr Pro Gly Lys Gly Leu Glu Trp Met
1               5                   10                  15

Gly Val Ile

<210> SEQ ID NO 378
<211> LENGTH: 41
<212> TYPE: PRT
<213> ORGANISM: Artificial Sequence
<220> FEATURE:
<223> OTHER INFORMATION: VH FR3 - AB329 (Chothia)

<400> SEQUENCE: 378

Thr Thr Tyr Asn Pro Pro Leu Lys Ser Arg Leu Ser Ile Ser Arg Asp
1               5                   10                  15
```

Thr Ser Lys Ser Gln Val Phe Leu Lys Met Ser Ser Leu Thr Glu
            20                  25                  30

Asp Thr Ala Thr Tyr Tyr Cys Ala Arg
        35                  40

<210> SEQ ID NO 379
<211> LENGTH: 11
<212> TYPE: PRT
<213> ORGANISM: Artificial Sequence
<220> FEATURE:
<223> OTHER INFORMATION: VH FR4 - AB329 (Chothia)

<400> SEQUENCE: 379

Trp Gly Gln Gly Ala Ser Val Thr Val Ser Ser
1               5                   10

<210> SEQ ID NO 380
<211> LENGTH: 23
<212> TYPE: PRT
<213> ORGANISM: Artificial Sequence
<220> FEATURE:
<223> OTHER INFORMATION: VL FR1 - AB330 (Chothia)

<400> SEQUENCE: 380

Asp Ile Gln Met Thr Gln Ser Pro Ser Ser Met Ser Ala Ser Leu Gly
1               5                   10                  15

Asp Arg Val Thr Ile Thr Cys
            20

<210> SEQ ID NO 381
<211> LENGTH: 15
<212> TYPE: PRT
<213> ORGANISM: Artificial Sequence
<220> FEATURE:
<223> OTHER INFORMATION: VL FR2 - AB330 (Chothia)

<400> SEQUENCE: 381

Trp Phe Gln Gln Lys Pro Gly Lys Ser Pro Arg Pro Leu Ile Tyr
1               5                   10                  15

<210> SEQ ID NO 382
<211> LENGTH: 32
<212> TYPE: PRT
<213> ORGANISM: Artificial Sequence
<220> FEATURE:
<223> OTHER INFORMATION: VL FR3 - AB330 (Chothia)

<400> SEQUENCE: 382

Gly Val Pro Ser Arg Phe Ser Gly Ser Arg Ser Gly Ser Glu Tyr Ser
1               5                   10                  15

Leu Thr Ile Thr Ser Leu Glu Ser Glu Asp Met Ala Asp Tyr His Cys
            20                  25                  30

<210> SEQ ID NO 383
<211> LENGTH: 11
<212> TYPE: PRT
<213> ORGANISM: Artificial Sequence
<220> FEATURE:
<223> OTHER INFORMATION: VL FR4 - AB330 (Chothia)

<400> SEQUENCE: 383

Phe Gly Ser Gly Thr Lys Leu Glu Ile Glu Arg
1               5                   10

```
<210> SEQ ID NO 384
<211> LENGTH: 25
<212> TYPE: PRT
<213> ORGANISM: Artificial Sequence
<220> FEATURE:
<223> OTHER INFORMATION: VH FR1 - AB330 (Chothia)

<400> SEQUENCE: 384

Glu Val Gln Val Val Glu Thr Gly Gly Gly Val Val Gln Pro Gly Lys
1               5                   10                  15

Ser Leu Glu Ile Thr Cys Ala Thr Ser
            20                  25

<210> SEQ ID NO 385
<211> LENGTH: 19
<212> TYPE: PRT
<213> ORGANISM: Artificial Sequence
<220> FEATURE:
<223> OTHER INFORMATION: VH FR2 - AB330 (Chothia)

<400> SEQUENCE: 385

Trp Met Tyr Trp Val Arg Gln Ser Ser Asp Arg Arg Leu Glu Trp Ile
1               5                   10                  15

Ala Arg Ile

<210> SEQ ID NO 386
<211> LENGTH: 41
<212> TYPE: PRT
<213> ORGANISM: Artificial Sequence
<220> FEATURE:
<223> OTHER INFORMATION: VH FR3 - AB330 (Chothia)

<400> SEQUENCE: 386

Ser Asp Tyr Val Glu Ser Val Arg Gly Arg Phe Thr Ile Ser Arg Asp
1               5                   10                  15

Asp Ser Arg Ser Ser Val Tyr Leu Gln Met Asn Asn Leu Lys Glu Glu
            20                  25                  30

Asp Thr Ala Thr Tyr Tyr Cys Thr Thr
        35                  40

<210> SEQ ID NO 387
<211> LENGTH: 11
<212> TYPE: PRT
<213> ORGANISM: Artificial Sequence
<220> FEATURE:
<223> OTHER INFORMATION: VH FR4 - AB330 (Chothia)

<400> SEQUENCE: 387

Trp Gly Gln Gly Val Met Val Thr Val Ser Ser
1               5                   10

<210> SEQ ID NO 388
<211> LENGTH: 23
<212> TYPE: PRT
<213> ORGANISM: Artificial Sequence
<220> FEATURE:
<223> OTHER INFORMATION: VL FR1 - AB331 (Chothia)

<400> SEQUENCE: 388

Asp Ile Gln Met Thr Gln Ser Pro Ser Ser Met Ser Ala Ser Leu Gly
1               5                   10                  15

Asp Arg Ile Thr Ile Thr Cys
            20
```

```
<210> SEQ ID NO 389
<211> LENGTH: 15
<212> TYPE: PRT
<213> ORGANISM: Artificial Sequence
<220> FEATURE:
<223> OTHER INFORMATION: VL FR2 - AB332 (Chothia)

<400> SEQUENCE: 389

Trp Tyr Gln Gln Lys Pro Gly Gln Pro Pro Lys Leu Leu Ile Tyr
1               5                   10                  15

<210> SEQ ID NO 390
<211> LENGTH: 32
<212> TYPE: PRT
<213> ORGANISM: Artificial Sequence
<220> FEATURE:
<223> OTHER INFORMATION: VL FR3 - AB332 (Chothia)

<400> SEQUENCE: 390

Gly Ile Pro Ala Arg Leu Ser Gly Ser Gly Ser Gly Thr Asp Phe Thr
1               5                   10                  15

Leu Asn Ile His Pro Val Glu Glu Asp Ala Ala Thr Tyr Tyr Cys
            20                  25                  30

<210> SEQ ID NO 391
<211> LENGTH: 11
<212> TYPE: PRT
<213> ORGANISM: Artificial Sequence
<220> FEATURE:
<223> OTHER INFORMATION: VL FR4 - AB332 (Chothia)

<400> SEQUENCE: 391

Phe Gly Gly Gly Thr Lys Leu Glu Ile Arg Arg
1               5                   10

<210> SEQ ID NO 392
<211> LENGTH: 25
<212> TYPE: PRT
<213> ORGANISM: Artificial Sequence
<220> FEATURE:
<223> OTHER INFORMATION: VH FR1 - AB332 (Chothia)

<400> SEQUENCE: 392

Glu Val Gln Leu Gln Gln Ser Gly Pro Glu Leu Val Lys Pro Gly Thr
1               5                   10                  15

Ser Val Lys Ile Ser Cys Lys Ala Ser
            20                  25

<210> SEQ ID NO 393
<211> LENGTH: 19
<212> TYPE: PRT
<213> ORGANISM: Artificial Sequence
<220> FEATURE:
<223> OTHER INFORMATION: VH FR2 - AB332 (Chothia)

<400> SEQUENCE: 393

Tyr Met Asn Trp Met Lys Gln Ser His Gly Lys Ser Leu Glu Trp Ile
1               5                   10                  15

Gly Asp Ile

<210> SEQ ID NO 394
<211> LENGTH: 42
<212> TYPE: PRT
<213> ORGANISM: Artificial Sequence
<220> FEATURE:
<223> OTHER INFORMATION: VH FR3 - AB332 (Chothia)
```

<400> SEQUENCE: 394

Thr Ser Tyr Asn Gln Lys Phe Lys Gly Lys Ala Thr Leu Thr Val Asp
1               5                   10                  15

Lys Ser Ser Ser Thr Ala Tyr Met Glu Leu Arg Ser Leu Thr Ser Glu
            20                  25                  30

Asp Ser Ala Val Tyr Tyr Cys Ala Arg Glu
        35                  40

<210> SEQ ID NO 395
<211> LENGTH: 108
<212> TYPE: PRT
<213> ORGANISM: Artificial Sequence
<220> FEATURE:
<223> OTHER INFORMATION: VL domain - Ab320

<400> SEQUENCE: 395

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
        35                  40                  45

Tyr Asn Ala Asn Ser Leu Glu Asp Gly Val Pro Ser Arg Phe Ser Gly
    50                  55                  60

Ser Gly Ser Gly Thr Gln Tyr Ser Met Lys Ile Asn Ser Met Gln Pro
65                  70                  75                  80

Glu Asp Thr Ala Thr Tyr Phe Cys Lys Gln Ala Tyr Asp Val Pro Phe
                85                  90                  95

Thr Phe Gly Ser Gly Thr Lys Leu Glu Ile Lys Arg
            100                 105

<210> SEQ ID NO 396
<211> LENGTH: 117
<212> TYPE: PRT
<213> ORGANISM: Artificial Sequence
<220> FEATURE:
<223> OTHER INFORMATION: VH domain - Ab320

<400> SEQUENCE: 396

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Tyr Tyr Gly Ser Lys Ala Tyr Trp Gly Gln Gly Thr Leu
            100                 105                 110

Val Thr Val Ser Ala
        115

<210> SEQ ID NO 397

```
<211> LENGTH: 108
<212> TYPE: PRT
<213> ORGANISM: Artificial Sequence
<220> FEATURE:
<223> OTHER INFORMATION: VL domain - Ab321

<400> SEQUENCE: 397

Ala Ile Gln Met Thr Gln Thr Thr Ser Ser Leu Ser Ala Ser Leu Gly
1               5                   10                  15

Asp Arg Val Thr Ile Ser Cys Ser Val Ser Gln Gly Ile Ser Asn Ser
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Leu
                85                  90                  95

Thr Phe Gly Ala Gly Thr Lys Leu Glu Leu Lys Arg
            100                 105

<210> SEQ ID NO 398
<211> LENGTH: 120
<212> TYPE: PRT
<213> ORGANISM: Artificial Sequence
<220> FEATURE:
<223> OTHER INFORMATION: VH domain - Ab321

<400> SEQUENCE: 398

Gln Val Gln Leu Gln Gln Pro Gly Ala Glu Phe Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Tyr Gly Ser Ser Tyr Arg Phe Ala Tyr Trp Gly Gln
            100                 105                 110

Gly Thr Leu Val Thr Val Ser Ala
        115                 120

<210> SEQ ID NO 399
<211> LENGTH: 110
<212> TYPE: PRT
<213> ORGANISM: Artificial Sequence
<220> FEATURE:
<223> OTHER INFORMATION: VL domain - Ab322

<400> SEQUENCE: 399

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30
```

```
Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Val Ser Asn Val Gln Ser
 65                  70                  75                  80

Glu Asp Leu Ala Glu Tyr Phe Cys Gln Gln Tyr Asn Ser Tyr Pro Tyr
                 85                  90                  95

Met Tyr Thr Phe Gly Gly Gly Thr Lys Leu Glu Ile Lys Arg
            100                 105                 110

<210> SEQ ID NO 400
<211> LENGTH: 120
<212> TYPE: PRT
<213> ORGANISM: Artificial Sequence
<220> FEATURE:
<223> OTHER INFORMATION: VH domain - Ab322

<400> SEQUENCE: 400

Gln Val Gln Leu Gln Gln Ser Gly Ala Glu Leu Ala Lys Pro Gly Ala
 1               5                  10                  15

Ser Val Lys Leu Ser Cys Lys Ala Ser Gly Tyr Thr Phe Thr Asn Tyr
             20                  25                  30

Trp Met His Trp Val Lys Gln Arg Pro Gly Gln Gly Leu Glu Trp Ile
         35                  40                  45

Gly Tyr Ile Asn Pro Ser Ser Gly Tyr Thr Lys Tyr Asn Gln Lys Phe
 50                  55                  60

Lys Asp Lys Ala Thr Leu Thr Ala Asp Lys Ser Ser Thr Ala Tyr
 65                  70                  75                  80

Met Gln Leu Ser Ser Leu Thr Tyr Glu Asp Ser Ala Val Tyr Tyr Cys
                 85                  90                  95

Ala Arg Asp Tyr Tyr Gly Ser Ser Ser Trp Phe Ala Tyr Trp Gly Gln
            100                 105                 110

Gly Thr Leu Val Thr Val Ser Ala
            115                 120

<210> SEQ ID NO 401
<211> LENGTH: 108
<212> TYPE: PRT
<213> ORGANISM: Artificial Sequence
<220> FEATURE:
<223> OTHER INFORMATION: VL domain - Ab323

<400> SEQUENCE: 401

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Pro Leu Ile
             35                  40                  45

Tyr Trp Ala Ser Thr Arg His Thr Gly Val Pro Asp Arg Phe Thr Gly
 50                  55                  60

Ser Gly Ser Gly Thr Asp Tyr Thr Leu Thr Ile Ser Ser Val Gln Thr
 65                  70                  75                  80

Glu Asp Leu Ala Leu Tyr Tyr Cys Gln Gln His Tyr Ser Thr Pro Arg
                 85                  90                  95

Thr Phe Gly Gly Gly Thr Lys Leu Glu Ile Lys Arg
            100                 105
```

<210> SEQ ID NO 402
<211> LENGTH: 117
<212> TYPE: PRT
<213> ORGANISM: Artificial Sequence
<220> FEATURE:
<223> OTHER INFORMATION: VH domain - Ab323

<400> SEQUENCE: 402

Gln Val Gln Leu Gln Gln Ser Gly Ala Glu Leu Val Lys Pro Gly Ala
1               5                   10                  15

Ser Val Lys Ile Ser Cys Lys Thr Ser Gly Tyr Thr Phe Ser Asn Tyr
            20                  25                  30

Trp Met Asn Trp Val Lys Gln Arg Pro Gly Lys Gly Leu Glu Trp Ile
        35                  40                  45

Gly Gln Ile Phe Pro Gly Asp Ala Asp Ala Asn Tyr Asn Gly Lys Phe
    50                  55                  60

Lys Gly Lys Ala Thr Leu Thr Ala Asp Lys Ser Ser Ala Ala Phe
65                  70                  75                  80

Met Gln Leu Ser Ser Leu Thr Ser Glu Asp Ser Ala Val Tyr Phe Cys
                85                  90                  95

Ala Arg Phe Ser Tyr Asp Gly Ala Phe Ala Tyr Trp Gly Gln Gly Thr
            100                 105                 110

Leu Val Thr Val Ser
        115

<210> SEQ ID NO 403
<211> LENGTH: 112
<212> TYPE: PRT
<213> ORGANISM: Artificial Sequence
<220> FEATURE:
<223> OTHER INFORMATION: VL domain - Ab324

<400> SEQUENCE: 403

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys Arg
            100                 105                 110

<210> SEQ ID NO 404
<211> LENGTH: 121
<212> TYPE: PRT
<213> ORGANISM: Artificial Sequence
<220> FEATURE:
<223> OTHER INFORMATION: VH domain - Ab324

<400> SEQUENCE: 404

Gln Val Gln Leu Gln Gln Ser Gly Ala Glu Leu Val Lys Pro Gly Ala
1               5                   10                  15

```
Ser Val Lys Ile Ser Cys Lys Ala Ser Gly Tyr Ala Phe Ser Ser Tyr
            20                  25                  30

Trp Val Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Ser Arg Gly Tyr Phe Tyr Gly Ser Thr Tyr Asp Ser Trp Gly
            100                 105                 110

Gln Gly Thr Thr Leu Thr Val Ser Ser
            115                 120

<210> SEQ ID NO 405
<211> LENGTH: 108
<212> TYPE: PRT
<213> ORGANISM: Artificial Sequence
<220> FEATURE:
<223> OTHER INFORMATION: VL domain - Ab325

<400> SEQUENCE: 405

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Arg
            85                  90                  95

Thr Phe Gly Gly Gly Thr Lys Leu Glu Ile Lys Arg
            100                 105

<210> SEQ ID NO 406
<211> LENGTH: 120
<212> TYPE: PRT
<213> ORGANISM: Artificial Sequence
<220> FEATURE:
<223> OTHER INFORMATION: VH domain - Ab325

<400> SEQUENCE: 406

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95
```

Ala Arg Trp Tyr Tyr Gly Ser Tyr Tyr Ala Met Asp Tyr Trp Gly Gln
            100                 105                 110

Gly Thr Ser Val Thr Val Ser Ser
        115                 120

<210> SEQ ID NO 407
<211> LENGTH: 110
<212> TYPE: PRT
<213> ORGANISM: Artificial Sequence
<220> FEATURE:
<223> OTHER INFORMATION: VL domain - Ab326

<400> SEQUENCE: 407

Asp Ile Val Met Thr Gln Ser Gln Arg Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Met Tyr Thr Phe Gly Gly Gly Thr Lys Leu Glu Ile Lys Arg
            100                 105                 110

<210> SEQ ID NO 408
<211> LENGTH: 120
<212> TYPE: PRT
<213> ORGANISM: Artificial Sequence
<220> FEATURE:
<223> OTHER INFORMATION: VH domain - Ab326

<400> SEQUENCE: 408

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Lys Pro Ser Ser Gly Tyr Thr Lys Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Tyr Glu Asp Ser Ala Val Tyr Tyr Cys
                85                  90                  95

Ala Arg Asp Tyr Tyr Gly Ser Ser Trp Phe Ala Tyr Trp Gly Gln
            100                 105                 110

Gly Thr Leu Val Thr Val Ser Ala
        115                 120

<210> SEQ ID NO 409
<211> LENGTH: 108
<212> TYPE: PRT
<213> ORGANISM: Artificial Sequence
<220> FEATURE:
<223> OTHER INFORMATION: VL domain - Ab327

<400> SEQUENCE: 409

```
Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Leu Lys Pro Gly Gln Ser Pro Lys Leu Leu Ile
        35                  40                  45

Tyr Ser Ala Ser Asn Arg Phe Thr Gly Val Pro Asp Arg Phe Thr Gly
50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ser Gly Thr Lys Leu Glu Ile Lys Arg
            100                 105
```

<210> SEQ ID NO 410
<211> LENGTH: 120
<212> TYPE: PRT
<213> ORGANISM: Artificial Sequence
<220> FEATURE:
<223> OTHER INFORMATION: VH domain - Ab327

<400> SEQUENCE: 410

```
Asp Val Lys Leu Val Glu Ser Gly Glu Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Thr Tyr Ile Ser Ser Gly Gly Asp Tyr Ile Tyr Tyr Ala Asp Thr Val
50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Glu Arg Ile Trp Leu Arg Arg Phe Phe Asp Val Trp Gly Thr
            100                 105                 110

Gly Thr Thr Val Thr Val Ser Ser
        115                 120
```

<210> SEQ ID NO 411
<211> LENGTH: 110
<212> TYPE: PRT
<213> ORGANISM: Artificial Sequence
<220> FEATURE:
<223> OTHER INFORMATION: VL domain - Ab328

<400> SEQUENCE: 411

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly His Ser Pro Lys Ala Leu Ile
        35                  40                  45

Tyr Ser Ala Ser Tyr Arg Tyr Ser Gly Val Pro Asp Arg Phe Thr Gly
50                  55                  60
```

Ser Gly Ser Gly Thr Asp Phe Thr Leu Thr Ile Ser Asn Val Gln Ser
65                  70                  75                  80

Glu Asp Leu Ala Glu Tyr Phe Cys Gln Arg Tyr Asn Ser Tyr Pro Tyr
                85                  90                  95

Met Phe Thr Phe Gly Gly Gly Thr Lys Leu Glu Ile Lys Arg
            100                 105                 110

<210> SEQ ID NO 412
<211> LENGTH: 120
<212> TYPE: PRT
<213> ORGANISM: Artificial Sequence
<220> FEATURE:
<223> OTHER INFORMATION: VH domain - Ab328

<400> SEQUENCE: 412

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Ser Gly Tyr Thr Lys Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Ala Arg Asp Tyr Tyr Gly Ser Ser Trp Phe Ala Tyr Trp Gly Gln
            100                 105                 110

Gly Thr Leu Val Thr Val Ser Ala
        115                 120

<210> SEQ ID NO 413
<211> LENGTH: 107
<212> TYPE: PRT
<213> ORGANISM: Artificial Sequence
<220> FEATURE:
<223> OTHER INFORMATION: VL domain - Ab329

<400> SEQUENCE: 413

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Asp Asn Tyr
                20                  25                  30

Leu Ser Trp Tyr Gln Gln Lys Pro Gly Lys Ser Pro His Leu Leu Ile
            35                  40                  45

His Ser Ala Thr Ser Leu Ala Asp Gly Val Pro Ser Arg Phe Ser Gly
        50                  55                  60

Gly Arg Ser Gly Thr Gln Phe Ser Leu Lys Ile Asn Arg Leu Gln Val
65                  70                  75                  80

Glu Asp Thr Gly Ile Tyr Tyr Cys Leu Gln His Tyr Ser Gly Trp Thr
                85                  90                  95

Phe Gly Gly Gly Thr Lys Leu Glu Leu Lys Arg
            100                 105

<210> SEQ ID NO 414
<211> LENGTH: 117
<212> TYPE: PRT

```
<213> ORGANISM: Artificial Sequence
<220> FEATURE:
<223> OTHER INFORMATION: VH domain - Ab329

<400> SEQUENCE: 414

Gln Val Gln Leu Lys Glu Ser Gly Pro Gly Leu Val Lys Pro Ser Ala
1               5                   10                  15

Thr Leu Ser Leu Thr Cys Thr Val Ser Gly Phe Ser Leu Thr Ser Tyr
            20                  25                  30

His Val Cys Trp Ile Arg Gln Thr Pro Gly Lys Gly Leu Glu Trp Met
        35                  40                  45

Gly Val Ile Trp Gly Asp Gly Arg Thr Thr Tyr Asn Pro Pro Leu Lys
    50                  55                  60

Ser Arg Leu Ser Ile Ser Arg Asp Thr Ser Lys Ser Gln Val Phe Leu
65                  70                  75                  80

Lys Met Ser Ser Leu Lys Thr Glu Asp Thr Ala Thr Tyr Tyr Cys Ala
                85                  90                  95

Arg Ala Thr Met Thr Gly His Gly Asp Ala Trp Gly Gln Gly Ala Ser
            100                 105                 110

Val Thr Val Ser Ser
        115

<210> SEQ ID NO 415
<211> LENGTH: 107
<212> TYPE: PRT
<213> ORGANISM: Artificial Sequence
<220> FEATURE:
<223> OTHER INFORMATION: VL domain - Ab330

<400> SEQUENCE: 415

Asp Ile Gln Met Thr Gln Ser Pro Ser Ser Met Ser Ala Ser Leu Gly
1               5                   10                  15

Asp Arg Val Thr Ile Thr Cys Gln Ala Ser Gln Asp Ile Gly Asn Tyr
            20                  25                  30

Leu Ile Trp Phe Gln Gln Lys Pro Gly Lys Ser Pro Arg Pro Leu Ile
        35                  40                  45

Tyr Tyr Ala Thr Asn Leu Ala Asn Gly Val Pro Ser Arg Phe Ser Gly
    50                  55                  60

Ser Arg Ser Gly Ser Glu Tyr Ser Leu Thr Ile Thr Ser Leu Glu Ser
65                  70                  75                  80

Glu Asp Met Ala Asp Tyr His Cys Leu Gln Tyr Lys Gln His Leu Thr
                85                  90                  95

Phe Gly Ser Gly Thr Lys Leu Glu Ile Glu Arg
            100                 105

<210> SEQ ID NO 416
<211> LENGTH: 116
<212> TYPE: PRT
<213> ORGANISM: Artificial Sequence
<220> FEATURE:
<223> OTHER INFORMATION: VH domain - Ab330

<400> SEQUENCE: 416

Glu Val Gln Val Val Glu Thr Gly Gly Gly Val Gln Pro Gly Lys
1               5                   10                  15

Ser Leu Glu Ile Thr Cys Ala Thr Ser Gly Leu Thr Phe Ser Thr Ala
            20                  25                  30

Trp Met Tyr Trp Val Arg Gln Ser Ser Asp Arg Arg Leu Glu Trp Ile
        35                  40                  45
```

Ala Arg Ile Lys Asp Lys Ser Asn Lys Phe Ala Ser Asp Tyr Val Glu
        50                  55                  60

Ser Val Arg Gly Arg Phe Thr Ile Ser Arg Asp Asp Ser Arg Ser Ser
65                  70                  75                  80

Val Tyr Leu Gln Met Asn Asn Leu Lys Glu Glu Asp Thr Ala Thr Tyr
                85                  90                  95

Tyr Cys Thr Thr Ser Tyr Gly Tyr Ala Trp Gly Gln Gly Val Met Val
            100                 105                 110

Thr Val Ser Ser
            115

<210> SEQ ID NO 417
<211> LENGTH: 107
<212> TYPE: PRT
<213> ORGANISM: Artificial Sequence
<220> FEATURE:
<223> OTHER INFORMATION: VL domain - Ab331

<400> SEQUENCE: 417

Asp Ile Gln Met Thr Gln Ser Pro Ser Ser Met Ser Ala Ser Leu Gly
1               5                   10                  15

Asp Arg Ile Thr Ile Thr Cys Gln Ala Ser Gln Asp Ile Gly Asn Tyr
            20                  25                  30

Leu Ile Trp Phe Gln Gln Lys Pro Gly Lys Ser Pro Arg Pro Leu Ile
        35                  40                  45

Tyr Tyr Ala Thr Asn Leu Ala Asn Gly Val Pro Ser Arg Phe Ser Gly
    50                  55                  60

Ser Arg Ser Gly Ser Glu Tyr Ser Leu Thr Ile Thr Ser Leu Glu Ser
65                  70                  75                  80

Glu Asp Met Ala Asp Tyr His Cys Leu Gln Tyr Lys Gln His Leu Thr
                85                  90                  95

Phe Gly Ser Gly Thr Lys Leu Glu Ile Glu Arg
            100                 105

<210> SEQ ID NO 418
<211> LENGTH: 116
<212> TYPE: PRT
<213> ORGANISM: Artificial Sequence
<220> FEATURE:
<223> OTHER INFORMATION: VH domain - Ab331

<400> SEQUENCE: 418

Glu Val Gln Val Val Glu Thr Gly Gly Gly Val Gln Pro Gly Lys
1               5                   10                  15

Ser Leu Glu Ile Thr Cys Ala Thr Ser Gly Leu Thr Phe Ser Thr Ala
            20                  25                  30

Trp Met Tyr Trp Val Arg Gln Ser Ser Asp Arg Arg Leu Glu Trp Ile
        35                  40                  45

Ala Arg Ile Lys Asp Lys Ser Asn Asn Phe Ala Ser Asp Tyr Val Glu
        50                  55                  60

Ser Val Arg Gly Arg Phe Thr Ile Ser Arg Asp Asp Ser Arg Ser Ser
65                  70                  75                  80

Val Tyr Leu Gln Met Asn Asn Leu Lys Glu Glu Asp Thr Ala Thr Tyr
                85                  90                  95

Tyr Cys Thr Thr Ser Tyr Gly Tyr Ala Trp Gly Gln Gly Val Met Val
            100                 105                 110

Thr Val Ser Ser

<210> SEQ ID NO 419
<211> LENGTH: 112
<212> TYPE: PRT
<213> ORGANISM: Artificial Sequence
<220> FEATURE:
<223> OTHER INFORMATION: VL domain - Ab332

<400> SEQUENCE: 419

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Leu Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Pro Thr Phe Gly Gly Gly Thr Lys Leu Glu Ile Arg Arg
            100                 105                 110

<210> SEQ ID NO 420
<211> LENGTH: 119
<212> TYPE: PRT
<213> ORGANISM: Artificial Sequence
<220> FEATURE:
<223> OTHER INFORMATION: VH domain - Ab332

<400> SEQUENCE: 420

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Thr Phe Thr Asp Tyr
            20                  25                  30

Tyr Met Asn Trp Met Lys Gln Ser His Gly Lys Ser Leu Glu Trp Ile
        35                  40                  45

Gly Asp Ile Asn Pro Asn Asn Gly Val Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Asp Tyr Gly Ser Asn Tyr Phe Asp Tyr Trp Gly Gln Gly
            100                 105                 110

Thr Thr Leu Thr Val Ser Ser
        115

<210> SEQ ID NO 421
<211> LENGTH: 109
<212> TYPE: PRT
<213> ORGANISM: Artificial Sequence
<220> FEATURE:
<223> OTHER INFORMATION: VL domain - Ab351

<400> SEQUENCE: 421

Glu Ile Val Met Thr Gln Ser Pro Ala Phe Leu Ser Val Thr Pro Gly
1               5                   10                  15

Glu Lys Val Thr Ile Thr Cys Lys Ala Ser Gln Asn Val Gly Thr Asn
            20                  25                  30

Val Ala Trp Tyr Gln Gln Lys Pro Asp Gln Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Glu Ala
65                  70                  75                  80

Glu Asp Ala Ala Thr Tyr Tyr Cys Gln Gln Tyr Asn Ser Tyr Pro Tyr
                85                  90                  95

Met Tyr Thr Phe Gly Gln Gly Thr Lys Leu Glu Ile Lys
            100                 105

<210> SEQ ID NO 422
<211> LENGTH: 109
<212> TYPE: PRT
<213> ORGANISM: Artificial Sequence
<220> FEATURE:
<223> OTHER INFORMATION: VL domain - Ab363

<400> SEQUENCE: 422

Asp Ile Val Met Thr Gln Ser Gln Ala Phe Met Ser Val Thr Val Gly
1               5                   10                  15

Glu Lys Val Thr Ile Thr Cys Lys Ala Ser Gln Asn Val Gly Thr Asn
            20                  25                  30

Val Ala Trp Tyr Gln Gln Lys Pro Asp Gln Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Glu Ala
65                  70                  75                  80

Glu Asp Ala Ala Thr Tyr Tyr Cys Gln Gln Tyr Asn Ser Tyr Pro Tyr
                85                  90                  95

Met Tyr Thr Phe Gly Gln Gly Thr Lys Leu Glu Ile Lys
            100                 105

<210> SEQ ID NO 423
<211> LENGTH: 109
<212> TYPE: PRT
<213> ORGANISM: Artificial Sequence
<220> FEATURE:
<223> OTHER INFORMATION: VL domain - Ab375

<400> SEQUENCE: 423

Glu Ile Val Met Thr Gln Ser Pro Ala Phe Met Ser Val Thr Val Gly
1               5                   10                  15

Glu Lys Val Thr Ile Thr Cys Lys Ala Ser Gln Asn Val Gly Thr Asn
            20                  25                  30

Val Ala Trp Tyr Gln Gln Lys Pro Asp Gln Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Glu Ala
65                  70                  75                  80

Glu Asp Ala Ala Thr Tyr Tyr Cys Gln Gln Tyr Asn Ser Tyr Pro Tyr
                85                  90                  95

Met Tyr Thr Phe Gly Gln Gly Thr Lys Leu Glu Ile Lys

-continued

```
<210> SEQ ID NO 424
<211> LENGTH: 109
<212> TYPE: PRT
<213> ORGANISM: Artificial Sequence
<220> FEATURE:
<223> OTHER INFORMATION: VL domain - Ab387

<400> SEQUENCE: 424

Glu Ile Val Met Thr Gln Ser Pro Ala Thr Leu Ser Thr Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Ala Leu Ile
        35                  40                  45

Tyr Ser Ala Ser Tyr Arg Tyr Ser Gly Val Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Tyr Cys Gln Gln Tyr Asn Ser Tyr Pro Tyr
                85                  90                  95

Met Tyr Thr Phe Gly Gln Gly Thr Lys Leu Glu Ile Lys
            100                 105

<210> SEQ ID NO 425
<211> LENGTH: 109
<212> TYPE: PRT
<213> ORGANISM: Artificial Sequence
<220> FEATURE:
<223> OTHER INFORMATION: VL domain - Ab399

<400> SEQUENCE: 425

Glu Ile Val Met Thr Gln Ser Gln Ala Thr Met Ser Thr Ser Val Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Tyr Cys Gln Gln Tyr Asn Ser Tyr Pro Tyr
                85                  90                  95

Met Tyr Thr Phe Gly Gln Gly Thr Lys Leu Glu Ile Lys
            100                 105

<210> SEQ ID NO 426
<211> LENGTH: 109
<212> TYPE: PRT
<213> ORGANISM: Artificial Sequence
<220> FEATURE:
<223> OTHER INFORMATION: VL domain - Ab411

<400> SEQUENCE: 426

Glu Ile Val Met Thr Gln Ser Gln Ala Thr Leu Ser Thr Ser Pro Gly
1               5                   10                  15

Glu Arg Ala Thr Leu Ser Cys Lys Ala Ser Gln Asn Val Gly Thr Asn
            20                  25                  30
```

```
Val Ala Trp Tyr Gln Gln Lys Pro Gly Gln Ala Pro Arg Ala Leu Ile
        35                  40                  45

Tyr Ser Ala Ser Tyr Arg Tyr Ser Gly Val Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Tyr Cys Gln Gln Tyr Asn Ser Tyr Pro Tyr
                85                  90                  95

Met Tyr Thr Phe Gly Gln Gly Thr Lys Leu Glu Ile Lys
                100                 105

<210> SEQ ID NO 427
<211> LENGTH: 109
<212> TYPE: PRT
<213> ORGANISM: Artificial Sequence
<220> FEATURE:
<223> OTHER INFORMATION: VL domain - Ab423

<400> SEQUENCE: 427

Glu Ile Val Met Thr Gln Ser Pro Ala Thr Leu Ser Thr Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Ala Leu Ile
        35                  40                  45

Tyr Ser Ala Ser Tyr Arg Tyr Ser Gly Val Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Tyr Cys Gln Gln Tyr Asn Ser Tyr Pro Tyr
                85                  90                  95

Met Tyr Thr Phe Gly Gln Gly Thr Lys Leu Glu Ile Lys
                100                 105

<210> SEQ ID NO 428
<211> LENGTH: 109
<212> TYPE: PRT
<213> ORGANISM: Artificial Sequence
<220> FEATURE:
<223> OTHER INFORMATION: VL domain - Ab435

<400> SEQUENCE: 428

Glu Ile Val Met Thr Gln Ser Gln Ala Thr Met Ser Thr Ser Val Gly
1               5                   10                  15

Glu Arg Ala Thr Leu Ser Cys Lys Ala Ser Gln Asn Val Gly Thr Asn
                20                  25                  30

Val Ala Trp Tyr Gln Gln Lys Pro Gly Gln Ser Pro Lys Ala Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Tyr Cys Gln Gln Tyr Asn Ser Tyr Pro Tyr
                85                  90                  95

Met Tyr Thr Phe Gly Gln Gly Thr Lys Leu Glu Ile Lys
                100                 105
```

```
<210> SEQ ID NO 429
<211> LENGTH: 120
<212> TYPE: PRT
<213> ORGANISM: Artificial Sequence
<220> FEATURE:
<223> OTHER INFORMATION: VH domain - Ab351

<400> SEQUENCE: 429
```

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Ser Tyr
                20                  25                  30

Trp Met His Trp Val Lys Gln Ala Pro Gly Gln Gly Leu Glu Trp Ile
            35                  40                  45

Gly Tyr Ile Lys Pro Ser Ser Gly Tyr Thr Lys Tyr Asn Gln Lys Phe
        50                  55                  60

Lys Asp Lys Val Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
                100                 105                 110

Gly Thr Leu Val Thr Val Ser Ser
        115                 120

```
<210> SEQ ID NO 430
<211> LENGTH: 120
<212> TYPE: PRT
<213> ORGANISM: Artificial Sequence
<220> FEATURE:
<223> OTHER INFORMATION: VH domain - Ab352

<400> SEQUENCE: 430
```

Glu Val Gln Leu Val Gln Ser Gly Pro Glu Val Lys Lys Pro Gly Thr
1               5                   10                  15

Ser Val Lys Leu Ser Cys Lys Ala Ser Gly Tyr Thr Phe Thr Ser Tyr
                20                  25                  30

Trp Met His Trp Val Arg Gln Ala Arg Gly Gln Arg Leu Glu Trp Ile
            35                  40                  45

Gly Tyr Ile Lys Pro Ser Ser Gly Tyr Thr Lys Tyr Asn Gln Lys Phe
        50                  55                  60

Lys Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
                100                 105                 110

Gly Thr Leu Val Thr Val Ser Ser
        115                 120

```
<210> SEQ ID NO 431
<211> LENGTH: 120
<212> TYPE: PRT
<213> ORGANISM: Artificial Sequence
<220> FEATURE:
<223> OTHER INFORMATION: VH domain - Ab353

<400> SEQUENCE: 431
```

Glu Val Gln Leu Val Gln Ser Gly Ala Glu Val Lys Lys Pro Gly Thr
1               5                   10                  15

```
Ser Val Lys Leu Ser Cys Lys Ala Ser Gly Tyr Thr Phe Thr Ser Ser
            20                  25                  30

Ala Met Gln Trp Val Lys Gln Ala Pro Gly Gln Gly Leu Glu Trp Ile
            35                  40                  45

Gly Tyr Ile Lys Pro Ser Ser Gly Tyr Thr Lys Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
            100                 105                 110

Gly Thr Leu Val Thr Val Ser Ser
            115                 120

<210> SEQ ID NO 432
<211> LENGTH: 120
<212> TYPE: PRT
<213> ORGANISM: Artificial Sequence
<220> FEATURE:
<223> OTHER INFORMATION: VH domain - Ab354

<400> SEQUENCE: 432

Glu Val Gln Leu Val Gln Ser Gly Ala Glu Val Lys Lys Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Arg Gly Gln Arg Leu Glu Trp Ile
            35                  40                  45

Gly Tyr Ile Lys Pro Ser Ser Gly Tyr Thr Lys Tyr Ala Gln Lys Phe
    50                  55                  60

Gln Glu Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
            100                 105                 110

Gly Thr Leu Val Thr Val Ser Ser
            115                 120

<210> SEQ ID NO 433
<211> LENGTH: 120
<212> TYPE: PRT
<213> ORGANISM: Artificial Sequence
<220> FEATURE:
<223> OTHER INFORMATION: VH domain - Ab355

<400> SEQUENCE: 433

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
            35                  40                  45

Gly Tyr Ile Lys Pro Ser Ser Gly Tyr Thr Lys Tyr Asn Gln Lys Phe
    50                  55                  60

Lys Asp Lys Ala Thr Leu Thr Ala Asp Lys Ser Thr Ser Thr Ala Tyr
```

```
                65                  70                  75                  80
Met Glu Leu Arg Ser Leu Arg Ser Asp Asp Thr Ala Val Tyr Tyr Cys
                    85                  90                  95

Ala Arg Asp Tyr Tyr Gly Ser Ser Trp Phe Ala Tyr Trp Gly Gln
                100                 105                 110

Gly Thr Leu Val Thr Val Ser Ser
            115                 120

<210> SEQ ID NO 434
<211> LENGTH: 120
<212> TYPE: PRT
<213> ORGANISM: Artificial Sequence
<220> FEATURE:
<223> OTHER INFORMATION: VH domain - Ab356

<400> SEQUENCE: 434

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Tyr Ile Lys Pro Ser Ser Gly Tyr Thr Lys Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Asp Tyr Tyr Gly Ser Ser Trp Phe Ala Tyr Trp Gly Gln
                100                 105                 110

Gly Thr Leu Val Thr Val Ser Ser
            115                 120

<210> SEQ ID NO 435
<211> LENGTH: 120
<212> TYPE: PRT
<213> ORGANISM: Artificial Sequence
<220> FEATURE:
<223> OTHER INFORMATION: VH domain - Ab357

<400> SEQUENCE: 435

Glu Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Tyr Ile Lys Pro Ser Ser Gly Tyr Thr Lys Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                    85                  90                  95

Ala Arg Asp Tyr Tyr Gly Ser Ser Trp Phe Ala Tyr Trp Gly Gln
                100                 105                 110

Gly Thr Leu Val Thr Val Ser Ser
            115                 120
```

-continued

<210> SEQ ID NO 436
<211> LENGTH: 120
<212> TYPE: PRT
<213> ORGANISM: Artificial Sequence
<220> FEATURE:
<223> OTHER INFORMATION: VH domain - Ab358

<400> SEQUENCE: 436

```
Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Tyr Ile Lys Pro Ser Ser Gly Tyr Thr Lys Tyr Ala Gln Lys Leu
    50                  55                  60

Gln Gly Arg Val Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Gly Ser Ser Ser Trp Phe Ala Tyr Trp Gly Gln
            100                 105                 110

Gly Thr Leu Val Thr Val Ser Ser
        115                 120
```

<210> SEQ ID NO 437
<211> LENGTH: 120
<212> TYPE: PRT
<213> ORGANISM: Artificial Sequence
<220> FEATURE:
<223> OTHER INFORMATION: VH domain - Ab359

<400> SEQUENCE: 437

```
Gln Val Gln Leu Val Gln Ser Gly Ala Glu Val Ala Lys Pro Gly Ser
1               5                   10                  15

Ser Val Lys Leu Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Tyr Ile Lys Pro Ser Ser Gly Tyr Thr Lys Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
            100                 105                 110

Gly Thr Leu Val Thr Val Ser Ser
        115                 120
```

<210> SEQ ID NO 438
<211> LENGTH: 120
<212> TYPE: PRT
<213> ORGANISM: Artificial Sequence
<220> FEATURE:
<223> OTHER INFORMATION: VH domain - Ab360

<400> SEQUENCE: 438

```
Glu Val Gln Leu Val Gln Ser Gly Ala Glu Val Lys Lys Pro Gly Ser
```

-continued

```
  1               5                  10                 15
Ser Val Lys Leu Ser Cys Lys Ala Ser Gly Tyr Thr Phe Thr Ser Tyr
                20                  25                 30

Trp Met His Trp Val Arg Gln Ala Pro Gly Gln Gly Leu Glu Trp Ile
            35                  40                 45

Gly Tyr Ile Lys Pro Ser Ser Gly Tyr Thr Lys Tyr Asn Gln Lys Phe
        50                  55                  60

Lys Asp Lys Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
                100                 105                110

Gly Thr Leu Val Thr Val Ser Ser
                115                 120
```

<210> SEQ ID NO 439
<211> LENGTH: 120
<212> TYPE: PRT
<213> ORGANISM: Artificial Sequence
<220> FEATURE:
<223> OTHER INFORMATION: VH domain - Ab361

<400> SEQUENCE: 439

```
Glu Val Gln Leu Val Gln Ser Gly Ala Glu Val Lys Lys Pro Gly Ser
 1               5                  10                 15

Ser Val Lys Val Ser Cys Lys Ala Ser Gly Tyr Thr Phe Ser Ser Tyr
                20                  25                 30

Trp Met His Trp Val Arg Gln Ala Pro Gly Gln Gly Leu Glu Trp Ile
            35                  40                 45

Gly Tyr Ile Lys Pro Ser Ser Gly Tyr Thr Lys Tyr Asn Gln Lys Phe
        50                  55                  60

Lys Asp Lys Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
                100                 105                110

Gly Thr Leu Val Thr Val Ser Ser
                115                 120
```

<210> SEQ ID NO 440
<211> LENGTH: 120
<212> TYPE: PRT
<213> ORGANISM: Artificial Sequence
<220> FEATURE:
<223> OTHER INFORMATION: VH domain - Ab362

<400> SEQUENCE: 440

```
Glu Val Gln Leu Val Gln Ser Gly Ala Glu Val Lys Lys Pro Gly Ser
 1               5                  10                 15

Ser Val Lys Leu Ser Cys Lys Ala Ser Gly Tyr Thr Phe Ser Ser Tyr
                20                  25                 30

Trp Met His Trp Val Lys Gln Ala Pro Gly Gln Gly Leu Glu Trp Ile
            35                  40                 45

Gly Tyr Ile Lys Pro Ser Ser Gly Tyr Thr Lys Tyr Ala Gln Lys Phe
        50                  55                  60
```

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Gly Ser Ser Ser Trp Phe Ala Tyr Trp Gly Gln
            100                 105                 110

Gly Thr Leu Val Thr Val Ser Ser
        115                 120

<210> SEQ ID NO 441
<211> LENGTH: 324
<212> TYPE: DNA
<213> ORGANISM: Artificial Sequence
<220> FEATURE:
<223> OTHER INFORMATION: VL domain - Ab320

<400> SEQUENCE: 441
gacatccaga tgactcagtc tccagcctcc ctggctgcat ctgtgggaga aactgtcacc    60
atcacatgtc gagcaagtga aaacatttac tacagtttag catggtatca gcagaagcaa   120
gggaaatctc ctcagctcct gatctataat gcaaacagct tggaagatgg tgtcccatcg   180
aggttcagtg gcagtggatc tgggacacag tattctatga gatcaacagc atgcagcct   240 gaagataccg caacttattt ctgtaaacag gcttatgacg ttccattcac gttcggctcg   300
gggacaaagt tggaaataaa acgg                                          324

<210> SEQ ID NO 442
<211> LENGTH: 351
<212> TYPE: DNA
<213> ORGANISM: Artificial Sequence
<220> FEATURE:
<223> OTHER INFORMATION: VH domain - Ab320

<400> SEQUENCE: 442
caggttcagc tgcagcagtc tggggctgag ctggtgaagc ctggggcctc agtgaagatt    60
tcctgcaaag cttctggcta cgcattcagt agctactgga tgaactgggt gaagcagagg   120
cctggaaagg gtcttgagtg gattggacag atttatcctg agatggtga tactaactac   180 aacggaaagt tcaagggcaa ggccacactg actgcagaca atcctccag cacagcctac   240 atgcagctca gcagcctgac ctctgaggac tctgcggtct atttctgtgc ctcttattac   300
tacggtagta aggcttactg gggccaaggg actctggtca ctgtctctgc a            351

<210> SEQ ID NO 443
<211> LENGTH: 324
<212> TYPE: DNA
<213> ORGANISM: Artificial Sequence
<220> FEATURE:
<223> OTHER INFORMATION: VL domain - Ab321

<400> SEQUENCE: 443
gctatccaga tgacacagac tacatcctcc ctgtctgcct ctctgggaga cagagtcacc    60
atcagttgca gtgtaagtca gggcattagc aattctttaa actggtatca gcagaaacca   120
gatggaactg ttaaactcct gatctattac acatcaagtt acactcagg agtcccatca   180 aggttcagtg gcagtgggtc tgggacagat tattctctca ccatcagcaa cctggaacct   240
gaagatattg ccacttacta ttgtcagcag tatagtaagc ttccgctcac gttcggtgct   300
gggaccaagc tggagctgaa acgg                                          324

```
<210> SEQ ID NO 444
<211> LENGTH: 360
<212> TYPE: DNA
<213> ORGANISM: Artificial Sequence
<220> FEATURE:
<223> OTHER INFORMATION: VH domain - Ab321

<400> SEQUENCE: 444
caggtccaac tgcagcagcc tggggctgag tttgtgaagc ctggggcttc agtgaagctg      60
tcctgcaagg cttctggcta caccttcacc agctactgga tgcactgggt gaagcagagg     120
cctggacgag ccttgagtg gattggaagg attgatccta atagtggtgg tactaagtac      180
aatgagaagt tcaagagcaa ggccacactg actgtagaca accctccag cacagcctac      240 atgcagctca gcagcctgac atctgaggac tctgcggtct attattgtgc aagagattac     300
tacggtagta gctaccggtt tgcttactgg ggccaaggga ctctggtcac tgtctctgca     360

<210> SEQ ID NO 445
<211> LENGTH: 330
<212> TYPE: DNA
<213> ORGANISM: Artificial Sequence
<220> FEATURE:
<223> OTHER INFORMATION: VL domain - Ab322

<400> SEQUENCE: 445
gacattgtga tgacccagtc tcaaagattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccgtcagcaa tgtgcagtct     240
gaagacttgg cagagtattt ctgtcagcaa tataacagct atccgtacat gtacacgttc     300 ggaggggggga ccaagctgga aataaaacgg                                     330

<210> SEQ ID NO 446
<211> LENGTH: 360
<212> TYPE: DNA
<213> ORGANISM: Artificial Sequence
<220> FEATURE:
<223> OTHER INFORMATION: VH domain - Ab322

<400> SEQUENCE: 446
caggtccagc tgcagcagtc tggggctgaa ctggcaaaac tggggcctc agtgaagctg       60 tcctgcaagg cttctggcta cacctttact aactactgga tgcactgggt aaaacagagg     120
cctggacagg gtctggaatg gattggatac attaatccta gcagtggtta tactaagtac     180
aatcagaagt tcaaggacaa ggccacattg actgcagaca atcctccag cacagcctac      240 atgcagctga gcagcctgac atatgaggac tctgcagtct attactgtgc aagagattac     300
tacggtagta gctcctggtt tgcttactgg ggccaaggga ctctggtcac tgtctctgca     360

<210> SEQ ID NO 447
<211> LENGTH: 324
<212> TYPE: DNA
<213> ORGANISM: Artificial Sequence
<220> FEATURE:
<223> OTHER INFORMATION: VL domain - Ab323

<400> SEQUENCE: 447
gacattgtga tgacccagtc tcacaaattc atgtccacat cagtaggaga cagggtcagc      60
atcacctgca aggccagtca ggatgtgagt actgctgtag cctggtatca acaaaaacca     120
```

```
gggcaatctc ccaaaccact gatttactgg gcatccaccc ggcacactgg agtccctgat        180
cgcttcacag gcagtggatc tgggacagat tatactctca ccatcagcag tgtgcagact        240
gaagacctgg cactttatta ctgtcagcaa cattatagca ctcctcggac gttcggtgga        300
ggcaccaagc tggaaatcaa acgg                                               324
```

```
<210> SEQ ID NO 448
<211> LENGTH: 354
<212> TYPE: DNA
<213> ORGANISM: Artificial Sequence
<220> FEATURE:
<223> OTHER INFORMATION: VH domain - Ab323

<400> SEQUENCE: 448
caggttcagc tgcagcagtc tggggctgag ctggtgaagc ctggggcctc agtgaagatt        60
tcctgcaaaa cttctggcta cacattcagc aactactgga tgaactgggt gaagcagagg        120
cctggaaagg gtcttgagtg gattggacag attttttcctg agatgctga tgctaactac        180 aacggaaagt tcaagggcaa ggccacactg actgcagaca atcctccag cgcagccttc        240 atgcagctca gcagcctgac ctctgaggac tctgcggtct atttctgtgc aagatttagt        300
tacgacgggg cgtttgctta ctggggccaa gggactctgg tcactgtctc tgca             354
```

```
<210> SEQ ID NO 449
<211> LENGTH: 336
<212> TYPE: DNA
<213> ORGANISM: Artificial Sequence
<220> FEATURE:
<223> OTHER INFORMATION: VL domain - Ab324

<400> SEQUENCE: 449
gacattgtgc tgacccaatc tccagcttct ttggctgtgt ctctagggca gagggccacc        60
atctcctgca gagccagcga agtgttgat aattatggca ttagttttat gaactggttc        120
caacagaaac caggacagcc acccaaactc ctcatctatg ctgcatccaa ccaaggatcc        180
ggggtccctg ccaggtttag tggcagtggg tctgggacag acttcagcct caacatccat        240
cctatggagg aggatgatac tgcaatgtat ttctgtcagc aaagtaagga ggttccgtgg        300
acgttcggtg gaggcaccaa gctggaaatc aaacgg                                  336
```

```
<210> SEQ ID NO 450
<211> LENGTH: 363
<212> TYPE: DNA
<213> ORGANISM: Artificial Sequence
<220> FEATURE:
<223> OTHER INFORMATION: VH domain - Ab324

<400> SEQUENCE: 450
caggttcagc tgcaacagtc tggggctgag ctggtgaagc ctggggcctc agtgaagatt        60
tcctgcaaag cttctggcta cgcattcagt agctactggg tgaactgggt gaagcagagg        120
cctggaaagg gtcttgagtg gattggacag atttatcctg agatggtga tactaactac        180 aacggaaagt tcaagggcaa ggccacactg actgcagaca atcctccag cacagcctac        240 atgcagctca gcagcctgac ctctgaggac tctgcggtct atttctgtgc aagatcaaga        300
gggtatttct acggtagtac ctacgactcc tggggccaag gcaccactct cacagtctcc        360
tca                                                                      363
```

```
<210> SEQ ID NO 451
<211> LENGTH: 324
```

```
<212> TYPE: DNA
<213> ORGANISM: Artificial Sequence
<220> FEATURE:
<223> OTHER INFORMATION: VL domain - Ab325

<400> SEQUENCE: 451
gatatccaga tgacacagac tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat acactcagg agtcccatca    180 aggttcagtg gcagtgggtc tggaacagat tattctctca ccattagcaa cctggagcaa   240
gaagatattg ccacttactt ttgccaacag ggtaatacgc ttcctcggac gttcggtgga   300
ggcaccaagc tggaaatcaa acgg                                          324

<210> SEQ ID NO 452
<211> LENGTH: 360
<212> TYPE: DNA
<213> ORGANISM: Artificial Sequence
<220> FEATURE:
<223> OTHER INFORMATION: VH domain - Ab325

<400> SEQUENCE: 452
caggttcagc tgcagcagtc tggggctgag ctggtgaagc ctggggcctc agtgaagatt    60
tcctgcaaag cttctggcta cgcattcagt agctactgga tgaactgggt gaagcagagg   120
cctggaaagg gtcttgagtg gattggacag atttatcctg agatggtga tactaactac    180 aacggaaagt tcaagggcaa ggccacactg actgcagaca atcctccag cacagcctac    240 atgcagctca gcagcctgac ctctgaggac tctgcggtct atttctgtgc aagatggtac   300
tacggtagtt actatgctat ggactactgg ggtcaaggaa cctcagtcac cgtctcctca   360

<210> SEQ ID NO 453
<211> LENGTH: 330
<212> TYPE: DNA
<213> ORGANISM: Artificial Sequence
<220> FEATURE:
<223> OTHER INFORMATION: VL domain - Ab326

<400> SEQUENCE: 453
gacattgtga tgacccagtc tcaaagattc atgtccacat cagtaggaga cagggtcagc    60
gtcacctgca aggccagtca gaatgtgggt actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcaacaa tataacagct atccgtacat gtacacgttc   300 ggaggggga ccaagctgga aataaaacgg                                     330

<210> SEQ ID NO 454
<211> LENGTH: 360
<212> TYPE: DNA
<213> ORGANISM: Artificial Sequence
<220> FEATURE:
<223> OTHER INFORMATION: VH domain - Ab326

<400> SEQUENCE: 454
caggtccagc tgcagcagtc tggggctgaa ctggcaaaac ctggggcctc agtgaagctg    60
tcctgcaagg cttctggcta caccttact agctactgga tgcactgggt aaaacagagg   120
cctggacagg gtctggaatg gattggatac attaagccta gcagtggtta tactaagtac   180
```

```
aatcagaagt tcaaggacaa ggccacattg actgcagaca atcctccag cacagcctac    240 atgcagctga gcagcctgac atatgaggac tctgcagtct attactgtgc aagagattac    300
tacggtagta gctcctggtt tgcttactgg ggccaaggga ctctggtcac tgtctctgca    360

<210> SEQ ID NO 455
<211> LENGTH: 324
<212> TYPE: DNA
<213> ORGANISM: Artificial Sequence
<220> FEATURE:
<223> OTHER INFORMATION: VL domain - Ab327

<400> SEQUENCE: 455
gacattgtga tgacccagtc tcaaaaattc atgtccacat cagtaggaga cagggtcagc     60
atcacctgta aggccagtca gaatgtgggt actgctgtag cctggtatca actgaaacca    120
ggacaatctc ctaaactact gatttactcg gcatccaatc ggttcactgg agtccctgat    180
cgcttcacag gcagtggatc tgggacagat ttcactctca ccatcagcaa tatgcagtct    240
gaagacctgg cagattattt ctgccagcaa tatagcagct atcctctcac gttcggctcg    300
gggacaaagt tggaaataaa acgg                                           324

<210> SEQ ID NO 456
<211> LENGTH: 360
<212> TYPE: DNA
<213> ORGANISM: Artificial Sequence
<220> FEATURE:
<223> OTHER INFORMATION: VH domain - Ab327

<400> SEQUENCE: 456
gacgtgaagc tggtggagtc tggggaaggc ttagtgaagc ctggagggtc cctgaaactc     60
tcctgtgcag cctctggatt cactttcagt agctatgcca tgtcttgggt tcgccagact    120
ccagagaaga ggctggagtg ggtcacatac attagtagtg gtggtgatta catctactat    180
gcagacactg tgaagggccg attcaccatc tccagagaca tgccaggaa cacccctgtac   240 ctgcaaatga gcagtctgaa gtctgaggac acagccatgt attactgtac aagagagcgg    300
atatggttac gacggttctt cgatgtctgg ggcacaggga ccacggtcac cgtctcctca    360

<210> SEQ ID NO 457
<211> LENGTH: 330
<212> TYPE: DNA
<213> ORGANISM: Artificial Sequence
<220> FEATURE:
<223> OTHER INFORMATION: VL domain - Ab328

<400> SEQUENCE: 457
gacattgtga tgacccagtc tcaaaaattc atgtccacat cagtaggaga cagggtcagc     60
gtcacctgca aggccagtca gaatgtgggt actaatgtag cctggtatca acagaaacca    120
gggcactctc ctaaagcact gatttactcg gcatcctacc ggtacagtgg agtccctgat    180
cgcttcacag gcagtggatc tgggacagat ttcactctca ccatcagcaa tgtgcagtct    240
gaagacttgg cagagtattt ctgtcagcga tataacagct atccgtacat gttcacgttc    300
ggagggggga ccaagctgga aataaaacgg                                    330

<210> SEQ ID NO 458
<211> LENGTH: 360
<212> TYPE: DNA
<213> ORGANISM: Artificial Sequence
<220> FEATURE:
<223> OTHER INFORMATION: VH domain - Ab328
```

<400> SEQUENCE: 458

```
caggtccagc tgcagcagtc tggggctgaa ctggcaaaac ctggggcctc agtgaagctg      60
tcctgcaagg cttctggcta cacctttact agctactgga tgcactgggt aaaacagagg     120
cctggacagg gtctggaatg gattggatac attaatccta gcagtggtta tactaagtac     180
aatcagaagt tcaaggacaa ggccacattg actgcagaca atcctccag cacagcctac      240
atgcagctga gcagcctgac atttgaggac tctgcagtct attactgtgc aagagattac     300
tacggtagta gctcctggtt tgcttactgg ggccaaggga ctctggtcac tgtctctgca     360
```

<210> SEQ ID NO 459
<211> LENGTH: 321
<212> TYPE: DNA
<213> ORGANISM: Artificial Sequence
<220> FEATURE:
<223> OTHER INFORMATION: VL domain - Ab329

<400> SEQUENCE: 459

```
gacatccaga tgacacagtc tcctgcctcc ctgtctgcat ctctggaaga aattgtcacc      60
atcacatgcc aggcaagcca ggacattgat aattacttat catggtatca gcagaaacca     120
gggaaatctc ctcacctcct gatccacagt gcaaccagct ggcagatggg gtcccatca      180
aggttcagcg gcggtagatc tggcacacag ttttctctta agatcaacag actacaggtt     240
gaagatactg ggatctatta ctgtctacaa cattatagtg ttggacgtt cggtggaggc      300
accaagttgg agttgaaacg g                                               321
```

<210> SEQ ID NO 460
<211> LENGTH: 351
<212> TYPE: DNA
<213> ORGANISM: Artificial Sequence
<220> FEATURE:
<223> OTHER INFORMATION: VH domain - Ab329

<400> SEQUENCE: 460

```
caggtgcagc tgaaggagtc aggacctggc ctggtgaagc cctcagcgac cctgtctctc      60
acctgcactg tctctggggtt ctcattaacc agttatcatg tgtgctggat tcgacagact    120
ccaggaaagg gtctgagtg gatgggagta atatggggtg atggaaggac aacatataat      180
ccacctctca atcccgact gagcatcagc agggacacct ccaagagcca gttttctta      240
aaaatgagca gtctgaaaac tgaagacaca gccacctatt actgtgccag agcgactatg     300
acgggccacg gggatgcctg ggtcaagga gcctcagtca ctgtctcctc a               351
```

<210> SEQ ID NO 461
<211> LENGTH: 321
<212> TYPE: DNA
<213> ORGANISM: Artificial Sequence
<220> FEATURE:
<223> OTHER INFORMATION: VL domain - Ab330

<400> SEQUENCE: 461

```
gacatccaga tgacccagtc tccatcctcc atgtctgcat ctctgggaga cagagtcact      60
attacttgcc aggcaagtca ggacattggg aattatttaa tctggtttca acagaaacca     120
gggaagtctc ctaggcctct gatttattat gcaaccaact ggcaaatggg gtcccatca      180
aggttcagtg gcagtaggtc tggctcagaa tattctctga ccattaccag cctggagtct     240
gaagatatgg cagactatca ctgtctacaa tataaacagc atctcacgtt cggctcaggg     300
```

```
acgaagttgg agatagaacg g                                              321
```

<210> SEQ ID NO 462
<211> LENGTH: 348
<212> TYPE: DNA
<213> ORGANISM: Artificial Sequence
<220> FEATURE:
<223> OTHER INFORMATION: VH domain - Ab330

<400> SEQUENCE: 462

```
gaggtacagg tcgtggaaac aggggaggc gtggtgcagc ctgggaaatc tcttgaaatc      60
acctgtgcca cgtcaggatt gaccttcagt acggcctgga tgtactgggt tcgccagtct    120
tcagataggc gactagagtg gattgctcga attaaagaca aatctaacaa gtttgcatcc    180
gactatgtgg aatctgtgag aggaagattc accatctcaa gagatgattc cagaagttcc    240
gtttacttgc agatgaacaa cttaaaagag gaagacactg ccacttatta ctgtactaca    300
tcttatggat atgcctgggg ccaaggagtc atggtcacag tctcctca                 348
```

<210> SEQ ID NO 463
<211> LENGTH: 321
<212> TYPE: DNA
<213> ORGANISM: Artificial Sequence
<220> FEATURE:
<223> OTHER INFORMATION: VL domain - Ab331

<400> SEQUENCE: 463

```
gacatccaga tgacccagtc tccatcctcc atgtctgcat ctctgggaga cagaatcact     60
attacttgcc aggcaagtca ggacattggg aattatttaa tctggtttca acagaaacca    120
gggaagtctc ctaggcctct gatttattat gcaaccaact ggcaaatggg gtcccatca     180
aggttcagtg gcagtaggtc tggctcagaa tattctctga ccattaccag cctggagtct    240
gaagatatgg cagactatca ctgtctacaa tataaacagc atctcacgtt cggctcaggg    300
acgaagttgg agatagaacg g                                              321
```

<210> SEQ ID NO 464
<211> LENGTH: 348
<212> TYPE: DNA
<213> ORGANISM: Artificial Sequence
<220> FEATURE:
<223> OTHER INFORMATION: VH domain - Ab331

<400> SEQUENCE: 464

```
gaggtacagg tcgtggaaac aggggaggc gtggtgcagc ctgggaaatc tcttgagatc      60
acctgtgcca cgtcaggatt gaccttcagt acggcctgga tgtactgggt tcgccagtct    120
tcagataggc gactagagtg gattgctcga attaaagaca aatctaacaa ttttgcatcc    180
gactatgtgg aatctgtgag aggaagattc accatctcaa gagatgattc cagaagttcc    240
gtttacttac agatgaacaa cttaaaagag gaagacactg ccacttatta ctgtactaca    300
tcttatggat atgcctgggg ccaaggagtc atggtcacag tctcctca                 348
```

<210> SEQ ID NO 465
<211> LENGTH: 358
<212> TYPE: DNA
<213> ORGANISM: Artificial Sequence
<220> FEATURE:
<223> OTHER INFORMATION: VL domain - Ab332

<400> SEQUENCE: 465

```
gaggtccagc tgcaacaatc tggacctgag ctggtgaagc ctgggacttc agtgaagata     60
```

```
tcctgtaagg cttctggata cacgttcact gactactaca tgaactggat gaagcagagc    120
catggaaaga gccttgagtg gattggagat attaatccta acaatggtgt tactagctac    180
aaccagaagt tcaagggcaa ggccacattg actgtagaca agtcctccag cacagcctac    240
atggagctcc gcagcctgac atctgaggac tctgcagtct attactgtgc aagagaggac    300
tacggtagta actactttga ctactggggc caaggcacca ctctcacagt ctcctcag     358
```

```
<210> SEQ ID NO 466
<211> LENGTH: 358
<212> TYPE: DNA
<213> ORGANISM: Artificial Sequence
<220> FEATURE:
<223> OTHER INFORMATION: VH domain - Ab332

<400> SEQUENCE: 466
```

```
gaggtccagc tgcaacaatc tggacctgag ctggtgaagc ctgggacttc agtgaagata    60
tcctgtaagg cttctggata cacgttcact gactactaca tgaactggat gaagcagagc   120
catggaaaga gccttgagtg gattggagat attaatccta acaatggtgt tactagctac   180
aaccagaagt tcaagggcaa ggccacattg actgtagaca agtcctccag cacagcctac   240
atggagctcc gcagcctgac atctgaggac tctgcagtct attactgtgc aagagaggac   300
tacggtagta actactttga ctactggggc caaggcacca ctctcacagt ctcctcag    358
```

```
<210> SEQ ID NO 467
<211> LENGTH: 1620
<212> TYPE: PRT
<213> ORGANISM: Homo sapiens
<220> FEATURE:
<223> OTHER INFORMATION: human ALK

<400> SEQUENCE: 467
```

```
Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190
```

```
Lys Lys Ala Ser Glu Val Gly Arg Glu Gly Arg Leu Ser Ala Ala Ile
            195                 200                 205

Arg Ala Ser Gln Pro Arg Leu Leu Phe Gln Ile Phe Gly Thr Gly His
        210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
                260                 265                 270

Glu Leu Glu Tyr Ser Pro Pro Leu His Asp Leu Arg Asn Gln Ser Trp
            275                 280                 285

Ser Trp Arg Arg Ile Pro Ser Glu Glu Ala Ser Gln Met Asp Leu Leu
        290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
                340                 345                 350

Arg His Leu Gln Pro Ser Gly Arg Tyr Ile Ala Gln Leu Leu Pro His
            355                 360                 365

Asn Glu Ala Ala Arg Glu Ile Leu Leu Met Pro Thr Pro Gly Lys His
        370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
        595                 600                 605

Leu Gln Met Val Ala Trp Trp Gly Gln Gly Ser Arg Ala Ile Val Ala
```

```
           610                 615                 620
    Phe Asp Asn Ile Ser Ile Ser Leu Asp Cys Tyr Leu Thr Ile Ser Gly
    625                 630                 635                 640

Glu Asp Lys Ile Leu Gln Asn Thr Ala Pro Lys Ser Arg Asn Leu Phe
                        645                 650                 655

Glu Arg Asn Pro Asn Lys Glu Leu Lys Pro Gly Glu Asn Ser Pro Arg
                        660                 665                 670

Gln Thr Pro Ile Phe Asp Pro Thr Val His Trp Leu Phe Thr Thr Cys
                    675                 680                 685

Gly Ala Ser Gly Pro His Gly Pro Thr Gln Ala Gln Cys Asn Asn Ala
                690                 695                 700

Tyr Gln Asn Ser Asn Leu Ser Val Glu Val Gly Ser Glu Gly Pro Leu
    705                 710                 715                 720

Lys Gly Ile Gln Ile Trp Lys Val Pro Ala Thr Asp Thr Tyr Ser Ile
                        725                 730                 735

Ser Gly Tyr Gly Ala Ala Gly Gly Lys Gly Gly Lys Asn Thr Met Met
                        740                 745                 750

Arg Ser His Gly Val Ser Val Leu Gly Ile Phe Asn Leu Glu Lys Asp
                    755                 760                 765

Asp Met Leu Tyr Ile Leu Val Gly Gln Gln Gly Glu Asp Ala Cys Pro
    770                 775                 780

Ser Thr Asn Gln Leu Ile Gln Lys Val Cys Ile Gly Glu Asn Asn Val
    785                 790                 795                 800

Ile Glu Glu Glu Ile Arg Val Asn Arg Ser Val His Glu Trp Ala Gly
                        805                 810                 815

Gly Gly Gly Gly Gly Gly Gly Ala Thr Tyr Val Phe Lys Met Lys Asp
                        820                 825                 830

Gly Val Pro Val Pro Leu Ile Ile Ala Ala Gly Gly Gly Gly Arg Ala
                    835                 840                 845

Tyr Gly Ala Lys Thr Asp Thr Phe His Pro Glu Arg Leu Glu Asn Asn
                850                 855                 860

Ser Ser Val Leu Gly Leu Asn Gly Asn Ser Gly Ala Ala Gly Gly Gly
    865                 870                 875                 880

Gly Gly Trp Asn Asp Asn Thr Ser Leu Leu Trp Ala Gly Lys Ser Leu
                        885                 890                 895

Gln Glu Gly Ala Thr Gly Gly His Ser Cys Pro Gln Ala Met Lys Lys
                        900                 905                 910

Trp Gly Trp Glu Thr Arg Gly Gly Phe Gly Gly Gly Gly Gly Gly Cys
                    915                 920                 925

Ser Ser Gly Gly Gly Gly Gly Tyr Ile Gly Gly Asn Ala Ala Ser
                930                 935                 940

Asn Asn Asp Pro Glu Met Asp Gly Glu Asp Gly Val Ser Phe Ile Ser
    945                 950                 955                 960

Pro Leu Gly Ile Leu Tyr Thr Pro Ala Leu Lys Val Met Glu Gly His
                    965                 970                 975

Gly Glu Val Asn Ile Lys His Tyr Leu Asn Cys Ser His Cys Glu Val
                    980                 985                 990

Asp Glu Cys His Met Asp Pro Glu Ser His Lys Val Ile Cys Phe Cys
                    995                 1000                1005

Asp His Gly Thr Val Leu Ala Glu Asp Gly Val Ser Cys Ile Val Ser
                1010                1015                1020

Pro Thr Pro Glu Pro His Leu Pro Leu Ser Leu Ile Leu Ser Val Val
    1025                1030                1035                1040
```

-continued

Thr Ser Ala Leu Val Ala Ala Leu Val Leu Ala Phe Ser Gly Ile Met
            1045                1050                1055

Ile Val Tyr Arg Arg Lys His Gln Glu Leu Gln Ala Met Gln Met Glu
            1060                1065                1070

Leu Gln Ser Pro Glu Tyr Lys Leu Ser Lys Leu Arg Thr Ser Thr Ile
            1075                1080                1085

Met Thr Asp Tyr Asn Pro Asn Tyr Cys Phe Ala Gly Lys Thr Ser Ser
            1090                1095                1100

Ile Ser Asp Leu Lys Glu Val Pro Arg Lys Asn Ile Thr Leu Ile Arg
1105                1110                1115                1120

Gly Leu Gly His Gly Ala Phe Gly Glu Val Tyr Glu Gly Gln Val Ser
            1125                1130                1135

Gly Met Pro Asn Asp Pro Ser Pro Leu Gln Val Ala Val Lys Thr Leu
            1140                1145                1150

Pro Glu Val Cys Ser Glu Gln Asp Glu Leu Asp Phe Leu Met Glu Ala
            1155                1160                1165

Leu Ile Ile Ser Lys Phe Asn His Gln Asn Ile Val Arg Cys Ile Gly
            1170                1175                1180

Val Ser Leu Gln Ser Leu Pro Arg Phe Ile Leu Leu Glu Leu Met Ala
1185                1190                1195                1200

Gly Gly Asp Leu Lys Ser Phe Leu Arg Glu Thr Arg Pro Arg Pro Ser
            1205                1210                1215

Gln Pro Ser Ser Leu Ala Met Leu Asp Leu Leu His Val Ala Arg Asp
            1220                1225                1230

Ile Ala Cys Gly Cys Gln Tyr Leu Glu Glu Asn His Phe Ile His Arg
            1235                1240                1245

Asp Ile Ala Ala Arg Asn Cys Leu Leu Thr Cys Pro Gly Pro Gly Arg
            1250                1255                1260

Val Ala Lys Ile Gly Asp Phe Gly Met Ala Arg Asp Ile Tyr Arg Ala
1265                1270                1275                1280

Ser Tyr Tyr Arg Lys Gly Gly Cys Ala Met Leu Pro Val Lys Trp Met
            1285                1290                1295

Pro Pro Glu Ala Phe Met Glu Gly Ile Phe Thr Ser Lys Thr Asp Thr
            1300                1305                1310

Trp Ser Phe Gly Val Leu Leu Trp Glu Ile Phe Ser Leu Gly Tyr Met
            1315                1320                1325

Pro Tyr Pro Ser Lys Ser Asn Gln Glu Val Leu Glu Phe Val Thr Ser
            1330                1335                1340

Gly Gly Arg Met Asp Pro Pro Lys Asn Cys Pro Gly Pro Val Tyr Arg
1345                1350                1355                1360

Ile Met Thr Gln Cys Trp Gln His Gln Pro Glu Asp Arg Pro Asn Phe
            1365                1370                1375

Ala Ile Ile Leu Glu Arg Ile Glu Tyr Cys Thr Gln Asp Pro Asp Val
            1380                1385                1390

Ile Asn Thr Ala Leu Pro Ile Glu Tyr Gly Pro Leu Val Glu Glu Glu
            1395                1400                1405

Glu Lys Val Pro Val Arg Pro Lys Asp Pro Glu Gly Val Pro Pro Leu
            1410                1415                1420

Leu Val Ser Gln Gln Ala Lys Arg Glu Glu Glu Arg Ser Pro Ala Ala
1425                1430                1435                1440

Pro Pro Pro Leu Pro Thr Thr Ser Ser Gly Lys Ala Ala Lys Lys Pro
            1445                1450                1455

-continued

```
Thr Ala Ala Glu Ile Ser Val Arg Val Pro Arg Gly Pro Ala Val Glu
            1460                1465                1470

Gly Gly His Val Asn Met Ala Phe Ser Gln Ser Asn Pro Pro Ser Glu
        1475                1480                1485

Leu His Lys Val His Gly Ser Arg Asn Lys Pro Thr Ser Leu Trp Asn
    1490                1495                1500

Pro Thr Tyr Gly Ser Trp Phe Thr Glu Lys Pro Thr Lys Asn Asn
1505                1510                1515                1520

Pro Ile Ala Lys Lys Glu Pro His Asp Arg Gly Asn Leu Gly Leu Glu
            1525                1530                1535

Gly Ser Cys Thr Val Pro Pro Asn Val Ala Thr Gly Arg Leu Pro Gly
        1540                1545                1550

Ala Ser Leu Leu Leu Glu Pro Ser Ser Leu Thr Ala Asn Met Lys Glu
            1555                1560                1565

Val Pro Leu Phe Arg Leu Arg His Phe Pro Cys Gly Asn Val Asn Tyr
    1570                1575                1580

Gly Tyr Gln Gln Gln Gly Leu Pro Leu Glu Ala Ala Thr Ala Pro Gly
1585                1590                1595                1600

Ala Gly His Tyr Glu Asp Thr Ile Leu Lys Ser Lys Asn Ser Met Asn
            1605                1610                1615

Gln Pro Gly Pro
            1620

<210> SEQ ID NO 468
<211> LENGTH: 11
<212> TYPE: PRT
<213> ORGANISM: Artificial Sequence
<220> FEATURE:
<223> OTHER INFORMATION: consensus sequence of VL CDR3 of
      antigen-binding fragment - specifically binds to an ECD of ALK
<220> FEATURE:
<221> NAME/KEY: VARIANT
<222> LOCATION: 2
<223> OTHER INFORMATION: Xaa = Gln or Arg
<220> FEATURE:
<221> NAME/KEY: VARIANT
<222> LOCATION: 10
<223> OTHER INFORMATION: Xaa = Tyr or Phe

<400> SEQUENCE: 468

Gln Xaa Tyr Asn Ser Tyr Pro Tyr Met Xaa Thr
1               5                   10

<210> SEQ ID NO 469
<211> LENGTH: 5
<212> TYPE: PRT
<213> ORGANISM: Artificial Sequence
<220> FEATURE:
<223> OTHER INFORMATION: consensus sequence of VH CDR1 of
      antigen-binding fragment - specifically binds to an ECD of ALK
<220> FEATURE:
<221> NAME/KEY: VARIANT
<222> LOCATION: 1
<223> OTHER INFORMATION: Xaa = Asn or Ser

<400> SEQUENCE: 469

Xaa Tyr Trp Met His
1               5

<210> SEQ ID NO 470
<211> LENGTH: 17
<212> TYPE: PRT
<213> ORGANISM: Artificial Sequence
<220> FEATURE:
```

```
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 3
<223> OTHER INFORMATION: Xaa = Asn or Lys

<400> SEQUENCE: 470

Tyr Ile Xaa Pro Ser Ser Gly Tyr Thr Lys Tyr Asn Gln Lys Phe Lys
1               5                   10                  15

Asp

<210> SEQ ID NO 471
<211> LENGTH: 19
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 8
<223> OTHER INFORMATION: Xaa = Asn or Lys

<400> SEQUENCE: 471

Arg Ile Lys Asp Lys Ser Asn Xaa Phe Ala Ser Asp Tyr Val Glu Ser
1               5                   10                  15

Val Arg Gly

<210> SEQ ID NO 472
<211> LENGTH: 8
<212> TYPE: PRT
<213> ORGANISM: Artificial Sequence
<220> FEATURE:
<223> OTHER INFORMATION: consensus sequence of VH CDR1 of
      antigen-binding fragment - specifically binds to an ECD of ALK
<220> FEATURE:
<221> NAME/KEY: VARIANT
<222> LOCATION: 6
<223> OTHER INFORMATION: Xaa = Asn or Ser

<400> SEQUENCE: 472

Gly Tyr Thr Phe Thr Xaa Tyr Trp
1               5

<210> SEQ ID NO 473
<211> LENGTH: 8
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 2
<223> OTHER INFORMATION: Xaa = Asn or Lys

<400> SEQUENCE: 473

Ile Xaa Pro Ser Ser Gly Tyr Thr
1               5

<210> SEQ ID NO 474
<211> LENGTH: 8
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
```

```
<221> NAME/KEY: VARIANT
<222> LOCATION: 7
<223> OTHER INFORMATION: Xaa = Asn or Lys

<400> SEQUENCE: 474

Ile Lys Asp Lys Ser Asn Xaa Phe
1               5

<210> SEQ ID NO 475
<211> LENGTH: 11
<212> TYPE: PRT
<213> ORGANISM: Artificial Sequence
<220> FEATURE:
<223> OTHER INFORMATION: consensus sequence of VL CDR3 of
      antigen-binding fragment - specifically binds to an ECD of ALK
<220> FEATURE:
<221> NAME/KEY: VARIANT
<222> LOCATION: 2
<223> OTHER INFORMATION: Xaa = Gln or Arg
<220> FEATURE:
<221> NAME/KEY: VARIANT
<222> LOCATION: 10
<223> OTHER INFORMATION: Xaa = Tyr or Phe

<400> SEQUENCE: 475

Gln Xaa Tyr Asn Ser Tyr Pro Tyr Met Xaa Thr
1               5                   10

<210> SEQ ID NO 476
<211> LENGTH: 7
<212> TYPE: PRT
<213> ORGANISM: Artificial Sequence
<220> FEATURE:
<223> OTHER INFORMATION: consensus sequence of VH CDR1 of
      antigen-binding fragment - specifically binds to an ECD of ALK
<220> FEATURE:
<221> NAME/KEY: VARIANT
<222> LOCATION: 6
<223> OTHER INFORMATION: Xaa = Asn or Ser

<400> SEQUENCE: 476

Gly Tyr Thr Phe Thr Xaa Tyr
1               5

<210> SEQ ID NO 477
<211> LENGTH: 6
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 1
<223> OTHER INFORMATION: Xaa = Asn or Lys

<400> SEQUENCE: 477

Xaa Pro Ser Ser Gly Tyr
1               5

<210> SEQ ID NO 478
<211> LENGTH: 8
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 6
<223> OTHER INFORMATION: Xaa = Asn or Lys
```

<400> SEQUENCE: 478

Lys Asp Lys Ser Asn Xaa Phe Ala
1               5

<210> SEQ ID NO 479
<211> LENGTH: 110
<212> TYPE: PRT
<213> ORGANISM: Artificial Sequence
<220> FEATURE:
<223> OTHER INFORMATION: consensus sequence of VL region of anti-ALK
      antibody
<220> FEATURE:
<221> NAME/KEY: VARIANT
<222> LOCATION: 9
<223> OTHER INFORMATION: Xaa = Lys or Arg
<220> FEATURE:
<221> NAME/KEY: VARIANT
<222> LOCATION: 42
<223> OTHER INFORMATION: Xaa = Gln or His
<220> FEATURE:
<221> NAME/KEY: VARIANT
<222> LOCATION: 75
<223> OTHER INFORMATION: Xaa = Val or Ile
<220> FEATURE:
<221> NAME/KEY: VARIANT
<222> LOCATION: 90
<223> OTHER INFORMATION: Xaa = Gln or Arg
<220> FEATURE:
<221> NAME/KEY: VARIANT
<222> LOCATION: 98
<223> OTHER INFORMATION: Xaa = Tyr or Phe

<400> SEQUENCE: 479

Asp Ile Val Met Thr Gln Ser Gln Xaa Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Xaa Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Xaa Ser Asn Val Gln Ser
65                  70                  75                  80

Glu Asp Leu Ala Glu Tyr Phe Cys Gln Xaa Tyr Asn Ser Tyr Pro Tyr
                85                  90                  95

Met Xaa Thr Phe Gly Gly Gly Thr Lys Leu Glu Ile Lys Arg
            100                 105                 110

<210> SEQ ID NO 480
<211> LENGTH: 120
<212> TYPE: PRT
<213> ORGANISM: Artificial Sequence
<220> FEATURE:
<223> OTHER INFORMATION: consensus sequence of VH region of anti-ALK
      antibody
<220> FEATURE:
<221> NAME/KEY: VARIANT
<222> LOCATION: 31
<223> OTHER INFORMATION: Xaa = Asn or Ser
<220> FEATURE:
<221> NAME/KEY: VARIANT
<222> LOCATION: 52
<223> OTHER INFORMATION: Xaa = Asn or Lys
<220> FEATURE:
<221> NAME/KEY: VARIANT
<222> LOCATION: 88
<223> OTHER INFORMATION: Xaa = Tyr or Phe

<400> SEQUENCE: 480

Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Xaa Tyr
            20                  25                  30

Trp Met His Trp Val Lys Gln Arg Pro Gly Gln Gly Leu Glu Trp Ile
        35                  40                  45

Gly Tyr Ile Xaa Pro Ser Ser Gly Tyr Thr Lys Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Xaa Glu Asp Ser Ala Val Tyr Tyr Cys
                85                  90                  95

Ala Arg Asp Tyr Tyr Gly Ser Ser Trp Phe Ala Tyr Trp Gly Gln
            100                 105                 110

Gly Thr Leu Val Thr Val Ser Ala
        115                 120

<210> SEQ ID NO 481
<211> LENGTH: 107
<212> TYPE: PRT
<213> ORGANISM: Artificial Sequence
<220> FEATURE:
<223> OTHER INFORMATION: consensus sequence of VL region of anti-ALK
      antibody
<220> FEATURE:
<221> NAME/KEY: VARIANT
<222> LOCATION: 19
<223> OTHER INFORMATION: Xaa = Val or Ile or their conservative
      substitution

<400> SEQUENCE: 481

Asp Ile Gln Met Thr Gln Ser Pro Ser Ser Met Ser Ala Ser Leu Gly
1               5                   10                  15

Asp Arg Xaa Thr Ile Thr Cys Gln Ala Ser Gln Asp Ile Gly Asn Tyr
            20                  25                  30

Leu Ile Trp Phe Gln Gln Lys Pro Gly Lys Ser Pro Arg Pro Leu Ile
        35                  40                  45

Tyr Tyr Ala Thr Asn Leu Ala Asn Gly Val Pro Ser Arg Phe Ser Gly
    50                  55                  60

Ser Arg Ser Gly Ser Glu Tyr Ser Leu Thr Ile Thr Ser Leu Glu Ser
65                  70                  75                  80

Glu Asp Met Ala Asp Tyr His Cys Leu Gln Tyr Lys Gln His Leu Thr
                85                  90                  95

Phe Gly Ser Gly Thr Lys Leu Glu Ile Glu Arg
            100                 105

<210> SEQ ID NO 482
<211> LENGTH: 116
<212> TYPE: PRT
<213> ORGANISM: Artificial Sequence
<220> FEATURE:
<223> OTHER INFORMATION: consensus sequence of VH region of anti-ALK
      antibody
<220> FEATURE:
<221> NAME/KEY: VARIANT
<222> LOCATION: 57
<223> OTHER INFORMATION: Xaa = Lys or Asn or their conservative
      substitution

<400> SEQUENCE: 482

-continued

```
Glu Val Gln Val Val Glu Thr Gly Gly Val Val Gln Pro Gly Lys
1               5                   10                  15

Ser Leu Glu Ile Thr Cys Ala Thr Ser Gly Leu Thr Phe Ser Thr Ala
            20                  25                  30

Trp Met Tyr Trp Val Arg Gln Ser Ser Asp Arg Arg Leu Glu Trp Ile
            35                  40                  45

Ala Arg Ile Lys Asp Lys Ser Asn Xaa Phe Ala Ser Asp Tyr Val Glu
        50                  55                  60

Ser Val Arg Gly Arg Phe Thr Ile Ser Arg Asp Ser Arg Ser Ser
65                  70                  75                  80

Val Tyr Leu Gln Met Asn Asn Leu Lys Glu Glu Asp Thr Ala Thr Tyr
                85                  90                  95

Tyr Cys Thr Thr Ser Tyr Gly Tyr Ala Trp Gly Gln Gly Val Met Val
            100                 105                 110

Thr Val Ser Ser
            115

<210> SEQ ID NO 483
<211> LENGTH: 11
<212> TYPE: PRT
<213> ORGANISM: Artificial Sequence
<220> FEATURE:
<223> OTHER INFORMATION: VL CDR1 - Ab423 (kabat)

<400> SEQUENCE: 483

Arg Ala Ser Gln Ser Val Ser Ser Asn Leu Ala
1               5                   10

<210> SEQ ID NO 484
<211> LENGTH: 7
<212> TYPE: PRT
<213> ORGANISM: Artificial Sequence
<220> FEATURE:
<223> OTHER INFORMATION: VL CDR2 - Ab435 (kabat)

<400> SEQUENCE: 484

Gly Ala Ser Thr Arg Ala Thr
1               5

<210> SEQ ID NO 485
<211> LENGTH: 5
<212> TYPE: PRT
<213> ORGANISM: Artificial Sequence
<220> FEATURE:
<223> OTHER INFORMATION: VH CDR1 - Ab353 (kabat)

<400> SEQUENCE: 485

Ser Ser Ala Met Gln
1               5

<210> SEQ ID NO 486
<211> LENGTH: 17
<212> TYPE: PRT
<213> ORGANISM: Artificial Sequence
<220> FEATURE:
<223> OTHER INFORMATION: VH CDR2 - Ab354 (kabat)

<400> SEQUENCE: 486

Tyr Ile Lys Pro Ser Ser Gly Tyr Thr Lys Tyr Ala Gln Lys Phe Gln
1               5                   10                  15

Glu
```

-continued

```
<210> SEQ ID NO 487
<211> LENGTH: 17
<212> TYPE: PRT
<213> ORGANISM: Artificial Sequence
<220> FEATURE:
<223> OTHER INFORMATION: VH CDR2 - Ab358 (kabat)

<400> SEQUENCE: 487

Tyr Ile Lys Pro Ser Ser Gly Tyr Thr Lys Tyr Ala Gln Lys Leu Gln
1               5                   10                  15
Gly

<210> SEQ ID NO 488
<211> LENGTH: 17
<212> TYPE: PRT
<213> ORGANISM: Artificial Sequence
<220> FEATURE:
<223> OTHER INFORMATION: VH CDR2 - Ab362 (kabat)

<400> SEQUENCE: 488

Tyr Ile Lys Pro Ser Ser Gly Tyr Thr Lys Tyr Ala Gln Lys Phe Gln
1               5                   10                  15
Gly

<210> SEQ ID NO 489
<211> LENGTH: 6
<212> TYPE: PRT
<213> ORGANISM: Artificial Sequence
<220> FEATURE:
<223> OTHER INFORMATION: VL CDR1 - Ab423 (IMGT)

<400> SEQUENCE: 489

Gln Ser Val Ser Ser Asn
1               5

<210> SEQ ID NO 490
<211> LENGTH: 3
<212> TYPE: PRT
<213> ORGANISM: Artificial Sequence
<220> FEATURE:
<223> OTHER INFORMATION: VL CDR2 - Ab435 (IMGT)

<400> SEQUENCE: 490

Gly Ala Ser
1

<210> SEQ ID NO 491
<211> LENGTH: 8
<212> TYPE: PRT
<213> ORGANISM: Artificial Sequence
<220> FEATURE:
<223> OTHER INFORMATION: VH CDR1 - Ab353 (IMGT)

<400> SEQUENCE: 491

Gly Tyr Thr Phe Thr Ser Ser Ala
1               5

<210> SEQ ID NO 492
<211> LENGTH: 8
<212> TYPE: PRT
<213> ORGANISM: Artificial Sequence
<220> FEATURE:
<223> OTHER INFORMATION: VH CDR1 - Ab362 (IMGT)

<400> SEQUENCE: 492

Gly Tyr Thr Phe Ser Ser Tyr Trp
```

```
1               5
```

```
<210> SEQ ID NO 493
<211> LENGTH: 11
<212> TYPE: PRT
<213> ORGANISM: Artificial Sequence
<220> FEATURE:
<223> OTHER INFORMATION: VL CDR1 - Ab423 (Chothia)

<400> SEQUENCE: 493

Arg Ala Ser Gln Ser Val Ser Ser Asn Leu Ala
1               5                   10

<210> SEQ ID NO 494
<211> LENGTH: 7
<212> TYPE: PRT
<213> ORGANISM: Artificial Sequence
<220> FEATURE:
<223> OTHER INFORMATION: VL CDR2 - Ab435 (Chothia)

<400> SEQUENCE: 494

Gly Ala Ser Thr Arg Ala Thr
1               5

<210> SEQ ID NO 495
<211> LENGTH: 7
<212> TYPE: PRT
<213> ORGANISM: Artificial Sequence
<220> FEATURE:
<223> OTHER INFORMATION: VH CDR1 - Ab353 (Chothia)

<400> SEQUENCE: 495

Gly Tyr Thr Phe Thr Ser Ser
1               5

<210> SEQ ID NO 496
<211> LENGTH: 7
<212> TYPE: PRT
<213> ORGANISM: Artificial Sequence
<220> FEATURE:
<223> OTHER INFORMATION: VH CDR1 - Ab362 (Chothia)

<400> SEQUENCE: 496

Gly Tyr Thr Phe Ser Ser Tyr
1               5

<210> SEQ ID NO 497
<211> LENGTH: 11
<212> TYPE: PRT
<213> ORGANISM: Artificial Sequence
<220> FEATURE:
<223> OTHER INFORMATION: consensus sequence of VH CDR3 of
      antigen-binding fragment - specifically binds to an ECD of ALK
<220> FEATURE:
<221> NAME/KEY: VARIANT
<222> LOCATION: 7
<223> OTHER INFORMATION: Xaa = Tyr or Ser
<220> FEATURE:
<221> NAME/KEY: VARIANT
<222> LOCATION: 8
<223> OTHER INFORMATION: Xaa = Arg or Trp

<400> SEQUENCE: 497

Asp Tyr Tyr Gly Ser Ser Xaa Xaa Phe Ala Tyr
1               5                   10

<210> SEQ ID NO 498
<211> LENGTH: 17
```

```
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 1
<223> OTHER INFORMATION: Xaa = Arg or Tyr
<220> FEATURE:
<221> NAME/KEY: VARIANT
<222> LOCATION: 3
<223> OTHER INFORMATION: Xaa = Asp or Lys
<220> FEATURE:
<221> NAME/KEY: VARIANT
<222> LOCATION: 5
<223> OTHER INFORMATION: Xaa = Asn or Ser
<220> FEATURE:
<221> NAME/KEY: VARIANT
<222> LOCATION: 8
<223> OTHER INFORMATION: Xaa = Gly or Tyr
<220> FEATURE:
<221> NAME/KEY: VARIANT
<222> LOCATION: 13
<223> OTHER INFORMATION: Xaa = Glu or Gln
<220> FEATURE:
<221> NAME/KEY: VARIANT
<222> LOCATION: 17
<223> OTHER INFORMATION: Xaa = Ser or Asp

<400> SEQUENCE: 498

Xaa Ile Xaa Pro Xaa Ser Gly Xaa Thr Lys Tyr Asn Xaa Lys Phe Lys
1               5                   10                  15

Xaa

<210> SEQ ID NO 499
<211> LENGTH: 5
<212> TYPE: PRT
<213> ORGANISM: Artificial Sequence
<220> FEATURE:
<223> OTHER INFORMATION: consensus sequence of VH CDR1 of
      antigen-binding fragment - specifically binds to an ECD of ALK
<220> FEATURE:
<221> NAME/KEY: VARIANT
<222> LOCATION: 4
<223> OTHER INFORMATION: Xaa = Met or Val

<400> SEQUENCE: 499

Ser Tyr Trp Xaa Asn
1               5

<210> SEQ ID NO 500
<211> LENGTH: 11
<212> TYPE: PRT
<213> ORGANISM: Artificial Sequence
<220> FEATURE:
<223> OTHER INFORMATION: consensus sequence of VL CDR1 of anti-ALK or an
       antigen- binding fragment
<220> FEATURE:
<221> NAME/KEY: VARIANT
<222> LOCATION: 5
<223> OTHER INFORMATION: Xaa = Asn or Asp
<220> FEATURE:
<221> NAME/KEY: VARIANT
<222> LOCATION: 7
<223> OTHER INFORMATION: Xaa = Gly or Ser
<220> FEATURE:
<221> NAME/KEY: VARIANT
<222> LOCATION: 9
<223> OTHER INFORMATION: Xaa = Ala or Asn

<400> SEQUENCE: 500

Lys Ala Ser Gln Xaa Val Xaa Thr Xaa Val Ala
```

```
1               5              10
```

<210> SEQ ID NO 501
<211> LENGTH: 5
<212> TYPE: PRT
<213> ORGANISM: Artificial Sequence
<220> FEATURE:
<223> OTHER INFORMATION: consensus sequence of VH CDR1 of anti-ALK or an
      antigen- binding fragment
<220> FEATURE:
<221> NAME/KEY: VARIANT
<222> LOCATION: 1
<223> OTHER INFORMATION: Xaa = Asn or Ser
<220> FEATURE:
<221> NAME/KEY: VARIANT
<222> LOCATION: 3
<223> OTHER INFORMATION: Xaa = Met or Val

<400> SEQUENCE: 501

```
Xaa Tyr Trp Xaa Asn
1               5
```

<210> SEQ ID NO 502
<211> LENGTH: 17
<212> TYPE: PRT
<213> ORGANISM: Artificial Sequence
<220> FEATURE:
<223> OTHER INFORMATION: consensus sequence of VH CDR2 of anti-ALK or an
      antigen- binding fragment
<220> FEATURE:
<221> NAME/KEY: VARIANT
<222> LOCATION: 3
<223> OTHER INFORMATION: Xaa = Phe or Tyr
<220> FEATURE:
<221> NAME/KEY: VARIANT
<222> LOCATION: 7
<223> OTHER INFORMATION: Xaa = Ala or Gly
<220> FEATURE:
<221> NAME/KEY: VARIANT
<222> LOCATION: 9
<223> OTHER INFORMATION: Xaa = Ala or Thr

<400> SEQUENCE: 502

```
Gln Ile Xaa Pro Gly Asp Xaa Asp Xaa Asn Tyr Asn Gly Lys Phe Lys
1               5                   10                  15

Gly
```

<210> SEQ ID NO 503
<211> LENGTH: 8
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 2
<223> OTHER INFORMATION: Xaa = Asp, Lys or Asn
<220> FEATURE:
<221> NAME/KEY: VARIANT
<222> LOCATION: 4
<223> OTHER INFORMATION: Xaa = Asn or Ser
<220> FEATURE:
<221> NAME/KEY: VARIANT
<222> LOCATION: 7
<223> OTHER INFORMATION: Xaa = Gly or Tyr

<400> SEQUENCE: 503

```
Ile Xaa Pro Xaa Ser Gly Xaa Thr
1               5
```

```
<210> SEQ ID NO 504
<211> LENGTH: 13
<212> TYPE: PRT
<213> ORGANISM: Artificial Sequence
<220> FEATURE:
<223> OTHER INFORMATION: consensus sequence of VH CDR3 of
      antigen-binding fragment - specifically binds to an ECD of ALK
<220> FEATURE:
<221> NAME/KEY: VARIANT
<222> LOCATION: 9
<223> OTHER INFORMATION: Xaa = Tyr or Ser
<220> FEATURE:
<221> NAME/KEY: VARIANT
<222> LOCATION: 10
<223> OTHER INFORMATION: Xaa = Arg or Trp

<400> SEQUENCE: 504

Ala Arg Asp Tyr Tyr Gly Ser Ser Xaa Xaa Phe Ala Tyr
1               5                   10

<210> SEQ ID NO 505
<211> LENGTH: 6
<212> TYPE: PRT
<213> ORGANISM: Artificial Sequence
<220> FEATURE:
<223> OTHER INFORMATION: consensus sequence of VL CDR1 of
      antigen-binding fragment - specifically binds to an ECD of ALK
<220> FEATURE:
<221> NAME/KEY: VARIANT
<222> LOCATION: 2
<223> OTHER INFORMATION: Xaa = Asn or Asp
<220> FEATURE:
<221> NAME/KEY: VARIANT
<222> LOCATION: 4
<223> OTHER INFORMATION: Xaa = Gly or Ser
<220> FEATURE:
<221> NAME/KEY: VARIANT
<222> LOCATION: 6
<223> OTHER INFORMATION: Xaa = Ala or Asn

<400> SEQUENCE: 505

Gln Xaa Val Xaa Thr Xaa
1               5

<210> SEQ ID NO 506
<211> LENGTH: 8
<212> TYPE: PRT
<213> ORGANISM: Artificial Sequence
<220> FEATURE:
<223> OTHER INFORMATION: consensus sequence of VH CDR1 of
      antigen-binding fragment - specifically binds to an ECD of ALK
<220> FEATURE:
<221> NAME/KEY: VARIANT
<222> LOCATION: 3
<223> OTHER INFORMATION: Xaa = Asn or Ser
<220> FEATURE:
<221> NAME/KEY: VARIANT
<222> LOCATION: 6
<223> OTHER INFORMATION: Xaa = Ala or Thr

<400> SEQUENCE: 506

Gly Tyr Xaa Phe Ser Xaa Tyr Trp
1               5

<210> SEQ ID NO 507
<211> LENGTH: 8
<212> TYPE: PRT
<213> ORGANISM: Artificial Sequence
<220> FEATURE:
<223> OTHER INFORMATION: consensus sequence of VL CDR2 of
      antigen-binding fragment - specifically binds to an ECD of ALK
<220> FEATURE:
<221> NAME/KEY: VARIANT
```

```
<222> LOCATION: 2
<223> OTHER INFORMATION: Xaa = Phe or Tyr
<220> FEATURE:
<221> NAME/KEY: VARIANT
<222> LOCATION: 6
<223> OTHER INFORMATION: Xaa = Ala or Gly
<220> FEATURE:
<221> NAME/KEY: VARIANT
<222> LOCATION: 8
<223> OTHER INFORMATION: Xaa = Ala or Thr

<400> SEQUENCE: 507

Ile Xaa Pro Gly Asp Xaa Asp Xaa
1               5

<210> SEQ ID NO 508
<211> LENGTH: 6
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 1
<223> OTHER INFORMATION: Xaa = Asp, Lys or Asn
<220> FEATURE:
<221> NAME/KEY: VARIANT
<222> LOCATION: 3
<223> OTHER INFORMATION: Xaa = Asn or Ser
<220> FEATURE:
<221> NAME/KEY: VARIANT
<222> LOCATION: 6
<223> OTHER INFORMATION: Xaa = Gly or Tyr

<400> SEQUENCE: 508

Xaa Pro Xaa Ser Gly Xaa
1               5

<210> SEQ ID NO 509
<211> LENGTH: 11
<212> TYPE: PRT
<213> ORGANISM: Artificial Sequence
<220> FEATURE:
<223> OTHER INFORMATION: consensus sequence of VH CDR3 of
      antigen-binding fragment - specifically binds to an ECD of ALK
<220> FEATURE:
<221> NAME/KEY: VARIANT
<222> LOCATION: 7
<223> OTHER INFORMATION: Xaa = Tyr or Ser
<220> FEATURE:
<221> NAME/KEY: VARIANT
<222> LOCATION: 8
<223> OTHER INFORMATION: Xaa = Arg or Trp

<400> SEQUENCE: 509

Asp Tyr Tyr Gly Ser Ser Xaa Xaa Phe Ala Tyr
1               5                   10

<210> SEQ ID NO 510
<211> LENGTH: 11
<212> TYPE: PRT
<213> ORGANISM: Artificial Sequence
<220> FEATURE:
<223> OTHER INFORMATION: consensus sequence of VL CDR1 of
      antigen-binding fragment - specifically binds to an ECD of ALK
<220> FEATURE:
<221> NAME/KEY: VARIANT
<222> LOCATION: 5
<223> OTHER INFORMATION: Xaa = Asn or Asp
<220> FEATURE:
<221> NAME/KEY: VARIANT
<222> LOCATION: 7
```

```
<223> OTHER INFORMATION: Xaa = Gly or Ser
<220> FEATURE:
<221> NAME/KEY: VARIANT
<222> LOCATION: 9
<223> OTHER INFORMATION: Xaa = Ala or Asn

<400> SEQUENCE: 510

Lys Ala Ser Gln Xaa Val Xaa Thr Xaa Val Ala
1               5                   10

<210> SEQ ID NO 511
<211> LENGTH: 7
<212> TYPE: PRT
<213> ORGANISM: Artificial Sequence
<220> FEATURE:
<223> OTHER INFORMATION: consensus sequence of VH CDR1 of
      antigen-binding fragment - specifically binds to an ECD of ALK
<220> FEATURE:
<221> NAME/KEY: VARIANT
<222> LOCATION: 3
<223> OTHER INFORMATION: Xaa = Asn or Ser
<220> FEATURE:
<221> NAME/KEY: VARIANT
<222> LOCATION: 6
<223> OTHER INFORMATION: Xaa = Ala or Thr

<400> SEQUENCE: 511

Gly Tyr Xaa Phe Ser Xaa Tyr
1               5

<210> SEQ ID NO 512
<211> LENGTH: 6
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 1
<223> OTHER INFORMATION: Xaa = Ala or Gly
<220> FEATURE:
<221> NAME/KEY: VARIANT
<222> LOCATION: 5
<223> OTHER INFORMATION: Xaa = Ala or Thr

<400> SEQUENCE: 512

Xaa Pro Gly Asp Xaa Asp
1               5

<210> SEQ ID NO 513
<211> LENGTH: 7
<212> TYPE: PRT
<213> ORGANISM: Artificial Sequence
<220> FEATURE:
<223> OTHER INFORMATION: consensus sequence of VH CDR3 of
      antigen-binding fragment - specifically binds to an ECD of ALK
<220> FEATURE:
<221> NAME/KEY: VARIANT
<222> LOCATION: 2
<223> OTHER INFORMATION: Xaa = Gln or Arg
<220> FEATURE:
<221> NAME/KEY: VARIANT
<222> LOCATION: 4
<223> OTHER INFORMATION: Xaa = Asn or Ser

<400> SEQUENCE: 513

Gln Xaa Tyr Xaa Ser Tyr Pro
1               5

<210> SEQ ID NO 514
```

```
<211> LENGTH: 17
<212> TYPE: PRT
<213> ORGANISM: Artificial Sequence
<220> FEATURE:
<223> OTHER INFORMATION: consensus sequence of VH CDR2 of
      antigen-binding fragment - specifically binds to an ECD of ALK
<220> FEATURE:
<221> NAME/KEY: VARIANT
<222> LOCATION: 12
<223> OTHER INFORMATION: Xaa = Asn or Ala
<220> FEATURE:
<221> NAME/KEY: VARIANT
<222> LOCATION: 15
<223> OTHER INFORMATION: Xaa = Phe or Leu
<220> FEATURE:
<221> NAME/KEY: VARIANT
<222> LOCATION: 16
<223> OTHER INFORMATION: Xaa = Lys or Gln
<220> FEATURE:
<221> NAME/KEY: VARIANT
<222> LOCATION: 17
<223> OTHER INFORMATION: Xaa = Asp, Glu or Gly

<400> SEQUENCE: 514

Tyr Ile Lys Pro Ser Ser Gly Tyr Thr Lys Tyr Xaa Gln Lys Xaa Xaa
1               5                   10                  15

Xaa

<210> SEQ ID NO 515
<211> LENGTH: 120
<212> TYPE: PRT
<213> ORGANISM: Artificial Sequence
<220> FEATURE:
<223> OTHER INFORMATION: consensus sequence of VL region of an anti-ALK
      antibody
<220> FEATURE:
<221> NAME/KEY: VARIANT
<222> LOCATION: 1
<223> OTHER INFORMATION: Xaa = Glu or Gln
<220> FEATURE:
<221> NAME/KEY: VARIANT
<222> LOCATION: 9
<223> OTHER INFORMATION: Xaa = Ala or Pro
<220> FEATURE:
<221> NAME/KEY: VARIANT
<222> LOCATION: 12
<223> OTHER INFORMATION: Xaa = Ala or Lys
<220> FEATURE:
<221> NAME/KEY: VARIANT
<222> LOCATION: 16
<223> OTHER INFORMATION: Xaa = Ala or Thr
<220> FEATURE:
<221> NAME/KEY: VARIANT
<222> LOCATION: 38
<223> OTHER INFORMATION: Xaa = Arg or Lys
<220> FEATURE:
<221> NAME/KEY: VARIANT
<222> LOCATION: 41
<223> OTHER INFORMATION: Xaa = Pro or Arg
<220> FEATURE:
<221> NAME/KEY: VARIANT
<222> LOCATION: 44
<223> OTHER INFORMATION: Xaa = Gly or Arg
<220> FEATURE:
<221> NAME/KEY: VARIANT
<222> LOCATION: 61
<223> OTHER INFORMATION: Xaa = Ala or Asn
<220> FEATURE:
<221> NAME/KEY: VARIANT
<222> LOCATION: 65
<223> OTHER INFORMATION: Xaa = Lys or Arg
<220> FEATURE:
<221> NAME/KEY: VARIANT
<222> LOCATION: 66
<223> OTHER INFORMATION: Xaa = Asp or Glu
<220> FEATURE:
```

```
<221> NAME/KEY: VARIANT
<222> LOCATION: 67
<223> OTHER INFORMATION: Xaa = Lys or Arg
<220> FEATURE:
<221> NAME/KEY: VARIANT
<222> LOCATION: 68
<223> OTHER INFORMATION: Xaa = Ala or Val
<220> FEATURE:
<221> NAME/KEY: VARIANT
<222> LOCATION: 84
<223> OTHER INFORMATION: Xaa = Arg or Ser
<220> FEATURE:
<221> NAME/KEY: VARIANT
<222> LOCATION: 89
<223> OTHER INFORMATION: Xaa = Asp or Glu

<400> SEQUENCE: 515
```

Xaa Val Gln Leu Val Gln Ser Gly Xaa Glu Val Xaa Lys Pro Gly Xaa
 1               5                  10                  15

Ser Val Lys Leu Ser Cys Lys Ala Ser Gly Tyr Thr Phe Thr Ser Tyr
            20                  25                  30

Trp Met His Trp Val Xaa Gln Ala Xaa Gly Gln Xaa Leu Glu Trp Ile
        35                  40                  45

Gly Tyr Ile Lys Pro Ser Ser Gly Tyr Thr Lys Tyr Xaa Gln Lys Phe
50                  55                  60

Xaa Xaa Xaa Xaa Thr Leu Thr Ala Asp Lys Ser Thr Ser Thr Ala Tyr
65                  70                  75                  80

Met Glu Leu Xaa Ser Leu Arg Ser Xaa Asp Thr Ala Val Tyr Tyr Cys
            85                  90                  95

Ala Arg Asp Tyr Tyr Gly Ser Ser Trp Phe Ala Tyr Trp Gly Gln
            100                 105                 110

Gly Thr Leu Val Thr Val Ser Ser
        115                 120

```
<210> SEQ ID NO 516
<211> LENGTH: 109
<212> TYPE: PRT
<213> ORGANISM: Artificial Sequence
<220> FEATURE:
<223> OTHER INFORMATION: consensus sequence of VH region of an anti-ALK
      antibody
<220> FEATURE:
<221> NAME/KEY: VARIANT
<222> LOCATION: 8
<223> OTHER INFORMATION: Xaa = Pro or Gln
<220> FEATURE:
<221> NAME/KEY: VARIANT
<222> LOCATION: 10
<223> OTHER INFORMATION: Xaa = Phe or Thr
<220> FEATURE:
<221> NAME/KEY: VARIANT
<222> LOCATION: 11
<223> OTHER INFORMATION: Xaa = Leu or Met
<220> FEATURE:
<221> NAME/KEY: VARIANT
<222> LOCATION: 13
<223> OTHER INFORMATION: Xaa = Val or Thr
<220> FEATURE:
<221> NAME/KEY: VARIANT
<222> LOCATION: 14
<223> OTHER INFORMATION: Xaa = Ser or Thr
<220> FEATURE:
<221> NAME/KEY: VARIANT
<222> LOCATION: 15
<223> OTHER INFORMATION: Xaa = Pro or Val
<220> FEATURE:
<221> NAME/KEY: VARIANT
<222> LOCATION: 18
<223> OTHER INFORMATION: Xaa = Lys or Arg
<220> FEATURE:
```

-continued

```
<221> NAME/KEY: VARIANT
<222> LOCATION: 19
<223> OTHER INFORMATION: Xaa = Ala or Val
<220> FEATURE:
<221> NAME/KEY: VARIANT
<222> LOCATION: 21
<223> OTHER INFORMATION: Xaa = Ile or Leu
<220> FEATURE:
<221> NAME/KEY: VARIANT
<222> LOCATION: 22
<223> OTHER INFORMATION: Xaa = Ser or Thr
<220> FEATURE:
<221> NAME/KEY: VARIANT
<222> LOCATION: 41
<223> OTHER INFORMATION: Xaa = Asp or Gly
<220> FEATURE:
<221> NAME/KEY: VARIANT
<222> LOCATION: 43, 60
<223> OTHER INFORMATION: Xaa = Ala or Ser
<220> FEATURE:
<221> NAME/KEY: VARIANT
<222> LOCATION: 78
<223> OTHER INFORMATION: Xaa = Ala or Pro
<220> FEATURE:
<221> NAME/KEY: VARIANT
<222> LOCATION: 80
<223> OTHER INFORMATION: Xaa = Ala or Pro
<220> FEATURE:
<221> NAME/KEY: VARIANT
<222> LOCATION: 83
<223> OTHER INFORMATION: Xaa = Ala or Phe
<220> FEATURE:
<221> NAME/KEY: VARIANT
<222> LOCATION: 85
<223> OTHER INFORMATION: Xaa = Thr or Val

<400> SEQUENCE: 516

Glu Ile Val Met Thr Gln Ser Xaa Ala Xaa Xaa Ser Xaa Xaa Xaa Gly
1               5                   10                  15

Glu Xaa Xaa Thr Xaa Xaa Cys Lys Ala Ser Gln Asn Val Gly Thr Asn
            20                  25                  30

Val Ala Trp Tyr Gln Gln Lys Pro Xaa Gln Xaa Pro Lys Ala Leu Ile
        35                  40                  45

Tyr Ser Ala Ser Tyr Arg Tyr Ser Gly Val Pro Xaa Arg Phe Ser Gly
    50                  55                  60

Ser Gly Ser Gly Thr Asp Phe Thr Leu Thr Ile Ser Ser Xaa Glu Xaa
65                  70                  75                  80

Glu Asp Xaa Ala Xaa Tyr Tyr Cys Gln Gln Tyr Asn Ser Tyr Pro Tyr
                85                  90                  95

Met Tyr Thr Phe Gly Gln Gly Thr Lys Leu Glu Ile Lys
            100                 105

<210> SEQ ID NO 517
<211> LENGTH: 1042
<212> TYPE: PRT
<213> ORGANISM: mouse
<220> FEATURE:
<223> OTHER INFORMATION: mouse ALK

<400> SEQUENCE: 517

Met Gly Ala Ala Gly Phe Leu Trp Leu Leu Pro Leu Leu Leu Ala
1               5                   10                  15

Ala Ala Ser Tyr Ser Gly Ala Ala Thr Asp Gln Arg Ala Gly Ser Pro
            20                  25                  30

Ala Ser Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
```

```
            50                  55                  60
Arg Val Tyr Ala Arg Asp Leu Leu Pro Gln Pro Arg Ser Pro Ser
 65                  70                  75                  80

Glu Pro Glu Ala Gly Gly Leu Glu Ala Arg Gly Ser Leu Ala Leu Asp
                     85                  90                  95

Cys Glu Pro Leu Leu Arg Leu Leu Gly Pro Leu Pro Gly Ile Ser Trp
                100                 105                 110

Ala Asp Gly Ala Ser Ser Pro Ser Pro Glu Ala Gly Pro Thr Leu Ser
                115                 120                 125

Arg Val Leu Lys Gly Gly Ser Val Arg Lys Leu Arg Arg Ala Lys Gln
                130                 135                 140

Leu Val Leu Glu Leu Gly Glu Glu Thr Ile Leu Glu Gly Cys Ile Gly
145                 150                 155                 160

Pro Pro Glu Glu Val Ala Ala Val Gly Ile Leu Gln Phe Asn Leu Ser
                165                 170                 175

Glu Leu Phe Ser Trp Trp Ile Leu His Gly Glu Gly Arg Leu Arg Ile
                180                 185                 190

Arg Leu Met Pro Glu Lys Lys Ala Ser Glu Val Gly Arg Glu Gly Arg
                195                 200                 205

Leu Ser Ser Ala Ile Arg Ala Ser Gln Pro Arg Leu Leu Phe Gln Ile
                210                 215                 220

Phe Gly Thr Gly His Ser Ser Met Glu Ser Pro Ser Glu Thr Pro Ser
225                 230                 235                 240

Pro Pro Gly Thr Phe Met Trp Asn Leu Thr Trp Thr Met Lys Asp Ser
                245                 250                 255

Phe Pro Phe Leu Ser His Arg Ser Arg Tyr Gly Leu Glu Cys Ser Phe
                260                 265                 270

Asp Phe Pro Cys Glu Leu Glu Tyr Ser Pro Pro Leu His Asn His Gly
                275                 280                 285

Asn Gln Ser Trp Ser Trp Arg His Val Pro Ser Glu Glu Ala Ser Arg
                290                 295                 300

Met Asn Leu Leu Asp Gly Pro Glu Ala Glu His Ser Gln Glu Met Pro
305                 310                 315                 320

Arg Gly Ser Phe Leu Leu Leu Asn Thr Ser Ala Asp Ser Lys His Thr
                325                 330                 335

Ile Leu Ser Pro Trp Met Arg Ser Ser Ser Asp His Cys Thr Leu Ala
                340                 345                 350

Val Ser Val His Arg His Leu Gln Pro Ser Gly Arg Tyr Val Ala Gln
                355                 360                 365

Leu Leu Pro His Asn Glu Ala Gly Arg Glu Ile Leu Leu Val Pro Thr
                370                 375                 380

Pro Gly Lys His Gly Trp Thr Val Leu Gln Gly Arg Val Gly Arg Pro
385                 390                 395                 400

Ala Asn Pro Phe Arg Val Ala Leu Glu Tyr Ile Ser Ser Gly Asn Arg
                405                 410                 415

Ser Leu Ser Ala Val Asp Phe Phe Ala Leu Lys Asn Cys Ser Glu Gly
                420                 425                 430

Thr Ser Pro Gly Ser Lys Met Ala Leu Gln Ser Ser Phe Thr Cys Trp
                435                 440                 445

Asn Gly Thr Val Leu Gln Leu Gly Gln Ala Cys Asp Phe His Gln Asp
                450                 455                 460

Cys Ala Gln Gly Glu Asp Glu Gly Gln Leu Cys Ser Lys Leu Pro Ala
465                 470                 475                 480
```

```
Gly Phe Tyr Cys Asn Phe Glu Asn Gly Phe Cys Gly Trp Thr Gln Ser
                485                 490                 495

Pro Leu Ser Pro His Met Pro Arg Trp Gln Val Arg Thr Leu Arg Asp
                500                 505                 510

Ala His Ser Gln Gly His Gln Gly Arg Ala Leu Leu Leu Ser Thr Thr
                515                 520                 525

Asp Ile Leu Ala Ser Glu Gly Ala Thr Val Thr Ser Ala Thr Phe Pro
                530                 535                 540

Ala Pro Met Lys Asn Ser Pro Cys Glu Leu Arg Met Ser Trp Leu Ile
545                 550                 555                 560

Arg Gly Val Leu Arg Gly Asn Val Ser Leu Val Leu Glu Asn Lys
                565                 570                 575

Thr Gly Lys Glu Gln Ser Arg Thr Val Trp His Val Ala Thr Asp Glu
                580                 585                 590

Gly Leu Ser Leu Trp Gln His Thr Val Leu Ser Leu Leu Asp Val Thr
                595                 600                 605

Asp Arg Phe Trp Leu Gln Ile Val Thr Trp Trp Gly Pro Gly Ser Arg
                610                 615                 620

Ala Thr Val Gly Phe Asp Asn Ile Ser Ile Ser Leu Asp Cys Tyr Leu
625                 630                 635                 640

Thr Ile Ser Gly Glu Glu Lys Met Ser Leu Asn Ser Val Pro Lys Ser
                645                 650                 655

Arg Asn Leu Phe Glu Lys Asn Pro Asn Lys Glu Ser Lys Ser Trp Ala
                660                 665                 670

Asn Ile Ser Gly Pro Thr Pro Ile Phe Asp Pro Thr Val His Trp Leu
                675                 680                 685

Phe Thr Thr Cys Gly Ala Ser Gly Pro His Gly Pro Thr Gln Ala Gln
                690                 695                 700

Cys Asn Asn Ala Tyr Gln Asn Ser Asn Leu Ser Val Val Gly Ser
705                 710                 715                 720

Glu Gly Pro Leu Lys Gly Val Gln Ile Trp Lys Val Pro Ala Thr Asp
                725                 730                 735

Thr Tyr Ser Ile Ser Gly Tyr Gly Ala Ala Gly Gly Lys Gly Gly Lys
                740                 745                 750

Asn Thr Met Met Arg Ser His Gly Val Ser Val Leu Gly Ile Phe Asn
                755                 760                 765

Leu Glu Lys Gly Asp Thr Leu Tyr Ile Leu Val Gly Gln Gln Gly Glu
                770                 775                 780

Asp Ala Cys Pro Arg Ala Asn Gln Leu Ile Gln Lys Val Cys Val Gly
785                 790                 795                 800

Glu Asn Asn Val Ile Glu Glu Ile Arg Val Asn Arg Ser Val His
                805                 810                 815

Glu Trp Ala Gly Gly Gly Gly Gly Gly Ala Thr Tyr Val Phe
                820                 825                 830

Lys Met Lys Asp Gly Val Pro Val Pro Leu Ile Ile Ala Ala Gly Gly
                835                 840                 845

Gly Gly Arg Ala Tyr Gly Ala Lys Thr Glu Thr Phe His Pro Glu Arg
                850                 855                 860

Leu Glu Ser Asn Ser Ser Val Leu Gly Leu Asn Gly Asn Ser Gly Ala
865                 870                 875                 880

Ala Gly Gly Gly Gly Gly Trp Asn Asp Asn Thr Ser Leu Leu Trp Ala
                885                 890                 895
```

```
Gly Lys Ser Leu Leu Glu Gly Ala Ala Gly His Ser Cys Pro Gln
            900                 905                 910
Ala Met Lys Lys Trp Gly Trp Glu Thr Arg Gly Phe Gly Gly Gly
            915                 920                 925
Gly Gly Gly Cys Ser Ser Gly Gly Gly Gly Tyr Ile Gly Gly
            930                 935                 940
Asn Ala Ala Ser Asn Asn Asp Pro Glu Met Asp Gly Glu Asp Gly Val
945                 950                 955                 960
Ser Phe Ile Ser Pro Leu Gly Ile Leu Tyr Thr Pro Ala Leu Lys Val
            965                 970                 975
Met Glu Gly His Gly Glu Val Asn Ile Lys His Tyr Leu Asn Cys Ser
            980                 985                 990
His Cys Glu Val Asp Glu Cys His Met Asp Pro Glu Ser His Lys Val
            995                 1000                1005
Ile Cys Phe Cys Asp His Gly Thr Val Leu Ala Asp Asp Gly Val Ser
            1010                1015                1020
Cys Ile Val Ser Pro Thr Pro Glu Pro His Leu Pro Leu Ser Leu Ile
1025                1030                1035                1040
Leu Ser

<210> SEQ ID NO 518
<211> LENGTH: 1038
<212> TYPE: PRT
<213> ORGANISM: rattus
<220> FEATURE:
<223> OTHER INFORMATION: rat ALK

<400> SEQUENCE: 518

Met Gly Ala Leu Gly Phe Leu Trp Leu Leu Pro Leu Leu Leu Thr
1               5                   10                  15
Ala Ala Ser Tyr Ser Gly Ala Ala Thr Asp Gln Arg Ala Gly Ser Pro
            20                  25                  30
Ala Ser Gly Pro Pro Leu Gln Pro Arg Glu Pro Leu Ser Tyr Ser Arg
            35                  40                  45
Leu Gln Arg Lys Ser Leu Ala Val Asp Phe Val Val Pro Ser Leu Phe
50                  55                  60
Arg Val Tyr Ala Arg Asp Leu Leu Pro Gln Pro Pro Ser Pro Ser
65              70                  75                  80
Glu Pro Gly Ala Gly Gly Leu Glu Ala Arg Gly Ser Leu Ala Leu Asp
                85                  90                  95
Cys Asp Pro Leu Leu Arg Leu Leu Gly Pro Ser Pro Gly Ile Ser Trp
            100                 105                 110
Ala Glu Gly Ala Ser Ser Pro Ser Pro Glu Ala Ala Pro Thr Leu Ser
            115                 120                 125
Arg Val Leu Lys Gly Gly Ser Val Arg Lys Leu Arg Arg Ala Lys Gln
            130                 135                 140
Leu Val Leu Glu Leu Gly Glu Glu Thr Ile Leu Glu Gly Cys Ile Gly
145                 150                 155                 160
Pro Pro Glu Glu Ala Ala Ala Val Gly Ile Leu Gln Phe Asn Leu Ser
                165                 170                 175
Glu Leu Phe Ser Trp Trp Ile Leu His Gly Gly Arg Leu Arg Ile
            180                 185                 190
Arg Leu Met Pro Glu Lys Lys Ala Ser Glu Val Gly Arg Glu Gly Arg
            195                 200                 205
Leu Ser Thr Ala Ile Arg Ala Ser Gln Pro Arg Leu Leu Phe Gln Ile
```

```
                 210                 215                 220
Phe Gly Thr Gly His Ser Ser Leu Glu Ser Pro Ser Glu Met Pro Ser
225                 230                 235                 240

Pro Pro Gly Asn Phe Leu Trp Asn Leu Thr Trp Thr Met Lys Asp Ser
                245                 250                 255

Phe Pro Phe Leu Ser His Arg Ser Arg Tyr Gly Leu Glu Cys Ser Phe
                260                 265                 270

Asp Phe Pro Cys Glu Leu Glu Tyr Ser Pro Pro Leu His Thr His Gly
            275                 280                 285

Asn Gln Ser Trp Ser Trp Arg Arg Val Pro Ser Glu Glu Ala Ser Arg
        290                 295                 300

Met Asn Leu Leu Asp Gly Pro Glu Ala Glu His Leu Lys Glu Met Pro
305                 310                 315                 320

Arg Gly Ser Phe Leu Leu Leu Asn Thr Ser Ala Asp Ser Lys His Thr
                325                 330                 335

Ile Leu Ser Pro Trp Met Arg Ser Ser Ser Glu His Cys Thr Leu Ala
                340                 345                 350

Val Ser Val His Arg His Leu Gln Pro Ser Gly Arg Tyr Val Ala Gln
            355                 360                 365

Leu Leu Pro His Asn Glu Ala Gly Arg Glu Ile Leu Leu Val Pro Thr
        370                 375                 380

Pro Gly Lys His Gly Trp Thr Val Leu His Gly Arg Val Gly Arg Pro
385                 390                 395                 400

Glu Asn Pro Phe Arg Val Ala Leu Glu Tyr Ile Ser Ser Gly Asn Arg
                405                 410                 415

Ser Leu Ser Ala Val Asp Phe Phe Ala Leu Lys Asn Cys Ser Glu Gly
            420                 425                 430

Thr Ser Pro Gly Ser Lys Met Ala Leu Gln Ser Ser Phe Thr Cys Trp
        435                 440                 445

Asn Gly Thr Val Leu Gln Leu Gly Gln Ala Cys Asp Phe His Gln Asn
    450                 455                 460

Cys Ala Gln Gly Glu Asp Glu Gly Gln Leu Cys Ser Lys Leu Pro Ala
465                 470                 475                 480

Gly Phe Tyr Cys Asn Phe Glu Asp Gly Phe Cys Gly Trp Thr Gln Ser
                485                 490                 495

Pro Leu Ser Pro Arg Val Pro Arg Trp Gln Val Lys Thr Leu Lys Asp
            500                 505                 510

Thr His Ser Gln Gly His Gln Gly His Ala Leu Leu Leu Ser Thr Thr
        515                 520                 525

Asp Asp Pro Thr Ser Glu Ser Ala Thr Val Thr Ser Ala Thr Phe Pro
    530                 535                 540

Ala Pro Met Lys Ser Ser Pro Cys Glu Leu Arg Met Ser Trp Leu Ile
545                 550                 555                 560

Arg Gly Val Leu Lys Gly Asn Val Ser Leu Val Leu Val Glu Asn Lys
                565                 570                 575

Thr Gly Lys Glu Gln Ser Arg Thr Val Trp His Val Ala Thr Asn Glu
            580                 585                 590

Gly Leu Ser Leu Trp Gln Trp Thr Val Leu Ser Leu Leu Asp Val Thr
        595                 600                 605

Asp Arg Phe Trp Leu Gln Ile Val Thr Trp Trp Gly Pro Gly Ser Arg
    610                 615                 620

Ala Thr Val Ala Phe Asp Asn Ile Ser Ile Ser Leu Asp Cys Tyr Leu
625                 630                 635                 640
```

```
Thr Ile Ser Gly Glu Glu Lys Met Ser Leu Asn Ala Val Pro Lys Ser
                645                 650                 655

Arg Asn Leu Phe Glu Lys Asn Pro Asn Lys Glu Pro Lys Pro Trp Ala
                660                 665                 670

Asn Ile Ser Gly Pro Thr Pro Ile Phe Asp Pro Thr Val His Trp Leu
                675                 680                 685

Phe Thr Thr Cys Gly Ala Ser Gly Pro His Gly Pro Thr Gln Ala Gln
                690                 695                 700

Cys Asn Asn Ala Tyr Gln Asn Ser Asn Leu Ser Val Val Val Gly Ser
705                 710                 715                 720

Glu Gly Pro Leu Arg Gly Ile Gln Ile Trp Lys Val Pro Ala Thr Asp
                725                 730                 735

Thr Tyr Ser Ile Ser Gly Tyr Gly Ala Ala Gly Gly Lys Gly Gly Lys
                740                 745                 750

Asn Thr Met Met Arg Ser His Gly Val Ser Val Leu Gly Ile Phe Asn
                755                 760                 765

Leu Glu Lys Asp Asp Thr Leu Tyr Ile Leu Val Gly Gln Gln Gly Glu
                770                 775                 780

Asp Ala Cys Pro Arg Ala Asn Gln Leu Ile Gln Lys Val Cys Val Gly
785                 790                 795                 800

Glu Asn Asn Val Ile Glu Glu Ile Arg Val Asn Arg Ser Val His
                805                 810                 815

Glu Trp Ala Gly Gly Gly Gly Gly Gly Ala Thr Tyr Val Phe
                820                 825                 830

Lys Met Lys Asp Gly Val Pro Val Pro Leu Ile Ile Ala Ala Gly Gly
                835                 840                 845

Gly Gly Arg Ala Tyr Gly Ala Lys Thr Glu Thr Phe His Pro Glu Arg
                850                 855                 860

Leu Glu Asn Asn Ser Ser Val Leu Gly Leu Asn Gly Asn Ser Gly Ala
865                 870                 875                 880

Ala Gly Gly Gly Gly Trp Asn Asp Asn Thr Ser Leu Leu Trp Ala
                885                 890                 895

Gly Lys Ser Leu Leu Glu Gly Ala Ala Gly Gly His Ser Cys Pro Gln
                900                 905                 910

Ala Met Lys Lys Trp Gly Trp Glu Thr Arg Gly Gly Phe Gly Gly Gly
                915                 920                 925

Gly Gly Gly Cys Ser Ser Gly Gly Gly Gly Gly Tyr Ile Gly Gly
                930                 935                 940

Asn Ala Ala Ser Asn Asn Asp Pro Glu Met Asp Gly Glu Asp Gly Val
945                 950                 955                 960

Ser Phe Ile Ser Pro Leu Gly Ile Leu Tyr Thr Pro Ala Leu Lys Val
                965                 970                 975

Met Glu Gly His Gly Glu Val Asn Ile Lys His Tyr Leu Asn Cys Ser
                980                 985                 990

His Cys Glu Val Asp Glu Cys His Met Asp Pro Glu Ser His Lys Val
                995                 1000                1005

Ile Cys Phe Cys Asp His Gly Thr Val Leu Ala Asp Asp Gly Val Ser
                1010                1015                1020

Cys Ile Val Ser Pro Thr Pro Glu Pro His Leu Pro Leu Ser
1025                1030                1035

<210> SEQ ID NO 519
<211> LENGTH: 1040
```

<212> TYPE: PRT
<213> ORGANISM: Homo sapiens
<220> FEATURE:
<223> OTHER INFORMATION: human ALK variant found in Fig. 9

<400> SEQUENCE: 519

```
Met Gly Ala Ile Gly Leu Leu Trp Leu Leu Pro Leu Leu Leu Ser Thr
 1               5                  10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
    370                 375                 380
```

```
Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
            405                 410                 415

Val Asp Phe Phe Ala Leu Lys Asn Cys Ser Glu Gly Thr Ser Pro Gly
        420                 425                 430

Ser Lys Met Ala Leu Gln Ser Ser Phe Thr Cys Trp Asn Gly Thr Val
    435                 440                 445

Leu Gln Leu Gly Gln Ala Cys Asp Phe His Gln Asp Cys Ala Gln Gly
    450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
            485                 490                 495

His Thr Pro Gln Trp Gln Val Arg Thr Leu Lys Asp Ala Arg Phe Gln
        500                 505                 510

Asp His Gln Asp His Ala Leu Leu Leu Ser Thr Thr Asp Val Pro Ala
    515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
            565                 570                 575

Gln Gly Arg Met Val Trp His Val Ala Ala Tyr Glu Gly Leu Ser Leu
        580                 585                 590

Trp Gln Trp Met Val Leu Pro Leu Leu Asp Val Ser Asp Arg Phe Trp
    595                 600                 605

Leu Gln Met Val Ala Trp Trp Gly Gln Gly Ser Arg Ala Ile Val Ala
610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
            645                 650                 655

Glu Arg Asn Pro Asn Lys Glu Leu Lys Pro Gly Glu Asn Ser Pro Arg
        660                 665                 670

Gln Thr Pro Ile Phe Asp Pro Thr Val His Trp Leu Phe Thr Thr Cys
    675                 680                 685

Gly Ala Ser Gly Pro His Gly Pro Thr Gln Ala Gln Cys Asn Asn Ala
690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
            725                 730                 735

Ser Gly Tyr Gly Ala Ala Gly Gly Lys Gly Gly Lys Asn Thr Met Met
        740                 745                 750

Arg Ser His Gly Val Ser Val Leu Gly Ile Phe Asn Leu Glu Lys Asp
    755                 760                 765

Asp Met Leu Tyr Ile Leu Val Gly Gln Gln Gly Glu Asp Ala Cys Pro
    770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
```

-continued

```
                805                 810                 815
Gly Gly Gly Gly Gly Gly Gly Ala Thr Tyr Val Phe Lys Met Lys Asp
            820                 825                 830

Gly Val Pro Val Pro Leu Ile Ile Ala Ala Gly Gly Gly Gly Arg Ala
            835                 840                 845

Tyr Gly Ala Lys Thr Asp Thr Phe His Pro Glu Arg Leu Glu Asn Asn
    850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
            885                 890                 895

Gln Glu Gly Ala Thr Gly Gly His Ser Cys Pro Gln Ala Met Lys Lys
            900                 905                 910

Trp Gly Trp Glu Thr Arg Gly Gly Phe Gly Gly Gly Gly Gly Gly Cys
            915                 920                 925

Ser Ser Gly Gly Gly Gly Gly Tyr Ile Gly Gly Asn Ala Ala Ser
    930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
            980                 985                 990

Asp Glu Cys His Met Asp Pro Glu Ser His Lys Val Ile Cys Phe Cys
            995                 1000                1005

Asp His Gly Thr Val Leu Ala Glu Asp Gly Val Ser Cys Ile Val Ser
    1010                1015                1020

Pro Thr Pro Glu Pro His Leu Pro Leu Ser Leu Ile Leu Ser Leu Glu
1025                1030                1035                1040
```

ANTI-ALK ANTIBODIES AND METHODS
FOR USE THEREOF

This application claims the benefit of U.S. Provisional Application No. 62/210,705, filed Aug. 27, 2015, the disclosure of which is incorporated by reference herein in its entirety.

REFERENCE TO SEQUENCE LISTING
SUBMITTED ELECTRONICALLY

This application incorporates by reference a Sequence Listing submitted with this application as text file entitled "Sequence_Listing_12638_115_228.txt" created on Aug. 26, 2016 and having a size of 225,594 bytes.

1. FIELD

Provided herein are compositions, methods and uses involving antibodies that specifically bind to ALK, a receptor tyrosine kinase, and modulate the expression and/or activity of ALK for treating, e.g., managing, disorders, such as cancer.

2. BACKGROUND

Anaplastic Lymphoma Kinase (ALK) is a receptor tyrosine kinase (RTK) involved in neurogenesis during embryonic development. ALK is transiently expressed in specific regions of the central and peripheral nervous system, for example the mid-brain, thalamus, olfactory bulb, and peripheral ganglia. This expression is essential and is highest in the neonatal brain. Expression is maintained at low levels in the adult brain.

ALK has also been shown to be expressed in cells exhibiting a number of disease states, such as cells involved in cancer and other hyperproliferative and neoplastic disorders. Overexpression and/or constitutive activation (such as by fusion proteins) of ALK has also been associated with oncogenic growth and the formation of tumors. In addition, aberrant ALK signaling has been implicated in driving several types of cancer. Genomic translocations resulting in the fusion of the ALK kinase domain with the oligomerization region of intracellular proteins (e.g., EML4-ALK, NPM-ALK, etc.) have been identified in approximately 5% of non-small cell lung cancers, and approximately 60% of anaplastic large-cell lymphomas. Furthermore, ALK activation through overexpression, somatic mutation, or germ-line mutation occurs in approximately 15% of neuroblastoma cases, the most common extra-cranial tumor type in children.

3. SUMMARY

In one aspect, provided herein are antigen-binding agents, e.g., antibodies, which specifically bind to an extracellular domain (ECD) of ALK such as human ALK. In one aspect, provided herein are antibodies (e.g., monoclonal antibodies), including antigen-binding fragments thereof, which specifically bind to the extracellular domain (ECD) of ALK, such as human ALK. In another specific aspect, such anti-ALK antibodies specifically bind to an ECD of human ALK (e.g., the NTR, MAM1, LDLa, MAM2 or EGF domains of ALK-ECD) and inhibit phosphorylation of ALK. In a specific aspect, such anti-ALK antibodies specifically bind to an ECD of human ALK (e.g., the NTR, MAM1, LDLa, MAM2 or EGF domains of human ALK-ECD) present on the surface of a cell, and is internalized by the cell. Also provided herein are polynucleotides and vectors comprising sequences encoding such antibodies, cells (e.g., host cells) comprising such polynucleotides or vectors, and compositions, reagents and kits comprising such antibodies. In another aspect, provided herein are methods for modulating ALK activity or ALK expression levels, diagnostic methods and uses, and therapeutic methods and uses of such anti-ALK antibodies.

In one aspect, provided herein is an antibody, e.g., a monoclonal antibody, or antigen-binding fragment thereof that binds to the ECD of human ALK, wherein the antibody or antigen-binding fragment thereof:
(a) inhibits ALK activity in cells as determined by inhibition of phosphorylation of ALK;
(b) binds to the ECD of human ALK present on a cell, and is internalized by the cell;
(c) induces ALK degradation in cells; and/or
(d) inhibits tumor cell proliferation or tumor growth.

In certain aspects, the antibody or antigen-binding fragment thereof comprises:
(a) a light chain variable region (VL) comprising VL complementary determining region 1 (CDR1), VL CDR2, and VL CDR3 of any one of antibodies Ab320-Ab332 and Ab351-Ab446, for example, as set forth in Table 1; and
(b) a heavy chain variable region (VH) comprising VH complementary determining region 1 (CDR1), VH CDR2, and VH CDR3 of any one of antibodies Ab320-Ab332 and Ab351-Ab446, for example as set forth in Table 2.

Also provided herein is a method of making an antibody or an antigen-binding fragment thereof which specifically binds to the ECD of human ALK, comprising culturing a cell provided herein to express the antibody or antigen-binding fragment.

Also provided herein is a method of making an antibody or an antigen-binding fragment thereof which specifically binds to the ECD of human ALK, comprising expressing a polynucleotide provided herein.

In certain aspects, the antibody or antigen-binding fragment thereof comprises:
(i) a light chain variable region (VL) comprising:
  (a) a VL complementarity determining region (CDR) 1 comprising the amino acid sequence of KASQNVGTNVA (SEQ ID NO:13);
  (b) a VL CDR2 comprising the amino acid sequence of SASYRYS (SEQ ID NO:14); and
  (c) a VL CDR3 comprising the amino acid sequence of QX$_1$YNSYPYMX$_2$T (SEQ ID NO:468), wherein X$_1$ is Q or R and X$_2$ is Y or F; and
(ii) a heavy chain variable region (VH) comprising:
  (a) a VH CDR1 comprising the amino acid sequence X$_3$YWMH (SEQ ID NO:469), wherein X$_3$ is N or S;
  (b) a VH CDR2 comprising the amino acid sequence of YIX$_4$PSSGYTKYNQKFKD (SEQ ID NO:470), wherein X$_4$ is N or K; and
  (c) a VH CDR3 comprising the amino acid sequence of DYYGSSSWFAY (SEQ ID NO:18).

In certain aspects, the antibody or antigen-binding fragment thereof comprises a VL comprising:
(a) a VL CDR1 comprising the amino acid sequence of KASQNVGTNVA (SEQ ID NO:13);
(b) a VL CDR2 comprising the amino acid sequence of SASYRYS (SEQ ID NO:14); and
(c) a VL CDR3 comprising the amino acid sequence of QQYNSYPYMYT (SEQ ID NO:15).

In certain aspects, the antibody or antigen-binding fragment thereof comprises a VL comprising:

(a) a VL CDR1 comprising the amino acid sequence of KASQNVGTNVA (SEQ ID NO:13);
(b) a VL CDR2 comprising the amino acid sequence of SASYRYS (SEQ ID NO:14); and
(c) a VL CDR3 comprising the amino acid sequence of QRYNSYPYMFT (SEQ ID NO:41).

In certain aspects, the antibody or antigen-binding fragment thereof comprises a VH comprising:
(a) a VH CDR1 comprising the amino acid sequence of SYWMH (SEQ ID NO:10);
(b) a VH CDR2 comprising the amino acid sequence of YIKPSSGYTKYNQKFKD (SEQ ID NO:34); and
(c) a VH CDR3 comprising the amino acid sequence of DYYGSSSWFAY (SEQ ID NO:18).

In certain aspects, the antibody or antigen-binding fragment thereof comprises a VH comprising:
(a) a VH CDR1 comprising the amino acid sequence of SYWMH (SEQ ID NO:10);
(b) a VH CDR2 comprising the amino acid sequence of YINPSSGYTKYNQKFKD (SEQ ID NO:17); and
(c) a VH CDR3 comprising the amino acid sequence of DYYGSSSWFAY (SEQ ID NO:18).

In certain aspects, the antibody or antigen-binding fragment thereof comprises a VH comprising:
(a) a VH CDR1 comprising the amino acid sequence of NYWMH (SEQ ID NO:16);
(b) a VH CDR2 comprising the amino acid sequence of YINPSSGYTKYNQKFKD (SEQ ID NO:17); and
(c) a VH CDR3 comprising the amino acid sequence of DYYGSSSWFAY (SEQ ID NO:18).

In certain aspects, the antibody or antigen-binding fragment thereof comprises:
(i) a VL comprising:
  (a) a VL CDR1 comprising the amino acid sequence of KASQNVGTNVA (SEQ ID NO:13);
  (b) a VL CDR2 comprising the amino acid sequence of SASYRYS (SEQ ID NO:14); and
  (c) a VL CDR3 comprising the amino acid sequence of QQYNSYPYMYT (SEQ ID NO:15); and
(ii) a VH comprising:
  (a) a VH CDR1 comprising the amino acid sequence of SYWMH (SEQ ID NO:10);
  (b) a VH CDR2 comprising the amino acid sequence of YIKPSSGYTKYNQKFKD (SEQ ID NO:34); and
  (c) a VH CDR3 comprising the amino acid sequence of DYYGSSSWFAY (SEQ ID NO:18).

In certain aspects, the antibody or antigen-binding fragment thereof comprises:
(i) a VL comprising:
  (a) a VL CDR1 comprising the amino acid sequence of KASQNVGTNVA (SEQ ID NO:13);
  (b) a VL CDR2 comprising the amino acid sequence of SASYRYS (SEQ ID NO:14); and
  (c) a VL CDR3 comprising the amino acid sequence of QQYNSYPYMYT (SEQ ID NO:15); and
(ii) a VH comprising:
  (a) a VH CDR1 comprising the amino acid sequence of SYWMH (SEQ ID NO:10);
  (b) a VH CDR2 comprising the amino acid sequence of YINPSSGYTKYNQKFKD (SEQ ID NO:17); and
  (c) a VH CDR3 comprising the amino acid sequence of DYYGSSSWFAY (SEQ ID NO:18).

In certain aspects, the antibody or antigen-binding fragment thereof comprises:
(i) a VL comprising:
  (a) a VL CDR1 comprising the amino acid sequence of KASQNVGTNVA (SEQ ID NO:13);
  (b) a VL CDR2 comprising the amino acid sequence of SASYRYS (SEQ ID NO:14); and
  (c) a VL CDR3 comprising the amino acid sequence of QQYNSYPYMYT (SEQ ID NO:15); and
(ii) a VH comprising:
  (a) a VH CDR1 comprising the amino acid sequence of NYWMH (SEQ ID NO:16);
  (b) a VH CDR2 comprising the amino acid sequence of YINPSSGYTKYNQKFKD (SEQ ID NO:17); and
  (c) a VH CDR3 comprising the amino acid sequence of DYYGSSSWFAY (SEQ ID NO:18).

In certain aspects, the antibody or antigen-binding fragment thereof comprises:
(i) a VL comprising:
  (a) a VL CDR1 comprising the amino acid sequence of KASQNVGTNVA (SEQ ID NO:13);
  (b) a VL CDR2 comprising the amino acid sequence of SASYRYS (SEQ ID NO:14); and
  (c) a VL CDR3 comprising the amino acid sequence of QRYNSYPYMFT (SEQ ID NO:41); and
(ii) a VH comprising:
  (a) a VH CDR1 comprising the amino acid sequence of SYWMH (SEQ ID NO:10);
  (b) a VH CDR2 comprising the amino acid sequence of YIKPSSGYTKYNQKFKD (SEQ ID NO:34); and
  (c) a VH CDR3 comprising the amino acid sequence of DYYGSSSWFAY (SEQ ID NO:18).

In certain aspects, the antibody or antigen-binding fragment thereof comprises:
(i) a VL comprising:
  (a) a VL CDR1 comprising the amino acid sequence of KASQNVGTNVA (SEQ ID NO:13);
  (b) a VL CDR2 comprising the amino acid sequence of SASYRYS (SEQ ID NO:14); and
  (c) a VL CDR3 comprising the amino acid sequence of QRYNSYPYMFT (SEQ ID NO:41); and
(ii) a VH comprising:
  (a) a VH CDR1 comprising the amino acid sequence of SYWMH (SEQ ID NO:10);
  (b) a VH CDR2 comprising the amino acid sequence of YINPSSGYTKYNQKFKD (SEQ ID NO:17); and
  (c) a VH CDR3 comprising the amino acid sequence of DYYGSSSWFAY (SEQ ID NO:18).

In certain aspects, the antibody or antigen-binding fragment thereof comprises:
(i) a VL comprising:
  (a) a VL CDR1 comprising the amino acid sequence of KASQNVGTNVA (SEQ ID NO:13);
  (b) a VL CDR2 comprising the amino acid sequence of SASYRYS (SEQ ID NO:14); and
  (c) a VL CDR3 comprising the amino acid sequence of QRYNSYPYMFT (SEQ ID NO:41); and
(ii) a VH comprising:
  (a) a VH CDR1 comprising the amino acid sequence of NYWMH (SEQ ID NO:16);
  (b) a VH CDR2 comprising the amino acid sequence of YINPSSGYTKYNQKFKD (SEQ ID NO:17); and
  (c) a VH CDR3 comprising the amino acid sequence of DYYGSSSWFAY (SEQ ID NO:18).

In certain aspects, the antibody or antigen-binding fragment thereof comprises a VL comprising an amino acid sequence at least 80% identical to the amino acid sequence of SEQ ID NO: 399, and a VH comprising an amino acid sequence at least 80% identical to the amino acid sequence of SEQ ID NO: 400.

In certain aspects, the antibody or antigen-binding fragment thereof comprises a VL comprising an amino acid sequence at least 80% identical to the amino acid sequence of SEQ ID NO: 407, and a VH comprising an amino acid sequence at least 80% identical to the amino acid sequence of SEQ ID NO: 408.

In certain aspects, the antibody or antigen-binding fragment thereof comprises a VL comprising an amino acid sequence at least 80% identical to the amino acid sequence of SEQ ID NO: 411, and a VH comprising an amino acid sequence at least 80% identical to the amino acid sequence of SEQ ID NO: 412.

In certain aspects, the antibody or antigen-binding fragment thereof comprises a VL comprising an amino acid sequence at least 80% identical to any one of the amino acid sequences of SEQ ID NOs: 421-428, and a VH comprising an amino acid sequence at least 80% identical to any one of the amino acid sequences of SEQ ID NOs: 429-440.

In certain aspects, the antibody or antigen-binding fragment thereof comprises a VL comprising an amino acid sequence at least 85% identical to the amino acid sequence of SEQ ID NO: 399, and a VH comprising an amino acid sequence at least 85% identical to the amino acid sequence of SEQ ID NO: 400.

In certain aspects, the antibody or antigen-binding fragment thereof comprises a VL comprising an amino acid sequence at least 85% identical to the amino acid sequence of SEQ ID NO: 407, and a VH comprising an amino acid sequence at least 85% identical to the amino acid sequence of SEQ ID NO: 408.

In certain aspects, the antibody or antigen-binding fragment thereof comprises a VL comprising an amino acid sequence at least 85% identical to the amino acid sequence of SEQ ID NO: 411, and a VH comprising an amino acid sequence at least 85% identical to the amino acid sequence of SEQ ID NO: 412.

In certain aspects, the antibody or antigen-binding fragment thereof comprises a VL comprising an amino acid sequence at least 85% identical to any one of the amino acid sequences of SEQ ID NOs: 421-428, and a VH comprising an amino acid sequence at least 85% identical to any one of the amino acid sequences of SEQ ID NOs: 429-440.

In certain aspects, the antibody or antigen-binding fragment thereof comprises a VL comprising an amino acid sequence at least 90% identical to the amino acid sequence of SEQ ID NO: 399, and a VH comprising an amino acid sequence at least 90% identical to the amino acid sequence of SEQ ID NO: 400.

In certain aspects, the antibody or antigen-binding fragment thereof comprises a VL comprising an amino acid sequence at least 90% identical to the amino acid sequence of SEQ ID NO: 407, and a VH comprising an amino acid sequence at least 90% identical to the amino acid sequence of SEQ ID NO: 408.

In certain aspects, the antibody or antigen-binding fragment thereof comprises a VL comprising an amino acid sequence at least 90% identical to the amino acid sequence of SEQ ID NO: 411, and a VH comprising an amino acid sequence at least 90% identical to the amino acid sequence of SEQ ID NO: 412.

In certain aspects, the antibody or antigen-binding fragment thereof comprises a VL comprising an amino acid sequence at least 90% identical to any one of the amino acid sequences of SEQ ID NOs: 421-428, and a VH comprising an amino acid sequence at least 90% identical to any one of the amino acid sequences of SEQ ID NOs: 429-440.

In certain aspects, the antibody or antigen-binding fragment thereof comprises a VL comprising an amino acid sequence at least 95% identical to the amino acid sequence of SEQ ID NO: 399, and a VH comprising an amino acid sequence at least 95% identical to the amino acid sequence of SEQ ID NO: 400.

In certain aspects, the antibody or antigen-binding fragment thereof comprises a VL comprising an amino acid sequence at least 95% identical to the amino acid sequence of SEQ ID NO: 407, and a VH comprising an amino acid sequence at least 95% identical to the amino acid sequence of SEQ ID NO: 408.

In certain aspects, the antibody or antigen-binding fragment thereof comprises a VL comprising an amino acid sequence at least 95% identical to the amino acid sequence of SEQ ID NO: 411, and a VH comprising an amino acid sequence at least 95% identical to the amino acid sequence of SEQ ID NO: 412.

In certain aspects, the antibody or antigen-binding fragment thereof comprises a VL comprising an amino acid sequence at least 95% identical to any one of the amino acid sequences of SEQ ID NOs: 421-428, and a VH comprising an amino acid sequence at least 95% identical to any one of the amino acid sequences of SEQ ID NOs: 429-440.

In certain aspects, the antibody or antigen-binding fragment thereof comprises a VL comprising SEQ ID NO: 399 and a VH comprising SEQ ID NO: 400.

In certain aspects, the antibody or antigen-binding fragment thereof comprises a VL comprising SEQ ID NO: 407 and a VH comprising SEQ ID NO: 408.

In certain aspects, the antibody or antigen-binding fragment thereof comprises a VL comprising SEQ ID NO: 411 and a VH comprising SEQ ID NO: 412.

In certain aspects, the antibody or antigen-binding fragment thereof comprises a VL comprising any one of the amino acid sequences of SEQ ID NOs: 421-428 and a VH comprising any one of the amino acid sequences of SEQ ID NOs: 429-440.

In certain aspects, the antibody or antigen-binding fragment thereof comprises the VL CDR1-3 and the VH CDR1-3 of any one of Ab320-Ab332, Ab353, Ab354, Ab358, Ab362, Ab423, or Ab435.

In certain aspects, the antibody or antigen-binding fragment thereof comprises the VL CDR1-3 and the VH CDR1-3 of any one of Ab320-Ab332, or Ab351-Ab446.

In certain aspects, the antibody or antigen-binding fragment thereof comprises a heavy chain constant region. In certain aspects, the heavy chain constant region is a human IgG constant region. In specific aspects, the heavy chain constant region is a human $IgG_1$ constant region.

In certain aspects, the antibody or antigen-binding fragment thereof comprises a light chain constant region selected from the group consisting of a human kappa constant region and a human lambda constant region.

In certain aspects, the antibody or antigen-binding fragment thereof is a human antibody, a humanized antibody, a chimeric antibody, a recombinant antibody, a multispecific antibody, or an antigen-binding fragment thereof. In certain aspects, the antigen-binding fragment is an Fv, Fab, F(ab')2, Fab', dsFv, scFv, or sc(Fv)2. In specific aspects, the antibody or antigen-binding fragment thereof is a monoclonal antibody or antigen-binding fragment thereof. In certain aspects, the antibody or antigen-binding fragment thereof is an antibody.

In certain aspects, provided herein are compositions comprising an antibody or antigen-binding fragment thereof provided herein and a pharmaceutically acceptable carrier.

In certain aspects, provided herein are nucleic acids comprising a sequence encoding an antibody or antigen-binding fragment provided herein. In certain aspects, provided herein is a vector comprising a nucleic acid encoding an antibody or antigen-binding fragment provided herein. In certain aspects, provided herein is a cell comprising a nucleic acid encoding an antibody or antigen-binding fragment provided herein.

In certain aspects, provided herein is a method of making an antibody or antigen-binding fragment thereof provided herein, comprising (a) culturing a cell comprising a nucleic acid encoding the antibody or antigen-binding fragment; and (b) isolating the antibody or antigen-binding fragment thereof.

In certain aspects, provided herein is a method of inhibiting the proliferation of a cell expressing ALK, said method comprising contacting the cell with an antibody or antigen-binding fragment provided herein.

In certain aspects, provided herein is a method of treating cancer in a subject, comprising administering to the subject a therapeutically effective amount of an antibody or antigen-binding fragment thereof provided herein. In certain aspects, the cancer is selected from the group consisting of anaplastic large cell lymphoma, inflammatory myofibroblastic tumors, lung cancer, for example, small cell lung carcinoma or non-small cell lung cancer, e.g., adenocarcinoma, such as bronchioalveolar carcinoma, squamous cell carcinoma or large-cell carcinoma, diffuse large B-cell lymphoma, squamous cell carcinoma, breast carcinoma, melanoma, pancreatic cancer, B-cell non-Hodgkin's lymphoma, thyroid carcinoma, retinoblastoma, Ewing sarcoma, prostate cancer, colon cancer, colorectal cancer, glioblastoma, rhabdomyosarcoma, ovarian cancer, head and neck cancer, e.g., head and neck squamous cell carcinomas, medulloblastoma and neuroblastoma. In specific aspects, the cancer is glioblastoma or neuroblastoma. In certain aspects the cancer comprises cells expressing ALK.

In specific aspects, the cancer comprises cells comprising an ALK mutation. In particular embodiments, the ALK mutation comprises a mutation of ALK amino acid residue 1174 (SEQ ID NO:467). In specific embodiments, the ALK mutation comprises a cysteine, isoleucine, leucine, serine, or valine amino acid substitution at ALK amino acid residue Phe1174 of SEQ ID NO:467. In specific embodiments, the ALK mutation comprises a leucine substitution at ALK amino acid residue Phe1174 of SEQ ID NO:467. In particular embodiments, the ALK mutation comprises a glutamine amino acid substitution at ALK amino acid residue Arg1275 of SEQ ID NO:467. In particular embodiments, the ALK mutation comprises a mutation of one or more of the following residues of SEQ ID NO:467: Pro36, Pro157, Val1198, Arg 259, Gly640, Leu684, Gly718, Met770, Asp993, Arg1060 (e.g., Arg1060His), Asp1091, Gly1128, Thr1151 (e.g., Thr1151Met), Met1166 (e.g., Met1166Arg), Ile1170 (e.g., Ile1170Asn or Ser), Ile1171 (e.g., Ile1171Asn), Phe1174, Arg1192, Leu1196 (e.g., Leu1196Met), Ala1200 (e.g., Ala1200Val), Leu1204 (e.g., Leu1204Phe), Glu1407, Glu1433, Leu1240 (e.g., Leu1240Val), Phe1245 (e.g., Phe1245Cys, Ile, Leu, or Val), Ile1250, Arg1464, Asp1270 (e.g., Asp1270Gly), Arg1275 (e.g., Arg1275Gln or Leu), Tyr1278 (e.g., Tyr1278Ser), Gly1286 (e.g., Gly1286Arg), Thr1343 (e.g, Thr1343Ile), Gly1494, or Ala1553. In particular embodiments, the ALK mutation is an ALK fusion gene, for example, an echinoderm microtubule-associated protein-like 4 (EML4)-ALK fusion gene, a nucleophosmin (NPM)-ALK fusion gene, or a tropomyosin 3 (TPM3)-ALK fusion gene. In specific embodiments, a EML4-ALK fusion gene is associated with lung cancer, for example, non-small cell lung cancer. In specific embodiments, a NPM-ALK fusion gene and/or a TPM3-ALK fusion gene is associated with anaplastic large-cell lymphoma.

In certain aspects, the subject being treated is a pediatric subject. For example, in certain aspects, provided herein is a method for treating cancer in a pediatric subject, comprising administering to the pediatric subject a therapeutically effective amount of an antibody or antigen-binding fragment thereof provided herein. In certain aspects, the cancer is glioblastoma, rhabdomyosarcoma, neuroblastoma, or medulloblastoma. In specific aspects, the cancer comprises cells comprising an ALK mutation. In particular embodiments, the ALK mutation comprises a mutation of ALK amino acid residue 1174 (SEQ ID NO:467). In specific embodiments, the ALK mutation comprises a cysteine, isoleucine, leucine, serine, or valine amino acid substitution at ALK amino acid residue Phe1174 of SEQ ID NO:467. In specific embodiments, the ALK mutation comprises a leucine substitution at ALK amino acid residue Phe1174 of SEQ ID NO:467. In particular embodiments, the ALK mutation comprises a glutamine amino acid substitution at ALK amino acid residue Arg1275 of SEQ ID NO:467. In particular embodiments, the ALK mutation comprises a mutation of one or more of the following residues of SEQ ID NO:467: Pro36, Pro157, Val1198, Arg 259, Gly640, Leu684, Gly718, Met770, Asp993, Arg1060 (e.g., Arg1060His), Asp1091, Gly1128, Thr1151 (e.g., Thr1151Met), Met1166 (e.g., Met1166Arg), Ile1170 (e.g., Ile1170Asn or Ser), Ile1171 (e.g., Ile1171Asn), Phe1174, Arg1192, Leu1196 (e.g., Leu1196Met), Ala1200 (e.g., Ala1200Val), Leu1204 (e.g., Leu1204Phe), Glu1407, Glu1433, Leu1240 (e.g., Leu1240Val), Phe1245 (e.g., Phe1245Cys, Ile, Leu, or Val), Ile1250, Arg1464, Asp1270 (e.g., Asp1270Gly), Arg1275 (e.g., Arg1275Gln or Leu), Tyr1278 (e.g., Tyr1278Ser), Gly1286 (e.g., Gly1286Arg), Thr1343 (e.g, Thr1343Ile), Gly1494, or Ala1553. In particular embodiments, the ALK mutation is an ALK fusion gene, for example, an echinoderm microtubule-associated protein-like 4 (EML4)-ALK fusion gene, a nucleophosmin (NPM)-ALK fusion gene, or a tropomyosin 3 (TPM3)-ALK fusion gene. In specific embodiments, a EML4-ALK fusion gene is associated with lung cancer, for example, non-small cell lung cancer. In specific embodiments, a NPM-ALK fusion gene and/or a TPM3-ALK fusion gene is associated with anaplastic large-cell lymphoma.

In certain aspects, provided herein is a method of treating neurofibromatosis in a subject, comprising administering to the subject a therapeutically effective amount of an antibody or antigen-binding fragment thereof provided herein. In certain aspects, the subject is a pediatric subject.

In certain aspects, provided herein is a kit comprising an antibody or antigen-binding fragment thereof provided herein.

In certain aspects, provided herein is a method of diagnosing a ALK-expressing cancer in a patient, wherein the method comprises the steps of:
(a) contacting a biological sample from the patient with an antibody or antigen-binding fragment provided herein;
(b) detecting binding of the antibody or antigen-binding fragment to ALK to determine an ALK protein level in the biological sample from the patient; and (c) comparing the ALK protein level with a standard ALK protein level.

In certain aspects, provided herein is a method of monitoring the ALK protein level during treatment of a ALK-expressing cancer in a patient, wherein the method comprises the steps of:
(a) administering to the patient an antibody or antigen-binding fragment provided herein;
(b) contacting a biological sample from the patient with the antibody or antigen-binding fragment;
(c) detecting binding of the antibody or antigen-binding fragment to ALK to determine an ALK protein level in the biological sample from the patient; and (d) comparing the ALK protein level with a standard ALK protein level.

4. BRIEF DESCRIPTION OF THE FIGURES

FIG. 1 depicts an exemplary amino acid sequence of human ALK (SEQ ID NO: 467), wherein amino acid residues 1-20 comprise the signal sequence.

Figure 3:
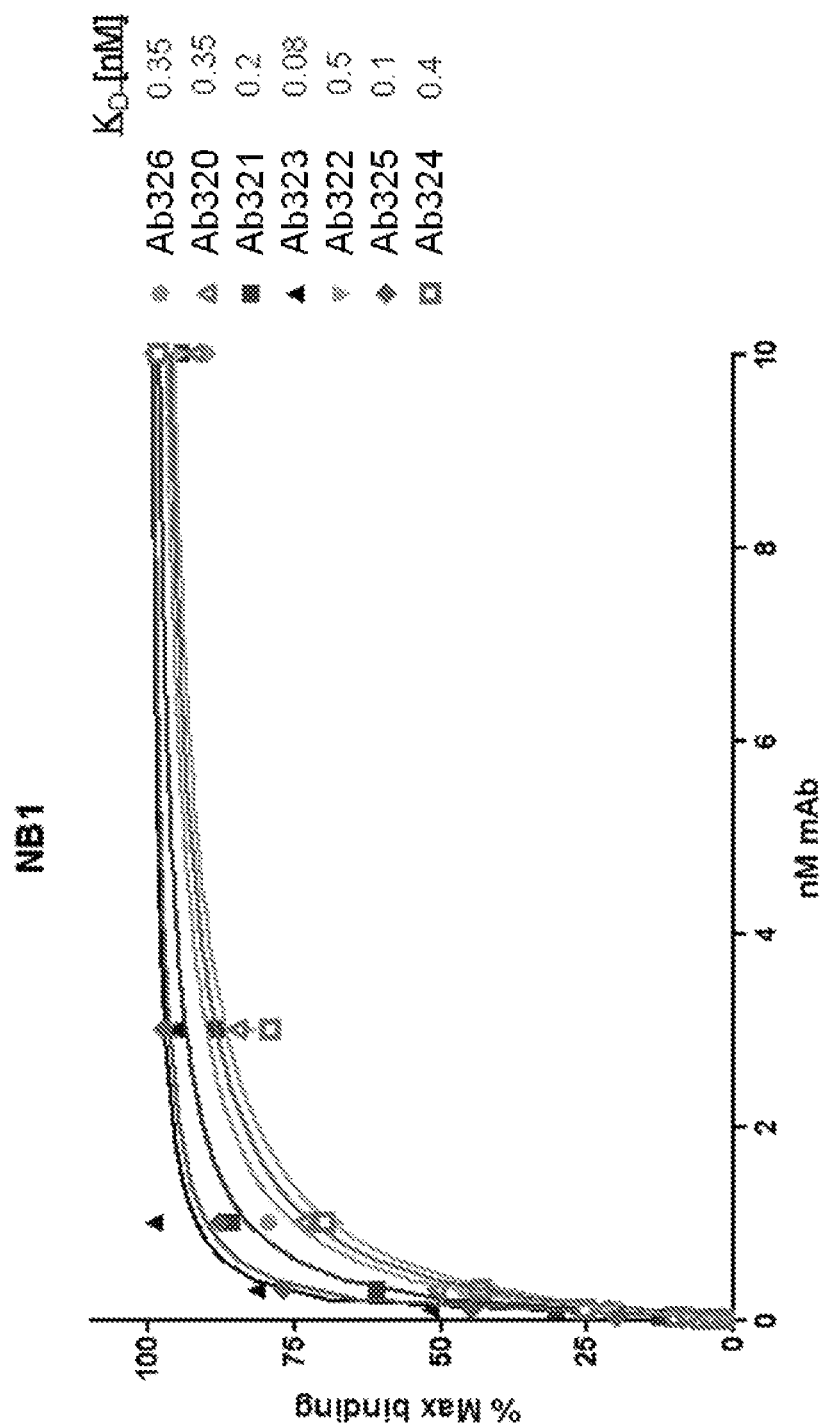

FIG. 3 depicts the apparent affinities ($K_D$) of ALK antibodies for ALK expression on the surface of NB1 cells. $K_D$ was determined by flow cytometry. Titration of each antibody on NB1 cells for 2-4 hours at 4° C. was followed by incubation with a fluorescently-labeled secondary antibody. The normalized mean fluorescent intensity (WI) shown as "% Max binding" was plotted as a function of antibody concentration.

Figure 4:
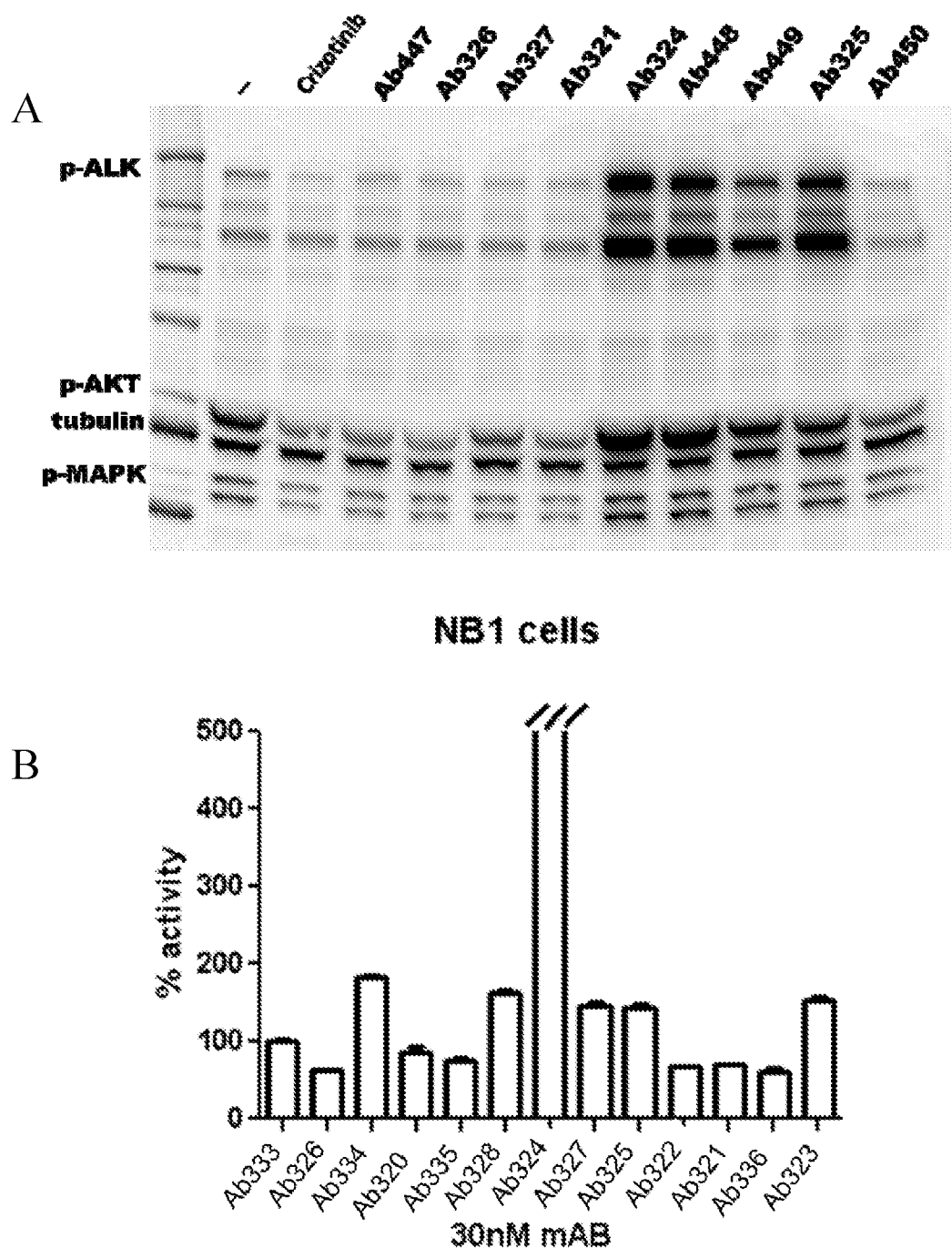

FIG. 4A depicts a Western blot depicting NB1 cells grown in media with reduced serum and treated with 30-100 nM of each antibody or the ALK inhibitor crizotinib for 1-2 hours. Lysed cells were subjected to SDS-PAGE, transferred to nitrocellulose and immunoblotted with antibodies against total, and phospho-specific ALK, AKT, and MAPK. FIG. 4B depicts an ELISA of NB1 cells grown in media with reduced serum and treated with 30-100 nM of each antibody for 1-2 hours. Cell lysates were incubated on ELISA plates with an anti-ALK antibody, followed by incubation with a pan phosphotyrosine antibody coupled to HRP.

Figure 5:
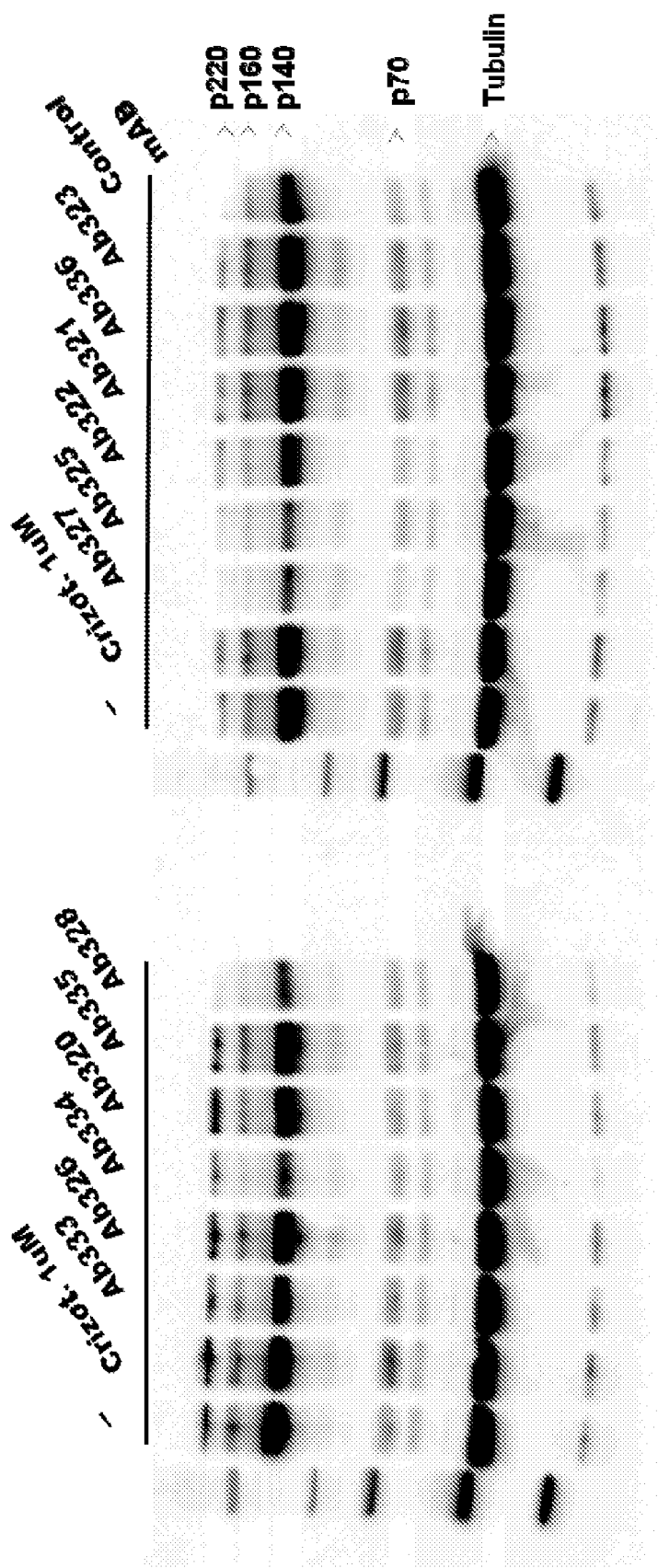

FIG. 5 depicts a Western blot of a panel of ALK antibodies. 24 hour treatment of NB1 cells with 100 nM of anti-ALK mAbs resulted in differences in ALK turnover (as measured by total protein levels).

Figure 6:
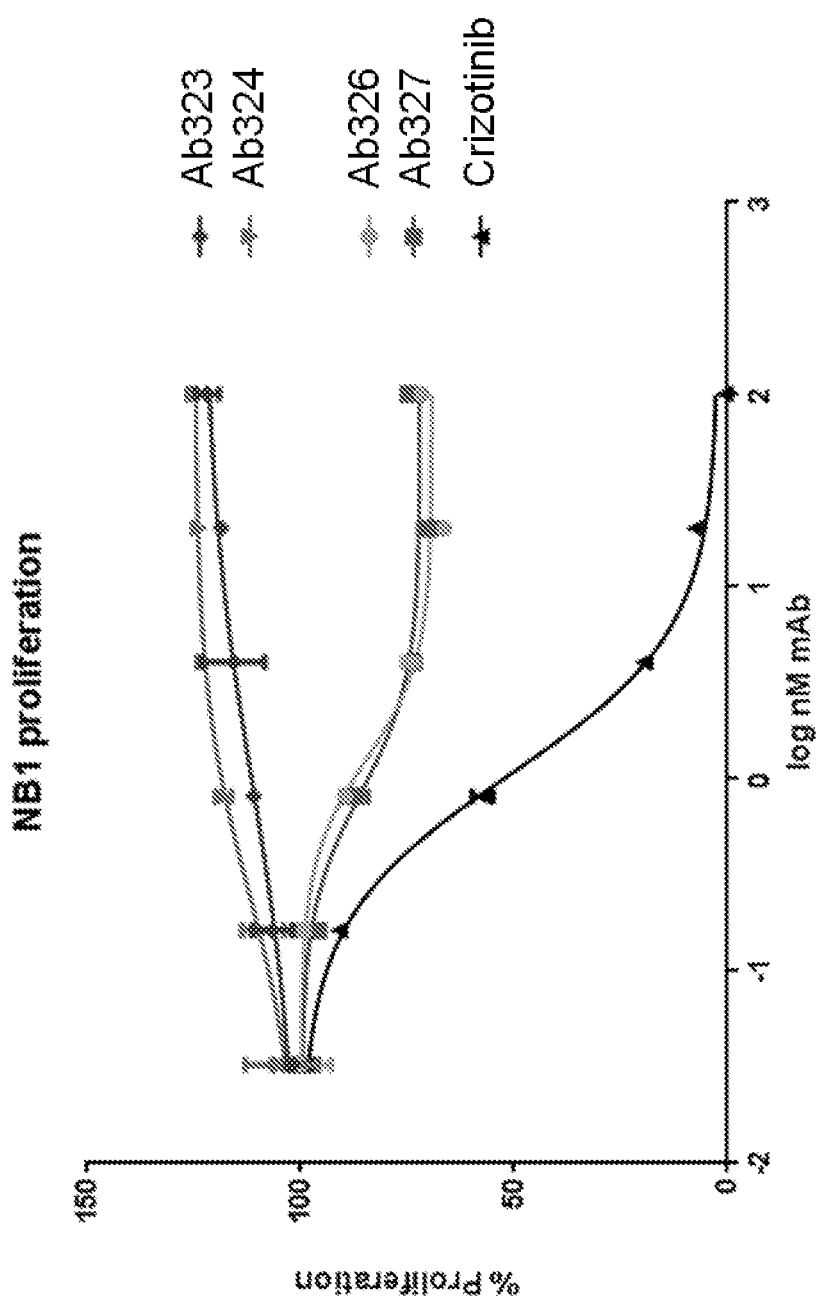

FIG. 6 depicts an ELISA showing the effect of ALK antibodies on the proliferation of NB1 cells. NB1 cells grown in media with reduced serum were treated with 30-100 nM of each antibody for 1-2 hours. Cell lysates were incubated on ELISA plates with an anti-ALK antibody, followed by incubation with a pan phosphotyrosine antibody coupled to HRP.

FIG. 7A depicts the effect of the titration of crizotinib, a small molecule ALK tyrosine kinase inhibitor, on the killing of NB1 cells. FIG. 7B depicts the co-titration of crizotinib with ALK inhibitory antibodies (Ab326 and Ab327) and ALK agonistic antibodies (Ab323 and Ab324).

Figure 8A:
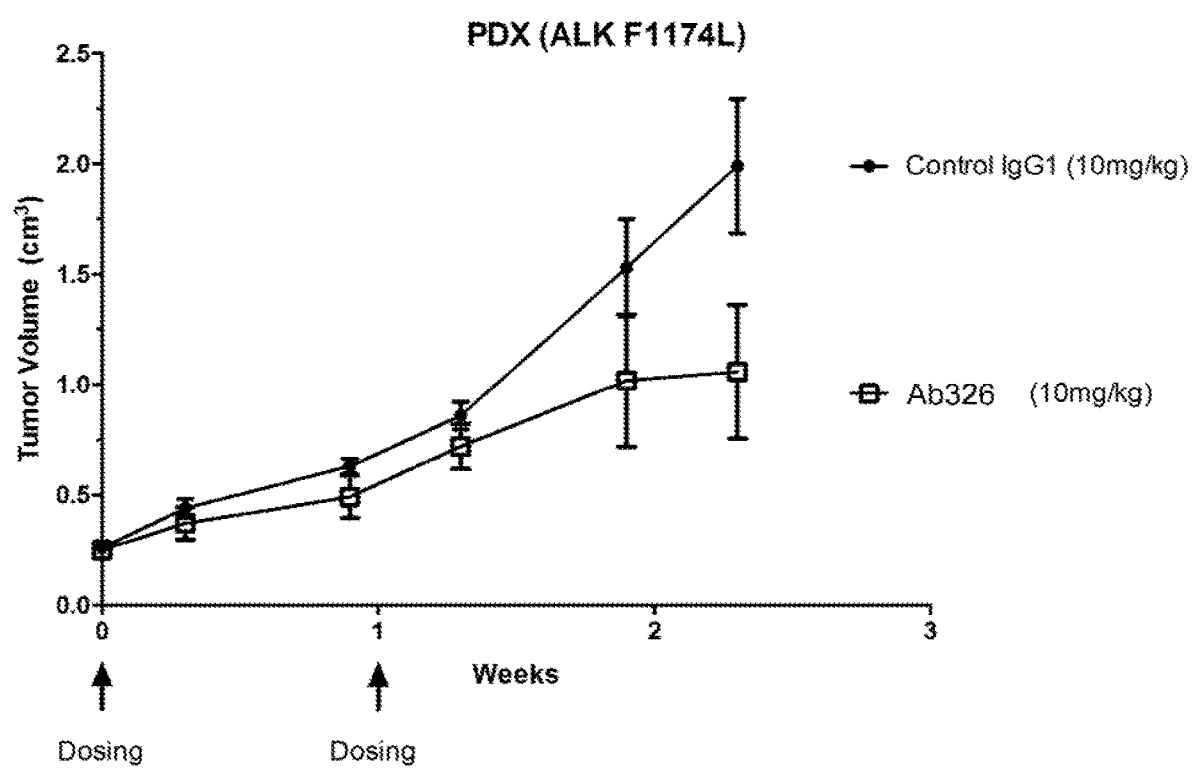
Figure 8B:
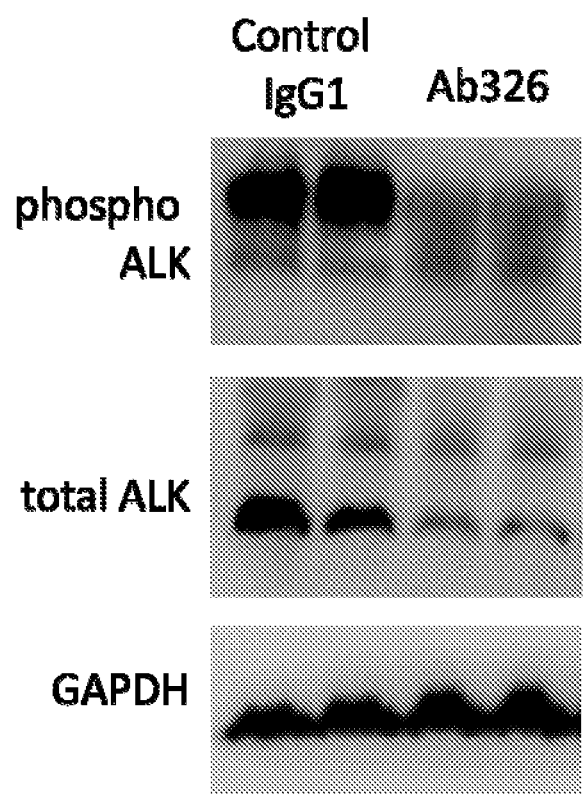

FIGS. 8A-B depict the in vivo antitumor activity of the Ab326 anti-ALK antibody in a patient-derived (PDX) neuroblastoma ALK F1174L tumor model compared with control IgG1 (A) and a western blot of tumor homogenates harvested from the patient-derived tumor model showing relative levels of total ALK and phosphorylated ALK in Ab326-treated and control IgG1-treated mice (B). GAPDH is included in the western blot of FIG. 8B as a control for protein level.

FIG. 9 depicts a sequence alignment of ALK species orthologs: human=hALK (SEQ ID NO: 519; see also SEQ ID NO: 467); mouse=mALK (SEQ ID NO: 517); rat=rALK (SEQ ID NO: 518). Boxed residues differ between rat and mouse ALK. Bold residues indicate the C-terminal ALK ECD antigen, used as an immunogen.

5. DETAILED DESCRIPTION

In one aspect, provided herein are antibodies ("ALK antibody" or "anti-ALK antibody), e.g., monoclonal antibodies, and antigen-binding fragments thereof, that specifically bind to an ALK polypeptide (e.g., an ECD of human ALK). In certain embodiments, such antibodies or antigen-binding fragments modulate ALK activity (e.g., ALK signaling) and/or ALK expression. In a specific embodiment, such antibodies or antigen-binding fragments, which specifically bind to an ECD of human ALK (e.g., the NTR, MAM1, LDLa, MAM2 or EGF domains of human ALK-ECD), bind to cell surface ALK and are internalized by the cell, and/or inhibit ALK activity (e.g., inhibit phosphorylation of ALK, induce ALK degradation, and/or inhibit tumor cell proliferation or tumor growth). Also provided are isolated nucleic acids (polynucleotides), such as complementary DNA (cDNA), encoding such antibodies, and antigen-binding fragments thereof. Further provided are vectors (e.g., expression vectors) and cells (e.g., host cells) comprising nucleic acids (polynucleotides) encoding such antibodies or antigen-binding fragments thereof. Also provided are methods of making such antibodies, antigen-binding fragments, and cells. In other aspects, provided herein are methods and uses for modulating ALK expression or ALK activity (e.g., inhibiting ALK expression or ALK activity), or treating or managing certain conditions or disorders described herein, such as treating or managing cancer. Related compositions (e.g., pharmaceutical compositions), kits, and diagnostic methods are also provided.

As used herein, the terms "ALK" or "ALK receptor" or "ALK polypeptide" refer to mammalian ALK, e.g., human ALK, including, for example, native ALK, ALK isoforms, and ALK fusion polypeptides resulting from genomic rearrangements, e.g., translocations. Native ALK is a transmembrane polypeptide that comprises an extracellular domain (ECD), a transmembrane domain, and a cytoplasmic domain. The ALK ECD comprises a basic N-terminal domain, two Meprin/A5/protein tyrosine phosphatase Mu (MAM) domains that flank a low-density lipoprotein class A (LDLa) domain, and a membrane-proximal glycine-rich domain. In a specific embodiment, the ALK is a human ALK of the amino acid sequence of SEQ ID NO: 467. GenBank™ accession numbers NP_004295.2 provides an exemplary human ALK amino acid sequence. GenBank™ accession number NM_004304.4 provides an exemplary human ALK nucleic acid. Unless otherwise specified herein, references to particular amino acid residues of ALK correspond to the amino acid residues of the human form of ALK set forth in SEQ ID NO: 467 and reproduced below:

```
  1 MGAIGLLWLL  PLLLSTAAVG  SGMGTGQRAG  SPAAGPPLQP  REPLSYSRLQ  RKSLAVDFVV
 61 PSLFRVYARD  LLLPPSSSEL  KAGRPEARGS  LALDCAPLLR  LLGPAPGVSW  TAGSPAPAEA
```

```
 121  RTLSRVLKGG  SVRKLRRAKQ  LVLELGEEAI  LEGCVGPPGE  AAVGLLQFNL  SELFSWWIRQ

181  GEGRLRIRLM  PEKKASEVGR  EGRLSAAIRA  SQPRLLFQIF  GTGHSSLESP  TNMPSPSPDY

241  FTWNLTWIMK  DSFPFLSHRS  RYGLECSFDF  PCELEYSPPL  HDLRNQSWSW  RRIPSEEASQ

301  MDLLDGPGAE  RSKEMPRGSF  LLLNTSADSK  HTILSPWMRS  SSEHCTLAVS  VHRHLQPSGR

361  YIAQLLPHNE  AAREILLMPT  PGKHGWTVLQ  GRIGRPDNPF  RVALEYISSG  NRSLSAVDFF

421  ALKNCSEGTS  PGSKMALQSS  FTCWNGTVLQ  LGQACDFHQD  CAQGEDESQM  CRKLPVGFYC

481  NFEDGFCGWT  QGTLSPHTPQ  WQVRTLKDAR  FQDHQDHALL  LSTTDVPASE  SATVTSATFP

541  APIKSSPCEL  RMSWLIRGVL  RGNVSLVLVE  NKTGKEQGRM  VWHVAAYEGL  SLWQWMVLPL

601  LDVSDRFWLQ  MVAWWGQGSR  AIVAFDNISI  SLDCYLTISG  EDKILQNTAP  KSRNLFERNP

661  NKELKPGENS  PRQTPIFDPT  VHWLFTTCGA  SGPHGPTQAQ  CNNAYQNSNL  SVEVGSEGPL

721  KGIQIWKVPA  TDTYSISGYG  AAGGKGGKNT  MMRSHGVSVL  GIFNLEKDDM  LYILVGQQGE

781  DACPSTNQLI  QKVCIGENNV  IEEEIRVNRS  VHEWAGGGGG  GGGATYVFKM  KDGVPVPLII

841  AAGGGGRAYG  AKTDTFHPER  LENNSSVLGL  NGNSGAAGGG  GGWNDNTSLL  WAGKSLQEGA

901  TGGHSCPQAM  KKWGWETRGG  FGGGGGGCSS  GGGGGGYIGG  NAASNNDPEM  DGEDGVSFIS

961  PLGILYTPAL  KVMEGHGEVN  IKHYLNCSHC  EVDECHMDPE  SHKVICFCDH  GTVLAEDGVS

1021  CIVSPTPEPH  LPLSLILSVV  TSALVAALVL  AFSGIMIVYR  RKHQELQAMQ  MELQSPEYKL

1081  SKLRTSTIMT  DYNPNYCFAG  KTSSISDLKE  VPRKNITLIR  GLGHGAFGEV  YEGQVSGMPN

1141  DPSPLQVAVK  TLPEVCSEQD  ELDFLMEALI  ISKFNHQNIV  RCIGVSLQSL  PRFILLELMA

1201  GGDLKSFLRE  TRPRPSQPSS  LAMLDLLHVA  RDIACGCQYL  EENHFIHRDI  AARNCLLTCP

1261  GPGRVAKIGD  FGMARDIYRA  SYYRKGGCAM  LPVKWMPPEA  FMEGIFTSKT  DTWSFGVLLW

1321  EIFSLGYMPY  PSKSNQEVLE  FVTSGGRMDP  PKNCPGPVYR  IMTQCWQHQP  EDRPNFAIIL

1381  ERIEYCTQDP  DVINTALPIE  YGPLVEEEEK  VPVRPKDPEG  VPPLLVSQQA  KREEERSPAA

1441  PPPLPTTSSG  KAAKKPTAAE  ISVRVPRGPA  VEGGHVNMAF  SQSNPPSELH  KVHGSRNKPT

1501  SLWNPTYGSW  FTEKPTKKNN  PIAKKEPHDR  GNLGLEGSCT  VPPNVATGRL  PGASLLLEPS

1561  SLTANMKEVP  LFRLRHFPCG  NVNYGYQQQG  LPLEAATAPG  AGHYEDTILK  SKNSMNQPGP
```

The ALK extracellular domain corresponds to amino acids 21-1038, the N-terminal domain corresponds to amino acids 21-263, the first MAM domain (MAM1) corresponds to amino acids 264-427, the LDLa domain corresponds to amino acids 437-473), the second MAM domain (MAM2) corresponds to amino acids 478-636, the glycine-rich domain corresponds to amino acids 816-940, the transmembrane domain corresponds to amino acids 1039-1059, the intracellular domain corresponds to amino acids 1060-1620, with the kinase domain corresponding to amino acids 1116-1392; the immature ALK sequence also includes a signal peptide at amino acids 1-20.

5.1 Antibodies

In a specific aspect, provided herein are antibodies (e.g., monoclonal antibodies, such as chimeric or humanized, for example, composite human, antibodies) which specifically bind to an extracellular domain (ECD) of human ALK (e.g., the NTR, MAM1, LDLa, MAM2 or EGF domains of human ALK-ECD). In particular embodiments, such antibodies modulate ALK expression and/or ALK activity. In particular embodiments, such antibodies bind to ALK on the surface of a cell, and are internalized.

In a specific aspect, provided herein are antigen-binding fragments of antibodies (e.g., antigen-binding fragments of monoclonal antibodies, such as chimeric or humanized, for example, composite human, antibodies) which specifically bind to an extracellular domain (ECD) of human ALK (e.g., the NTR, MAM1, LDLa, MAM2 or EGF domains of human ALK-ECD). In particular embodiments, such antigen-binding fragments modulate ALK expression and/or ALK activity. In particular embodiments, such antigen-binding fragments bind to ALK on the surface of a cell, and are internalized.

In certain embodiments, an anti-ALK antibody described herein, or an antigen-binding fragment thereof, inhibits ALK activity (e.g., ligand-dependent ALK activity and ligand-independent ALK activity) in a cell, for example, as determined by inhibition of phosphorylation of ALK, cell proliferation, and/or cell morphology. In certain embodiments, an anti-ALK antibody described herein or an antigen-binding fragment thereof inhibits ALK ligand binding to ALK receptor. In certain embodiments, an anti-ALK antibody described herein or an antigen-binding fragment thereof inhibits dimerization of the ALK receptor. In certain embodiments, an anti-ALK antibody described herein or an antigen-binding fragment thereof induces ALK receptor degradation. In certain embodiments, an anti-ALK antibody described herein or an antigen-binding fragment thereof inhibits tumor cell proliferation or tumor growth.

In certain embodiments, an anti-ALK antibody described herein, or an antigen-binding fragment thereof, increases ALK activity in a cell, for example, as determined by increase in phosphorylation of ALK, increased cell proliferation, and/or change in cell morphology. In certain embodiments, an anti-ALK antibody described herein or an antigen-binding fragment thereof increases ALK ligand binding to ALK receptor. In certain embodiments, an anti-ALK antibody described herein or an antigen-binding fragment thereof reduces ALK receptor degradation. In certain embodiments, an anti-ALK antibody described herein or an antigen-binding fragment thereof increases cell growth or proliferation.

In certain embodiments, an anti-ALK antibody described herein or an antigen-binding fragment thereof specifically binds to human ALK, but not mouse ALK. In certain embodiments, antibodies or antigen-binding fragments described herein can comprise sequences that do not naturally exist within the antibody germline repertoire of an animal or mammal (e.g., human) in vivo. As used herein and unless otherwise specified, the terms "about" or "approximately" mean within plus or minus 10% of a given value or range. In instances where an integer is required, the terms mean within plus or minus 10% of a given value or range, rounded either up or down to the nearest integer.

The term "antigen-binding agent" or "binding agent" or "binding protein" refers to an agent (e.g., a protein) comprising a portion (e.g., one or more binding regions such as CDRs) that binds to ALK (e.g., the ECD of ALK), and, optionally, a scaffold or framework portion (e.g., one or more scaffold or framework regions) that allows the binding portion to adopt a conformation that promotes binding of the antigen-binding agent to an ALK polypeptide, fragment, or epitope. Examples of such antigen-binding agents include antibodies, such as a human antibody, a humanized antibody, a chimeric antibody, a recombinant antibody, a single chain antibody, a diabody, a triabody, a tetrabody, a Fab fragment, a F(ab')$_2$ fragment, an IgD antibody, an IgE antibody, an IgM antibody, an IgG1 antibody, an IgG2 antibody, an IgG3 antibody, or an IgG4 antibody, and fragments thereof. The antigen-binding agent can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics 53(1):121-29; and Roque et al., 2004, Biotechnol. Prog. 20:639-54. In addition, peptide antibody mimetics ("PAMs") can be used, as well as scaffolds based on antibody mimetics utilizing fibronectin components as a scaffold.

As used herein, the terms "antibody" and "immunoglobulin" and "Ig" are terms of art and can be used interchangeably herein and refer to a molecule with an antigen binding site that specifically binds an antigen.

Antibodies can include, for example, monoclonal antibodies, recombinantly produced antibodies, monospecific antibodies, multispecific antibodies (including bispecific antibodies), human antibodies, humanized antibodies, such as composite human antibodies or deimmunized antibodies, murine antibodies (e.g., mouse or rat antibodies), chimeric antibodies, synthetic antibodies, and tetrameric antibodies comprising two heavy chain and two light chain molecules. In specific embodiments, antibodies can include, but are not limited to an antibody light chain monomer, an antibody heavy chain monomer, an antibody light chain dimer, an antibody heavy chain dimer, an antibody light chain/antibody heavy chain pair, an antibody with two light chain/heavy chain pairs (e.g., identical pairs), intrabodies, heteroconjugate antibodies, single domain antibodies, monovalent antibodies, bivalent antibodies, single chain antibodies or single-chain Fvs (scFv) (e.g., including monospecific, bispecific, etc.), camelized antibodies, and affybodies. Antigen-binding fragments can include antigen-binding fragments or epitope binding fragments such as, but not limited to, Fab fragments, F(ab') fragments, F(ab')$_2$ fragments, and disulfide-linked Fvs (sdFv). In certain embodiments, antibodies described herein refer to polyclonal antibody populations.

Antibodies can be of any type (e.g., IgG, IgE, IgM, IgD, IgA or IgY), any class, (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies (e.g., human IgG), or a class (e.g., human IgG$_1$, IgG$_2$, IgG$_3$, or IgG$_4$) or subclass thereof.

In a particular embodiment, an antibody is a 4-chain antibody unit comprising two heavy (H) chain/light (L) chain pairs, wherein the amino acid sequences of the H chains are identical and the amino acid sequences of the L chains are identical. In a specific embodiment, the H and L chain comprise constant regions, for example, human constant regions. In a yet more specific embodiment, the L chain constant region of such antibodies is a kappa or lambda light chain constant region, for example, a human kappa or lambda light chain constant region. In another specific embodiment, the H chain constant region of such antibodies comprise a gamma heavy chain constant region, for example, a human gamma heavy chain constant region. In a particular embodiment, such antibodies comprise IgG constant regions, for example, human IgG constant regions.

As used herein, an "antigen" is a moiety or molecule that contains an epitope to which an antibody can specifically bind. As such, an antigen is also specifically bound by an antibody. In a particular embodiment, the antigen to which an antibody described herein binds, is human ALK, or a fragment thereof, for example, an ECD domain of human ALK.

As used herein, an "epitope" is a term in the art and refers to a localized region of an antigen to which an antibody can specifically bind. An epitope can be a linear epitope or a conformational, non-linear, or discontinuous, epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, an antibody binds to a group of amino acids regardless of whether they are folded in a natural three dimensional protein structure. In other embodiments, an antibody requires amino acid residues making up the epitope to exhibit a particular conformation (e.g., bend, twist, turn or fold) in order to recognize and bind the epitope.

As used herein, the terms "immunospecifically binds," "immunospecifically recognizes," "specifically binds," and "specifically recognizes" are analogous terms in the context of antibodies and refer to molecules that bind to an antigen/ epitope as such binding is understood by one skilled in the art. For example, a molecule that specifically binds to an antigen may bind to other peptides or polypeptides, generally with lower affinity as determined by, e.g., immunoassays, surface plasmon resonance assays, for example, Biacore™, KinExA platform (Sapidyne Instruments, Boise, Id.), or other assays known in the art. In a specific embodiment, molecules that specifically bind to an antigen bind to the antigen with a $K_a$ that is at least 2 logs, 2.5 logs, 3 logs, 4 logs or greater than the $K_a$ when the molecules bind to another antigen. In another specific embodiment, molecules that specifically bind to an antigen do not cross react with other proteins. In another specific embodiment, molecules that specifically bind to an antigen do not cross react with other non-ALK proteins.

As used herein, the term "monoclonal antibody" is a well known term of art that refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single cell or cell line wherein the antibody immunospecifically binds to an ALK epitope (e.g., an epitope of the extracellular domain of human ALK) as determined, e.g., by ELISA or other antigen-binding or competitive binding assay known in the art or in the Examples provided herein. In particular embodiments, a monoclonal antibody can be a chimeric antibody or a humanized antibody. In particular embodiments, a monoclonal antibody can be a composite human antibody. In particular embodiments, a monoclonal antibody can be a deimmunized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody).

As used herein, the term "polyclonal antibodies" refers to an antibody population that includes a variety of different antibodies that immunospecifically bind to the same and/or to different epitopes within an antigen or antigens.

As used herein, the terms "variable region" or "variable domain" refer to a portion of an antibody, generally, a portion of an antibody light or heavy chain, typically corresponding to about the amino-terminal 110 to 120 amino acids in a mature heavy chain and about the amino-terminal 90 to 100 amino acids in a mature light chain. Variable regions comprise complementarity determining regions (CDRs) flanked by framework regions (FRs). Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction of the antibody with antigen and for the specificity of the antibody for an epitope. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242. In certain embodiments, the variable region is a human variable region. In certain embodiments, the variable region comprises murine (e.g., mouse or rat) CDRs and human framework regions (FRs). In particular embodiments, the variable region is a primate (e.g., human or non-human primate) variable region. In certain embodiments, the variable region comprises murine (e.g., mouse or rat) CDRs and primate (e.g., human or non-human primate) framework regions (FRs). As a non-limiting example, a variable region described herein is obtained from assembling two or more fragments of human sequences into a composite human sequence.

In certain aspects, the CDRs of an antibody can be determined according to (i) the Kabat numbering system (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226); or (iii) the ImMunoGeneTics (IMGT) numbering system, for example, as described in Lefranc, M.-P., 1999, The Immunologist, 7:132-136 and Lefranc, M.-P. et al., 1999, Nucleic Acids Res., 27:209-212 ("IMGT CDRs"); or (iv) MacCallum et al., 1996, J. Mol. Biol., 262:732-745. See also, e.g., Martin, A., "Protein Sequence and Structure Analysis of Antibody Variable Domains," in *Antibody Engineering*, Kontermann and Dithel, eds., Chapter 31, pp. 422-439, Springer-Verlag, Berlin (2001).

With respect to the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

In a specific embodiment, an anti-ALK antibody provided herein or an antigen-binding fragment thereof comprises CDRs of a VL region and CDRs of a VH region of any one of antibodies Ab320-Ab332 and Ab351-Ab446 described herein, and specifically binds ALK, e.g., human ALK, for example, ALK ECD, e.g. human ALK ECD. For example, provided herein are antibodies, and antigen-binding fragments thereof, that specifically bind ALK and comprise CDRs of a VL domain in Table 13, below, and CDRs of a VH domain in Table 14, below. In a specific embodiment, an anti-ALK antibody provided herein, or an antigen-binding fragment thereof, comprises a VL region and a VH region of any one of antibodies Ab320-Ab332 and Ab351-Ab446 described herein. For example, provided herein are antibodies, and antigen-binding fragments thereof, that specifically bind ALK and comprise a VL domain in Table 13, below, and VH domain in Table 14, below.

In certain embodiments, an antibody described herein comprises a VL domain as described herein, wherein the VL domain does not comprise a signal sequence. In certain embodiments, an antibody described herein comprises a VH domain as described herein, wherein the VH domain does not comprise a signal sequence. In certain embodiments, an antibody described herein comprises a VL domain and a VH domain, wherein the VL domain does not comprise a signal sequence, and wherein the VH domain does not comprise a signal sequence. In certain embodiments, an antibody described herein comprises a VL domain, wherein the VL domain comprises a signal sequence. In certain embodiments, an antibody described herein comprises a VH domain, wherein the VH domain comprises a signal sequence. In certain embodiments, an antibody described herein comprises a VL domain and a VH domain, wherein the VL domain comprises a signal sequence, and wherein the VH domain comprises a signal sequence.

In a specific embodiment, an anti-ALK antibody described herein or an antigen-binding fragment thereof comprises a VL region comprising SEQ ID NO: 395 and a VH region comprising SEQ ID NO: 396 (e.g., antibody Ab320). In a specific embodiment, an anti-ALK antibody described herein or an antigen-binding fragment thereof comprises a VL region comprising SEQ ID NO: 397 and a VH region comprising SEQ ID NO: 398 (e.g., antibody Ab321). In a specific embodiment, an anti-ALK antibody described herein or an antigen-binding fragment thereof comprises a VL region comprising SEQ ID NO: 399 and a VH region comprising SEQ ID NO: 400 (e.g., antibody Ab322). In a specific embodiment, an anti-ALK antibody described herein or an antigen-binding fragment thereof comprises a VL region comprising SEQ ID NO: 401 and a VH region comprising SEQ ID NO: 402 (e.g., antibody Ab323). In a specific embodiment, an anti-ALK antibody described herein or an antigen-binding fragment thereof comprises a VL region comprising SEQ ID NO: 403 and a VH region comprising SEQ ID NO: 404 (e.g., antibody Ab324). In a specific embodiment, an anti-ALK antibody described herein or an antigen-binding fragment thereof comprises a VL region comprising SEQ ID NO: 405 and a VH region comprising SEQ ID NO: 406 (e.g., antibody Ab325). In a specific embodiment, an anti-ALK antibody described herein or an antigen-binding fragment thereof comprises a VL region comprising SEQ ID NO: 407 and a VH region comprising SEQ ID NO: 408 (e.g., antibody Ab326). In a specific embodiment, an anti-ALK antibody described herein or an antigen-binding fragment thereof comprises a VL region comprising SEQ ID NO: 409 and a VH region comprising SEQ ID NO: 410 (e.g., antibody Ab327). In a specific embodiment, an anti-ALK antibody described herein or an antigen-binding fragment thereof comprises a VL region comprising SEQ ID NO: 411 and a VH region comprising SEQ ID NO: 412 (e.g., antibody Ab328). In a specific embodiment, an anti-ALK antibody described herein or an antigen-binding fragment thereof comprises a VL region comprising SEQ ID NO: 413 and a VH region comprising SEQ ID NO: 414 (e.g., antibody Ab329). In a specific embodiment, an anti-ALK antibody described herein or an antigen-binding fragment thereof comprises a VL region comprising SEQ ID NO: 415 and a VH region comprising SEQ ID NO: 416 (e.g., antibody Ab330). In a specific embodiment, an anti-ALK antibody described herein or an antigen-binding fragment thereof comprises a VL region comprising SEQ ID NO: 417 and a VH region comprising SEQ ID NO: 418 (e.g., antibody Ab331). In a specific embodiment, an anti-ALK antibody described herein or an antigen-binding fragment thereof comprises a VL region comprising SEQ ID NO: 419 and a VH region comprising SEQ ID NO: 420 (e.g., antibody Ab332).

In a specific embodiment, an anti-ALK antibody described herein or an antigen-binding fragment thereof comprises a VL region comprising SEQ ID NO: 421 and a VH region comprising SEQ ID NO: 429 (e.g., antibody Ab351). In a specific embodiment, an anti-ALK antibody described herein or an antigen-binding fragment thereof comprises a VL region comprising SEQ ID NO: 421 and a VH region comprising SEQ ID NO: 430 (e.g., antibody Ab352). In a specific embodiment, an anti-ALK antibody described herein or an antigen-binding fragment thereof comprises a VL region comprising SEQ ID NO: 421 and a VH region comprising SEQ ID NO: 431 (e.g., antibody Ab353). In a specific embodiment, an anti-ALK antibody described herein or an antigen-binding fragment thereof comprises a VL region comprising SEQ ID NO: 421 and a VH region comprising SEQ ID NO: 432 (e.g., antibody Ab354). In a specific embodiment, an anti-ALK antibody described herein or an antigen-binding fragment thereof comprises a VL region comprising SEQ ID NO: 421 and a VH region comprising SEQ ID NO: 433 (e.g., antibody Ab355). In a specific embodiment, an anti-ALK antibody described herein or an antigen-binding fragment thereof comprises a VL region comprising SEQ ID NO: 421 and a VH region comprising SEQ ID NO: 434 (e.g., antibody Ab356). In a specific embodiment, an anti-ALK antibody described herein or an antigen-binding fragment thereof comprises a VL region comprising SEQ ID NO: 421 and a VH region comprising SEQ ID NO: 435 (e.g., antibody Ab357). In a specific embodiment, an anti-ALK antibody described herein or an antigen-binding fragment thereof comprises a VL region comprising SEQ ID NO: 421 and a VH region comprising SEQ ID NO: 436 (e.g., antibody Ab358). In a specific embodiment, an anti-ALK antibody described herein or an antigen-binding fragment thereof comprises a VL region comprising SEQ ID NO: 421 and a VH region comprising SEQ ID NO: 437 (e.g., antibody Ab359). In a specific embodiment, an anti-ALK antibody described herein or an antigen-binding fragment thereof comprises a VL region comprising SEQ ID NO: 421 and a VH region comprising SEQ ID NO: 438 (e.g., antibody Ab360). In a specific embodiment, an anti-ALK antibody described herein or an antigen-binding fragment thereof comprises a VL region comprising SEQ ID NO: 421 and a VH region comprising SEQ ID NO: 439 (e.g., antibody Ab361). In a specific embodiment, an anti-ALK antibody described herein or an antigen-binding fragment thereof comprises a VL region comprising SEQ ID NO: 421 and a VH region comprising SEQ ID NO: 440 (e.g., antibody Ab362).

In a specific embodiment, an anti-ALK antibody described herein or an antigen-binding fragment thereof comprises a VL region comprising SEQ ID NO: 422 and a VH region comprising SEQ ID NO: 429 (e.g., antibody Ab363). In a specific embodiment, an anti-ALK antibody described herein or an antigen-binding fragment thereof comprises a VL region comprising SEQ ID NO: 422 and a VH region comprising SEQ ID NO: 430 (e.g., antibody Ab364). In a specific embodiment, an anti-ALK antibody described herein or an antigen-binding fragment thereof comprises a VL region comprising SEQ ID NO: 422 and a VH region comprising SEQ ID NO: 431 (e.g., antibody Ab365). In a specific embodiment, an anti-ALK antibody described herein or an antigen-binding fragment thereof comprises a VL region comprising SEQ ID NO: 422 and a VH region comprising SEQ ID NO: 432 (e.g., antibody Ab366). In a specific embodiment, an anti-ALK antibody described herein or an antigen-binding fragment thereof comprises a VL region comprising SEQ ID NO: 422 and a VH region comprising SEQ ID NO: 433 (e.g., antibody Ab367). In a specific embodiment, an anti-ALK antibody described herein or an antigen-binding fragment thereof comprises a VL region comprising SEQ ID NO: 422 and a VH region comprising SEQ ID NO: 434 (e.g., antibody Ab368). In a specific embodiment, an anti-ALK antibody described herein or an antigen-binding fragment thereof comprises a VL region comprising SEQ ID NO: 422 and a VH region comprising SEQ ID NO: 435 (e.g., antibody Ab369). In a specific embodiment, an anti-ALK antibody described herein or an antigen-binding fragment thereof comprises a VL region comprising SEQ ID NO: 422 and a VH region comprising SEQ ID NO: 436 (e.g., antibody Ab370). In a specific embodiment, an anti-ALK antibody described herein or an antigen-binding fragment thereof comprises a VL region comprising SEQ ID NO: 422 and a VH region comprising SEQ ID NO: 437 (e.g., antibody Ab371). In a specific embodiment, an anti-ALK antibody described herein or an antigen-binding fragment thereof comprises a VL region comprising SEQ ID NO: 422 and a VH region comprising SEQ ID NO: 438 (e.g., antibody Ab372). In a specific embodiment, an anti-ALK antibody described herein or an antigen-binding fragment thereof comprises a VL region comprising SEQ ID NO: 422 and a VH region comprising SEQ ID NO: 439 (e.g., antibody Ab373). In a specific embodiment, an anti-ALK antibody described herein or an antigen-binding fragment thereof comprises a VL region comprising SEQ ID NO: 422 and a VH region comprising SEQ ID NO: 440 (e.g., antibody Ab374).

In a specific embodiment, an anti-ALK antibody described herein or an antigen-binding fragment thereof comprises a VL region comprising SEQ ID NO: 423 and a VH region comprising SEQ ID NO: 429 (e.g., antibody Ab375). In a specific embodiment, an anti-ALK antibody described herein or an antigen-binding fragment thereof comprises a VL region comprising SEQ ID NO: 423 and a VH region comprising SEQ ID NO: 430 (e.g., antibody Ab376). In a specific embodiment, an anti-ALK antibody described herein or an antigen-binding fragment thereof comprises a VL region comprising SEQ ID NO: 423 and a VH region comprising SEQ ID NO: 431 (e.g., antibody Ab377). In a specific embodiment, an anti-ALK antibody described herein or an antigen-binding fragment thereof comprises a VL region comprising SEQ ID NO: 423 and a VH region comprising SEQ ID NO: 432 (e.g., antibody Ab378). In a specific embodiment, an anti-ALK antibody described herein or an antigen-binding fragment thereof comprises a VL region comprising SEQ ID NO: 423 and a VH region comprising SEQ ID NO: 433 (e.g., antibody Ab379). In a specific embodiment, an anti-ALK antibody described herein or an antigen-binding fragment thereof comprises a VL region comprising SEQ ID NO: 423 and a VH region comprising SEQ ID NO: 434 (e.g., antibody Ab380). In a specific embodiment, an anti-ALK antibody described herein or an antigen-binding fragment thereof comprises a VL region comprising SEQ ID NO: 423 and a VH region comprising SEQ ID NO: 435 (e.g., antibody Ab381). In a specific embodiment, an anti-ALK antibody described herein or an antigen-binding fragment thereof comprises a VL region comprising SEQ ID NO: 423 and a VH region comprising SEQ ID NO: 436 (e.g., antibody Ab382). In a specific embodiment, an anti-ALK antibody described herein or an antigen-binding fragment thereof comprises a VL region comprising SEQ ID NO: 423 and a VH region comprising SEQ ID NO: 437 (e.g., antibody Ab383). In a specific embodiment, an anti-ALK antibody described herein or an antigen-binding fragment thereof comprises a VL region comprising SEQ ID NO: 423 and a VH region comprising SEQ ID NO: 438 (e.g., antibody Ab384). In a specific embodiment, an anti-ALK antibody described herein or an antigen-binding fragment thereof comprises a VL region comprising SEQ ID NO: 423 and a VH region comprising SEQ ID NO: 439 (e.g., antibody Ab385). In a specific embodiment, an anti-ALK antibody described herein or an antigen-binding fragment thereof comprises a VL region comprising SEQ ID NO: 423 and a VH region comprising SEQ ID NO: 440 (e.g., antibody Ab386).

In a specific embodiment, an anti-ALK antibody described herein or an antigen-binding fragment thereof comprises a VL region comprising SEQ ID NO: 424 and a VH region comprising SEQ ID NO: 429 (e.g., antibody Ab387). In a specific embodiment, an anti-ALK antibody described herein or an antigen-binding fragment thereof comprises a VL region comprising SEQ ID NO: 424 and a VH region comprising SEQ ID NO: 430 (e.g., antibody Ab388). In a specific embodiment, an anti-ALK antibody described herein or an antigen-binding fragment thereof comprises a VL region comprising SEQ ID NO: 424 and a VH region comprising SEQ ID NO: 431 (e.g., antibody Ab389). In a specific embodiment, an anti-ALK antibody described herein or an antigen-binding fragment thereof comprises a VL region comprising SEQ ID NO: 424 and a VH region comprising SEQ ID NO: 432 (e.g., antibody Ab390). In a specific embodiment, an anti-ALK antibody described herein or an antigen-binding fragment thereof comprises a VL region comprising SEQ ID NO: 424 and a VH region comprising SEQ ID NO: 433 (e.g., antibody Ab391). In a specific embodiment, an anti-ALK antibody described herein or an antigen-binding fragment thereof comprises a VL region comprising SEQ ID NO: 424 and a VH region comprising SEQ ID NO: 434 (e.g., antibody Ab392). In a specific embodiment, an anti-ALK antibody described herein or an antigen-binding fragment thereof comprises a VL region comprising SEQ ID NO: 424 and a VH region comprising SEQ ID NO: 435 (e.g., antibody Ab393). In a specific embodiment, an anti-ALK antibody described herein or an antigen-binding fragment thereof comprises a VL region comprising SEQ ID NO: 424 and a VH region comprising SEQ ID NO: 436 (e.g., antibody Ab394). In a specific embodiment, an anti-ALK antibody described herein or an antigen-binding fragment thereof comprises a VL region comprising SEQ ID NO: 424 and a VH region comprising SEQ ID NO: 437 (e.g., antibody Ab395). In a specific embodiment, an anti-ALK antibody described herein or an antigen-binding fragment thereof comprises a VL region comprising SEQ ID NO: 424 and a VH region comprising SEQ ID NO: 438 (e.g., antibody Ab396). In a specific embodiment, an anti-ALK antibody described herein or an antigen-binding fragment thereof comprises a VL region comprising SEQ ID NO: 424 and a VH region comprising SEQ ID NO: 439 (e.g., antibody Ab397). In a specific embodiment, an anti-ALK antibody described herein or an antigen-binding fragment thereof comprises a VL region comprising SEQ ID NO: 424 and a VH region comprising SEQ ID NO: 440 (e.g., antibody Ab398).

In a specific embodiment, an anti-ALK antibody described herein or an antigen-binding fragment thereof comprises a VL region comprising SEQ ID NO: 425 and a VH region comprising SEQ ID NO: 429 (e.g., antibody Ab399). In a specific embodiment, an anti-ALK antibody described herein or an antigen-binding fragment thereof comprises a VL region comprising SEQ ID NO: 425 and a VH region comprising SEQ ID NO: 430 (e.g., antibody Ab400). In a specific embodiment, an anti-ALK antibody described herein or an antigen-binding fragment thereof comprises a VL region comprising SEQ ID NO: 425 and a VH region comprising SEQ ID NO: 431 (e.g., antibody Ab401). In a specific embodiment, an anti-ALK antibody described herein or an antigen-binding fragment thereof comprises a VL region comprising SEQ ID NO: 425 and a VH region comprising SEQ ID NO: 432 (e.g., antibody Ab402). In a specific embodiment, an anti-ALK antibody described herein or an antigen-binding fragment thereof comprises a VL region comprising SEQ ID NO: 425 and a VH region comprising SEQ ID NO: 433 (e.g., antibody Ab403). In a specific embodiment, an anti-ALK antibody described herein or an antigen-binding fragment thereof comprises a VL region comprising SEQ ID NO: 425 and a VH region comprising SEQ ID NO: 434 (e.g., antibody Ab404). In a specific embodiment, an anti-ALK antibody described herein or an antigen-binding fragment thereof comprises a VL region comprising SEQ ID NO: 425 and a VH region comprising SEQ ID NO: 435 (e.g., antibody Ab405). In a specific embodiment, an anti-ALK antibody described herein or an antigen-binding fragment thereof comprises a VL region comprising SEQ ID NO: 425 and a VH region comprising SEQ ID NO: 436 (e.g., antibody Ab406). In a specific embodiment, an anti-ALK antibody described herein or an antigen-binding fragment thereof comprises a VL region comprising SEQ ID NO: 425 and a VH region comprising SEQ ID NO: 437 (e.g., antibody Ab407). In a specific embodiment, an anti-ALK antibody described herein or an antigen-binding fragment thereof comprises a VL region comprising SEQ ID NO: 425 and a VH region comprising SEQ ID NO: 438 (e.g., antibody Ab408). In a specific embodiment, an anti-ALK antibody described herein or an antigen-binding fragment thereof comprises a VL region comprising SEQ ID NO: 425 and a VH region comprising SEQ ID NO: 439 (e.g., antibody Ab409). In a specific embodiment, an anti-ALK antibody described herein or an antigen-binding fragment thereof comprises a VL region comprising SEQ ID NO: 425 and a VH region comprising SEQ ID NO: 440 (e.g., antibody Ab410).

In a specific embodiment, an anti-ALK antibody described herein or an antigen-binding fragment thereof comprises a VL region comprising SEQ ID NO: 426 and a VH region comprising SEQ ID NO: 429 (e.g., antibody Ab411). In a specific embodiment, an anti-ALK antibody described herein or an antigen-binding fragment thereof comprises a VL region comprising SEQ ID NO: 426 and a VH region comprising SEQ ID NO: 430 (e.g., antibody Ab412). In a specific embodiment, an anti-ALK antibody described herein or an antigen-binding fragment thereof comprises a VL region comprising SEQ ID NO: 426 and a VH region comprising SEQ ID NO: 431 (e.g., antibody Ab413). In a specific embodiment, an anti-ALK antibody described herein or an antigen-binding fragment thereof comprises a VL region comprising SEQ ID NO: 426 and a VH region comprising SEQ ID NO: 432 (e.g., antibody Ab414). In a specific embodiment, an anti-ALK antibody described herein or an antigen-binding fragment thereof comprises a VL region comprising SEQ ID NO: 426 and a VH region comprising SEQ ID NO: 433 (e.g., antibody Ab415). In a specific embodiment, an anti-ALK antibody described herein or an antigen-binding fragment thereof comprises a VL region comprising SEQ ID NO: 426 and a VH region comprising SEQ ID NO: 434 (e.g., antibody Ab416). In a specific embodiment, an anti-ALK antibody described herein or an antigen-binding fragment thereof comprises a VL region comprising SEQ ID NO: 426 and a VH region comprising SEQ ID NO: 435 (e.g., antibody Ab417). In a specific embodiment, an anti-ALK antibody described herein or an antigen-binding fragment thereof comprises a VL region comprising SEQ ID NO: 426 and a VH region comprising SEQ ID NO: 436 (e.g., antibody Ab418). In a specific embodiment, an anti-ALK antibody described herein or an antigen-binding fragment thereof comprises a VL region comprising SEQ ID NO: 426 and a VH region comprising SEQ ID NO: 437 (e.g., antibody Ab419). In a specific embodiment, an anti-ALK antibody described herein or an antigen-binding fragment thereof comprises a VL region comprising SEQ ID NO: 426 and a VH region comprising SEQ ID NO: 438 (e.g., antibody Ab420). In a specific embodiment, an anti-ALK antibody described herein or an antigen-binding fragment thereof comprises a VL region comprising SEQ ID NO: 426 and a VH region comprising SEQ ID NO: 439 (e.g., antibody Ab421). In a specific embodiment, an anti-ALK antibody described herein or an antigen-binding fragment thereof comprises a VL region comprising SEQ ID NO: 426 and a VH region comprising SEQ ID NO: 440 (e.g., antibody Ab422).

In a specific embodiment, an anti-ALK antibody described herein or an antigen-binding fragment thereof comprises a VL region comprising SEQ ID NO: 427 and a VH region comprising SEQ ID NO: 429 (e.g., antibody Ab423). In a specific embodiment, an anti-ALK antibody described herein or an antigen-binding fragment thereof comprises a VL region comprising SEQ ID NO: 427 and a VH region comprising SEQ ID NO: 430 (e.g., antibody Ab424). In a specific embodiment, an anti-ALK antibody described herein or an antigen-binding fragment thereof comprises a VL region comprising SEQ ID NO: 427 and a VH region comprising SEQ ID NO: 431 (e.g., antibody Ab425). In a specific embodiment, an anti-ALK antibody described herein or an antigen-binding fragment thereof comprises a VL region comprising SEQ ID NO: 427 and a VH region comprising SEQ ID NO: 432 (e.g., antibody Ab426). In a specific embodiment, an anti-ALK antibody described herein or an antigen-binding fragment thereof comprises a VL region comprising SEQ ID NO: 427 and a VH region comprising SEQ ID NO: 433 (e.g., antibody Ab427). In a specific embodiment, an anti-ALK antibody described herein or an antigen-binding fragment thereof comprises a VL region comprising SEQ ID NO: 427 and a VH region comprising SEQ ID NO: 434 (e.g., antibody Ab428). In a specific embodiment, an anti-ALK antibody described herein or an antigen-binding fragment thereof comprises a VL region comprising SEQ ID NO: 427 and a VH region comprising SEQ ID NO: 435 (e.g., antibody Ab429). In a specific embodiment, an anti-ALK antibody described herein or an antigen-binding fragment thereof comprises a VL region comprising SEQ ID NO: 427 and a VH region comprising SEQ ID NO: 436 (e.g., antibody Ab430). In a specific embodiment, an anti-ALK antibody described herein or an antigen-binding fragment thereof comprises a VL region comprising SEQ ID NO: 427 and a VH region comprising SEQ ID NO: 437 (e.g., antibody Ab431). In a specific embodiment, an anti-ALK antibody described herein or an antigen-binding fragment thereof comprises a VL region comprising SEQ ID NO: 427 and a VH region comprising SEQ ID NO: 438 (e.g., antibody Ab432). In a specific embodiment, an anti-ALK antibody described herein or an antigen-binding fragment thereof comprises a VL region comprising SEQ ID NO: 427 and a VH region comprising SEQ ID NO: 439 (e.g., antibody Ab433). In a specific embodiment, an anti-ALK antibody described herein or an antigen-binding fragment thereof comprises a VL region comprising SEQ ID NO: 427 and a VH region comprising SEQ ID NO: 440 (e.g., antibody Ab434).

In a specific embodiment, an anti-ALK antibody described herein or an antigen-binding fragment thereof comprises a VL region comprising SEQ ID NO: 428 and a VH region comprising SEQ ID NO: 429 (e.g., antibody 435). In a specific embodiment, an anti-ALK antibody described herein or an antigen-binding fragment thereof comprises a VL region comprising SEQ ID NO: 428 and a VH region comprising SEQ ID NO: 430 (e.g., antibody Ab436). In a specific embodiment, an anti-ALK antibody described herein or an antigen-binding fragment thereof comprises a VL region comprising SEQ ID NO: 428 and a VH region comprising SEQ ID NO: 431 (e.g., antibody Ab437). In a specific embodiment, an anti-ALK antibody described herein or an antigen-binding fragment thereof comprises a VL region comprising SEQ ID NO: 428 and a VH region comprising SEQ ID NO: 432 (e.g., antibody Ab438). In a specific embodiment, an anti-ALK antibody described herein or an antigen-binding fragment thereof comprises a VL region comprising SEQ ID NO: 428 and a VH region comprising SEQ ID NO: 433 (e.g., antibody Ab439). In a specific embodiment, an anti-ALK antibody described herein or an antigen-binding fragment thereof comprises a VL region comprising SEQ ID NO: 428 and a VH region comprising SEQ ID NO: 434 (e.g., antibody Ab440). In a specific embodiment, an anti-ALK antibody described herein or an antigen-binding fragment thereof comprises a VL region comprising SEQ ID NO: 428 and a VH region comprising SEQ ID NO: 435 (e.g., antibody Ab441). In a specific embodiment, an anti-ALK antibody described herein or an antigen-binding fragment thereof comprises a VL region comprising SEQ ID NO: 428 and a VH region comprising SEQ ID NO: 436 (e.g., antibody Ab442). In a specific embodiment, an anti-ALK antibody described herein or an antigen-binding fragment thereof comprises a VL region comprising SEQ ID NO: 428 and a VH region comprising SEQ ID NO: 437 (e.g., antibody Ab443). In a specific embodiment, an anti-ALK antibody described herein or an antigen-binding fragment thereof comprises a VL region comprising SEQ ID NO: 428 and a VH region comprising SEQ ID NO: 438 (e.g., antibody Ab444). In a specific embodiment, an anti-ALK antibody described herein or an antigen-binding fragment thereof comprises a VL region comprising SEQ ID NO: 428 and a VH region comprising SEQ ID NO: 439 (e.g., antibody Ab445). In a specific embodiment, an anti-ALK antibody described herein or an antigen-binding fragment thereof comprises a VL region comprising SEQ ID NO: 428 and a VH region comprising SEQ ID NO: 440 (e.g., antibody Ab446).

In a specific embodiment, an anti-ALK antibody described herein or an antigen-binding fragment thereof comprises a VL region comprising SEQ ID NO: 395 (e.g., the VL region of antibody Ab320). In a specific embodiment, an anti-ALK antibody described herein or an antigen-binding fragment thereof comprises a VL region comprising SEQ ID NO: 397 (e.g., the VL region of antibody Ab321). In a specific embodiment, an anti-ALK antibody described herein or an antigen-binding fragment thereof comprises a VL region comprising SEQ ID NO: 399 (e.g., the VL region of antibody Ab322). In a specific embodiment, an anti-ALK antibody described herein or an antigen-binding fragment thereof comprises a VL region comprising SEQ ID NO: 401 (e.g., the VL region of antibody Ab323). In a specific embodiment, an anti-ALK antibody described herein or an antigen-binding fragment thereof comprises a VL region comprising SEQ ID NO: 403 (e.g., the VL region of antibody Ab324). In a specific embodiment, an anti-ALK antibody described herein or an antigen-binding fragment thereof comprises a VL region comprising SEQ ID NO: 405 (e.g., the VL region of antibody Ab325). In a specific embodiment, an anti-ALK antibody described herein or an antigen-binding fragment thereof comprises a VL region comprising SEQ ID NO: 407 (e.g., the VL region of antibody Ab326). In a specific embodiment, an anti-ALK antibody described herein or an antigen-binding fragment thereof comprises a VL region comprising SEQ ID NO: 409 (e.g., the VL region of antibody Ab327). In a specific embodiment, an anti-ALK antibody described herein or an antigen-binding fragment thereof comprises a VL region comprising SEQ ID NO: 411 (e.g., the VL region of antibody Ab328). In a specific embodiment, an anti-ALK antibody described herein or an antigen-binding fragment thereof comprises a VL region comprising SEQ ID NO: 413 (e.g., the VL region of antibody Ab329). In a specific embodiment, an anti-ALK antibody described herein or an antigen-binding fragment thereof comprises a VL region comprising SEQ ID NO: 415 (e.g., the VL region of antibody Ab330). In a specific embodiment, an anti-ALK antibody described herein or an antigen-binding fragment thereof comprises a VL region comprising SEQ ID NO: 417 (e.g., the VL region of antibody Ab331). In a specific embodiment, an anti-ALK antibody described herein or an antigen-binding fragment thereof comprises a VL region comprising SEQ ID NO: 419 (e.g., the VL region of antibody Ab332).

In a specific embodiment, an anti-ALK antibody described herein or an antigen-binding fragment thereof comprises a VL region comprising SEQ ID NO: 421 (e.g., the VL region of antibody Ab351). In a specific embodiment, an anti-ALK antibody described herein or an antigen-binding fragment thereof comprises a VL region comprising SEQ ID NO: 422 (e.g., the VL region of antibody Ab363). In a specific embodiment, an anti-ALK antibody described herein or an antigen-binding fragment thereof comprises a VL region comprising SEQ ID NO: 423 (e.g., the VL region of antibody Ab375). In a specific embodiment, an anti-ALK antibody described herein or an antigen-binding fragment thereof comprises a VL region comprising SEQ ID NO: 424 (e.g., the VL region of antibody Ab387). In a specific embodiment, an anti-ALK antibody described herein or an antigen-binding fragment thereof comprises a VL region comprising SEQ ID NO: 425 (e.g., the VL region of antibody Ab399). In a specific embodiment, an anti-ALK antibody described herein or an antigen-binding fragment thereof comprises a VL region comprising SEQ ID NO: 426 (e.g., the VL region of antibody Ab411). In a specific embodiment, an anti-ALK antibody described herein or an antigen-binding fragment thereof comprises a VL region comprising SEQ ID NO: 427 (e.g., the VL region of antibody Ab423). In a specific embodiment, an anti-ALK antibody described herein or an antigen-binding fragment thereof comprises a VL region comprising SEQ ID NO: 428 (e.g., the VL region of antibody Ab435).

In a specific embodiment, an anti-ALK antibody described herein or an antigen-binding fragment thereof comprises a VH region comprising SEQ ID NO: 396 (e.g., the VH region of antibody Ab320). In a specific embodiment, an anti-ALK antibody described herein or an antigen-binding fragment thereof comprises a VH region comprising SEQ ID NO: 398 (e.g., the VH region of antibody Ab321). In a specific embodiment, an anti-ALK antibody described herein or an antigen-binding fragment thereof comprises a VH region comprising SEQ ID NO:400 (e.g., the VH region of antibody Ab322). In a specific embodiment, an anti-ALK antibody described herein or an antigen-binding fragment thereof comprises a VH region comprising SEQ ID NO: 402 (e.g., the VH region of antibody Ab323). In a specific embodiment, an anti-ALK antibody described herein or an antigen-binding fragment thereof comprises a VH region comprising SEQ ID NO: 404 (e.g., the VH region of antibody Ab324). In a specific embodiment, an anti-ALK antibody described herein or an antigen-binding fragment thereof comprises a VH region comprising SEQ ID NO: 406 (e.g., the VH region of antibody Ab325). In a specific embodiment, an anti-ALK antibody described herein or an antigen-binding fragment thereof comprises a VH region comprising SEQ ID NO: 408 (e.g., the VH region of antibody Ab326). In a specific embodiment, an anti-ALK antibody described herein or an antigen-binding fragment thereof comprises a VH region comprising SEQ ID NO: 410 (e.g., the VH region of antibody Ab327). In a specific embodiment, an anti-ALK antibody described herein or an antigen-binding fragment thereof comprises a VH region comprising SEQ ID NO: 412 (e.g., the VH region of antibody Ab328). In a specific embodiment, an anti-ALK antibody described herein or an antigen-binding fragment thereof comprises a VH region comprising SEQ ID NO: 414 (e.g., the VH region of antibody Ab329). In a specific embodiment, an anti-ALK antibody described herein or an antigen-binding fragment thereof comprises a VH region comprising SEQ ID NO: 416 (e.g., the VH region of antibody Ab330). In a specific embodiment, an anti-ALK antibody described herein or an antigen-binding fragment thereof comprises a VH region comprising SEQ ID NO: 418 (e.g., the VH region of antibody Ab331). In a specific embodiment, an anti-ALK antibody described herein or an antigen-binding fragment thereof comprises a VH region comprising SEQ ID NO: 420 (e.g., the VH region of antibody Ab332).

In a specific embodiment, an anti-ALK antibody described herein or an antigen-binding fragment thereof comprises a VH region comprising SEQ ID NO: 429 (e.g., the VH region of antibody Ab351). In a specific embodiment, an anti-ALK antibody described herein or an antigen-binding fragment thereof comprises a VH region comprising SEQ ID NO: 430 (e.g., the VH region of antibody Ab352). In a specific embodiment, an anti-ALK antibody described herein or an antigen-binding fragment thereof comprises a VH region comprising SEQ ID NO:431 (e.g., the VH region of antibody Ab353). In a specific embodiment, an anti-ALK antibody described herein or an antigen-binding fragment thereof comprises a VH region comprising SEQ ID NO: 432 (e.g., the VH region of antibody Ab354). In a specific embodiment, an anti-ALK antibody described herein or an antigen-binding fragment thereof comprises a VH region comprising SEQ ID NO: 433 (e.g., the VH region of antibody Ab355). In a specific embodiment, an anti-ALK antibody described herein or an antigen-binding fragment thereof comprises a VH region comprising SEQ ID NO: 434 (e.g., the VH region of antibody Ab356). In a specific embodiment, an anti-ALK antibody described herein or an antigen-binding fragment thereof comprises a VH region comprising SEQ ID NO: 435 (e.g., the VH region of antibody Ab357). In a specific embodiment, an anti-ALK antibody described herein or an antigen-binding fragment thereof comprises a VH region comprising SEQ ID NO: 436 (e.g., the VH region of antibody Ab358). In a specific embodiment, an anti-ALK antibody described herein or an antigen-binding fragment thereof comprises a VH region comprising SEQ ID NO: 437 (e.g., the VH region of antibody Ab359). In a specific embodiment, an anti-ALK antibody described herein or an antigen-binding fragment thereof comprises a VH region comprising SEQ ID NO: 438 (e.g., the VH region of antibody Ab360). In a specific embodiment, an anti-ALK antibody described herein or an antigen-binding fragment thereof comprises a VH region comprising SEQ ID NO: 439 (e.g., the VH region of antibody Ab361). In a specific embodiment, an anti-ALK antibody described herein or an antigen-binding fragment thereof comprises a VH region comprising SEQ ID NO: 440 (e.g., the VH region of antibody Ab362).

In certain embodiments, provided herein is an anti-ALK antibody or an antigen-binding fragment thereof which specifically binds to an ECD of human ALK and comprises VL CDRs (e.g., Kabat CDRs, Chothia CDRs, or IMGT CDRs) of a VL comprising the amino acid sequence as set forth in Table 13 and VH CDRs (e.g., Kabat CDRs, Chothia CDRs, or IMGT CDRs) of a VH comprising the amino acid sequence as set forth in Table 14.

In certain embodiments, provided herein is an antibody or an antigen-binding fragment thereof which specifically binds to an ECD of human ALK and comprises VL and VH CDRs of any of the anti-ALK antibodies provided herein, for example as set forth in Tables 1 and 2.

TABLE 1

VL CDR Amino Acid Sequences (Kabat)

| Antibody | VL CDR1 (SEQ ID NO:) | VL CDR2 (SEQ ID NO:) | VL CDR3 (SEQ ID NO:) |
|---|---|---|---|
| Ab320 | RASENIYYSLA (1) | NANSLED (2) | KQAYDVPFT (3) |
| Ab321 | SVSQGISNSLN (7) | YTSSLHS (8) | QQYSKLPLT (9) |
| Ab322 | KASQNVGTNVA (13) | SASYRYS (14) | QQYNSYPYMYT (15) |
| Ab323 | KASQDVSTAVA (19) | WASTRHT (20) | QQHYSTPRT (21) |
| Ab324 | RASESVDNYGISFMN (25) | AASNQGS (26) | QQSKEVPWT (27) |
| Ab325 | RASQDISNYLN (30) | YTSRLHS (31) | QQGNTLPRT (32) |
| Ab326 | KASQNVGTNVA (13) | SASYRYS (14) | QQYNSYPYMYT (15) |

TABLE 1-continued

VL CDR Amino Acid Sequences (Kabat)

| Antibody | VL CDR1 (SEQ ID NO:) | VL CDR2 (SEQ ID NO:) | VL CDR3 (SEQ ID NO:) |
|---|---|---|---|
| Ab327 | KASQNVGTAVA (35) | SASNRFT (36) | QQYSSYPLT (37) |
| Ab328 | KASQNVGTNVA (13) | SASYRYS (14) | QRYNSYPYMFT (41) |
| Ab329 | QASQDIDNYLS (42) | SATSLAD (43) | LQHYSGWT (44) |
| Ab330 | QASQDIGNYLI (48) | YATNLAN (49) | LQYKQHLT (50) |
| Ab331 | QASQDIGNYLI (48) | YATNLAN (49) | LQYKQHLT (50) |
| Ab332 | KASQSVDYDGDSYMN (55) | AASNLES (56) | QQSNEDPPT (57) |
| Ab423 | RASQSVSSNLA (483) | SASYRYS (14) | QQYNSYPYMYT (15) |
| Ab435 | KASQNVGTNVA (13) | GASTRAT (484) | QQYNSYPYMYT (15) |

TABLE 2

VH CDR Amino Acid Sequences (Kabat)

| Antibody | VH CDR1 (SEQ ID NO:) | VH CDR2 (SEQ ID NO:) | VH CDR3 (SEQ ID NO:) |
|---|---|---|---|
| Ab320 | SYWMN (4) | QIYPGDGDTNYNGKFKG (5) | YYYGSKAY (6) |
| Ab321 | SYWMH (10) | RIDPNSGGTKYNEKFKS (11) | DYYGSSYRFAY (12) |
| Ab322 | NYWMH (16) | YINPSSGYTKYNQKFKD (17) | DYYGSSSWFAY (18) |
| Ab323 | NYWMN (22) | QIFPGDADANYNGKFKG (23) | FSYDGAFAY (24) |
| Ab324 | SYWVN (28) | QIYPGDGDTNYNGKFKG (5) | SRGYFYGSTYDS (29) |
| Ab325 | SYWMN (4) | QIYPGDGDTNYNGKFKG (5) | WYYGSYYAMDY (33) |
| Ab326 | SYWMH (10) | YIKPSSGYTKYNQKFKD (34) | DYYGSSSWFAY (18) |
| Ab327 | SYAMS (38) | YISSGGDYIYYADTVKG (39) | ERIWLRRFFDV (40) |
| Ab328 | SYWMH (10) | YINPSSGYTKYNQKFKD (17) | DYYGSSSWFAY (18) |
| Ab329 | SYHVC (45) | VIWGDGRTTYNPPLKS (46) | ATMTGHGDA (47) |
| Ab330 | TAWMY (51) | RIKDKSNKFASDYVESVRG (52) | SYGYA (53) |
| Ab331 | TAWMY (51) | RIKDKSNNFASDYVESVRG (54) | SYGYA (53) |
| Ab332 | DYYMN (58) | DINPNNGVTSYNQKFK (59) | EDYGSNYFDY (60) |
| Ab353 | SSAMQ (485) | YIKPSSGYTKYNQKFKD (34) | DYYGSSSWFAY (18) |
| Ab354 | SYWMH (10) | YIKPSSGYTKYAQKFQE (486) | DYYGSSSWFAY (18) |
| Ab358 | SYWMH (10) | YIKPSSGYTKYAQKLQG (487) | DYYGSSSWFAY (18) |
| Ab362 | SYWMH (10) | YIKPSSGYTKYAQKFQG (488) | DYYGSSSWFAY (18) |

TABLE 3

VL FR Amino Acid Sequences (Kabat)

| Antibody | VL FR1 (SEQ ID NO:) | VL FR2 (SEQ ID NO;) | VL FR3 (SEQ ID NO:) | VL FR4 (SEQ ID NO:) |
|---|---|---|---|---|
| Ab320 | DIQMTQSPASLAASVGETVTITC (61) | WYQQKQGKSPQLLIY (62) | GVPSRFSGSGSGTQYSMKINSMQPEDTATYFC (63) | FGSGTKLEIKR (64) |
| Ab321 | AIQMTQTTSSLSASLGDRVTISC (69) | WYQQKPDGTVKLLIY (70) | GVPSRFSGSGSGTDYSLTISNLEPEDIATYYC (71) | FGAGTKLELKR (72) |

TABLE 3-continued

VL FR Amino Acid Sequences (Kabat)

| Antibody | VL FR1 (SEQ ID NO:) | VL FR2 (SEQ ID NO;) | VL FR3 (SEQ ID NO:) | VL FR4 (SEQ ID NO:) |
|---|---|---|---|---|
| Ab322 | DIVMTQSQRFMSTSVG DRVSVTC (76) | WYQQKPGQSPKALIY (77) | GVPDRFTGSGSGTDFTL TVSNVQSEDLAEYFC (78) | FGGGTKLEIKR (79) |
| Ab323 | DIVMTQSHKFMSTSVG DRVSITC (83) | WYQQKPGQSPKPLIY (84) | GVPDRFTGSGSGTDYTL TISSVQTEDLALYYC (85) | FGGGTKLEIKR (79) |
| Ab324 | DIVLTQSPASLAVSLG QRATISC (88) | WFQQKPGQPPKLLIY (89) | GVPARFSGSGSGTDFSL NIHPMEEDDTAMYFC (90) | FGGGTKLEIKR (79) |
| Ab325 | DIQMTQTTSSLSASLG DRVTISC (93) | WYQQKPDGTVKLLIY (70) | GVPSRFSGSGSGTDYSL TISNLEQEDIATYFC (94) | FGGGTKLEIKR (79) |
| Ab326 | DIVMTQSQRFMSTSVG DRVSVTC (76) | WYQQKPGQSPKALIY (77) | GVPDRFTGSGSGTDFTL TISNVQSEDLAEYFC (96) | FGGGTKLEIKR (79) |
| Ab327 | DIVMTQSQKFMSTSVG DRVSITC (97) | WYQLKPGQSPKLLIY (98) | GVPDRFTGSGSGTDFTL TISNMQSEDLADYFC (99) | FGSGTKLEIKR (64) |
| Ab328 | DIVMTQSQKFMSTSVG DRVSVTC (104) | WYQQKPGHSPKALIY (105) | GVPDRFTGSGSGTDFTL TISNVQSEDLAEYFC (96) | FGGGTKLEIKR (79) |
| Ab329 | DIQMTQSPASLSASLE EIVTITC (107) | WYQQKPGKSPHLLIH (108) | GVPSRFSGGRSGTQFSL KINRLQVEDTGIYYC (109) | FGGGTKLELKR (110) |
| Ab330 | DIQMTQSPSSMSASLG DRVTITC (115) | WFQQKPGKSPRPLIY (116) | GVPSRFSGSRSGSEYSL TITSLESEDMADYHC (117) | FGSGTKLEIER (118) |
| Ab331 | DIQMTQSPSSMSASLG DRITITC (123) | WFQQKPGKSPRPLIY (116) | GVPSRFSGSRSGSEYSL TITSLESEDMADYHC (117) | FGSGTKLEIER (118) |
| Ab332 | DIVLTQSPASLAVSLG QRATISC (88) | WYQQKPGQPPKLLIY (89) | GIPARLSGSGSGTDFTL NIHPVEEEDAATYYC (124) | FGGGTKLEIRR (125) |

TABLE 4

VH FR Amino Acid Sequences (Kabat)

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab320 | QVQLQQSGAELVKPGA SVKISCKASGYAFS (65) | WVKQRPGKGLEWIG (66) | KATLTADKSSSTAYMQL SSLTSEDSAVYFCAS (67) | WGQGTLVTVSA (68) |
| Ab321 | QVQLQQPGAEFVKPGA SVKLSCKASGYTFT (73) | WVKQRPGRGLEWIG (74) | KATLTVDKPSSTAYMQL SSLTSEDSAVYYCAR (75) | WGQGTLVTVSA (68) |
| Ab322 | QVQLQQSGAELAKPGA SVKLSCKASGYTFT (80) | WVKQRPGQGLEWIG (81) | KATLTADKSSSTAYMQL SSLTYEDSAVYYCAR (82) | WGQGTLVTVSA (68) |
| Ab323 | QVQLQQSGAELVKPGA SVKISCKTSGYTFS (86) | WVKQRPGKGLEWIG (66) | KATLTADKSSSAAFMQL SSLTSEDSAVYFCAR (87) | WGQGTLVTVSA (68) |
| Ab324 | QVQLQQSGAELVKPGA SVKISCKASGYAFS (65) | WVKQRPGKGLEWIG (66) | KATLTADKSSSTAYMQL SSLTSEDSAVYFCAR (91) | WGQGTTLTVSS (92) |

TABLE 4-continued

VH FR Amino Acid Sequences (Kabat)

| Anti-body | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab325 | QVQLQQSGAELVKPGA SVKISCKASGYAFS (65) | WVKQRPGKGLEWIG (66) | KATLTADKSSSTAYMQL SSLTSEDSAVYFCAR (91) | WGQGTSVTVSS (95) |
| Ab326 | QVQLQQSGAELAKPGA SVKLSCKASGYTFT (80) | WVKQRPGQGLEWIG (81) | KATLTADKSSSTAYMQL SSLTYEDSAVYYCAR (82) | WGQGTLVTVSA (68) |
| Ab327 | DVKLVESGEGLVKPGG SLKLSCAASGFTFS (100) | WVRQTPEKRLEWVT (101) | RFTISRDNARNTLYLQM SSLKSEDTAMYYCTR (102) | WGTGTTVTVSS (103) |
| Ab328 | QVQLQQSGAELAKPGA SVKLSCKASGYTFT (80) | WVKQRPGQGLEWIG (81) | KATLTADKSSSTAYMQL SSLTFEDSAVYYCAR (106) | WGQGTLVTVSA (68) |
| Ab329 | QVQLKESGPGLVKPSA TLSLTCTVSGFSLT (111) | WIRQTPGKGLEWMG (112) | RLSISRDTSKSQVFLKM SSLKTEDTATYYCAR (113) | WGQGASVTVSS (114) |
| Ab330 | EVQVVETGGGVVQPGK SLEITCATSGLTFS (119) | WVRQSSDRRLEWIA (120) | RFTISRDDSRSSVYLQM NNLKEEDTATYYCTT (121) | WGQGVMVTVSS (122) |
| Ab331 | EVQVVETGGGVVQPGK SLEITCATSGLTFS (119) | WVRQSSDRRLEWIA (120) | RFTISRDDSRSSVYLQM NNLKEEDTATYYCTT (121) | WGQGVMVTVSS (122) |
| Ab332 | EVQLQQSGPELVKPGT SVKISCKASGYTFT (126) | WMKQSHGKSLEWIG (127) | GKATLTVDKSSSTAYME LRSLTSEDSAVYYCAR (128) | WGQGTTLTVSS (92) |

In a particular embodiment, an antibody described herein, or an antigen-binding fragment thereof, which specifically binds to an ECD of ALK comprises:
(a) a VL CDR1 comprising the amino acid sequence of KASQNVGTNVA (SEQ ID NO:13);
(b) a VL CDR2 comprising the amino acid sequence of SASYRYS (SEQ ID NO:14); and
(c) a VL CDR3 comprising the amino acid sequence of QX$_1$YNSYPYMX$_2$T (SEQ ID NO:468), wherein X$_1$ is any amino acid, for example, Q or R and X$_2$ is any amino acid, for example, an amino acid with an aromatic side chain, e.g., Y or F. In certain embodiments, any one of X$_1$ and X$_2$ is any amino acid sequence. In specific embodiments, X$_1$ is a conservative substitution of Q or R, and X$_2$ is a conservative substitution of Y or F. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK comprises:
(a) a VL CDR1 comprising the amino acid sequence of KASQZ$_{10}$VZ$_{11}$TZ$_{12}$VA (SEQ ID NO:500), wherein Z$_{10}$ is any amino acid, for example, N or D, Z$_{11}$ is any amino acid, for example, G or S, and Z$_{12}$ is any amino acid, for example, A or N;
(b) a VL CDR2 comprising the amino acid sequence of SASYRYS (SEQ ID NO:14) or WASTRHT (SEQ ID NO:20) or SASNRFT (SEQ ID NO:36); and
(c) a VL CDR3 comprising the amino acid sequence of QQHYSTPRT (SEQ ID NO:21) or QQYSSYPLT (SEQ ID NO:37) or QX$_1$YNSYPYMX$_2$T (SEQ ID NO:468), wherein X$_1$ is any amino acid, for example, Q or R and X$_2$ is any amino acid, for example, an amino acid with an aromatic side chain, Y or F. In certain embodiments, any one of X$_1$ and X$_2$ and Z$_{10}$-Z$_{12}$ is any amino acid sequence. In specific embodiments, X$_1$ is a conservative substitution of Q or R, X$_2$ is a conservative substitution of Y or F, Z$_{10}$ is a conservative substitution of N or D, Z$_{11}$ is a conservative substitution of G or S, and Z$_{12}$ is a conservative substitution of A or N. In specific embodiments, X$_1$ is a conservative substitution of Q or R, X$_2$ is a conservative substitution of Y or F, Z$_{10}$ is N, Z$_{11}$ is G, and Z$_{12}$ is A or N. In specific embodiments, X$_1$ is a conservative substitution of Q or R, X$_2$ is a conservative substitution of Y or F, Z$_{10}$ is D, Z$_{11}$ is S, and Z$_{12}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK comprises:
(a) a VL CDR1 comprising the amino acid sequence of KASQZ$_{10}$VZ$_{11}$TZ$_{12}$VA (SEQ ID NO:500), wherein Z$_{10}$ is N or D, Z$_{11}$ is G or S, and Z$_{12}$ is A or N;
(b) a VL CDR2 comprising the amino acid sequence of SASYRYS (SEQ ID NO:14); and
(c) a VL CDR3 comprising the amino acid sequence of QQYNSYPYMYT (SEQ ID NO:15). In specific embodiments, Z$_{10}$ is N, Z$_{11}$ is G, and Z$_{12}$ is A or N. In specific embodiments, Z$_{10}$ is D, Z$_{11}$ is S, and Z$_{12}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK comprises:

(a) a VL CDR1 comprising the amino acid sequence of KASQZ$_{10}$VZ$_{11}$TZ$_{12}$VA (SEQ ID NO:500), wherein Z$_{10}$ is N or D, Z$_{11}$ is G or S, and Z$_{12}$ is A or N;
(b) a VL CDR2 comprising the amino acid sequence of WASTRHT (SEQ ID NO:20); and
(c) a VL CDR3 comprising the amino acid sequence of QQHYSTPRT (SEQ ID NO:21. In specific embodiments, Z$_{10}$ is N, Z$_{11}$ is G, and Z$_{12}$ is A or N. In specific embodiments, Z$_{10}$ is D, Z$_{11}$ is S, and Z$_{12}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK comprises:
(a) a VL CDR1 comprising the amino acid sequence of KASQZ$_{10}$VZ$_{11}$TZ$_{12}$VA (SEQ ID NO:500), wherein Z$_{10}$ is N or D, Z$_{11}$ is G or S, and Z$_{12}$ is A or N;
(b) a VL CDR2 comprising the amino acid sequence of SASNRFT (SEQ ID NO:36); and
(c) a VL CDR3 comprising the amino acid sequence of QQYSSYPLT (SEQ ID NO:37). In specific embodiments, Z$_{10}$ is N, Z$_{11}$ is G, and Z$_{12}$ is A or N. In specific embodiments, Z$_{10}$ is D, Z$_{11}$ is S, and Z$_{12}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK comprises:
(a) a VL CDR1 comprising the amino acid sequence of KASQZ$_{10}$VZ$_{11}$TZ$_{12}$VA (SEQ ID NO:500), wherein Z$_{10}$ N or D, Z$_{11}$ is G or S, and Z$_{12}$ is A or N;
(b) a VL CDR2 comprising the amino acid sequence of SASYRYS (SEQ ID NO:14); and
(c) a VL CDR3 comprising the amino acid sequence of QRYNSYPYMFT (SEQ ID NO:41). In specific embodiments, Z$_{10}$ is N, Z$_{11}$ is G, and Z$_{12}$ is A or N. In specific embodiments, Z$_{10}$ is D, Z$_{11}$ is S, and Z$_{12}$ is A or N. In a particular embodiment the antibody or an antigen-binding fragment thereof is an antibody which specifically binds to an ECD of ALK.

As used herein, a "conservative amino acid substitution" is one in which the amino acid residue is replaced with an amino acid residue having a side chain with a similar charge. Families of amino acid residues having side chains with similar charges have been defined in the art. These families include amino acids with charged side chains (lysine, arginine, histidine, aspartic acid, glutamic acid), acidic side chains (aspartic acid, glutamic acid), basic side chains (lysine, arginine, histidine), uncharged polar side chains (glycine, asparagine, glutamine, serine, threonine, tyrosine, cysteine), hydrophobic side chains (methionine, alanine, valine, leucine, isoleucine), neutral hydrophilic side chains (cysteine, serine, threonine, asparagine, glutamine), nonpolar side chains (alanine, valine, leucine, isoleucine, proline, phenylalanine, methionine, tryptophan), beta-branched side chains (threonine, valine, isoleucine) aromatic side chains (tyrosine, phenylalanine, tryptophan, histidine), and residues that influence chain orientation (glycine, proline).

In a particular embodiment, an antibody described herein, or an antigen-binding fragment thereof, which specifically binds to an ECD of ALK comprises:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15 or 41. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK comprises:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15, 41, or 468. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 13, 19, 35, or 500;
(b) a VL CDR2 comprising the amino acid sequence of SEQ ID NO:14, 20, or 36; and
(c) a VL CDR3 comprising the amino acid sequence of SEQ ID NO:15, 21, 41, or 468. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK comprises:
(a) a VL CDR1 comprising the amino acid sequence of SEQ ID NO: 13 or 483;
(b) a VL CDR2 comprising the amino acid sequence of SEQ ID NO:14 or 484; and
(c) a VL CDR3 comprising the amino acid sequence of SEQ ID NO:15. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a light chain variable region (VL) comprising:
(a) a VL CDR1 comprising the amino acid sequence of SEQ ID NO:483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab320, for example, the VL CDR1, VL CDR2, and VL CDR3 of Ab320 as set forth in Table 1 (SEQ ID NOS: 1, 2, and 3, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab321, for example, the VL CDR1, VL CDR2, and VL CDR3 of Ab321 as set forth in Table 1 (SEQ ID NOS: 7, 8, and 9, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab322, for example, the VL CDR1, VL CDR2, and VL CDR3 of Ab322 as set forth in Table 1 (SEQ ID NOS: 13, 14, and 15, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab323, for example, the VL CDR1, VL CDR2, and VL CDR3 of Ab323 as set forth in Table 1 (SEQ ID NOS: 19, 20, and 21, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab324, for example, the VL CDR1, VL CDR2, and VL CDR3 of Ab324 as set forth in Table 1 (SEQ ID NOS: 25, 26, and 27, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab325, for example, the VL CDR1, VL CDR2, and VL CDR3 of Ab325 as set forth in Table 1 (SEQ ID NOS: 30, 31, and 32, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab326, for example, the VL CDR1, VL CDR2, and VL CDR3 of Ab326 as set forth in Table 1 (SEQ ID NOS: 13, 14, and 15, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab327, for example, the VL CDR1, VL CDR2, and VL CDR3 of Ab327 as set forth in Table 1 (SEQ ID NOS: 35, 36, and 37, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab328, for example, the VL CDR1, VL CDR2, and VL CDR3 of Ab328 as set forth in Table 1 (SEQ ID NOS: 13, 14, and 41, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab329, for example, the VL CDR1, VL CDR2, and VL CDR3 of Ab329 as set forth in Table 1 (SEQ ID NOS: 42, 43, and 44, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab330, for example, the VL CDR1, VL CDR2, and VL CDR3 of Ab330 as set forth in Table 1 (SEQ ID NOS: 48, 49, and 50, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab331, for example, the VL CDR1, VL CDR2, and VL CDR3 of Ab331 as set forth in Table 1 (SEQ ID NOS: 48, 49, and 50, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab332, for example, the VL CDR1, VL CDR2, and VL CDR3 of Ab332 as set forth in Table 1 (SEQ ID NOS: 55, 56, and 57, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab423, for example, the VL CDR1, VL CDR2, and VL CDR3 of Ab423 as set forth in Table 1 (SEQ ID NOS: 483, 14, and 15, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab435, for example, the VL CDR1, VL CDR2, and VL CDR3 of Ab435 as set forth in Table 1 (SEQ ID NOS: 13, 484, and 15, respectively). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence $X_3$YWMH (SEQ ID NO:469), wherein $X_3$ is any amino acid, for example, an amino acid with an uncharged polar side chain, e.g., N or S;
(b) a VH CDR2 comprising the amino acid sequence of YIX$_4$PSSGYTKYNQKFKD (SEQ ID NO:470), wherein $X_4$ is any amino acid, for example N or K; and
(c) a VH CDR3 comprising the amino acid sequence of DYYGSSSWFAY (SEQ ID NO:18). In certain embodiments, any one of $X_3$ or $X_4$ is any amino acid sequence. In specific embodiments, $X_3$ is a conservative substitution of N or S, $X_4$ is a conservative substitution of N or K. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of TAWMY (SEQ ID NO:51;
(b) a VH CDR2 comprising the amino acid sequence of RIKDKSNX$_5$FASDYVESVRG (SEQ ID NO: 471), wherein $X_5$ is any amino acid, for example N or K; and
(c) a VH CDR3 comprising the amino acid sequence of SYGYA (SEQ ID NO:53). In certain embodiments, $X_5$ is any amino acid sequence. In specific embodiments, $X_5$ is a conservative substitution of N or K. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence $X_3$YWMH (SEQ ID NO:469), wherein $X_3$ is any amino acid, for example, an amino acid with an uncharged polar side chain, e.g., N or S;
(b) a VH CDR2 comprising the amino acid sequence of $Z_1IZ_2PZ_3SGZ_4TKYNZ_5KFKZ_6$ (SEQ ID NO: 498), wherein $Z_1$ is any amino acid, for example R or Y, $Z_2$ is any amino acid, for example D, K, or N, $Z_3$ is any amino acid, for example, N or S, $Z_4$ is any amino acid, for example, G or Y, $Z_5$ is any amino acid, for example, E or Q, and $Z_6$ is any amino acid, for example, S or D; and
(c) a VH CDR3 comprising the amino acid sequence of DYYGSS$Z_7Z_8$FAY (SEQ ID NO:497), wherein $Z_7$ is any amino acid, for example, Y or S and $Z_8$ is any amino acid, for example, R or W. In certain embodiments, any one of $X_3$ and $Z_1$-$Z_8$ is any amino acid sequence. In specific embodiments, $X_3$ is a conservative substitution of N or S, $Z_1$ is a conservative substitution of R or Y, $Z_2$ is a conservative substitution of D, K, or N, $Z_3$ is a conservative substitution of N or S, $Z_4$ is a conservative substitution of G or Y, $Z_5$ is a conservative substitution of E or Q, $Z_6$ is a conservative substitution of S or D, $Z_7$ is a conservative substitution of Y or S, and $Z_8$ is a conservative substitution of R or W. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of SYW$Z_9$N (SEQ ID NO:499), wherein $Z_9$ is any amino acid, for example M or V;
(b) a VH CDR2 comprising the amino acid sequence of QIYPGDGDTNYNGKFKG (SEQ ID NO: 5); and
(c) a VH CDR3 comprising the amino acid sequence of YYYGSKAY (SEQ ID NO:6) or SRGYFYGSTYDS (SEQ ID NO:29) or WYYGSYYAMDY (SEQ ID NO:33). In certain embodiments, $Z_9$ is any amino acid. In specific embodiments, $Z_9$ is a conservative substitution of M or V. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}$YW$Z_{14}$N (SEQ ID NO:501), wherein $Z_{13}$ is any amino acid, for example N or S and $Z_{14}$ is any amino acid, for example M or V;
(b) a VH CDR2 comprising the amino acid sequence of QI$Z_{15}$PGD$Z_{16}$D$Z_{17}$NYNGKFKG (SEQ ID NO: 502) wherein $Z_{15}$ is any amino acid, for example, an aromatic amino acid, F or Y, $Z_{16}$ is any amino acid, for example A or G, and $Z_{17}$ is any amino acid, for example, A or T; and
(c) a VH CDR3 comprising the amino acid sequence of FSYDGAFAY (SEQ ID NO:24) or SRGYFYGSTYDS (SEQ ID NO:29) or WYYGSYYAMDY (SEQ ID NO:33). In certain embodiments, $Z_{13}$-$Z_{17}$ are any amino acid. In specific embodiments, $Z_{13}$ is a conservative substitution of N or S, $Z_{14}$ is a conservative substitution of M or V, $Z_{15}$ is a conservative substitution of F or Y, $Z_{16}$ is a conservative substitution of A or G, and $Z_{17}$ is a conservative substitution of A or T. In specific embodiments, $Z_{13}$ is N or S, $Z_{14}$ is M or V, $Z_{15}$ is F or Y, $Z_{16}$ is A or G, and $Z_{17}$ is A or T. In specific embodiments, $Z_{13}$ is 5, $Z_{14}$ is M or V, $Z_{15}$ is F or Y, $Z_{16}$ is A or G, and $Z_{17}$ is A or T. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of SYWMH (SEQ ID NO:10);
(b) a VH CDR2 comprising the amino acid sequence of YIKPSSGYTKY$Z_{45}$QK$Z_{46}Z_{47}Z_{48}$ (SEQ ID NO: 514) wherein $Z_{45}$ is N or A, $Z_{46}$ is F or L, $Z_{47}$ is K or Q, and $Z_{48}$ is D, E, or G; wherein $Z_{45}$ is any amino acid, for example, N or A, $Z_{46}$ is any amino acid, for example F or L, $Z_{47}$ is any amino acid, for example, K or Q, and $Z_{48}$ is any amino acid, for example D, E, or G; and
(c) a VH CDR3 comprising the amino acid sequence of DYYGSSSWFAY (SEQ ID NO:18). In certain embodiments, $Z_{45}$-$Z_{48}$ are any amino acid. In specific embodiments, $Z_{45}$ is a conservative substitution of N or A, $Z_{46}$ is a conservative substitution of F or L, $Z_{47}$ is a conservative substitution of K or Q, and $Z_{48}$ is a conservative substitution of D, E or G. In specific embodiments, $Z_{45}$ is N or A, $Z_{46}$ is F or L, $Z_{47}$ is K or Q, and $Z_{48}$ is D, E, or G. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}$YW$_{14}$N (SEQ ID NO:501), wherein $Z_{13}$ is N or S and $X_{14}$ is M or V;
(b) a VH CDR2 comprising the amino acid sequence of QI$Z_{15}$PGD$Z_{16}$D$Z_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of FSYDGAFAY (SEQ ID NO:24). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}$YW$Z_{14}$N (SEQ ID NO:501), wherein $Z_{13}$ is N or S and $Z_{14}$ is M or V;
(b) a VH CDR2 comprising the amino acid sequence of QI$Z_{15}$PGD$Z_{16}$D$Z_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of SRGYFYGSTYDS (SEQ ID NO:29). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}$YW$Z_{14}$N (SEQ ID NO:501), wherein $Z_{13}$ is N or S and $Z_{14}$ is M or V;
(b) a VH CDR2 comprising the amino acid sequence of QI$Z_{15}$PGD$Z_{16}$D$Z_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of WYYGSYYAMDY (SEQ ID NO:33). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of QIFPGDADANYNGKFKG (SEQ ID NO:23); and
(c) a VH CDR3 comprising the amino acid sequence of FSYDGAFAY (SEQ ID NO:24). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of QIYPGDGDTNYNGKFKG (SEQ ID NO: 5); and
(c) a VH CDR3 comprising the amino acid sequence of SRGYFYGSTYDS (SEQ ID NO:29). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of QIYPGDGDTNYNGKFKG (SEQ ID NO: 5); and
(c) a VH CDR3 comprising the amino acid sequence of WYYGSYYAMDY (SEQ ID NO:33). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of QIYPGDGDTNYNGKFKG (SEQ ID NO: 5); and
(c) a VH CDR3 comprising the amino acid sequence of SRGYFYGSTYDS (SEQ ID NO:29). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of QIYPGDGDTNYNGKFKG (SEQ ID NO: 5); and
(c) a VH CDR3 comprising the amino acid sequence of WYYGSYYAMDY (SEQ ID NO:33). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of $QIZ_{15}PGDZ_{16}DZ_{17}NYNGKFKG$ (SEQ ID NO: 502) wherein $Z_{15}$ is F or Y, $Z_{16}$ is A or G, and $Z_{17}$ is A or T; and
(c) a VH CDR3 comprising the amino acid sequence of SRGYFYGSTYDS (SEQ ID NO:29). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of $QIZ_{15}PGDZ_{16}DZ_{17}NYNGKFKG$ (SEQ ID NO: 502) wherein $Z_{15}$ is F or Y, $Z_{16}$ is A or G, and $Z_{17}$ is A or T; and
(c) a VH CDR3 comprising the amino acid sequence of WYYGSYYAMDY (SEQ ID NO:33). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of SYWMH (SEQ ID NO:10);
(b) a VH CDR2 comprising the amino acid sequence of $YIKPSSGYTKYZ_{45}QKZ_{46}Z_{47}Z_{48}$ (SEQ ID NO: 514) wherein $Z_{45}$ is N or A, $Z_{46}$ is F or L, $Z_{47}$ is K or Q, and $Z_{48}$ is D, E, or G; and
(c) a VH CDR3 comprising the amino acid sequence of DYYGSSSWFAY (SEQ ID NO:18). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 4 or 469;
(b) a VH CDR2 comprising the amino acid sequence of SEQ ID NO:5; and
(c) a VH CDR3 comprising the amino acid sequence of SEQ ID NO:6 or 33. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 10, 16, or 469;
(b) a VH CDR2 comprising the amino acid sequence of SEQ ID NO:17, 34, 470, or 497; and
(c) a VH CDR3 comprising the amino acid sequence of SEQ ID NO:18 or 498. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 10 or 469;
(b) a VH CDR2 comprising the amino acid sequence of SEQ ID NO:11 or 497; and
(c) a VH CDR3 comprising the amino acid sequence of SEQ ID NO:12 or 498. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 4, 28, or 499;
(b) a VH CDR2 comprising the amino acid sequence of SEQ ID NO:5; and
(c) a VH CDR3 comprising the amino acid sequence of SEQ ID NO:6, 29, or 33. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 10 or 485;
(b) a VH CDR2 comprising the amino acid sequence of SEQ ID NO: 34, 486, 487, or 488; and
(c) a VH CDR3 comprising the amino acid sequence of SEQ ID NO:18. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 485;
(b) a VH CDR2 comprising the amino acid sequence of SEQ ID NO: 486; and
(c) a VH CDR3 comprising the amino acid sequence of SEQ ID NO:18. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 485;
(b) a VH CDR2 comprising the amino acid sequence of SEQ ID NO: 487; and
(c) a VH CDR3 comprising the amino acid sequence of SEQ ID NO:18. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 485;
(b) a VH CDR2 comprising the amino acid sequence of SEQ ID NO: 488; and
(c) a VH CDR3 comprising the amino acid sequence of SEQ ID NO:18. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 10;
(b) a VH CDR2 comprising the amino acid sequence of SEQ ID NO: 34, 486, 487, or 488; and
(c) a VH CDR3 comprising the amino acid sequence of SEQ ID NO: 18. In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab320, for example, the VH CDR1, VH CDR2, and VH CDR3 of Ab320 as set forth in Table 2 (SEQ ID NOS: 4, 5, and 6, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab321, for example, the VH CDR1, VH CDR2, and VH CDR3 of Ab321 as set forth in Table 2 (SEQ ID NOS: 10, 11, and 12, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab322, for example, the VH CDR1, VH CDR2, and VH CDR3 of Ab322 as set forth in Table 2 (SEQ ID NOS: 16, 17, and 18, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab323, for example, the VH CDR1, VH CDR2, and VH CDR3 of Ab323 as set forth in Table 2 (SEQ ID NOS: 22, 23, and 24, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab324, for example, the VH CDR1, VH CDR2, and VH CDR3 of Ab324 as set forth in Table 2 (SEQ ID NOS: 28, 5, and 29, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab325, for example, the VH CDR1, VH CDR2, and VH CDR3 of Ab325 as set forth in Table 2 (SEQ ID NOS: 4, 5, and 33, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab326, for example, the VH CDR1, VH CDR2, and VH CDR3 of Ab326 as set forth in Table 2 (SEQ ID NOS: 10, 34, and 18, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab327, for example, the VH CDR1, VH CDR2, and VH CDR3 of Ab327 as set forth in Table 2 (SEQ ID NOS: 38, 39, and 40, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab328, for example, the VH CDR1, VH CDR2, and VH CDR3 of Ab328 as set forth in Table 2 (SEQ ID NOS: 10, 17, and 18, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab329, for example, the VH CDR1, VH CDR2, and VH CDR3 of Ab329 as set forth in Table 2 (SEQ ID NOS: 45, 46 and 47, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab330, for example, the VH CDR1, VH CDR2, and VH CDR3 of Ab330 as set forth in Table 2 (SEQ ID NOS: 51, 52, and 53, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab331, for example, the VH CDR1, VH CDR2, and VH CDR3 of Ab331 as set forth in Table 2 (SEQ ID NOS: 51, 54, and 53, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab332, for example, the VH CDR1, VH CDR2, and VH CDR3 of Ab332 as set forth in Table 2 (SEQ ID NOS: 58, 59, and 60, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab353, for example, the VH CDR1, VH CDR2, and VH CDR3 of Ab353 as set forth in Table 2 (SEQ ID NOS: 485, 34, and 18, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab354, for example, the VH CDR1, VH CDR2, and VH CDR3 of Ab354 as set forth in Table 2 (SEQ ID NOS: 10, 486, and 18, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab358, for example, the VH CDR1, VH CDR2, and VH CDR3 of Ab358 as set forth in Table 2 (SEQ ID NOS: 10, 487, and 18, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab362, for example, the VH CDR1, VH CDR2, and VH CDR3 of Ab362 as set forth in Table 2 (SEQ ID NOS: 10, 488, and 18, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:16;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:469;
(b) a VH CDR2 comprising the amino acid sequence of SEQ ID NO:17; and (c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:16;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:41. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:41. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:469;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:41. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:16;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:468. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:468. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:469;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:468. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:469;
(b) a VH CDR2 comprising the amino acid sequence of SEQ ID NO:5; and (c) a VH CDR3 comprising the amino acid sequence of SEQ ID NO:6; and
(ii) a light chain variable region (VL) comprising:
(a) a VL CDR1 comprising the amino acid sequence of SEQ ID NO: 1;
(b) a VL CDR2 comprising the amino acid sequence of SEQ ID NO:2; and
(c) a VL CDR3 comprising the amino acid sequence of SEQ ID NO:3. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:4;
(b) a VH CDR2 comprising the amino acid sequence of SEQ ID NO:5; and
(c) a VH CDR3 comprising the amino acid sequence of SEQ ID NO:33; and
(ii) a light chain variable region (VL) comprising:
(a) a VL CDR1 comprising the amino acid sequence of SEQ ID NO: 1;
(b) a VL CDR2 comprising the amino acid sequence of SEQ ID NO:2; and
(c) a VL CDR3 comprising the amino acid sequence of SEQ ID NO:3. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:485;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:485;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:485;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:485;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:486; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:486; and (c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:486; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:486; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:488; and (c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:488; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:488; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:488; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:485;
(b) a VH CDR2 comprising the amino acid sequence of SEQ ID NO:486; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:485;
(b) a VH CDR2 comprising the amino acid sequence of SEQ ID NO:486; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:486; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:486; and (c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:487; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:488; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:488; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:488; and (c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO: 485;
(b) a VH CDR2 comprising the amino acid sequence of SEQ ID NO:488; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:14; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 483;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of SEQ ID NO: 13;
(b) a VL CDR2 comprising the amino acid sequence of SEQ ID NO:484; and
(c) a VL CDR3 comprising the amino acid sequence of SEQ ID NO:15. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:16;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of KASQZ$_{10}$VZ$_{11}$TZ$_{12}$VA (SEQ ID NO:500), wherein Z$_{10}$ is N or D, Z$_{11}$ is G or S, and Z$_{12}$ is A or N;
(b) a VL CDR2 comprising the amino acid sequence of SEQ ID NO:14; and
(c) a VL CDR3 comprising the amino acid sequence of SEQ ID NO:15. In specific embodiments, Z$_{10}$ is N, Z$_{11}$ is G, and Z$_{12}$ is A or N. In specific embodiments, Z$_{10}$ is D, Z$_{11}$ is S, and Z$_{12}$ is A or N. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:34; and
(c) a VH CDR3 comprising the amino acid sequence of SEQ ID NO:18; and
(ii) a light chain variable region (VL) comprising:
(a) a VL CDR1 comprising the amino acid sequence of KASQZ$_{10}$VZ$_{11}$TZ$_{12}$VA (SEQ ID NO:500), wherein Z$_{10}$ is N or D, Z$_{11}$ is G or S, and Z$_{12}$ is A or N;
(b) a VL CDR2 comprising the amino acid sequence of SEQ ID NO:14; and
(c) a VL CDR3 comprising the amino acid sequence of SEQ ID NO:15. In specific embodiments, Z$_{10}$ is N, Z$_{11}$ is G, and Z$_{12}$ is A or N. In specific embodiments, Z$_{10}$ is D, Z$_{11}$ is S, and Z$_{12}$ is A or N. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:38;
(b) a VH CDR2 comprising the amino acid sequence of SEQ ID NO:39; and
(c) a VH CDR3 comprising the amino acid sequence of SEQ ID NO:40; and
(ii) a light chain variable region (VL) comprising:
(a) a VL CDR1 comprising the amino acid sequence of KASQ$Z_{10}$V$Z_{11}$T$Z_{12}$VA (SEQ ID NO:500), wherein $Z_{10}$ is N or D, $Z_{11}$ is G or S, and $Z_{12}$ is A or N;
(b) a VL CDR2 comprising the amino acid sequence of SEQ ID NO:36; and
(c) a VL CDR3 comprising the amino acid sequence of SEQ ID NO:37. In specific embodiments, $Z_{10}$ is N, $Z_{11}$ is G, and $Z_{12}$ is A or N. In specific embodiments, $Z_{10}$ is D, $Z_{11}$ is S, and $Z_{12}$ is A or N. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:10;
(b) a VH CDR2 comprising the amino acid sequence of SEQ ID NO:17; and
(c) a VH CDR3 comprising the amino acid sequence of SEQ ID NO:18; and
(ii) a light chain variable region (VL) comprising:
(a) a VL CDR1 comprising the amino acid sequence of KASQ$Z_{10}$V$Z_{11}$T$Z_{12}$VA (SEQ ID NO:500), wherein $Z_{10}$ is N or D, $Z_{11}$ is G or S, and $Z_{12}$ is A or N;
(b) a VL CDR2 comprising the amino acid sequence of SEQ ID NO:14; and
(c) a VL CDR3 comprising the amino acid sequence of SEQ ID NO:41. In specific embodiments, $Z_{10}$ is N, $Z_{11}$ is G, and $Z_{12}$ is A or N. In specific embodiments, $Z_{10}$ is D, $Z_{11}$ is S, and $Z_{12}$ is A or N. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of SEQ ID NO:22;
(b) a VH CDR2 comprising the amino acid sequence of SEQ ID NO:23; and
(c) a VH CDR3 comprising the amino acid sequence of SEQ ID NO:24; and
(ii) a light chain variable region (VL) comprising:
(a) a VL CDR1 comprising the amino acid sequence of KASQ$Z_{10}$V$Z_{11}$T$Z_{12}$VA (SEQ ID NO:500), wherein $Z_{10}$ is N or D, $Z_{11}$ is G or S, and $Z_{12}$ is A or N;
(b) a VL CDR2 comprising the amino acid sequence of SEQ ID NO:20; and
(c) a VL CDR3 comprising the amino acid sequence of SEQ ID NO:21. In specific embodiments, $Z_{10}$ is N, $Z_{11}$ is G, and $Z_{12}$ is A or N. In specific embodiments, $Z_{10}$ is D, $Z_{11}$ is S, and $Z_{12}$ is A or N. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}$YW$Z_{14}$N (SEQ ID NO:501), wherein $Z_{13}$ is N or S and $Z_{14}$ is M or V;
(b) a VH CDR2 comprising the amino acid sequence of QI$Z_{15}$PGD$Z_{16}$D$Z_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of SEQ ID NO:24; and
(ii) a light chain variable region (VL) comprising:
(a) a VL CDR1 comprising the amino acid sequence of KASQ$Z_{10}$V$Z_{11}$T$Z_{12}$VA (SEQ ID NO:500), wherein $Z_{10}$ is N or D, $Z_{11}$ is G or S, and $Z_{12}$ is A or N;
(b) a VL CDR2 comprising the amino acid sequence of SEQ ID NO:20; and
(c) a VL CDR3 comprising the amino acid sequence of SEQ ID NO:21. In specific embodiments, $Z_{10}$ is N, $Z_{11}$ is G, and $Z_{12}$ is A or N. In specific embodiments, $Z_{10}$ is D, $Z_{11}$ is S, and $Z_{12}$ is A or N. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}$YW$Z_{14}$N (SEQ ID NO:501), wherein $Z_{13}$ is N or S and $Z_{14}$ is M or V;
(b) a VH CDR2 comprising the amino acid sequence of SEQ ID NO:23; and
(c) a VH CDR3 comprising the amino acid sequence of SEQ ID NO:24; and
(ii) a light chain variable region (VL) comprising:
(a) a VL CDR1 comprising the amino acid sequence of KASQ$Z_{10}$V$Z_{11}$T$Z_{12}$VA (SEQ ID NO:500), wherein $Z_{10}$ is N or D, $Z_{11}$ is G or S, and $Z_{12}$ is A or N;
(b) a VL CDR2 comprising the amino acid sequence of SEQ ID NO:20; and
(c) a VL CDR3 comprising the amino acid sequence of SEQ ID NO:21. In specific embodiments, $Z_{10}$ is N, $Z_{11}$ is G, and $Z_{12}$ is A or N. In specific embodiments, $Z_{10}$ is D, $Z_{11}$ is S, and $Z_{12}$ is A or N. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}$YW$Z_{14}$N (SEQ ID NO:501), wherein $Z_{13}$ is N or S and $Z_{14}$ is M or V;
(b) a VH CDR2 comprising the amino acid sequence of QI$Z_{15}$PGD$Z_{16}$D$Z_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of SEQ ID NO:24; and
(ii) a light chain variable region (VL) comprising:
(a) a VL CDR1 comprising the amino acid sequence of SEQ ID NO: 19;
(b) a VL CDR2 comprising the amino acid sequence of SEQ ID NO:20; and
(c) a VL CDR3 comprising the amino acid sequence of SEQ ID NO:21. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of SEQ ID NO:23; and
(c) a VH CDR3 comprising the amino acid sequence of SEQ ID NO:24; and
(ii) a light chain variable region (VL) comprising:
(a) a VL CDR1 comprising the amino acid sequence of SEQ ID NO: 19;
(b) a VL CDR2 comprising the amino acid sequence of SEQ ID NO:20; and
(c) a VL CDR3 comprising the amino acid sequence of SEQ ID NO:21. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of QIZ$_{15}$PGDZ$_{16}$DZ$_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of SEQ ID NO:29; and
(ii) a light chain variable region (VL) comprising:
(a) a VL CDR1 comprising the amino acid sequence of SEQ ID NO: 25;
(b) a VL CDR2 comprising the amino acid sequence of SEQ ID NO:26; and
(c) a VL CDR3 comprising the amino acid sequence of SEQ ID NO:27. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of SEQ ID NO:5; and
(c) a VH CDR3 comprising the amino acid sequence of SEQ ID NO:29; and
(ii) a light chain variable region (VL) comprising:
(a) a VL CDR1 comprising the amino acid sequence of SEQ ID NO: 25;
(b) a VL CDR2 comprising the amino acid sequence of SEQ ID NO:26; and
(c) a VL CDR3 comprising the amino acid sequence of SEQ ID NO:27. In a particular embodiment the antibody or an antigen-binding fragment thereof is an antibody which specifically binds to an ECD of ALK.

In a specific embodiment, an anti-ALK antibody described herein or an antigen-binding fragment thereof comprises:

(i) a heavy chain variable region (VH) comprising:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of SEQ ID NO:5; and
(c) a VH CDR3 comprising the amino acid sequence of SEQ ID NO:29; and
(ii) a light chain variable region (VL) comprising:
(a) a VL CDR1 comprising the amino acid sequence of SEQ ID NO: 25;
(b) a VL CDR2 comprising the amino acid sequence of SEQ ID NO:26; and
(c) a VL CDR3 comprising the amino acid sequence of SEQ ID NO:27. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of QIZ$_{15}$PGDZ$_{16}$DZ$_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of SEQ ID NO:29; and
(ii) a light chain variable region (VL) comprising:
(a) a VL CDR1 comprising the amino acid sequence of SEQ ID NO: 25;
(b) a VL CDR2 comprising the amino acid sequence of SEQ ID NO:26; and
(c) a VL CDR3 comprising the amino acid sequence of SEQ ID NO:27. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of QIZ$_{15}$PGDZ$_{16}$DZ$_{17}$NYNGKFKG (SEQ ID NO: 502) wherein $Z_{15}$ is F or Y, $Z_{16}$ is A or G, and $Z_{17}$ is A or T; and
(c) a VH CDR3 comprising the amino acid sequence of SEQ ID NO:33; and
(ii) a light chain variable region (VL) comprising:
(a) a VL CDR1 comprising the amino acid sequence of SEQ ID NO: 30;
(b) a VL CDR2 comprising the amino acid sequence of SEQ ID NO:31; and
(c) a VL CDR3 comprising the amino acid sequence of SEQ ID NO:32. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is N or S and $Z_{14}$ is M or V;
(b) a VH CDR2 comprising the amino acid sequence of SEQ ID NO:5; and (c) a VH CDR3 comprising the amino acid sequence of SEQ ID NO:33; and
(ii) a light chain variable region (VL) comprising:
(a) a VL CDR1 comprising the amino acid sequence of SEQ ID NO: 30;
(b) a VL CDR2 comprising the amino acid sequence of SEQ ID NO:31; and
(c) a VL CDR3 comprising the amino acid sequence of SEQ ID NO:32. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of SEQ ID NO:5; and
(c) a VH CDR3 comprising the amino acid sequence of SEQ ID NO:33; and
(ii) a light chain variable region (VL) comprising:
(a) a VL CDR1 comprising the amino acid sequence of SEQ ID NO: 30;
(b) a VL CDR2 comprising the amino acid sequence of SEQ ID NO:31; and
(c) a VL CDR3 comprising the amino acid sequence of SEQ ID NO:32. In a particular embodiment the antibody or an antigen-binding fragment thereof is an antibody which specifically binds to an ECD of ALK.

In a specific embodiment, an anti-ALK antibody described herein or an antigen-binding fragment thereof comprises:
(i) a heavy chain variable region (VH) comprising:
(a) a VH CDR1 comprising the amino acid sequence of $Z_{13}YWZ_{14}N$ (SEQ ID NO:501), wherein $Z_{13}$ is S and $Z_{14}$ is M or V;
(b) a VH CDR2 comprising the amino acid sequence of $QIZ_{15}PGDZ_{16}DZ_{17}NYNGKFKG$ (SEQ ID NO: 502) wherein $Z_{15}$ is F or Y, $Z_{16}$ is A or G, and $Z_{17}$ is A or T; and
(c) a VH CDR3 comprising the amino acid sequence of SEQ ID NO:33; and
(ii) a light chain variable region (VL) comprising:
(a) a VL CDR1 comprising the amino acid sequence of SEQ ID NO: 30;
(b) a VL CDR2 comprising the amino acid sequence of SEQ ID NO:31; and
(c) a VL CDR3 comprising the amino acid sequence of SEQ ID NO:32. In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab320, for example, the VH CDR1, VH CDR2, and VH CDR3 of Ab320 as set forth in Table 2 (SEQ ID NOS: 4, 5, and 6, respectively); and (ii) the VL CDR1, VL CDR2, and VL CDR3 of Ab320, for example, the VL CDR1, VL CDR2, and VL CDR3 of Ab320 as set forth in Table 1 (SEQ ID NOS: 1, 2, and 3, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab321, for example, the VH CDR1, VH CDR2, and VH CDR3 of Ab321 as set forth in Table 2 (SEQ ID NOS: 10, 11, and 12, respectively); and (ii) the VL CDR1, VL CDR2, and VL CDR3 of Ab321, for example, the VL CDR1, VL CDR2, and VL CDR3 of Ab321 as set forth in Table 1 (SEQ ID NOS: 7, 8, and 9, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab322, for example, the VH CDR1, VH CDR2, and VH CDR3 of Ab322 as set forth in Table 2 (SEQ ID NOS: 16, 17, and 18, respectively); and (ii) the VL CDR1, VL CDR2, and VL CDR3 of Ab322, for example, the VL CDR1, VL CDR2, and VL CDR3 of Ab322 as set forth in Table 1 (SEQ ID NOS: 13, 14, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab323, for example, the VH CDR1, VH CDR2, and VH CDR3 of Ab323 as set forth in Table 2 (SEQ ID NOS: 22, 23, and 24, respectively); and (ii) the VL CDR1, VL CDR2, and VL CDR3 of Ab323, for example, the VL CDR1, VL CDR2, and VL CDR3 of Ab323 as set forth in Table 1 (SEQ ID NOS: 19, 20, and 21, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab324, for example, the VH CDR1, VH CDR2, and VH CDR3 of Ab324 as set forth in Table 2 (SEQ ID NOS: 28, 5, and 29, respectively); and (ii) the VL CDR1, VL CDR2, and VL CDR3 of Ab324, for example, the VL CDR1, VL CDR2, and VL CDR3 of Ab324 as set forth in Table 1 (SEQ ID NOS: 25, 26, and 27, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab325, for example, the VH CDR1, VH CDR2, and VH CDR3 of Ab325 as set forth in Table 2 (SEQ ID NOS: 4, 5, and 33, respectively); and (ii) the VL CDR1, VL CDR2, and VL CDR3 of Ab325, for example, the VL CDR1, VL CDR2, and VL CDR3 of Ab325 as set forth in Table 1 (SEQ ID NOS: 30, 31, and 32, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab326, for example, the VH CDR1, VH CDR2, and VH CDR3 of Ab326 as set forth in Table 2 (SEQ ID NOS: 10, 34, and 18, respectively); and (ii) the VL CDR1, VL CDR2, and VL CDR3 of Ab326, for example, the VL CDR1, VL CDR2, and VL CDR3 of Ab326 as set forth in Table 1 (SEQ ID NOS: 13, 14, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab327, for example, the VH CDR1, VH CDR2, and VH CDR3 of Ab327 as set forth in Table 2 (SEQ ID NOS: 38, 39, and 40, respectively); and (ii) the VL CDR1, VL CDR2, and VL CDR3 of Ab327, for example, the VL CDR1, VL CDR2, and VL CDR3 of Ab327 as set forth in Table 1 (SEQ ID NOS: 35, 36, and 37, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab328, for example, the VH CDR1, VH CDR2, and VH CDR3 of Ab328 as set forth in Table 2 (SEQ ID NOS: 10, 17, and 18, respectively); and (ii) the VL CDR1, VL CDR2, and VL CDR3 of Ab328, for example, the VL CDR1, VL CDR2, and VL CDR3 of Ab328 as set forth in Table 1 (SEQ ID NOS: 13, 14, and 41, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab329, for example, the VH CDR1, VH CDR2, and VH CDR3 of Ab329 as set forth in Table 2 (SEQ ID NOS: 45, 46, and 47, respectively); and (ii) the VL CDR1, VL CDR2, and VL CDR3 of Ab329, for example, the VL CDR1, VL CDR2, and VL CDR3 of Ab329 as set forth in Table 1 (SEQ ID NOS: 42, 43, and 44, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab330, for example, the VH CDR1, VH CDR2, and VH CDR3 of Ab330 as set forth in Table 2 (SEQ ID NOS: 51, 52, and 53, respectively); and (ii) the VL CDR1, VL CDR2, and VL CDR3 of Ab330, for example, the VL CDR1, VL CDR2, and VL CDR3 of Ab330 as set forth in Table 1 (SEQ ID NOS: 48, 49, and 50, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab331, for example, the VH CDR1, VH CDR2, and VH CDR3 of Ab331 as set forth in Table 2 (SEQ ID NOS: 51, 54, and 53, respectively); and (ii) the VL CDR1, VL CDR2, and VL CDR3 of Ab331, for example, the VL CDR1, VL CDR2, and VL CDR3 of Ab331 as set forth in Table 1 (SEQ ID NOS: 48, 49, and 50, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab332, for example, the VH CDR1, VH CDR2, and VH CDR3 of Ab332 as set forth in Table 2 (SEQ ID NOS: 58, 59, and 60, respectively); and (ii) the VL CDR1, VL CDR2, and VL CDR3 of Ab332, for example, the VL CDR1, VL CDR2, and VL CDR3 of Ab332 as set forth in Table 1 (SEQ ID NOS: 55, 56, and 57, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab423 (SEQ ID NOS: 10, 34, and 18, respectively); and (ii) the VL CDR1, VL CDR2, and VL CDR3 of Ab423, for example, the VL CDR1, VL CDR2, and VL CDR3 of Ab423 as set forth in Table 1 (SEQ ID NOS: 483, 14, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab435 (SEQ ID NOS: 10, 34, and 18, respectively); and (ii) the VL CDR1, VL CDR2, and VL CDR3 of Ab435, for example, the VL CDR1, VL CDR2, and VL CDR3 of Ab435 as set forth in Table 1 (SEQ ID NOS: 13, 484, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab353, for example, the VH CDR1, VH CDR2, and VH CDR3 of Ab353, as set forth in Table 2 (SEQ ID NOS: 485, 34, and 18, respectively); and (ii) the VL CDR1, VL CDR2, and VL CDR3 of Ab353 (SEQ ID NOS: 13, 14, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab354, for example, the VH CDR1, VH CDR2, and VH CDR3 of Ab354 as set forth in Table 2 (SEQ ID NOS: 10, 486, and 18, respectively); and (ii) the VL CDR1, VL CDR2, and VL CDR3 of Ab354 (SEQ ID NOS: 13, 14, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab358, for example, the VH CDR1, VH CDR2, and VH CDR3 of Ab358 as set forth in Table 2 (SEQ ID NOS: 10, 487, and 18, respectively); and (ii) the VL CDR1, VL CDR2, and VL CDR3 of Ab358 (SEQ ID NOS: 13, 14, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of Ab362, for example, the VH CDR1, VH CDR2, and VH CDR3 of Ab362 as set forth in Table 2 (SEQ ID NOS: 10, 488, and 18, respectively); and (ii) the VL CDR1, VL CDR2, and VL CDR3 of Ab362 (SEQ ID NOS: 13, 14, and 15, respectively). In a particular embodiment the antibody or an antigen-binding fragment thereof is an antibody which specifically binds to an ECD of ALK.

In a specific embodiment, an anti-ALK antibody described herein or an antigen-binding fragment thereof comprises (i) the VH CDR1, VH CDR2, and VH CDR3 of any of Ab320-Ab332, for example, the VH CDR1, VH CDR2, and VH CDR3 of any of Ab320-Ab332 as set forth in Table 2 (SEQ ID NOS: 10, 34, and 18, respectively); and (ii) the VL CDR1, VL CDR2, and VL CDR3 of any of Ab320-Ab332, for example, the VL CDR1, VL CDR2, and VL CDR3 of any of Ab320-Ab332 as set forth in Table 1 (SEQ ID NOS: 13, 14, and 15, respectively). In a particular embodiment the antibody or an antigen-binding fragment thereof is an antibody which specifically binds to an ECD of ALK.

In certain embodiments, an antibody described herein or an antigen-binding fragment thereof comprising Kabat VL and VH CDRS (e.g., Kabat VL CDR 1, 2, and 3, and Kabat VH CDR 1, 2, and 3 for any of antibodies Ab320-Ab332 as described in Tables 1 and 2, respectively) further comprises framework regions surrounding the CDRs in the variable region (e.g., variable region in Tables 13 and 14) in the format, from the N-terminus to C-terminus: FR1-CDR1-FR2-CDR2-FR3-CDR3-FR4. For example, FR1, FR2, FR3, and/or FR4 sequences can be any of those FR1, FR2, FR3 and/or FR4 sequences of Tables 3 and/or 4. In a particular embodiment the antibody or an antigen-binding fragment thereof is an antibody which specifically binds to an ECD of ALK.

In certain embodiments, an anti-ALK antibody, or antigen-binding fragment thereof, described herein comprises CDRs of any of antibodies Ab320-Ab332 and Ab351-Ag446, as determined by the IMGT (Immunogenetics) numbering system; see, e.g., Lefranc, M.-P., 1999, The Immunologist, 7:132-136 and Lefranc, M.-P. et al., 1999, Nucleic Acids Res., 27:209-212), both of which are incorporated herein by reference in their entirety. Using the IMGT numbering system, CDRs within an antibody heavy chain molecule are typically present at amino acid positions 27 to 38 (CDR1; 5-12 amino acids in length), amino acid positions 56 to 65 (CDR2; 0-10 amino acid positions in length), and amino acid positions 105 to 117 (CDR3; 2-12 amino acids in length). Using Kabat numbering, these heavy chain amino acid positions correspond to amino acid positions 26-35 for CDR1, 51-57 for CDR2 and 93-102 for CDR3. Using the IMGT numbering system, CDRs within an antibody light chain molecule are typically present at amino acid positions 27 to 38 (CDR1; 5-12 amino acids in length), amino acid positions 56 to 65 (CDR2; 0-10 amino acid positions in length), and amino acid positions 105 to 117 (CDR3; 2-12 amino acids in length). Using Kabat numbering, these light chain amino acid positions correspond to amino acid positions 27-32 for CDR1, 50-52 for CDR2, and 89-97 for CDR3.

In certain embodiments, provided herein is an antibody or antigen-binding fragment thereof, which specifically binds to an ECD of human ALK and comprises VL and VH CDRs of any of Ab320-Ab332, for example as set forth in Tables 5 and 6.

TABLE 5

VL CDR Amino Acid Sequences (IMGT)

| Antibody | VL CDR1 (SEQ ID NO:) | VL CDR2 (SEQ ID NO:) | VL CDR3 (SEQ ID NO:) |
|---|---|---|---|
| Ab320 | ENIYYS (129) | NAN (130) | KQAYDVP (131) |
| Ab321 | QGISNS (135) | YTS (136) | QQYSKLP (137) |
| Ab322 | QNVGTN (141) | SAS (142) | QQYNSYP (143) |
| Ab323 | QDVSTA (147) | WAS (148) | QQHYSTP (149) |
| Ab324 | ESVDNYGISF (153) | AAS (154) | QQSKEVP (155) |

TABLE 5-continued

VL CDR Amino Acid Sequences (IMGT)

| Antibody | VL CDR1 (SEQ ID NO:) | VL CDR2 (SEQ ID NO:) | VL CDR3 (SEQ ID NO:) |
|---|---|---|---|
| Ab325 | QDISNY (157) | YTS (136) | QQGNTLP (158) |
| Ab326 | QNVGTN (141) | SAS (142) | QQYNSYP (143) |
| Ab327 | QNVGTAVA (161) | SAS (142) | QQYSSYP (162) |
| Ab328 | QNVGTNVA (166) | SAS (142) | QRYNSYP (167) |
| Ab329 | QDIDNY (168) | SAT (169) | LQHY (170) |
| Ab330 | QDIGNY (174) | YAT (175) | LQYKQ (176) |
| Ab331 | QDIGNY (174) | YAT (175) | LQYKQ (176) |
| Ab332 | QSVDYDGDSY (181) | AAS (154) | QQSNEDP (182) |
| Ab423 | QSVSSN (489) | SAS (142) | QQYNSYP (143) |
| Ab435 | QNVGTN (141) | GAS (490) | QQYNSYP (143) |

TABLE 6

VH CDR Amino Acid Sequences (IMGT)

| Antibody | VH CDR1 (SEQ ID NO:) | VH CDR2 (SEQ ID NO:) | VH CDR3 (SEQ ID NO:) |
|---|---|---|---|
| Ab320 | GYAFSSYW (132) | IYPGDGDT (133) | ASYYYGSKAY (134) |
| Ab321 | GYTFTSYW (138) | IDPNSGGT (139) | ARDYYGSSYRFAY (140) |
| Ab322 | GYTFTNYW (144) | INPSSGYT (145) | ARDYYGSSSWFAY (146) |
| Ab323 | GYTFSNYW (150) | IFPGDADA (151) | ARFSYDGAFAY (152) |
| Ab324 | GYAFSSYW (132) | IYPGDGDT (133) | ARSRGYFYGSTYDS (156) |
| Ab325 | GYAFSSYW (132) | IYPGDGDT (133) | ARWYYGSYYAMDY (159) |
| Ab326 | GYTFTSYW (138) | IKPSSGYT (160) | ARDYYGSSSWFAY (146) |
| Ab327 | GFTFSSYA (163) | ISSGGDYI (164) | TRERIWLRRFFDV (165) |
| Ab328 | GYTFTSYW (138) | INPSSGYT (145) | ARDYYGSSSWFAY (146) |
| Ab329 | GFSLTSYH (171) | IWGDGRTT (172) | ARATMTGHGDA (173) |
| Ab330 | GLTFSTAW (177) | IKDKSNKF (178) | TTSYGYA (179) |
| Ab331 | GLTFSTAW (177) | IKDKSNNF (180) | TTSYGYA (179) |
| Ab332 | GYTFTDYY (183) | INPNNGVT (184) | AREDYGSNYFDY (185) |
| Ab353 | GYTFTSSA (491) | IKPSSGYT (160) | ARDYYGSSSWFAY (146) |
| Ab362 | GYTFSSYW (492) | IKPSSGYT (160) | ARDYYGSSSWFAY (146) |

TABLE 7

VL FR Amino Acid Sequences (IMGT)

| Antibody | VL FR1 (SEQ ID NO:) | VL FR2 (SEQ ID NO;) | VL FR3 (SEQ ID NO:) | VL FR4 (SEQ ID NO:) |
|---|---|---|---|---|
| Ab320 | DIQMTQSPASLAASVG ETVTITCRAS (186) | LAWYQQKQGKSPQLLI Y (187) | SLEDGVPSRFSGSGSGT QYSMKINSMQPEDTATY FC (188) | FTFGSGTKLEIKR (189) |
| Ab321 | AIQMTQTTSSLSASLG DRVTISCSVS (194) | LNWYQQKPDGTVKLLI Y (195) | SLHSGVPSRFSGSGSGT DYSLTISNLEPEDIATY YC (196) | LTFGAGTKLELKR (197) |
| Ab322 | DIVMTQSQRFMSTSVG DRVSVTCKAS (201) | VAWYQQKPGQSPKALI Y (202) | YRYSGVPDRFTGSGSGT DFTLTVSNVQSEDLAEY FC (203) | YMYTFGGGTKLE IKR (204) |
| Ab323 | DIVMTQSHKFMSTSVG DRVSITCKAS (208) | VAWYQQKPGQSPKPLI Y (209) | TRHTGVPD RFTGSGSGTDYTLTISS VQTEDLALYYC (210) | RTFGGGTKLEIKR (211) |
| Ab324 | DIVLTQSPASLAVSLG QRATISCRAS (214) | MNWFQQKPGQPPKLLI Y (215) | NQGSGVPARFSGSGSGT DFSLNIHPMEEDDTAMY FC (216) | WTFGGGTKLEIKR (217) |
| Ab325 | DIQMTQTTSSLSASLG DRVTISCRAS (220) | LNWYQQKPDGTVKLLI Y (195) | RLHSGVPSRFSGSGSGT DYSLTISNLEQEDIATY FC (221) | RTFGGGTKLEIKR (211) |
| Ab326 | DIVMTQSQRFMSTSVG DRVSVTCKAS (201) | VAWYQQKPGQSPKALI Y (202) | YRYSGVPDRFTGSGSGT DFTLTISNVQSEDLAEY FC (203) | YMYTFGGGTKLE IKR (204) |
| Ab327 | DIVMTQSQKFMSTSVG DRVSITCKAS (223) | WYQLKPGQSPKLLIY (224) | NRFTGVPDRFTGSGSGT DFTLTISNMQSEDLADY FC (225) | LTFGSGTKLEIK R (226) |
| Ab328 | DIVMTQSQKFMSTSVG DRVSVTCKAS (231) | WYQQKPGHSPKALIY (232) | YRYSGVPDRFTGSGSGT DFTLTISNVQSEDLAEY FC (233) | YMFTFGGGTKLE IKR (234) |
| Ab329 | DIQMTQSPASLSASLE EIVTITCQAS (237) | LSWYQQKPGKSPHLLI H (238) | SLADGVPSRFSGGRSGT QFSLKINRLQVEDTGIY YC (239) | SGWTFGGGTKLE LKR (240) |
| Ab330 | DIQMTQSPSSMSASLG DRVTITCQAS (245) | LIWFQQKPGKSPRPLI Y (246) | NLANGVPSRFSGSRSGS EYSLTITSLESEDMADY HC (247) | HLTFGSGTKLEI ER (248) |
| Ab331 | DIQMTQSPSSMSASLG DRITITCQAS (253) | LIWFQQKPGKSPRPLI Y (246) | NLANGVPSRFSGSRSGS EYSLTITSLESEDMADY HC (247) | HLTFGSGTKLEI ER (248) |
| Ab332 | DIVLTQSPASLAVSLG QRATISCKAS (254) | MNWYQQKPGQPPKLLI Y (255) | NLESGIPARLSGSGSGT DFTLNIHPVEEEDAATY YC (256) | PTFGGGTKLEIR R (257) |

TABLE 8

VH FR Amino Acid Sequences (IMGT)

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab320 | QVQLQQSGAELVKPGA SVKISCKAS (190) | MNWVKQRPGKGLEW IGQ (191) | NYNGKFKGKATLTADKSSS TAYMQLSSLTSEDSAVYFC (192) | WGQGTLVTVSA (193) |
| Ab321 | QVQLQQPGAEFVKPGA SVKLSCKAS (198) | MHWVKQRPGRGLEW IGR (199) | KYNEKFKSKATLTVDKPSS TAYMQLSSLTSEDSAVYYC (200) | WGQGTLVTVSA (193) |
| Ab322 | QVQLQQSGAELAKPGA SVKLSCKAS (205) | MHWVKQRPGQGLEW IGY (206) | KYNQKFKDKATLTADKSSS TAYMQLSSLTYEDSAVYYC (207) | WGQGTLVTVSA (193) |

TABLE 8-continued

VH FR Amino Acid Sequences (IMGT)

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab323 | QVQLQQSGAELVKPGA SVKISCKTS (212) | MNWVKQRPGKGLEW IGQ (191) | NYNGKFKGKATLTADKSSS AAFMQLSSLTSEDSAVYFC (213) | WGQGTLVTVSA (193) |
| Ab324 | QVQLQQSGAELVKPGA SVKISCKAS (190) | VNWVKQRPGKGLEW IGQ (218) | NYNGKFKGKATLTADKSSS TAYMQLSSLTSEDSAVYFC (219) | WGQGTTLTVSS (192) |
| Ab325 | QVQLQQSGAELVKPGA SVKISCKAS (190) | MNWVKQRPGKGLEW IGQ (191) | NYNGKFKGKATLTADKSSS TAYMQLSSLTSEDSAVYFC (222) | WGQGTSVTVSS (192) |
| Ab326 | QVQLQQSGAELAKPGA SVKLSCKAS (205) | MHWVKQRPGQGLEW IGY (206) | KYNQKFKDKATLTADKSSS TAYMQLSSLTYEDSAVYYC (207) | WGQGTLVTVSA (193) |
| Ab327 | DVKLVESGEGLVKPGG SLKLSCAAS (227) | MSWVRQTPEKRLEW VTY (228) | YYADTVKGRFTISRDNARN TLYLQMSSLKSEDTAMYYC (229) | WGTGTTVTVSS (230) |
| Ab328 | QVQLQQSGAELAKPGA SVKLSCKAS (205) | MHWVKQRPGQGLEW IGY (235) | KYNQKFKDKATLTADKSSS TAYMQLSSLTFEDSAVYYC (236) | WGQGTLVTVSA (193) |
| Ab329 | QVQLKESGPGLVKPSA TLSLTCTVS (241) | VCWIRQTPGKGLEW MGV (242) | YNPPLKSRLSISRDTSKSQ VFLKMSSLKTEDTATYYC (243) | WGQGASVTVSS (244) |
| Ab330 | EVQVVETGGGVVQPGK SLEITCATS (249) | MYWVRQSSDRRLEW IAR (250) | ASDYVESVRGRFTISRDDS RSSVYLQMNNLKEEDTATY YC (251) | WGQGVMVTVSS (252) |
| Ab331 | EVQVVETGGGVVQPGK SLEITCATS (249) | MYWVRQSSDRRLEW IAR (250) | ASDYVESVRGRFTISRDDS RSSVYLQMNNLKEEDTATY YC (251) | WGQGVMVTVSS (252) |
| Ab332 | EVQLQQSGPELVKPGT SVKISCKAS (258) | MNWMKQSHGKSLEW IGD (259) | SYNQKFKGKATLTVDKSSS TAYMELRSLTSEDSAVYYC (260) | WGQGTTLTVSS (261) |

In a particular embodiment, an antibody described herein, or an antigen-binding fragment thereof, which specifically binds to an ECD of ALK, comprises:
(a) a VL CDR1 comprising the amino acid sequence of QNVGTN (SEQ ID NO:141);
(b) a VL CDR2 comprising the amino acid sequence of SAS (SEQ ID NO:142); and
(c) a VL CDR3 comprising the amino acid sequence of $QZ_{18}YZ_{19}SYP$ (SEQ ID NO:513), wherein $Z_{18}$ is any amino acid, for example, Q or R and $Z_{19}$ is any amino acid, for example, N or S. In certain embodiments, $Z_{18}$ and $Z_{19}$ are any amino acid. In specific embodiments, $Z_{18}$ is a conservative substitution of Q or R and $Z_{19}$ is a conservative substitution of N or S. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of $QZ_{20}VZ_{21}TZ_{22}$ (SEQ ID NO:505), wherein $Z_{20}$ is any amino acid, for example, N or D, $Z_{21}$ is any amino acid, for example, G or S, and $Z_{22}$ is any amino acid, for example, A or N;
(b) a VL CDR2 comprising the amino acid sequence of SAS (SEQ ID NO:142) or WAS (SEQ ID NO:148); and
(c) a VL CDR3 comprising the amino acid sequence of QQHYSTP (SEQ ID NO:149) or QQYSSYP (SEQ ID NO:162) or $QZ_{18}YNSYP$ (SEQ ID NO:513), wherein $Z_{18}$ is any amino acid, for example, Q or R. In certain embodiments, any one of $Z_{18}$-$Z_{22}$ is any amino acid. In specific embodiments, $Z_{18}$ is a conservative substitution of Q or R, $Z_{19}$ is a conservative substitution of N or S, $Z_{20}$ is a conservative substitution of N or D, $Z_{21}$ is a conservative substitution of G or S, and $Z_{22}$ is a conservative substitution of A or N. In specific embodiments, $Z_{18}$ is a conservative substitution of Q or R, $Z_{19}$ is a conservative substitution of N or S, $Z_{20}$ is N, $Z_{21}$ is G, and $Z_{22}$ is A or N. In specific embodiments, $Z_{18}$ is a conservative substitution of Q or R, $Z_{19}$ is a conservative substitution of N or S, $Z_{20}$ is D, $Z_{21}$ is S, and $Z_{22}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of $QZ_{20}VZ_{21}TZ_{22}$ (SEQ ID NO:505), wherein $Z_{20}$ is N or D, $Z_{21}$ is G or S, and $Z_{22}$ is A or N;
(b) a VL CDR2 comprising the amino acid sequence of SAS (SEQ ID NO:142); and
(c) a VL CDR3 comprising the amino acid sequence of QQYNSYP (SEQ ID NO:143). In specific embodiments, $Z_{20}$ is N, $Z_{21}$ is G, and $Z_{22}$ is A or N. In specific embodiments, $Z_{20}$ is D, $Z_{21}$ is S, and $Z_{22}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of $QZ_{20}VZ_{21}TZ_{22}$ (SEQ ID NO:505), wherein $Z_{20}$ is N or D, $Z_{21}$ is G or S, and $Z_{22}$ is A or N;
(b) a VL CDR2 comprising the amino acid sequence of WAS (SEQ ID NO:148); and
(c) a VL CDR3 comprising the amino acid sequence of QQHYSTP (SEQ ID NO:149). In specific embodiments, $Z_{20}$ is N, $Z_{21}$ is G, and $Z_{22}$ is A or N. In specific embodiments, $Z_{20}$ is N, $Z_{21}$ is G, and $Z_{22}$ is A or N. In specific embodiments, $Z_{20}$ is D, $Z_{21}$ is S, and $Z_{22}$ is A or N.

In a particular embodiment, an antibody described herein, or an antigen-binding fragment thereof, which specifically binds to an ECD of ALK, comprises:
(a) a VL CDR1 comprising the amino acid sequence of $QZ_{20}VZ_{21}TZ_{22}$ (SEQ ID NO:505), wherein $Z_{20}$ is N or D, $Z_{21}$ is G or S, and $Z_{22}$ is A or N;
(b) a VL CDR2 comprising the amino acid sequence of SAS (SEQ ID NO:142); and
(c) a VL CDR3 comprising the amino acid sequence of QQYSSYP (SEQ ID NO:162). In specific embodiments, $Z_{20}$ is N, $Z_{21}$ is G, and $Z_{22}$ is A or N. In specific embodiments, $Z_{20}$ is D, $Z_{21}$ is S, and $Z_{22}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of $QZ_{20}VZ_{21}TZ_{22}$ (SEQ ID NO:505), wherein $Z_{20}$ is N or D, $Z_{21}$ is G or S, and $Z_{22}$ is A or N;
(b) a VL CDR2 comprising the amino acid sequence of SAS (SEQ ID NO:142); and
(c) a VL CDR3 comprising the amino acid sequence of QRYNSYP (SEQ ID NO:167). In specific embodiments, $Z_{20}$ is N, $Z_{21}$ is G, and $Z_{22}$ is A or N. In specific embodiments, $Z_{20}$ is D, $Z_{21}$ is S, and $Z_{22}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 141, 161, or 166;
(b) a VL CDR2 comprising the amino acid sequence of SEQ ID NO:142; and
(c) a VL CDR3 comprising the amino acid sequence of SEQ ID NO:143, 162, or 167. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 141, 161, or 166;
(b) a VL CDR2 comprising the amino acid sequence of SEQ ID NO:142; and
(c) a VL CDR3 comprising the amino acid sequence of SEQ ID NO:143, 162, 167, or 513. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 141, 161, 166, or 505;
(b) a VL CDR2 comprising the amino acid sequence of SEQ ID NO:142; and
(c) a VL CDR3 comprising the amino acid sequence of SEQ ID NO: 143, 162, 167, or 513. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 141 or 489;
(b) a VL CDR2 comprising the amino acid sequence of SEQ ID NO:142 or 490; and
(c) a VL CDR3 comprising the amino acid sequence of SEQ ID NO: 143. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 489;
(b) a VL CDR2 comprising the amino acid sequence of SEQ ID NO: 490; and
(c) a VL CDR3 comprising the amino acid sequence of SEQ ID NO: 143. In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab320, for example, the VL CDR1, VL CDR2, and VL CDR3 of Ab320 as set forth in Table 5 (SEQ ID NOS: 129, 130, and 131, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab321, for example, the VL CDR1, VL CDR2, and VL CDR3 of Ab321 as set forth in Table 5 (SEQ ID NOS: 135, 136, and 137, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab322, for example, the VL CDR1, VL CDR2, and VL CDR3 of Ab322 as set forth in Table 5 (SEQ ID NOS: 141, 142, and 143, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab323, for example, the VL CDR1, VL CDR2, and VL CDR3 of Ab323 as set forth in Table 5 (SEQ ID NOS: 147, 148, and 149, respectively).

In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab324, for example, the VL CDR1, VL CDR2, and VL CDR3 of Ab324 as set forth in Table 5 (SEQ ID NOS: 153, 154, and 155, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab325, for example, the VL CDR1, VL CDR2, and VL CDR3 of Ab325 as set forth in Table 5 (SEQ ID NOS: 157, 136, and 158, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab326, for example, the VL CDR1, VL CDR2, and VL CDR3 of Ab326 as set forth in Table 5 (SEQ ID NOS: 141, 142, and 143, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab327, for example, the VL CDR1, VL CDR2, and VL CDR3 of Ab327 as set forth in Table 5 (SEQ ID NOS: 161, 142, and 162, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab328, for example, the VL CDR1, VL CDR2, and VL CDR3 of Ab328 as set forth in Table 5 (SEQ ID NOS: 166, 142, and 167, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab329, for example, the VL CDR1, VL CDR2, and VL CDR3 of Ab329 as set forth in Table 5 (SEQ ID NOS: 168, 169, and 170, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab330, for example, the VL CDR1, VL CDR2, and VL CDR3 of Ab330 as set forth in Table 5 (SEQ ID NOS: 174, 175, and 176, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab331, for example, the VL CDR1, VL CDR2, and VL CDR3 of Ab331 as set forth in Table 5 (SEQ ID NOS: 174, 175, and 176, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab332, for example, the VL CDR1, VL CDR2, and VL CDR3 of Ab332 as set forth in Table 5 (SEQ ID NOS: 181, 154, and 182, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab423, for example, the VL CDR1, VL CDR2, and VL CDR3 of Ab423 as set forth in Table 5 (SEQ ID NOS: 489, 142, and 143, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab435, for example, the VL CDR1, VL CDR2, and VL CDR3 of Ab435 as set forth in Table 5 (SEQ ID NOS: 141, 490, and 143, respectively). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence GYTFTX$_6$YW (SEQ ID NO:472), wherein X$_6$ is any amino acid, for example, an amino acid with an uncharged polar side chain, e.g., N or S;
(b) a VH CDR2 comprising the amino acid sequence of IX$_7$PSSGYT (SEQ ID NO:473), wherein X$_7$ is any amino acid, for example N or K; and
(c) a VH CDR3 comprising the amino acid sequence of ARDYYGSSSWFAY (SEQ ID NO:146). In certain embodiments, any one of X$_6$ or X$_7$ is any amino acid sequence. In specific embodiments, X$_6$ is a conservative substitution of N or S, X$_7$ is a conservative substitution of N or K. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GLTFSTAW (SEQ ID NO:177);
(b) a VH CDR2 comprising the amino acid sequence of IKDKSNX$_8$F (SEQ ID NO: 474), wherein X$_8$ is any amino acid, for example N or K; and
(c) a VH CDR3 comprising the amino acid sequence of TTSYGYA (SEQ ID NO:179). In certain embodiments, X$_8$ is any amino acid sequence. In specific embodiments, X$_8$ is a conservative substitution of N or K. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence GYTFTX$_6$YW (SEQ ID NO:472), wherein X$_6$ is any amino acid, for example, an amino acid with an uncharged polar side chain, e.g., N or S;
(b) a VH CDR2 comprising the amino acid sequence of IZ$_{23}$PZ$_{24}$SGZ$_{25}$T (SEQ ID NO: 503), wherein Z$_{23}$ is any amino acid, for example D, K, or N, $Z_{24}$ is any amino acid, for example, N or S, $Z_{25}$ is any amino acid, for example, G or Y; and (c) a VH CDR3 comprising the amino acid sequence of ARDYYGSS$Z_{26}Z_{27}$FAY (SEQ ID NO:504), wherein $Z_{26}$ is any amino acid, for example, Y or S and $Z_{27}$ is any amino acid, for example, R or W. In certain embodiments, any one of $Z_{23}$-$Z_{27}$ is any amino acid. In specific embodiments, $X_3$ is a conservative substitution of N or S, $Z_{23}$ is a conservative substitution of D, K, or N, $Z_{24}$ is a conservative substitution of N or S, $Z_{25}$ is a conservative substitution of G or Y, $Z_{26}$ is a conservative substitution of Y or S, and $Z_{27}$ is a conservative substitution of R or W. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYAFSSYW (SEQ ID NO:132);
(b) a VH CDR2 comprising the amino acid sequence of IYPGDGDT (SEQ ID NO: 133); and
(c) a VH CDR3 comprising the amino acid sequence of ASYYYGSKAY (SEQ ID NO:134) or ARSRGYFYGSTYDS (SEQ ID NO:156) or ARWYYGSYYAMDY (SEQ ID NO:159). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GY$Z_{43}$FS$Z_{28}$YW (SEQ ID NO:506), wherein $Z_{28}$ is any amino acid, for example N or S and $Z_{43}$ is any amino acid, for example A or T and;
(b) a VH CDR2 comprising the amino acid sequence of I$Z_{29}$PGD$Z_{30}$D$Z_{31}$ (SEQ ID NO: 507) wherein $Z_{29}$ is any amino acid, for example, an aromatic amino acid, F or Y, $Z_{30}$ is any amino acid, for example A or G, and $Z_{31}$ is any amino acid, for example, A or T; and
(c) a VH CDR3 comprising the amino acid sequence of ARFSYDGAFAY (SEQ ID NO:152) or ARSRGYFYGSTYDS (SEQ ID NO:156) or ARWYYGSYYAMDY (SEQ ID NO:159). In certain embodiments, $Z_{28}$-$Z_{31}$ and $Z_{43}$ are any amino acid. In specific embodiments, $Z_{28}$ is a conservative substitution of N or S, $Z_{29}$ is a conservative substitution of F or Y, $Z_{30}$ is a conservative substitution of A or G, $Z_{31}$ is a conservative substitution of A or T, and $Z_{43}$ is a conservative substitution of A or T. In specific embodiments, $Z_{28}$ is N or S, $Z_{29}$ is F or Y, $Z_{30}$ is A or G, $Z_{31}$ is A or T, and $Z_{43}$ is A or T. In specific embodiments, $Z_{28}$ is 5, $Z_{29}$ is F or Y, $Z_{30}$ is A or G, $Z_{31}$ is A or T, and $Z_{43}$ is A or T. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GY$Z_{43}$FS$Z_{28}$YW (SEQ ID NO:506), wherein $Z_{28}$ is N or S and $Z_{43}$ is A or T;
(b) a VH CDR2 comprising the amino acid sequence of I$Z_{29}$PGD$Z_{30}$D$Z_{31}$ (SEQ ID NO: 507) wherein $Z_{29}$ is F or Y, $Z_{30}$ is A or G, and $Z_{31}$ is A or T; and
(c) a VH CDR3 comprising the amino acid sequence of ARFSYDGAFAY (SEQ ID NO:152). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GY$Z_{43}$FS$Z_{28}$YW (SEQ ID NO:506), wherein $Z_{28}$ is N or S and $Z_{43}$ is A or T;
(b) a VH CDR2 comprising the amino acid sequence of I$Z_{29}$PGD$Z_{30}$D$Z_{31}$ (SEQ ID NO: 507) wherein $Z_{29}$ is F or Y, $Z_{30}$ is A or G, and $Z_{31}$ is A or T; and
(c) a VH CDR3 comprising the amino acid sequence of ARSRGYFYGSTYDS (SEQ ID NO:156). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GY$Z_{43}$FS$Z_{28}$YW (SEQ ID NO:506), wherein $Z_{28}$ is N or S and $Z_{43}$ is A or T;
(b) a VH CDR2 comprising the amino acid sequence of I$Z_{29}$PGD$Z_{30}$D$Z_{31}$ (SEQ ID NO: 507) wherein $Z_{29}$ is F or Y, $Z_{30}$ is A or G, and $Z_{31}$ is A or T; and
(c) a VH CDR3 comprising the amino acid sequence of ARWYYGSYYAMDY (SEQ ID NO:159). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GY$Z_{43}$FS$Z_{28}$YW (SEQ ID NO:506), wherein $Z_{28}$ is N or S and $Z_{43}$ is A or T;
(b) a VH CDR2 comprising the amino acid sequence of IFPGDADA (SEQ ID NO: 151); and
(c) a VH CDR3 comprising the amino acid sequence of ARFSYDGAFAY (SEQ ID NO:152).

In a particular embodiment, an antibody described herein, or an antigen-binding fragment thereof, which specifically binds to an ECD of ALK, comprises:
(a) a VH CDR1 comprising the amino acid sequence of GY$Z_{43}$FS$Z_{28}$YW (SEQ ID NO:506), wherein $Z_{28}$ is N or S and $Z_{43}$ is A or T;
(b) a VH CDR2 comprising the amino acid sequence of IYPGDGDT (SEQ ID NO: 133); and
(c) a VH CDR3 comprising the amino acid sequence of ARSRGYFYGSTYDS (SEQ ID NO:156). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GY$Z_{43}$FS$Z_{28}$YW (SEQ ID NO:506), wherein $Z_{28}$ is N or S and $Z_{43}$ is A or T;
(b) a VH CDR2 comprising the amino acid sequence of IYPGDGDT (SEQ ID NO: 133); and
(c) a VH CDR3 comprising the amino acid sequence of ARWYYGSYYAMDY (SEQ ID NO:159). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{43}$FSZ$_{28}$YW (SEQ ID NO:506), wherein Z$_{28}$ is S and Z$_{43}$ is A or T;
(b) a VH CDR2 comprising the amino acid sequence of IZ$_{29}$PGDZ$_{30}$DZ$_{31}$ (SEQ ID NO: 507) wherein Z$_{29}$ is F or Y, Z$_{30}$ is A or G, and Z$_{31}$ is A or T; and
(c) a VH CDR3 comprising the amino acid sequence of ARSRGYFYGSTYDS (SEQ ID NO:156). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{43}$FSZ$_{28}$YW (SEQ ID NO:506), wherein Z$_{28}$ is S and Z$_{43}$ is A or T;
(b) a VH CDR2 comprising the amino acid sequence of IZ$_{29}$PGDZ$_{30}$DZ$_{31}$ (SEQ ID NO: 507) wherein Z$_{29}$ is F or Y, Z$_{30}$ is A or G, and Z$_{31}$ is A or T; and
(c) a VH CDR3 comprising the amino acid sequence of ARWYYGSYYAMDY (SEQ ID NO:159). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 132 or 472;
(b) a VH CDR2 comprising the amino acid sequence of SEQ ID NO:133; and
(c) a VH CDR3 comprising the amino acid sequence of SEQ ID NO:134 or 159. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 138 or 144 or 472;
(b) a VH CDR2 comprising the amino acid sequence of SEQ ID NO:145 or 160 or 473 or 504; and
(c) a VH CDR3 comprising the amino acid sequence of SEQ ID NO:146 or 503. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 138 or 472;
(b) a VH CDR2 comprising the amino acid sequence of SEQ ID NO:139 or 504; and
(c) a VH CDR3 comprising the amino acid sequence of SEQ ID NO:140 or 503. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 132;
(b) a VH CDR2 comprising the amino acid sequence of SEQ ID NO:133; and
(c) a VH CDR3 comprising the amino acid sequence of SEQ ID NO:134 or 156 or 159. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 138, 491, or 492;
(b) a VH CDR2 comprising the amino acid sequence of SEQ ID NO:160; and
(c) a VH CDR3 comprising the amino acid sequence of SEQ ID NO:146. In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab320, for example, the VH CDR1, VH CDR2, and VH CDR3 of Ab320 as set forth in Table 6 (SEQ ID NOS: 132, 133, and 134, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab321, for example, the VH CDR1, VH CDR2, and VH CDR3 of Ab321 as set forth in Table 6 (SEQ ID NOS: 138, 139, and 140, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab322, for example, the VH CDR1, VH CDR2, and VH CDR3 of Ab322 as set forth in Table 6 (SEQ ID NOS: 144, 145, and 146, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab323, for example, the VH CDR1, VH CDR2, and VH CDR3 of Ab323 as set forth in Table 6 (SEQ ID NOS: 150, 151, and 152, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab324, for example, the VH CDR1, VH CDR2, and VH CDR3 of Ab324 as set forth in Table 6 (SEQ ID NOS: 132, 133, and 156, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab325, for example, the VH CDR1, VH CDR2, and VH CDR3 of Ab325 as set forth in Table 6 (SEQ ID NOS: 132, 133, and 159, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab326, for example, the VH CDR1, VH CDR2, and VH CDR3 of Ab326 as set forth in Table 6 (SEQ ID NOS: 138, 160, and 146, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab327, for example, the VH CDR1, VH CDR2, and VH CDR3 of Ab327 as set forth in Table 6 (SEQ ID NOS: 163, 164, and 165, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab328, for example, the VH CDR1, VH CDR2, and VH CDR3 of Ab328 as set forth in Table 6 (SEQ ID NOS: 138, 145, and 146, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab329, for example, the VH CDR1, VH CDR2, and VH CDR3 of Ab329 as set forth in Table 6 (SEQ ID NOS: 171, 172, and 172, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab330, for example, the VH CDR1, VH CDR2, and VH CDR3 of Ab330 as set forth in Table 6 (SEQ ID NOS:177, 178, and 179, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab331, for example, the VH CDR1, VH CDR2, and VH CDR3 of Ab331 as set forth in Table 6 (SEQ ID NOS: 177, 180, and 179, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab332, for example, the VH CDR1, VH CDR2, and VH CDR3 of Ab332 as set forth in Table 6 (SEQ ID NOS: 183, 184, and 185, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab353, for example, the VH CDR1, VH CDR2, and VH CDR3 of Ab353 as set forth in Table 6 (SEQ ID NOS: 491, 160, and 146, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab362, for example, the VH CDR1, VH CDR2, and VH CDR3 of Ab362 as set forth in Table 6 (SEQ ID NOS: 492, 160, and 146, respectively). In a particular embodiment the antibody or an antigen-binding fragment thereof is an antibody which specifically binds to an ECD of ALK.

In certain embodiments, an antibody described herein or an antigen-binding fragment thereof comprising IMGT VL and VH CDRS (e.g., IMGT VL CDR 1, 2, and 3, and IMGT VH CDR 1, 2, and 3 for any of antibodies Ab320-Ab332 as described in Tables 5 and 6, respectively) further comprises framework regions surrounding the CDRs in the variable region (e.g., variable region in Tables 13 and 14) in the format, from the N-terminus to C-terminus: FR1-CDR1-FR2-CDR2-FR3-CDR3-FR4. For example, FR1, FR2, FR3, and/or FR4 sequences can be any of those FR1, FR2, FR3 and/or FR4 sequences of Tables 7 and/or 8.

In certain aspects, the CDRs of an antibody described herein are Chothia CDRs (see, e.g., Chothia and Lesk, 1987, J. Mol. Biol., 196:901-917; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in *Antibody Engineering*, Kontermann and Dithel, eds., Chapter 31, pp. 422-439, Springer-Verlag, Berlin (2001)). Using the Kabat numbering system of numbering amino acid residues in the VH region and VL region, Chothia CDRs within an antibody heavy chain molecule are typically present at amino acid positions 26 to 32 (CDR1), amino acid positions 53 to 55 (CDR2), and amino acid positions 96 to 101 (CDR3). Using the Kabat numbering system of numbering amino acid residues in the VH region and VL region, Chothia CDRs within an antibody light chain molecule are typically present at amino acid positions 26 to 33 (CDR1), amino acid positions 50 to 52 (CDR2), and amino acid positions 91 to 96 (CDR3). In a specific embodiment, using the Kabat numbering system of numbering amino acid residues in the VH chain region and VL chain region, the Chothia CDRs within an antibody heavy chain molecule are at amino acid positions 26 to 32 or 34 (CDR1), amino acid positions 52 to 56 (CDR2; in one embodiment, CDR2 is at positions 52A-56, wherein 52A follows position 52), and amino acid positions 95 to 102 (CDR3; in one embodiment, there is no amino acid at one or more positions numbered 96-100); and the Chothia CDRs within an antibody light chain molecule are at amino acid positions 24 to 34 (CDR1), amino acid positions 50 to 56 (CDR2), and amino acid positions 89 to 97 (CDR3). These Chothia CDR positions may vary depending on the antibody, and may be determined according to methods known in the art.

In certain aspects, also described herein are antibodies that immunospecifically bind to an ALK polypeptide that comprise one or more Chothia VL CDRs of a VL of any one of antibodies Ab320-Ab332 and Ab351-Ab446 (see Table 9) and/or one or more Chothia VH CDRs of a VH of any one of antibodies Ab320-Ab332 and Ab351-Ab446 (see Table 10). In certain embodiments, antibodies described herein that immunospecifically bind to an ALK polypeptide comprise one or more CDRs, in which the Chothia and Kabat CDRs have the same amino acid sequence. In certain embodiments, provided herein are antibodies that immunospecifically bind to an ALK polypeptide and which comprise combinations of Kabat CDRs and Chothia CDRs.

TABLE 9

VL CDR Amino Acid Sequences (Chothia)

| Antibody | VL CDR1 (SEQ ID NO:) | VL CDR2 (SEQ ID NO:) | VL CDR3 (SEQ ID NO:) |
|---|---|---|---|
| Ab320 | RASENIYYSLA (262) | NANSLED (263) | KQAYDVPF (264) |
| Ab321 | SVSQGISNSLN (268) | YTSSLHS (269) | QQYSKLPL (270) |
| Ab322 | KASQNVGTNVA (274) | SASYRYS (275) | QQYNSYPYMYT (276) |
| Ab323 | KASQDVSTAVA (280) | WASTRHT (281) | QQHYSTPRT (282) |
| Ab324 | RASESVDNYGISFMN (286) | AASNQGS (287) | QQSKEVPWT (288) |
| Ab325 | RASQDISNYLN (290) | YTSRLHS (291) | QQGNTLPRT (292) |
| Ab326 | KASQNVGTNVA (274) | SASYRYS (275) | QQYNSYPYMYT (276) |
| Ab327 | KASQNVGTAVA (296) | SASNRFT (297) | QQYSSYPLT (298) |
| Ab328 | KASQNVGTNVA (274) | SASYRYS (275) | QRYNSYPYMFT (302) |
| Ab329 | QASQDIDNYLS (303) | SATSLAD (304) | LQHYSGWT (305) |
| Ab330 | QASQDIGNYLI (309) | YATNLAN (310) | LQYKQHLT (311) |
| Ab331 | QASQDIGNYLI (309) | YATNLAN (310) | LQYKQHLT (311) |
| Ab332 | KASQSVDYDGDSYMN (316) | AASNLES (317) | QQSNEDPPT (318) |
| Ab423 | RASQSVSSNLA (493) | SASYRYS (275) | QQYNSYPYMYT (276) |
| Ab435 | KASQNVGTNVA (274) | GASTRAT (494) | QQYNSYPYMYT (276) |

TABLE 10

VH CDR Amino Acid Sequences (Chothia)

| Antibody | VH CDR1 (SEQ ID NO:) | VH CDR2 (SEQ ID NO:) | VH CDR3 (SEQ ID NO:) |
|---|---|---|---|
| Ab320 | GYAFSSY (265) | YPGDGD (266) | YYYGSKAY (267) |
| Ab321 | GYTFTSY (271) | DPNSGG (272) | DYYGSSYRFAY (273) |
| Ab322 | GYTFTNY (277) | NPSSGY (278) | DYYGSSSWFAY (279) |
| Ab323 | GYTFSNY (283) | FPGDAD (284) | FSYDGAFAY (285) |
| Ab324 | GYAFSSY (265) | YPGDGD (266) | SRGYFYGSTYDS (289) |
| Ab325 | YAFSSY (293) | YPGDGD (266) | WYYGSYYAMDY (294) |
| Ab326 | GYTFTSY (271) | KPSSGY (295) | DYYGSSSWFAY (279) |
| Ab327 | GFTFSSY (299) | SSGGDY (300) | ERIWLRRFFDV (301) |
| Ab328 | GYTFTSY (271) | NPSSGY (278) | DYYGSSSWFAY (279) |
| Ab329 | GFSLTSY (306) | WGDGR (307) | ATMTGHGDA (308) |
| Ab330 | GLTFSTA (312) | KDKSNKFA (313) | SYGYA (314) |
| Ab331 | GLTFSTA (312) | KDKSNNFA (315) | SYGYA (314) |
| Ab332 | GYTFTDY (319) | NPNNGV (320) | DYGSNYFDY (321) |
| Ab353 | GYTFTSS (495) | KPSSGY (295) | DYYGSSSWFAY (279) |
| Ab362 | GYTFSSY (496) | KPSSGY (295) | DYYGSSSWFAY (279) |

TABLE 11

VL FR Amino Acid Sequences (Chothia)

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| Ab320 | DIQMTQSPASLAASVGETVTITC (322) | WYQQKGKSPQLLIY (323) | GVPSRFSGSGSGTQYSMKINSMQPEDTATYFC (324) | TFGSGTKLEIKR (325) |
| Ab321 | AIQMTQTTSSLSASLGDRVTISC (330) | WYQQKPDGTVKLLIY (331) | GVPSRFSGSGSGTDYSLTISNLEPEDIATYYC (332) | TFGAGTKLELKR (333) |
| Ab322 | DIVMTQSQRFMSTSVGDRVSVTC (337) | WYQQKPGQSPKALIY (338) | GVPDRFTGSGSGTDFTLTVSNVQSEDLAEYFC (339) | FGGGTKLEIKR (340) |

TABLE 11-continued

VL FR Amino Acid Sequences (Chothia)

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| Ab323 | DIVMTQSHKFMSTSVGDRVSITC (344) | WYQQKPGQSPKPLIY (345) | GVPDRFTGSGSGTDYTLTISSVQTEDLALYYC (346) | FGGGTKLEIKR (340) |
| Ab324 | DIVLTQSPASLAVSLGQRATISC (349) | WFQQKPGQPPKLLIY (350) | GVPARFSGSGSGTDFSLNIHPMEEDDTAMYFC (351) | FGGGTKLEIKR (340) |
| Ab325 | DIQMTQTTSSLSASLGDRVTISC (355) | WYQQKPDGTVKLLIY (331) | GVPSRFSGSGSGTDYSLTISNLEQEDIATYFC (356) | FGGGTKLEIKR (340) |
| Ab326 | DIVMTQSQRFMSTSVGDRVSVTC (337) | WYQQKPGQSPKALIY (338) | GVPDRFTGSGSGTDFTLTISNVQSEDLAEYFC (359) | FGGGTKLEIKR (340) |
| Ab327 | DIVMTQSQKFMSTSVGDRVSITC (360) | WYQLKPGQSPKLLIY (361) | GVPDRFTGSGSGTDFTLTISNMQSEDLADYFC (362) | FGSGTKLEIKR (363) |
| Ab328 | DIVMTQSQKFMSTSVGDRVSVTC (368) | WYQQKPGHSPKALIY (369) | GVPDRFTGSGSGTDFTLTISNVQSEDLAEYFC (359) | FGGGTKLEIKR (340) |
| Ab329 | DIQMTQSPASLSASLEEIVTITC (372) | WYQQKPGKSPHLLIH (373) | GVPSRFSGGRSGTQFSLKINRLQVEDTGIYYC (374) | FGGGTKLELKR (375) |
| Ab330 | DIQMTQSPSSMSASLGDRVTITC (380) | WFQQKPGKSPRPLIY (381) | GVPSRFSGSRSGSEYSLTITSLESEDMADYHC (382) | FGSGTKLEIER (383) |
| Ab331 | DIQMTQSPSSMSASLGDRITITC (388) | WFQQKPGKSPRPLIY (381) | GVPSRFSGSRSGSEYSLTITSLESEDMADYHC (382) | FGSGTKLEIER (383) |
| Ab332 | DIVLTQSPASLAVSLGQRATISC (349) | WYQQKPGQPPKLLIY (389) | GIPARLSGSGSGTDFTLNIHPVEEEDAATYYC (390) | FGGGTKLEIRR (391) |

TABLE 12

VH FR Amino Acid Sequences (Chothia)

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab320 | QVQLQQSGAELVKPGASVKISCKAS (326) | WMNWVKQRPGKGLEWIGQI (327) | TNYNGKFKGKATLTADKSSSTAYMQLSSLTSEDSAVYFCAS (328) | WGQGTLVTVSA (329) |
| Ab321 | QVQLQQPGAEFVKPGASVKLSCKAS (334) | WMHWVKQRPGRGLEWIGRI (335) | TKYNEKFKSKATLTVDKPSSTAYMQLSSLTSEDSAVYYCAR (336) | WGQGTLVTVSA (329) |
| Ab322 | QVQLQQSGAELAKPGASVKLSCKAS (341) | WMHWVKQRPGQGLEWIGYI (342) | TKYNQKFKDKATLTADKSSSTAYMQLSSLTYEDSAVYYCAR (343) | WGQGTLVTVSA (329) |
| Ab323 | QVQLQQSGAELVKPGASVKISCKTS (347) | WMNWVKQRPGKGLEWIGQI (327) | ANYNGKFKGKATLTADKSSSAAFMQLSSLTSEDSAVYFCAR (348) | WGQGTLVTVSA (329) |
| Ab324 | QVQLQQSGAELVKPGASVKISCKAS (326) | WVNWVKQRPGKGLEWIGQI (352) | TNYNGKFKGKATLTADKSSSTAYMQLSSLTSEDSAVYFCAR (353) | WGQGTTLTVSS (354) |
| Ab325 | QVQLQQSGAELVKPGASVKISCKASG (357) | WMNWVKQRPGKGLEWIGQI (327) | TNYNGKFKGKATLTADKSSSTAYMQLSSLTSEDSAVYFCAR (353) | WGQGTSVTVSS (358) |

TABLE 12-continued

VH FR Amino Acid Sequences (Chothia)

| Anti-body | VH FR1 (SEQ ID NO:) | VH FR2 (SEQ ID NO:) | VH FR3 (SEQ ID NO:) | VH FR4 (SEQ ID NO:) |
|---|---|---|---|---|
| Ab326 | QVQLQQSGAELAKPGA SVKLSCKAS (341) | WMHWVKQRPGQGLEWI GYI (342) | TKYNQKFKDKATLTADK SSSTAYMQLSSLTYEDS AVYYCAR (343) | WGQGTLVTVSA (329) |
| Ab327 | DVKLVESGEGLVKPGG SLKLSCAAS (364) | AMSWVRQTPEKRLEWV TYI (365) | IYYADTVKGRFTISRDN ARNTLYLQMSSLKSEDT AMYYCTR (366) | WGTGTTVTVSS (367) |
| Ab328 | QVQLQQSGAELAKPGA SVKLSCKAS (341) | WMHWVKQRPGQGLEWI GYI (370) | TKYNQKFKDKATLTADK SSSTAYMQLSSLTFEDS AVYYCAR (371) | WGQGTLVTVSA (329) |
| Ab329 | QVQLKESGPGLVKPSA TLSLTCTVS (376) | HVCWIRQTPGKGLEWM GVI (377) | TTYNPPLKSRLSISRDT SKSQVFLKMSSLKTEDT ATYYCAR (378) | WGQGASVTVSS (379) |
| Ab330 | EVQVVETGGGVVQPGK SLEITCATS (384) | WMYWVRQSSDRRLEWI ARI (385) | SDYVESVRGRFTISRDD SRSSVYLQMNNLKEEDT ATYYCTT (386) | WGQGVMVTVSS (387) |
| Ab331 | EVQVVETGGGVVQPGK SLEITCATS (384) | WMYWVRQSSDRRLEWI ARI (385) | SDYVESVRGRFTISRDD SRSSVYLQMNNLKEEDT ATYYCTT (386) | WGQGVMVTVSS (387) |
| Ab332 | EVQLQQSGPELVKPGT SVKISCKAS (392) | YMNWMKQSHGKSLEWI GDI (393) | TSYNQKFKGKATLTVDK SSSTAYMELRSLTSEDS AVYYCARE (394) | WGQGTTLTVSS (354) |

In a particular embodiment, an antibody described herein, or an antigen-binding fragment thereof, which specifically binds to an ECD of ALK, comprises:
(a) a VL CDR1 comprising the amino acid sequence of KASQNVGTNVA (SEQ ID NO:274);
(b) a VL CDR2 comprising the amino acid sequence of SASYRYS (SEQ ID NO:275); and
(c) a VL CDR3 comprising the amino acid sequence of QX$_9$YNSYPYMX$_{10}$T (SEQ ID NO:475), wherein X$_9$ is any amino acid, for example, Q or R and X$_{10}$ is any amino acid, for example, an amino acid with an aromatic side chain, Y or F. In certain embodiments, any one of X$_9$ and X$_{10}$ is any amino acid sequence. In specific embodiments, X$_9$ is a conservative substitution of Q or R, and X$_{10}$ is a conservative substitution of Y or F. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of KASQZ$_{32}$VZ$_{33}$TZ$_{34}$VA (SEQ ID NO:510), wherein Z$_{32}$ is any amino acid, for example, N or D, Z$_{33}$ is any amino acid, for example, G or S, and Z$_{34}$ is any amino acid, for example, A or N;
(b) a VL CDR2 comprising the amino acid sequence of SASYRYS (SEQ ID NO:275) or WASTRHT (SEQ ID NO:281) or SASNRFT (SEQ ID NO:297); and
(c) a VL CDR3 comprising the amino acid sequence of QQHYSTPRT (SEQ ID NO:282) or QQYSSYPLT (SEQ ID NO:298) or QX$_9$YNSYPYMX$_{10}$T (SEQ ID NO:475), wherein X$_9$ is any amino acid, for example, Q or R and X$_{10}$ is any amino acid, for example, an amino acid with an aromatic side chain, Y or F. In certain embodiments, any one of X$_9$ and X$_{10}$ and Z$_{32}$-Z$_{34}$ is any amino acid sequence. In specific embodiments, X$_9$ is a conservative substitution of Q or R, X$_{10}$ is a conservative substitution of Y or F, Z$_{32}$ is a conservative substitution of N or D, Z$_{33}$ is a conservative substitution of G or S, and Z$_{34}$ is a conservative substitution of A or N. In specific embodiments, X$_9$ is a conservative substitution of Q or R, X$_{10}$ is a conservative substitution of Y or F, Z$_{32}$ is N, Z$_{33}$ is G, and Z$_{34}$ is A or N. In specific embodiments, X$_9$ is a conservative substitution of Q or R, X$_{10}$ is a conservative substitution of Y or F, Z$_{32}$ is D, Z$_{33}$ is S, and Z$_{34}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of KASQZ$_{32}$VZ$_{33}$TZ$_{34}$VA (SEQ ID NO:510), wherein Z$_{32}$ is N or D, Z$_{33}$ is G or S, and Z$_{34}$ is A or N;
(b) a VL CDR2 comprising the amino acid sequence of SASYRYS (SEQ ID NO:275); and
(c) a VL CDR3 comprising the amino acid sequence of QQYNSYPYMYT (SEQ ID NO:276). In specific embodiments, Z$_{32}$ is N, Z$_{33}$ is G, and Z$_{34}$ is A or N. In specific embodiments, Z$_{32}$ is D, Z$_{33}$ is S, and Z$_{34}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of KASQZ$_{32}$VZ$_{33}$TZ$_{34}$VA (SEQ ID NO:510), wherein Z$_{32}$ is N or D, Z$_{33}$ is G or S, and Z$_{34}$ is A or N;
(b) a VL CDR2 comprising the amino acid sequence of WASTRHT (SEQ ID NO:281); and
(c) a VL CDR3 comprising the amino acid sequence of QQHYSTPRT (SEQ ID NO:282). In specific embodiments, Z$_{32}$ is N, Z$_{33}$ is G, and Z$_{34}$ is A or N. In specific embodiments, Z$_{32}$ is D, Z$_{33}$ is S, and Z$_{34}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of KASQZ$_{32}$VZ$_{33}$TZ$_{34}$VA (SEQ ID NO:510), wherein Z$_{32}$ is N or D, Z$_{33}$ is G or S, and Z$_{34}$ is A or N;
(b) a VL CDR2 comprising the amino acid sequence of SASNRFT (SEQ ID NO:297); and
(c) a VL CDR3 comprising the amino acid sequence of QQYSSYPLT (SEQ ID NO:298). In specific embodiments, Z$_{32}$ is N, Z$_{33}$ is G, and Z$_{34}$ is A or N. In specific embodiments, Z$_{32}$ is D, Z$_{33}$ is S, and Z$_{34}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of KASQZ$_{32}$VZ$_{33}$TZ$_{34}$VA (SEQ ID NO:510), wherein Z$_{32}$ is N or D, Z$_{33}$ is G or S, and Z$_{34}$ is A or N;
(b) a VL CDR2 comprising the amino acid sequence of SASYRYS (SEQ ID NO:275); and
(c) a VL CDR3 comprising the amino acid sequence of QRYNSYPYMFT (SEQ ID NO:302). In specific embodiments, Z$_{32}$ is N, Z$_{33}$ is G, and Z$_{34}$ is A or N. In specific embodiments, Z$_{32}$ is D, Z$_{33}$ is S, and Z$_{34}$ is A or N. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 274;
(b) a VL CDR2 comprising the amino acid sequence of SEQ ID NO:275; and
(c) a VL CDR3 comprising the amino acid sequence of SEQ ID NO:276 or 302. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 274;
(b) a VL CDR2 comprising the amino acid sequence of SEQ ID NO:275; and
(c) a VL CDR3 comprising the amino acid sequence of SEQ ID NO:276, 302, or 475. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 274, 280, 296, or 510;
(b) a VL CDR2 comprising the amino acid sequence of SEQ ID NO:275, 281, or 297; and
(c) a VL CDR3 comprising the amino acid sequence of SEQ ID NO:276, 282, 302, or 475. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 274 or 493;
(b) a VL CDR2 comprising the amino acid sequence of SEQ ID NO:275 or 494; and
(c) a VL CDR3 comprising the amino acid sequence of SEQ ID NO:276. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VL CDR1 comprising the amino acid sequence of SEQ ID NO: 493;
(b) a VL CDR2 comprising the amino acid sequence of SEQ ID NO: 494; and
(c) a VL CDR3 comprising the amino acid sequence of SEQ ID NO:276. In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab320, for example, the VL CDR1, VL CDR2, and VL CDR3 of Ab320 as set forth in Table 9 (SEQ ID NOS: 262, 263, and 264, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab321, for example, the VL CDR1, VL CDR2, and VL CDR3 of Ab321 as set forth in Table 9 (SEQ ID NOS: 268, 269, and 270, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab322, for example, the VL CDR1, VL CDR2, and VL CDR3 of Ab322 as set forth in Table 9 (SEQ ID NOS: 274, 275, and 276, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab323, for example, the VL CDR1, VL CDR2, and VL CDR3 of Ab323 as set forth in Table 9 (SEQ ID NOS: 280, 281, and 282, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab324, for example, the VL CDR1, VL CDR2, and VL CDR3 of Ab324 as set forth in Table 9 (SEQ ID NOS: 286, 287, and 288, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab325, for example, the VL CDR1, VL CDR2, and VL CDR3 of Ab325 as set forth in Table 9 (SEQ ID NOS: 290, 291, and 292, respectively).

In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab326, for example, the VL CDR1, VL CDR2, and VL CDR3 of Ab326 as set forth in Table 9 (SEQ ID NOS: 274, 275, and 276, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab327, for example, the VL CDR1, VL CDR2, and VL CDR3 of Ab327 as set forth in Table 9 (SEQ ID NOS: 296, 297, and 298, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab328, for example, the VL CDR1, VL CDR2, and VL CDR3 of Ab328 as set forth in Table 9 (SEQ ID NOS: 274, 275, and 302, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab329, for example, the VL CDR1, VL CDR2, and VL CDR3 of Ab329 as set forth in Table 9 (SEQ ID NOS: 303, 304, and 305, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab330, for example, the VL CDR1, VL CDR2, and VL CDR3 of Ab330 as set forth in Table 9 (SEQ ID NOS: 309, 310, and 311, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab331, for example, the VL CDR1, VL CDR2, and VL CDR3 of Ab331 as set forth in Table 9 (SEQ ID NOS: 309, 310, and 311, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab332, for example, the VL CDR1, VL CDR2, and VL CDR3 of Ab332 as set forth in Table 9 (SEQ ID NOS: 316, 317, and 318, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab423, for example, the VL CDR1, VL CDR2, and VL CDR3 of Ab423 as set forth in Table 9 (SEQ ID NOS: 493, 275, and 276, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VL CDR1, VL CDR2, and VL CDR3 of Ab435, for example, the VL CDR1, VL CDR2, and VL CDR3 of Ab435 as set forth in Table 9 (SEQ ID NOS: 274, 494, and 276, respectively). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK:
(a) a VH CDR1 comprising the amino acid sequence GYTFTX$_{11}$Y (SEQ ID NO:476), wherein X$_{11}$ is any amino acid, for example, an amino acid with an uncharged polar side chain, e.g., N or S;
(b) a VH CDR2 comprising the amino acid sequence of X$_{12}$PSSGY (SEQ ID NO:477), wherein X$_{12}$ is any amino acid, for example N or K; and
(c) a VH CDR3 comprising the amino acid sequence of DYYGSSSWFAY (SEQ ID NO:279). In certain embodiments, any one of X$_{11}$ or X$_{12}$ is any amino acid sequence. In specific embodiments, X$_{11}$ is a conservative substitution of N or S, X$_{12}$ is a conservative substitution of N or K. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GLTFSTA (SEQ ID NO:312;
(b) a VH CDR2 comprising the amino acid sequence of KDKSNX$_{13}$FA (SEQ ID NO: 478), wherein X$_{13}$ is any amino acid, for example N or K; and
(c) a VH CDR3 comprising the amino acid sequence of SYGYA (SEQ ID NO:314). In certain embodiments, X$_{13}$ is any amino acid sequence. In specific embodiments, X$_{13}$ is a conservative substitution of N or K. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence GYTFTX$_{11}$Y (SEQ ID NO:476), wherein X$_{11}$ is any amino acid, for example, an amino acid with an uncharged polar side chain, e.g., N or S;
(b) a VH CDR2 comprising the amino acid sequence of Z$_{35}$PZ$_{36}$SGZ$_{37}$ (SEQ ID NO: 508), wherein Z$_{35}$ is any amino acid, for example D, K, or N, Z$_{36}$ is any amino acid, for example, N or S, and Z$_{37}$ is any amino acid, for example, G or Y; and
(c) a VH CDR3 comprising the amino acid sequence of DYYGSSZ$_{38}$Z$_{39}$FAY (SEQ ID NO:509), wherein Z$_{38}$ is any amino acid, for example, Y or S and Z$_{39}$ is any amino acid, for example, R or W. In certain embodiments, any one of X$_{11}$ and Z$_{35}$-Z$_{39}$ is any amino acid sequence. In specific embodiments, X$_{11}$ is a conservative substitution of N or S, Z$_{35}$ is a conservative substitution of D, K, or N, Z$_{36}$ is a conservative substitution of N or S, Z$_{37}$ is a conservative substitution of G or Y, Z$_{38}$ is a conservative substitution of Y or S, and Z$_{39}$ is a conservative substitution of R or W. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYAFSSY (SEQ ID NO:265) or YAFSSY (SEQ ID NO: 293);
(b) a VH CDR2 comprising the amino acid sequence of YPGDGD (SEQ ID NO: 266); and
(c) a VH CDR3 comprising the amino acid sequence of YYYGSKAY (SEQ ID NO:267) or SRGYFYGSTYDS (SEQ ID NO:289) or WYYGSYYAMDY (SEQ ID NO:294). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is any amino acid, for example N or S and Z$_{44}$ is any amino acid, for example A or T;
(b) a VH CDR2 comprising the amino acid sequence of Z$_{41}$PGDZ$_{42}$D (SEQ ID NO: 512) wherein Z$_{41}$ is any amino acid, for example A or G, and Z$_{42}$ is any amino acid, for example, A or T; and
(c) a VH CDR3 comprising the amino acid sequence of FSYDGAFAY (SEQ ID NO:285) or SRGYFYGSTYDS (SEQ ID NO:289) or WYYGSYYAMDY (SEQ ID NO:294). In certain embodiments, Z$_{40}$-Z$_{42}$ and Z$_{44}$ are any amino acid. In specific embodiments, Z$_{40}$ is a conservative substitution of N or S, Z$_{41}$ is a conservative substitution of A or G, Z$_{42}$ is a conservative substitution of A or T, and Z$_{44}$ is a conservative substitution of A or T. In specific embodiments, Z$_{40}$ is N or S, Z$_{41}$ is A or G, Z$_{42}$ is A or T, and Z$_{44}$ is A or T. In specific embodiments, Z$_{40}$ is 5, Z$_{41}$ is A or G, Z$_{42}$ is A or T, and Z$_{44}$ is A or T. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is N or S and Z$_{44}$ is A or T;
(b) a VH CDR2 comprising the amino acid sequence of Z$_{41}$PGDZ$_{42}$D (SEQ ID NO: 512) wherein Z$_{41}$ is A or G, and Z$_{42}$ is A or T; and
(c) a VH CDR3 comprising the amino acid sequence of FSYDGAFAY (SEQ ID NO:285). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is N or S and Z$_{44}$ is A or T;
(b) a VH CDR2 comprising the amino acid sequence of Z$_{41}$PGDZ$_{42}$D (SEQ ID NO: 512) wherein Z$_{41}$ is A or G, and Z$_{42}$ is A or T; and
(c) a VH CDR3 comprising the amino acid sequence of SRGYFYGSTYDS (SEQ ID NO:289). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is N or S and Z$_{44}$ is A or T;
(b) a VH CDR2 comprising the amino acid sequence of Z$_{41}$PGDZ$_{42}$D (SEQ ID NO: 512) wherein Z$_{41}$ is A or G, and Z$_{42}$ is A or T; and
(c) a VH CDR3 comprising the amino acid sequence of WYYGSYYAMDY (SEQ ID NO:294). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is N or S and Z$_{44}$ is A or T;
(b) a VH CDR2 comprising the amino acid sequence of FPGDAD (SEQ ID NO:284); and
(c) a VH CDR3 comprising the amino acid sequence of FSYDGAFAY (SEQ ID NO:285). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is N or S and Z$_{44}$ is A or T;
(b) a VH CDR2 comprising the amino acid sequence of YPGDGD (SEQ ID NO: 266); and
(c) a VH CDR3 comprising the amino acid sequence of SRGYFYGSTYDS (SEQ ID NO:289). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is N or S and Z$_{44}$ is A or T;
(b) a VH CDR2 comprising the amino acid sequence of YPGDGD (SEQ ID NO: 266); and
(c) a VH CDR3 comprising the amino acid sequence of WYYGSYYAMDY (SEQ ID NO:294). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is S and Z$_{44}$ is A or T;
(b) a VH CDR2 comprising the amino acid sequence of YPGDGD (SEQ ID NO: 266); and
(c) a VH CDR3 comprising the amino acid sequence of SRGYFYGSTYDS (SEQ ID NO:289). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is S and Z$_{44}$ is A or T;
(b) a VH CDR2 comprising the amino acid sequence of YPGDGD (SEQ ID NO: 266); and
(c) a VH CDR3 comprising the amino acid sequence of WYYGSYYAMDY (SEQ ID NO:294).
In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is S and Z$_{44}$ is A or T;
(b) a VH CDR2 comprising the amino acid sequence of Z$_{41}$PGDZ$_{42}$D (SEQ ID NO: 512) wherein Z$_{41}$ is A or G, and Z$_{42}$ is A or T; and
(c) a VH CDR3 comprising the amino acid sequence of SRGYFYGSTYDS (SEQ ID NO:289). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises:
(a) a VH CDR1 comprising the amino acid sequence of GYZ$_{44}$FSZ$_{40}$Y (SEQ ID NO:511), wherein Z$_{40}$ is S and Z$_{44}$ is A or T;
(b) a VH CDR2 comprising the amino acid sequence of Z$_{41}$PGDZ$_{42}$D (SEQ ID NO: 512) wherein Z$_{41}$ is A or G, and Z$_{42}$ is A or T; and
(c) a VH CDR3 comprising the amino acid sequence of WYYGSYYAMDY (SEQ ID NO:294). In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 265 or 476;
(b) a VH CDR2 comprising the amino acid sequence of SEQ ID NO:266; and
(c) a VH CDR3 comprising the amino acid sequence of SEQ ID NO:267 or 294. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 271, 277, or 476;
(b) a VH CDR2 comprising the amino acid sequence of SEQ ID NO:278, 295, 477, or 508; and
(c) a VH CDR3 comprising the amino acid sequence of SEQ ID NO:279 or 509. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 271 or 476;
(b) a VH CDR2 comprising the amino acid sequence of SEQ ID NO:272 or 508; and
(c) a VH CDR3 comprising the amino acid sequence of SEQ ID NO:273 or 509. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 265 or 293;
(b) a VH CDR2 comprising the amino acid sequence of SEQ ID NO:266; and
(c) a VH CDR3 comprising the amino acid sequence of SEQ ID NO:267, 289, or 294. In a particular embodiment the antibody or an antigen-binding fragment thereof is an antibody which specifically binds to an ECD of ALK.

In a particular embodiment, an antibody described herein, or an antigen-binding fragment thereof, which specifically binds to an ECD of ALK, comprises a heavy chain variable region (VH) comprising:
(a) a VH CDR1 comprising the amino acid sequence of SEQ ID NO: 271, 495, or 496;
(b) a VH CDR2 comprising the amino acid sequence of SEQ ID NO:295; and
(c) a VH CDR3 comprising the amino acid sequence of SEQ ID NO:279. In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab320, for example, the VH CDR1, VH CDR2, and VH CDR3 of Ab320 as set forth in Table 10 (SEQ ID NOS: 262, 263, and 264, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab321, for example, the VH CDR1, VH CDR2, and VH CDR3 of Ab321 as set forth in Table 10 (SEQ ID NOS: 271, 272, and 273, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab322, for example, the VH CDR1, VH CDR2, and VH CDR3 of Ab322 as set forth in Table 10 (SEQ ID NOS: 277, 278, and 279, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab323, for example, the VH CDR1, VH CDR2, and VH CDR3 of Ab323 as set forth in Table 10 (SEQ ID NOS: 283, 284, and 285, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab324, for example, the VH CDR1, VH CDR2, and VH CDR3 of Ab324 as set forth in Table 10 (SEQ ID NOS: 265, 266, and 289, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab325, for example, the VH CDR1, VH CDR2, and VH CDR3 of Ab325 as set forth in Table 10 (SEQ ID NOS: 293, 266, and 294, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab326, for example, the VH CDR1, VH CDR2, and VH CDR3 of Ab326 as set forth in Table 10 (SEQ ID NOS: 271, 295, and 279, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab327, for example, the VH CDR1, VH CDR2, and VH CDR3 of Ab327 as set forth in Table 10 (SEQ ID NOS: 299, 300, and 301, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab328, for example, the VH CDR1, VH CDR2, and VH CDR3 of Ab328 as set forth in Table 10 (SEQ ID NOS: 271, 278, and 279, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab329, for example, the VH CDR1, VH CDR2, and VH CDR3 of Ab329 as set forth in Table 10 (SEQ ID NOS: 306, 307, and 308, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab330, for example, the VH CDR1, VH CDR2, and VH CDR3 of Ab330 as set forth in Table 10 (SEQ ID NOS: 312, 313, and 314, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab331, for example, the VH CDR1, VH CDR2, and VH CDR3 of Ab331 as set forth in Table 10 (SEQ ID NOS: 312, 315, and 314, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab332, for example, the VH CDR1, VH CDR2, and VH CDR3 of Ab332 as set forth in Table 10 (SEQ ID NOS: 319, 320, and 321, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab353, for example, the VH CDR1, VH CDR2, and VH CDR3 of Ab353 as set forth in Table 10 (SEQ ID NOS: 495, 295, and 279, respectively). In a particular embodiment the antibody or an antigen-binding fragment thereof is an antibody which specifically binds to an ECD of ALK.

In a particular embodiment, an antibody described herein, or an antigen-binding fragment thereof, comprises the VH CDR1, VH CDR2, and VH CDR3 of Ab362, for example, the VH CDR1, VH CDR2, and VH CDR3 of Ab362 as set forth in Table 10 (SEQ ID NOS: 496, 295, and 279, respectively). In a particular embodiment the antibody or an antigen-binding fragment thereof is an antibody which specifically binds to an ECD of ALK.

In certain embodiments, an antibody described herein or an antigen-binding fragment thereof comprising Chothia VL and VH CDRS (e.g., Chothia VL CDR 1, 2, and 3, and Chothia VH CDR 1, 2, and 3 for any of antibodies Ab320-Ab332 as described in Tables 9 and 10, respectively) further comprises framework regions surrounding the CDRs in the variable region (e.g., variable region in Tables 13 and 14) in the format, from the N-terminus to C-terminus: FR1-CDR1-FR2-CDR2-FR3-CDR3-FR4. For example, FR1, FR2, FR3, and/or FR4 sequences can be any of those FR1, FR2, FR3 and/or FR4 sequences of Tables 11 and/or 12.

In a specific embodiment, an anti-ALK antibody described herein comprises a VL region comprising DIVMTQSQX$_{14}$FMSTSVGDRVSVTCKASQNVGTNVA WYQQKPGX$_{15}$ SPKALIYSASYRYS GVPDRFTGSGSGTDFTLTX$_{16}$SNVQSEDLAEYFCQX$_{17}$ YNSYPYMX$_{18}$TFGGGTKLEIKR (SEQ ID NO:479), wherein $X_{14}$ is any amino acid, for example, an amino acid with a basic side chain, e.g., K or R, $X_{15}$ is any amino acid, for example, Q or H, $X_{16}$ is any amino acid, for example, an amino acid with a nonpolar side chain, for example, e.g., V or I, $X_{17}$ is any amino acid, for example, Q or R, $X_{18}$ is any amino acid, for example, any amino acid with an aromatic side chain, e.g., Y or F. In certain embodiments, any one of $X_{14}$ to $X_{18}$ is any amino acid sequence. In specific embodiments, $X_{14}$ is a conservative substitution of K or R, $X_{15}$ is a conservative substitution of Q or H, $X_{16}$ is a conservative substitution of V or I, $X_{17}$ is a conservative substitution of Q or R, and $X_{18}$ is a conservative substitution of Y or F.

In a specific embodiment, an anti-ALK antibody described herein comprises a VH region comprising QVQLQQSGAELAKPGASVKLSCKASGYTFTX$_{19}$YWM HWVKQRPGQGLEWIGYIX$_{20}$PSS GYTKYNQKFKDKATLTADKSSSTAYMQLSSLTX$_{21}$ED SAVYYCARDYYGSSSWFAYWG QGTLVTVSA (SEQ ID NO:480), wherein $X_{19}$ is any amino acid, for example, any amino acid with an uncharged polar side chain, e.g., N or S, $X_{20}$ is any amino acid, for example, N or K, $X_{21}$ is any amino acid, for example, an amino acid with an aromatic side chain, e.g., Y or F. In certain embodiments, any one of $X_{19}$ to $X_{21}$ is any amino acid sequence. In specific embodiments, $X_{19}$ is a conservative substitution of N or S, $X_{20}$ is a conservative substitution of N or K, and $X_{21}$ is a conservative substitution of Y or F.

In a specific embodiment, an anti-ALK antibody described herein comprises (a) VL region comprising DIVMTQSQX$_{14}$FMSTSVGDRVSVTCKASQNVGTNVAWYQQKPGX$_{15}$SPKALIYSASYRYS GVPDRFTGSGSGTDFTLTX$_{16}$SNVQSEDLAEYFCQX$_{17}$YNSYPYMX$_{18}$TFGGGTKLEIKR (SEQ ID NO:479), wherein X$_{14}$ is any amino acid, for example, an amino acid with a basic side chain, e.g., K or R, X$_{15}$ is any amino acid, for example, Q or H, X$_{16}$ is any amino acid, for example, an amino acid with a nonpolar side chain, for example, e.g., V or I, X$_{17}$ is any amino acid, for example, Q or R, X$_{18}$ is any amino acid, for example, any amino acid with an aromatic side chain, e.g., Y or F; and (b) a VH region comprising QVQLQQSGAELAKPGASVKLSCKASGYTFTX$_{19}$YWMHWVKQRPGQGLEWIGYIX$_{20}$PSSGYTKYNQKFKDKATLTADKSSSTAYMQLSSLTX$_{21}$EDSAVYYCARDYYGSSSWFAYWG QGTLVTVSA (SEQ ID NO:480), wherein X$_{19}$ is any amino acid, for example, any amino acid with an uncharged polar side chain, e.g., N or S, X$_{20}$ is any amino acid, for example, N or K, X$_{21}$ is any amino acid, for example, an amino acid with an aromatic side chain, e.g., Y or F. In certain embodiments, any one of X$_{14}$ to X$_{18}$ and X$_{19}$ to X$_{21}$ is any amino acid sequence. In specific embodiments, X$_{14}$ is a conservative substitution of K or R, X$_{15}$ is a conservative substitution of Q or H, X$_{16}$ is a conservative substitution of V or I, X$_{17}$ is a conservative substitution of Q or R, X$_{18}$ is a conservative substitution of Y or F, X$_{19}$ is a conservative substitution of N or S, X$_{20}$ is a conservative substitution of N or K, and X$_{21}$ is a conservative substitution of Y or F.

In a specific embodiment, an anti-ALK antibody described herein comprises a VL region comprising

```
                                      (SEQ ID NO: 481)
DIQMTQSPSSMSASLGDRX22TITCQASQDIGNYLIWFQQKPGKSPRPL

IYYATNLANGVPSRFSGSRSGSEYSLTITSLESEDMADYHCLQYKQHLT

FGSGTKLEIER,
``` wherein X$_{22}$ is any amino acid, for example, an amino acid with a nonpolar side chain, e.g., V or I. In certain embodiments X$_{22}$ is any amino acid. In specific embodiments, X$_{22}$ is a conservative substitution of V or I.

In a specific embodiment, an anti-ALK antibody described herein comprises a VH region comprising EVQVVETGGGVVQPGKSLEITCATSGLTF-STAWMYWVRQSSDRRLEWIARIKDKSNX$_{23}$FASDYVESVRGRFTISRDDSRSSVYLQMNNLKEED-TATYYCTTSYGYAWGQGVMVTVS S (SEQ ID NO: 482), wherein X$_{23}$ is any amino acid, for example, K or N. In certain embodiments X$_{23}$ is any amino acid sequence. In specific embodiments, X$_{23}$ is a conservative substitution of K or N.

In a specific embodiment, an anti-ALK antibody described herein comprises (a) VL region comprising

```
                                      (SEQ ID NO: 481)
DIQMTQSPSSMSASLGDRX22TITCQASQDIGNYLIWFQQKPGKSPRPL

IYYATNLANGVPSRFSGSRSGSEYSLTITSLESEDMADYHCLQYKQHLT

FGSGTKLEIER,
``` wherein X$_{22}$ is any amino acid, for example, an amino acid with a nonpolar side chain, e.g., V or I; and (b) a VH region comprising EVQVVETGGGVVQPGKSLEITCATSGLTF-STAWMYWVRQSSDRRLEWIARIKDKSNX$_{23}$FASDYVESVRGRFTISRDDSRSSVYLQMNNLKEED-TATYYCTTSYGYAWGQGVMVTVS S (SEQ ID NO: 482), wherein X$_{23}$ is any amino acid, for example, K or N. In certain embodiments, any one of X$_{22}$ to X$_{23}$ is any amino acid. In specific embodiments, X$_{22}$ is a conservative substitution of V or I, and X$_{23}$ is a conservative substitution of K or N.

In a specific embodiment, an anti-ALK antibody described herein or an antigen-binding fragment thereof comprises a VL as described in Table 13. In a specific embodiment, an anti-ALK antibody described herein or an antigen-binding fragment thereof comprises a VH as described in Table 14. Further combinations of the VL and VH sequences for humanized antibodies are listed in Table 15.

TABLE 13

VL Domain Amino Acid Sequences

| Antibody | VL (SEQ ID NO:) |
|---|---|
| Ab320 | DIQMTQSPASLAASVGETVTITCRASENIYYSLAWYQQKQGKSPQLLIYNANSLEDGVPSRFSGSGSGTQYSMKINSMQPEDTATYFCKQAYDVPFTFGSGTKLEIKR (SEQ ID NO: 395) |
| Ab321 | AIQMTQTTSSLSASLGDRVTISCSVSQGISNSLNWYQQKPDGTVKLLIYYTSSLHSGVPSRFSGSGSGTDYSLTISNLEPEDIATYYCQQYSKLPLTFGAGTKLELKR (SEQ ID NO: 397) |
| Ab322 | DIVMTQSQRFMSTSVGDRVSVTCKASQNVGTNVAWYQQKPGQSPKALIYSASYRYSGVPDRFTGSGSGTDFTLTVSNVQSEDLAEYFCQQYNSYPYMYTFGGGTKLEIKR (SEQ ID NO: 399) |
| Ab323 | DIVMTQSHKFMSTSVGDRVSITCKASQDVSTAVAWYQQKPGQSPKPLIYWASTRHTGVPDRFTGSGSGTDYTLTISSVQTEDLALYYCQQHYSTPRTFGGGTKLEIKR (SEQ ID NO: 401) |
| Ab324 | DIVLTQSPASLAVSLGQRATISCRASESVDNYGISFMNWFQQKPGQPPKLLIYAASNQGSGVPARFSGSGSGTDFSLNIHPMEEDDTAMYFCQQSKEVPWTFGGGTKLEIKR (SEQ ID NO: 403) |
| Ab325 | DIQMTQTTSSLSASLGDRVTISCRASQDISNYLNWYQQKPDGTVKLLIYYTSRLHSGVPSRFSGSGSGTDYSLTISNLEQEDIATYFCQQGNTLPRTFGGGTKLEIKR (SEQ ID NO: 405) |
| Ab326 | DIVMTQSQRFMSTSVGDRVSVTCKASQNVGTNVAWYQQKPGQSPKALIYSASYRYSGVPDRFTGSGSGTDFTLTISNVQSEDLAEYFCQQYNSYPYMYTFGGGTKLEIKR (SEQ ID NO: 407) |

TABLE 13-continued

VL Domain Amino Acid Sequences

| Antibody | VL (SEQ ID NO:) |
|---|---|
| Ab327 | DIVMTQSQKFMSTSVGDRVSITCKASQNVGTAVAWYQLKPGQSPKLLIYSASNRFTGVPDRFTGSGSG<br>TDFTLTISNMQSEDLADYFCQQYSSYPLTFGSGTKLEIKR (SEQ ID NO: 409) |
| Ab328 | DIVMTQSQKFMSTSVGDRVSVTCKASQNVGTNVAWYQQKPGHSPKALIYSASYRYSGVPDRFTGSGSG<br>TDFTLTISNVQSEDLAEYFCQRYNSYPYMFTFGGGTKLEIKR (SEQ ID NO: 411) |
| Ab329 | DIQMTQSPASLSASLEEIVTITCQASQDIDNYLSWYQQKPGKSPHLLIHSATSLADGVPSRFSGGRSG<br>TQFSLKINRLQVEDTGIYYCLQHYSGWTFGGGTKLELKR (SEQ ID NO: 413) |
| Ab330 | DIQMTQSPSSMSASLGDRVTITCQASQDIGNYLIWFQQKPGKSPRPLIYYATNLANGVPSRFSGSRSG<br>SEYSLTITSLESEDMADYHCLQYKQHLTFGSGTKLEIER (SEQ ID NO: 415) |
| Ab331 | DIQMTQSPSSMSASLGDRITITCQASQDIGNYLIWFQQKPGKSPRPLIYYATNLANGVPSRFSGSRSG<br>SEYSLTITSLESEDMADYHCLQYKQHLTFGSGTKLEIER (SEQ ID NO: 417) |
| Ab332 | DIVLTQSPASLAVSLGQRATISCKASQSVDYDGDSYMNWYQQKPGQPPKLLIYAASNLESGIPARLSG<br>SGSGTDFTLNIHPVEEEDAATYYCQQSNEDPPTFGGGTKLEIRR (SEQ ID NO: 419) |
| Ab351 | EIVMTQSPAFLSVTPGEKVTITCKASQNVGTNVAWYQQKPDQAPKALIYSASYRYSGVPSRFSGSGSG<br>TDFTLTISSLEAEDAATYYCQQYNSYPYMYTFGQGTKLEIK (SEQ ID NO: 421) |
| Ab363 | DIVMTQSQAFMSVTVGEKVTITCKASQNVGTNVAWYQQKPDQAPKALIYSASYRYSGVPSRFSGSGSG<br>TDFTLTISSLEAEDAATYYCQQYNSYPYMYTFGQGTKLEIK (SEQ ID NO: 422) |
| Ab375 | EIVMTQSPAFMSVTVGEKVTITCKASQNVGTNVAWYQQKPDQSPKALIYSASYRYSGVPSRFSGSGSG<br>TDFTLTISSLEAEDAATYYCQQYNSYPYMYTFGQGTKLEIK (SEQ ID NO: 423) |
| Ab387 | EIVMTQSPATLSTSPGERATLSCKASQNVGTNVAWYQQKPGQAPRALIYSASYRYSGVPARFSGSGSG<br>TDFTLTISSVEPEDFAVYYCQQYNSYPYMYTFGQGTKLEIK (SEQ ID NO: 424) |
| Ab399 | EIVMTQSQATMSTSVGERATLSCKASQNVGTNVAWYQQKPGQSPKALIYSASYRYSGVPARFSGSGSG<br>TDFTLTISSVEPEDFAVYYCQQYNSYPYMYTFGQGTKLEIK (SEQ ID NO: 425) |
| Ab411 | EIVMTQSQATLSTSPGERATLSCKASQNVGTNVAWYQQKPGQAPRALIYSASYRYSGVPARFSGSGSG<br>TDFTLTISSVEPEDFAVYYCQQYNSYPYMYTFGQGTKLEIK (SEQ ID NO: 426) |
| Ab423 | EIVMTQSPATLSTSPGERATLSCRASQSVSSNLAWYQQKPGQAPRALIYSASYRYSGVPARFSGSGSG<br>TDFTLTISSVEPEDFAVYYCQQYNSYPYMYTFGQGTKLEIK (SEQ ID NO: 427) |
| Ab435 | EIVMTQSQATMSTSVGERATLSCKASQNVGTNVAWYQQKPGQSPKALIYGASTRATGVPARFSGSGSG<br>TDFTLTISSVEPEDFAVYYCQQYNSYPYMYTFGQGTKLEIK (SEQ ID NO: 428) |

TABLE 14

VH Domain Amino Acid Sequences

| Antibody | VH (SEQ ID NO:) |
|---|---|
| Ab320 | QVQLQQSGAELVKPGASVKISCKASGYAFSSYWMNWVKQRPGKGLEWIGQIYPGDGDTNYNGKFKGKA<br>TLTADKSSSTAYMQLSSLTSEDSAVYFCASYYYGSKAYWGQGTLVTVSA (SEQ ID NO: 396) |
| Ab321 | QVQLQQPGAEFVKPGASVKLSCKASGYTFTSYWMHWVKQRPGRGLEWIGRIDPNSGGTKYNEKFKSKA<br>TLTVDKPSSTAYMQLSSLTSEDSAVYYCARDYYGSSYRFAYWGQGTLVTVSA (SEQ ID NO: 398) |
| Ab322 | QVQLQQSGAELAKPGASVKLSCKASGYTFTNYWMHWVKQRPGQGLEWIGYINPSSGYTKYNQKFKDKA<br>TLTADKSSSTAYMQLSSLTYEDSAVYYCARDYYGSSSWFAYWGQGTLVTVSA (SEQ ID NO: 400) |
| Ab323 | QVQLQQSGAELVKPGASVKISCKTSGYTFSNYWMNWVKQRPGKGLEWIGQIFPGDADANYNGKFKGKA<br>TLTADKSSSAAFMQLSSLTSEDSAVYFCARFSYDGAFAYWGQGTLVTVS (SEQ ID NO: 402) |
| Ab324 | QVQLQQSGAELVKPGASVKISCKASGYAFSSYWVNWVKQRPGKGLEWIGQIYPGDGDTNYNGKFKGKA<br>TLTADKSSSTAYMQLSSLTSEDSAVYFCARSRGYFYGSTYDSWGQGTTLTVSS (SEQ ID NO: 404) |
| Ab325 | QVQLQQSGAELVKPGASVKISCKASGYAFSSYWMNWVKQRPGKGLEWIGQIYPGDGDTNYNGKFKGKA<br>TLTADKSSSTAYMQLSSLTSEDSAVYFCARWYYGSYYAMDYWGQGTSVTVSS (SEQ ID NO: 406) |
| Ab326 | QVQLQQSGAELAKPGASVKLSCKASGYTFTSYWMHWVKQRPGQGLEWIGYIKPSSGYTKYNQKFKDKA<br>TLTADKSSSTAYMQLSSLTYEDSAVYYCARDYYGSSSWFAYWGQGTLVTVSA (SEQ ID NO: 408) |

TABLE 14-continued

VH Domain Amino Acid Sequences

| Antibody | VH (SEQ ID NO:) |
|---|---|
| Ab327 | DVKLVESGEGLVKPGGSLKLSCAASGFTFSSYAMSWVRQTPEKRLEWVTYISSGGDYIYYADTVKGRF<br>TISRDNARNTLYLQMSSLKSEDTAMYYCTRERIWLRRFEDVWGTGTTVTVSS (SEQ ID NO: 410) |
| Ab328 | QVQLQQSGAELAKPGASVKLSCKASGYTFTSYWMHWVKQRPGQGLEWIGYINPSSGYTKYNQKFKDKA<br>TLTADKSSSTAYMQLSSLTFEDSAVYYCARDYYGSSSWFAYWGQGTLVTVSA (SEQ ID NO: 412) |
| Ab329 | QVQLKESGPGLVKPSATLSLTCTVSGFSLTSYHVCWIRQTPGKGLEWMGVIWGDGRTTYNPPLKSRLS<br>ISRDTSKSQVFLKMSSLKTEDTATYYCARATMTGHGDAWGQGASVTVSS (SEQ ID NO: 414) |
| Ab330 | EVQVVETGGGVVQPGKSLEITCATSGLTFSTAWMYWVRQSSDRRLEWIARIKDKSNKFASDYVESVRG<br>RFTISRDDSRSSVYLQMNNLKEEDTATYYCTTSYGYAWGQGVMVTVSS (SEQ ID NO: 416) |
| Ab331 | EVQVVETGGGVVQPGKSLEITCATSGLTFSTAWMYWVRQSSDRRLEWIARIKDKSNNFASDYVESVRG<br>RFTISRDDSRSSVYLQMNNLKEEDTATYYCTTSYGYAWGQGVMVTVSS (SEQ ID NO: 418) |
| Ab332 | EVQLQQSGPELVKPGTSVKISCKASGYTFTDYYMNWMKQSHGKSLEWIGDINPNNGVTSYNQKFKGKA<br>TLTVDKSSSTAYMELRSLTSEDSAVYYCAREDYGSNYFDYWGQGTTLTVSS (SEQ ID NO: 420) |
| Ab351 | QVQLVQSGAEVAKPGTSVKLSCKASGYTFTSYWMHWVKQAPGQGLEWIGYIKPSSGYTKYNQKFKDKV<br>TLTADKSTSTAYMELSSLRSEDTAVYYCARDYYGSSSWFAYWGQGTLVTVSS (SEQ ID NO: 429) |
| Ab352 | EVQLVQSGPEVKPGTSVKLSCKASGYTFTSYWMHWVRQARGQRLEWIGYIKPSSGYTKYNQKFKDRA<br>TLTADKSTSTAYMELSSLRSEDTAVYYCARDYYGSSSWFAYWGQGTLVTVSS (SEQ ID NO: 430) |
| Ab353 | EVQLVQSGAEVKKPGTSVKLSCKASGYTFTSSAMQWVKQAPGQGLEWIGYIKPSSGYTKYNQKFKDKA<br>TLTADKSTSTAYMELSSLRSEDTAVYYCARDYYGSSSWFAYWGQGTLVTVSS (SEQ ID NO: 431) |
| Ab354 | EVQLVQSGAEVKKPGTSVKLSCKASGYTFTSYWMHWVRQARGQRLEWIGYIKPSSGYTKYAQKFQERV<br>TLTADKSTSTAYMELSSLRSEDTAVYYCARDYYGSSSWFAYWGQGTLVTVSS (SEQ ID NO: 432) |
| Ab355 | QVQLVQSGAEVAKPGASVKLSCKASGYTFTSYWMHWVKQAPGQGLEWIGYIKPSSGYTKYNQKFKDKA<br>TLTADKSTSTAYMELRSLRSDDTAVYYCARDYYGSSSWFAYWGQGTLVTVSS (SEQ ID NO: 433) |
| Ab356 | EVQLVQSGAEVKKPGASVKLSCKASGYTFTSYWMHWVRQAPGQGLEWIGYIKPSSGYTKYNQKFKDKA<br>TLTADKSTSTAYMELRSLRSDDTAVYYCARDYYGSSSWFAYWGQGTLVTVSS (SEQ ID NO: 434) |
| Ab357 | EVQLVQSGAEVKKPGASVKLSCKASGYTFTSYWMHWVRQAPGQGLEWIGYIKPSSGYTKYNQKFKDKA<br>TLTADKSTSTAYMELRSLRSDDTAVYYCARDYYGSSSWFAYWGQGTLVTVSS (SEQ ID NO: 435) |
| Ab358 | EVQLVQSGAEVKKPGASVKLSCKASGYTFTSYWMHWVRQAPGQGLEWIGYIKPSSGYTKYAQKLQGRV<br>TLTADKSTSTAYMELRSLRSDDTAVYYCARDYYGSSSWFAYWGQGTLVTVSS (SEQ ID NO: 436) |
| Ab359 | QVQLVQSGAEVAKPGSSVKLSCKASGYTFTSYWMHWVKQAPGQGLEWIGYIKPSSGYTKYNQKFKDKA<br>TLTADKSTSTAYMELSSLRSEDTAVYYCARDYYGSSSWFAYWGQGTLVTVSS (SEQ ID NO: 437) |
| Ab360 | EVQLVQSGAEVKKPGSSVKLSCKASGYTFTSYWMHWVRQAPGQGLEWIGYIKPSSGYTKYNQKFKDKA<br>TLTADKSTSTAYMELSSLRSEDTAVYYCARDYYGSSSWFAYWGQGTLVTVSS (SEQ ID NO: 438) |
| Ab361 | EVQLVQSGAEVKKPGSSVKVSCKASGYTFSSYWMHWVRQAPGQGLEWIGYIKPSSGYTKYNQKFKDKA<br>TLTADKSTSTAYMELSSLRSEDTAVYYCARDYYGSSSWFAYWGQGTLVTVSS (SEQ ID NO: 439) |
| Ab362 | EVQLVQSGAEVKKPGSSVKLSCKASGYTFSSYWMHWVKQAPGQGLEWIGYIKPSSGYTKYAQKFQGRV<br>TLTADKSTSTAYMELSSLRSEDTAVYYCARDYYGSSSWFAYWGQGTLVTVSS (SEQ ID NO: 440) |

TABLE 15

Humanized Antibody sequences

| Humanized Antibody | VL SEQ ID NO: | VH SEQ ID NO: |
|---|---|---|
| Ab351 | 421 | 429 |
| Ab352 | 421 | 430 |
| Ab353 | 421 | 431 |
| Ab354 | 421 | 432 |
| Ab355 | 421 | 433 |
| Ab356 | 421 | 434 |
| Ab357 | 421 | 435 |
| Ab358 | 421 | 436 |
| Ab359 | 421 | 437 |
| Ab360 | 421 | 438 |
| Ab361 | 421 | 439 |
| Ab362 | 421 | 440 |
| Ab363 | 422 | 429 |
| Ab364 | 422 | 430 |
| Ab365 | 422 | 431 |
| Ab366 | 422 | 432 |
| Ab367 | 422 | 433 |
| Ab368 | 422 | 434 |
| Ab369 | 422 | 435 |
| Ab370 | 422 | 436 |

TABLE 15-continued

Humanized Antibody sequences

| Humanized Antibody | VL SEQ ID NO: | VH SEQ ID NO: |
|---|---|---|
| Ab371 | 422 | 437 |
| Ab372 | 422 | 438 |
| Ab373 | 422 | 439 |
| Ab374 | 422 | 440 |
| Ab375 | 423 | 429 |
| Ab376 | 423 | 430 |
| Ab377 | 423 | 431 |
| Ab378 | 423 | 432 |
| Ab379 | 423 | 433 |
| Ab380 | 423 | 434 |
| Ab381 | 423 | 435 |
| Ab382 | 423 | 436 |
| Ab383 | 423 | 437 |
| Ab384 | 423 | 438 |
| Ab385 | 423 | 439 |
| Ab386 | 423 | 440 |
| Ab387 | 424 | 429 |
| Ab388 | 424 | 430 |
| Ab389 | 424 | 431 |
| Ab390 | 424 | 432 |
| Ab391 | 424 | 433 |
| Ab392 | 424 | 434 |
| Ab393 | 424 | 435 |
| Ab394 | 424 | 436 |
| Ab395 | 424 | 437 |
| Ab396 | 424 | 438 |
| Ab397 | 424 | 439 |
| Ab398 | 424 | 440 |
| Ab399 | 425 | 429 |
| Ab400 | 425 | 430 |
| Ab401 | 425 | 431 |
| Ab402 | 425 | 432 |
| Ab403 | 425 | 433 |
| Ab404 | 425 | 434 |
| Ab405 | 425 | 435 |
| Ab406 | 425 | 436 |
| Ab407 | 425 | 437 |
| Ab408 | 425 | 438 |
| Ab409 | 425 | 439 |
| Ab410 | 425 | 440 |
| Ab411 | 426 | 429 |
| Ab412 | 426 | 430 |
| Ab413 | 426 | 431 |
| Ab414 | 426 | 432 |
| Ab415 | 426 | 433 |
| Ab416 | 426 | 434 |
| Ab417 | 426 | 435 |
| Ab418 | 426 | 436 |
| Ab419 | 426 | 437 |
| Ab420 | 426 | 438 |
| Ab421 | 426 | 439 |
| Ab422 | 426 | 440 |
| Ab423 | 427 | 429 |
| Ab424 | 427 | 430 |
| Ab425 | 427 | 431 |
| Ab426 | 427 | 432 |
| Ab427 | 427 | 433 |
| Ab428 | 427 | 434 |
| Ab429 | 427 | 435 |
| Ab430 | 427 | 436 |
| Ab431 | 427 | 437 |
| Ab432 | 427 | 438 |
| Ab433 | 427 | 439 |
| Ab434 | 427 | 440 |
| Ab435 | 428 | 429 |
| Ab436 | 428 | 430 |
| Ab437 | 428 | 431 |
| Ab438 | 428 | 432 |
| Ab439 | 428 | 433 |
| Ab440 | 428 | 434 |
| Ab441 | 428 | 435 |
| Ab442 | 428 | 436 |
| Ab443 | 428 | 437 |
| Ab444 | 428 | 438 |
| Ab445 | 428 | 439 |
| Ab446 | 428 | 440 |

In a specific embodiment, an anti-ALK antibody described herein comprises a VH region comprising $X_{24}$VQLVQSG$X_{25}$EV$X_{26}$KPG$X_{27}$SVKLSCKASGYTFTS YWMHWV$X_{28}$QA$X_{29}$GQ$X_{30}$LEWIG YIKPSSGYTKY$X_{31}$QKF$X_{32}X_{33}X_{34}X_{35}$TLTADKSTSTAY MEL$X_{36}$SLRS$X_{37}$DTAVYYCARD YYGSSSW-FAYWGQGTLVTVSS (SEQ ID NO: 515), wherein $X_{24}$ is any amino acid, for example, an amino acid with a polar side chain, e.g., E or Q, $X_{25}$ is any amino acid, for example, an amino acid with a nonpolar side chain, e.g., A or P, $X_{26}$ is any amino acid, for example A or K, $X_{27}$ is any amino acid, for example, A or T, $X_{28}$ is any amino acid, for example, any amino acid with a positively charged side chain, e.g., R or K, $X_{29}$ is any amino acid, for example, P or R, $X_{30}$ is any amino acid, for example, G or R, $X_{31}$ is any amino acid, for example, A or N, $X_{32}$ is any amino acid, for example, any amino acid with a positively charged side chain, e.g., K or R, $X_{33}$ is any amino acid, for example, any amino acid with a negatively charged side chain, e.g., D or E, $X_{34}$ is any amino acid, for example, any amino acid with a positively charged side chain, e.g., K or R, $X_{35}$ is any amino acid, for example, any amino acid with a nonpolar side chain, e.g., A or V, $X_{36}$ is any amino acid, for example, an amino acid with a polar side chain, e.g., R or S, $X_{37}$ is any amino acid, for example, any amino acid with a negatively charged side chain, e.g., D or E. In certain embodiments $X_{24}$ is any amino acid. In specific embodiments, $X_{24}$ is a conservative substitution of E or Q. In certain embodiments $X_{25}$ is any amino acid. In specific embodiments, $X_{25}$ is a conservative substitution of P or A. In certain embodiments $X_{26}$ is any amino acid. In specific embodiments, $X_{26}$ is a conservative substitution of K or A. In certain embodiments $X_{27}$ is any amino acid. In specific embodiments, $X_{27}$ is a conservative substitution of T or A. In certain embodiments $X_{28}$ is any amino acid. In specific embodiments, $X_{28}$ is a conservative substitution of K or R. In certain embodiments $X_{29}$ is any amino acid. In specific embodiments, $X_{29}$ is a conservative substitution of P or R. In certain embodiments $X_{30}$ is any amino acid. In specific embodiments, $X_{30}$ is a conservative substitution of G or R. In certain embodiments $X_{31}$ is any amino acid. In specific embodiments, $X_{31}$ is a conservative substitution of A or N. In certain embodiments $X_{32}$ is any amino acid. In specific embodiments, $X_{32}$ is a conservative substitution of R or K. In certain embodiments $X_{33}$ is any amino acid. In specific embodiments, $X_{33}$ is a conservative substitution of D or E. In certain embodiments $X_{34}$ is any amino acid. In specific embodiments, $X_{34}$ is a conservative substitution of R or K. In certain embodiments $X_{35}$ is any amino acid. In specific embodiments, $X_{35}$ is a conservative substitution of A or V. In certain embodiments $X_{36}$ is any amino acid. In specific embodiments, $X_{36}$ is a conservative substitution of S or R. In certain embodiments $X_{37}$ is any amino acid. In specific embodiments, $X_{37}$ is a conservative substitution of D or E.

In a specific embodiment, an anti-ALK antibody described herein comprises a VL region comprising EIVMTQS$X_{38}$A$X_{39}X_{40}$S$X_{41}X_{42}X_{43}$GE$X_{44}X_{45}$T$X_{46}X_{47}$CK ASQNVGTNVAWYQQKPX$_{48}$QX$_{49}$P
KALIYSASYRYSGVPX$_{50}$RFSGSGSGTDFTLTISSX$_{51}$
EX$_{52}$EDX$_{53}$AX$_{54}$YYCQQYNSYPYMY TFGQGTKLEIK (SEQ ID NO: 516), wherein X$_{38}$ is any amino acid, for example, P or Q, X$_{39}$ is any amino acid, for example, F or T, X$_{40}$ is any amino acid, for example, L or M, X$_{41}$ is any amino acid, for example, V or T, X$_{42}$ is any amino acid, for example, an amino acid with a polar side chain, e.g., S or T, X$_{43}$ is any amino acid, for example, an amino acid with a nonpolar side chain, e.g., P or V, X$_{44}$ is any amino acid, for example, an amino acid with a positively charged side chain, e.g., K or R, X$_{45}$ is any amino acid, for example, an amino acid with a nonpolar side chain, e.g., A or V, X$_{46}$ is any amino acid, for example, an amino acid with a nonpolar side chain, e.g., I or L, X$_{47}$ is any amino acid, for example, an amino acid with a polar side chain, e.g., S or T, X$_{48}$ is any amino acid, for example, D or G, X$_{49}$ is any amino acid, for example, A or S, X$_{50}$ is any amino acid, for example, A or S, X$_{51}$ is any amino acid, for example, an amino acid with a nonpolar side chain, e.g., V or L, X$_{52}$ is any amino acid, for example, an amino acid with a nonpolar side chain, e.g., A or P, X$_{53}$ is any amino acid, for example, an amino acid with a nonpolar side chain, e.g., A or F, X$_{54}$ is any amino acid, for example, T or V. In certain embodiments X$_{38}$ is any amino acid sequence. In specific embodiments, X$_{38}$ is a conservative substitution of P or Q. In certain embodiments X$_{39}$ is any amino acid sequence. In specific embodiments, X$_{39}$ is a conservative substitution of F or T. In certain embodiments X$_{40}$ is any amino acid sequence. In specific embodiments, X$_{40}$ is a conservative substitution of L or M. In certain embodiments X$_{41}$ is any amino acid sequence. In specific embodiments, X$_{41}$ is a conservative substitution of V or T. In certain embodiments X$_{42}$ is any amino acid sequence. In specific embodiments, X$_{42}$ is a conservative substitution of S or T. In certain embodiments X$_{43}$ is any amino acid sequence. In specific embodiments, X$_{43}$ is a conservative substitution of P or V. In certain embodiments X$_{44}$ is any amino acid sequence. In specific embodiments, X$_{44}$ is a conservative substitution of K or R. In certain embodiments X$_{45}$ is any amino acid sequence. In specific embodiments, X$_{45}$ is a conservative substitution of V or A. In certain embodiments X$_{46}$ is any amino acid sequence. In specific embodiments, X$_{46}$ is a conservative substitution of I or L. In certain embodiments X$_{47}$ is any amino acid sequence. In specific embodiments, X$_{47}$ is a conservative substitution of S or T. In certain embodiments X$_{48}$ is any amino acid sequence. In specific embodiments, X$_{48}$ is a conservative substitution of D or G. In certain embodiments X$_{49}$ is any amino acid sequence. In specific embodiments, X$_{49}$ is a conservative substitution of A or S. In certain embodiments X$_{50}$ is any amino acid sequence. In specific embodiments, X$_{50}$ is a conservative substitution of A or S. In certain embodiments X$_{51}$ is any amino acid sequence. In specific embodiments, X$_{51}$ is a conservative substitution of L or V. In certain embodiments X$_{52}$ is any amino acid sequence. In specific embodiments, X$_{52}$ is a conservative substitution of A or P. In certain embodiments X$_{53}$ is any amino acid sequence. In specific embodiments, X$_{53}$ is a conservative substitution of A or F. In certain embodiments X$_{54}$ is any amino acid sequence. In specific embodiments, X$_{54}$ is a conservative substitution of T or V.

In a specific embodiment, an anti-ALK antibody described herein comprises
(a) VL region comprising
EIVMTQSX$_{38}$AX$_{39}$X$_{40}$SX$_{41}$X$_{42}$X$_{43}$GEX$_{44}$X$_{45}$TX$_{46}$X$_{47}$CK ASQNVGTNVAWYQQKPX$_{48}$QX$_{49}$P
KALIYSASYRYSGVPX$_{50}$RFSGSGSGTDFTLTISSX$_{51}$ EX$_{52}$EDX$_{53}$AX$_{54}$YYCQQYNSYPYMY TFGQGTKLEIK (SEQ ID NO: 516), wherein X$_{38}$ is any amino acid, for example, P or Q, X$_{39}$ is any amino acid, for example, F or T, X$_{40}$ is any amino acid, for example, L or M, X$_{41}$ is any amino acid, for example, V or T, X$_{42}$ is any amino acid, for example, an amino acid with a polar side chain, e.g., S or T, X$_{43}$ is any amino acid, for example, an amino acid with a nonpolar side chain, e.g., P or V, X$_{44}$ is any amino acid, for example, an amino acid with a positively charged side chain, e.g., K or R, X$_{45}$ is any amino acid, for example, an amino acid with a nonpolar side chain, e.g., A or V, X$_{46}$ is any amino acid, for example, an amino acid with a nonpolar side chain, e.g., I or L, X$_{47}$ is any amino acid, for example, an amino acid with a polar side chain, e.g., S or T, X$_{48}$ is any amino acid, for example, D or G, X$_{49}$ is any amino acid, for example, A or S, X$_{50}$ is any amino acid, for example, A or S, X$_{51}$ is any amino acid, for example, an amino acid with a nonpolar side chain, e.g., V or L, X$_{52}$ is any amino acid, for example, an amino acid with a nonpolar side chain, e.g., A or P, X$_{53}$ is any amino acid, for example, an amino acid with a nonpolar side chain, e.g., A or F, X$_{54}$ is any amino acid, for example, T or V; and
(b) a VH region comprising
X$_{24}$VQLVQSGX$_{25}$EVX$_{26}$KPGX$_{27}$SVKLSCKASGYTFTS YWMHWVX$_{28}$QAX$_{29}$GQX$_{30}$LEWIG
YIKPSSGYTKYX$_{31}$QKFX$_{32}$X$_{33}$X$_{34}$X$_{35}$TLTADKSTSTAY MELX$_{36}$SLRSX$_{37}$DTAVYYCARDY YGSSSW-FAYWGQGTLVTVSS (SEQ ID NO: 515), wherein X$_{24}$ is any amino acid, for example, an amino acid with a polar side chain, e.g., E or Q, X$_{25}$ is any amino acid, for example, an amino acid with a nonpolar side chain, e.g., A or P, X$_{26}$ is any amino acid, for example A or K, X$_{27}$ is any amino acid, for example, A or T, X$_{28}$ is any amino acid, for example, an amino acid with a positively charged side chain, e.g., R or K, X$_{29}$ is any amino acid, for example, P or R, X$_{30}$ is any amino acid, for example, G or R, X$_{31}$ is any amino acid, for example, A or N, X$_{32}$ is any amino acid, for example, any amino acid with a positively charged side chain, e.g., K or R, X$_{33}$ is any amino acid, for example, any amino acid with a negatively charged side chain, e.g., D or E, X$_{34}$ is any amino acid, for example, any amino acid with a positively charged side chain, e.g., K or R, X$_{35}$ is any amino acid, for example, any amino acid with a nonpolar side chain, e.g., A or V, X$_{36}$ is any amino acid, for example, an amino acid with a polar side chain, e.g., R or S, X$_{37}$ is any amino acid, for example, any amino acid with a negatively charged side chain, e.g., D or E.

In certain aspects, an antibody described herein may be described by its VL region alone, or its VH region alone, or by its 3 VL CDRs alone, or its 3 VH CDRs alone. See, for example, Rader et al., 1998, Proc. Natl. Acad. Sci. USA, 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson et al., 1991, Nature 352:624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also, Kim & Hong, 2007, J. Microbiol. 45:572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In a specific embodiment, the position of one or more CDRs along the VH (e.g., CDR1, CDR2, or CDR3) and/or VL (e.g., CDR1, CDR2, or CDR3) region of an antibody described herein may vary by one, two, three, four, five, or six amino acid positions so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). For example, in one embodiment, the position defining a CDR of any of antibody Ab320-Ab332 and Ab351-Ab446 may vary by shifting the N-terminal and/or C-terminal boundary of the CDR by one, two, three, four, five, or six amino acids, relative to the CDR position in the VL or VH (see, e.g., Tables 13 or 14, respectively), so long as immunospecific binding to ALK (e.g., human ALK) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antibody described herein may vary (e.g., be shorter or longer) by one, two, three, four, five, or more amino acids, so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). For example, in one embodiment, a VH and/or VL CDR1, CDR2, and/or CDR3 described herein may be one, two, three, four, five or more amino acids shorter than one or more of the CDRs described by SEQ ID NO: 1-60, so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). In another embodiment, a VH and/or VL CDR1, CDR2, and/or CDR3 described herein may be one, two, three, four, five or more amino acids longer than one or more of the CDRs described by SEQ ID NOS: 1-60, so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). In another embodiment, the amino terminus of a VH and/or VL CDR1, CDR2, and/or CDR3 described herein may be extended by one, two, three, four, five or more amino acids compared to one or more of the CDRs described by SEQ ID NOS: 1-60, so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). In another embodiment, the carboxy terminus of a VH and/or VL CDR1, CDR2, and/or CDR3 described herein may be extended by one, two, three, four, five or more amino acids compared to one or more of the CDRs described by SEQ ID NOS: 1-60, so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). In another embodiment, the amino terminus of a VH and/or VL CDR1, CDR2, and/or CDR3 described herein may be shortened by one, two, three, four, five or more amino acids compared to one or more of the CDRs described by SEQ ID NOS: 1-60, so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). In one embodiment, the carboxy terminus of a VH and/or VL CDR1, CDR2, and/or CDR3 described herein may be shortened by one, two, three, four, five or more amino acids compared to one or more of the CDRs described by SEQ ID NOS: 1-60, so long as immunospecific binding to ALK (e.g., human ALK ECD, e.g., amino acid residues 21-1038 of SEQ ID NO: 467) is maintained (e.g., substantially maintained, for example, at least 50%, at least 60%, at least 70%, at least 80%, at least 90%, at least 95%). Any method known in the art can be used to ascertain whether immunospecific binding to ALK (e.g., human ALK ECD, e.g., amino acid residues 21-1038 of SEQ ID NO: 467) is maintained, for example, the binding assays and conditions described in the "Examples" section (Section 6) provided herein. For example, Section 6 provided herein describes a flow cytometry utilized to measure the affinity at steady state ($K_D$) with which different ALK antibodies binds to their target on the surface of NB1 cells.

In specific aspects, provided herein is an antibody comprising an antibody light chain and heavy chain, e.g., a separate light chain and heavy chain. With respect to the light chain, in a specific embodiment, the light chain of an antibody described herein is a kappa (κ) light chain. In another specific embodiment, the light chain of an antibody described herein is a lambda (λ) light chain. In another embodiment, light chain is a mixed sequence, e.g., the variable portion of the light chain comprises kappa light chain sequences and the constant region of the light chain comprises lambda light chain sequences, or vice versa. In certain embodiments, the light chain of an antibody described herein is a human kappa light chain or a human lambda light chain. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a particular embodiment, an antibody described herein, which immunospecifically binds to an ALK polypeptide (e.g., an ECD of ALK, for example human ALK) comprises a light chain wherein the amino acid sequence of the VL chain region comprises any amino acid sequence described herein (e.g., any of the sequences in Table 13), and comprises a light chain constant region, wherein the constant region of the light chain comprises the amino acid sequence of a human kappa light chain constant region. In another particular embodiment, an antibody described herein, which immunospecifically binds an ALK polypeptide (e.g., an ECD of ALK, for example human ALK) comprises a light chain wherein the amino acid sequence of the VL chain region can comprise any amino acid sequence described herein (e.g., any of the sequences in Table 13), and comprises a light chain constant region, wherein the constant region of the light chain comprises the amino acid sequence of a human lambda light chain constant region.

With respect to the heavy chain, in a specific embodiment, the heavy chain of an antibody described herein comprises a constant region and can be an alpha (α), delta (δ), epsilon (ε), gamma (γ) or mu (μ) heavy chain. In another specific embodiment, the heavy chain of an antibody described can comprise a human alpha (α), delta (δ), epsilon (ε), gamma (γ) or mu (μ) heavy chain. In a particular embodiment, an antibody described herein, which immunospecifically binds to an ALK polypeptide (e.g., an ECD of ALK, for example human ALK), comprises a heavy chain wherein the amino acid sequence of the VH chain region can comprise any amino acid sequence described herein (e.g., any of the sequences in Table 14), and a constant region, wherein the constant region of the heavy chain comprises the amino acid sequence of a human gamma (γ) heavy chain constant region. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a specific embodiment, an antibody described herein, which immunospecifically binds to an ALK polypeptide (e.g., an ECD of ALK, for example human ALK) comprises a VL chain region and a VH chain region comprising any amino acid sequences described herein, and constant regions, wherein the constant regions comprise amino acid sequences of constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which immunospecifically binds to an ALK polypeptide (e.g., an ECD of ALK, for example human ALK) comprises a VL chain region and a VH chain region comprising any amino acid sequences described herein, and constant regions, wherein the constant regions comprise amino acid sequences of constant regions of an IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_{2a}$ and $IgG_{2b}$, or a mixture thereof) of immunoglobulin molecule. In a particular embodiment, the constant regions comprise the amino acid sequences of the constant regions of a human IgG, IgE, IgM, IgD, IgA or IgY immunoglobulin molecule, any class (e.g., $IgG_1$, $IgG_2$, $IgG_3$, $IgG_4$, $IgA_1$ and $IgA_2$), or any subclass (e.g., $IgG_{2a}$ and $IgG_{2b}$, or a mixture thereof) of immunoglobulin molecule.

In yet another specific embodiment, an antibody described herein, which immunospecifically binds to an ALK polypeptide (e.g., an ECD of ALK, for example human ALK), comprises a VL chain region and a VH chain region comprising any amino acid sequences described herein, and constant regions, wherein the constant regions comprise the amino acid sequences of the constant regions of a human $IgG_1$ (e.g., isotype a, z, or f), human $IgG_2$ (e.g., isotype a or b) or human $IgG_4$. In a particular embodiment, an antibody described herein, which immunospecifically binds to an ALK polypeptide (e.g., an ECD of ALK, for example human ALK) comprises a VL chain region and a VH chain region comprising any amino acid sequences described herein, and constant regions, wherein the constant regions comprise the amino acid sequences of the constant region of a human $IgG_1$. Non-limiting examples of human constant regions are described in the art, e.g., see Kabat et al. (1991) *Sequences of Proteins of Immunological Interest*, Fifth Edition, U.S. Department of Health and Human Services, NIH Publication No. 91-3242.

Framework regions described herein are determined based upon the boundaries of the CDR numbering system. In other words, if the CDRs are determined by, e.g., Kabat, IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, or the Chothia numbering system, FR2 is defined as the amino acid residues between CDR1 and CDR2 amino acid residues as defined by, e.g., the Kabat numbering system, the IMGT numbering system, or the Chothia numbering system, FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In certain embodiments, an antibody described herein comprises one or more VL framework regions (FRs) having the amino acid sequence described herein for any one of antibodies Ab320-Ab332 (e.g., see Table 3), wherein the antibody immunospecifically binds to ALK (e.g., human ALK ECD, e.g., amino acid residues 21-1038 of SEQ ID NO: 467). In specific aspects, VL FRs are in the following positions relative to VL CDRs in a VL sequence: FR1-CDR1-FR2-CDR2-FR3-CDR3-FR4. In specific aspects, VH FRs are in the following positions relative to VH CDRs in a VH sequence: FR1-CDR1-FR2-CDR2-FR3-CDR3-FR4.

In certain embodiments, an antibody described herein comprises one or more VL framework regions (FRs) having the amino acid sequence described herein for Ab320 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 61, and VL CDRs of Ab320. In some embodiments, the VL FR2 has the amino acid sequence of SEQ ID NO: 62, and VL CDRs of Ab320. In some embodiments, the VL FR3 has the amino acid sequence of SEQ ID NO: 63, and VL CDRs of Ab320. In some embodiments, the VL FR4 has the amino acid sequence of SEQ ID NO: 64, and VL CDRs of Ab320. In certain embodiments, the an antibody described herein comprises one or more of the VL FR1 having the amino acid sequence of SEQ ID NO: 61, the VL FR 2 having the amino acid sequence of SEQ ID NO: 62, the VL FR3 having the amino acid sequence of SEQ ID NO: 63, and the VL FR4 having the amino acid sequence of SEQ ID NO: 64, and VL CDRs of Ab320.

In certain embodiments, an antibody described herein comprises one or more VL framework regions (FRs) having the amino acid sequence described herein for Ab321 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 69 and VL CDRs of Ab321. In some embodiments, the VL FR2 has the amino acid sequence of SEQ ID NO: 70 and VL CDRs of Ab321. In some embodiments, the VL FR3 has the amino acid sequence of SEQ ID NO: 71 and VL CDRs of Ab321. In some embodiments, the VL FR4 has the amino acid sequence of SEQ ID NO: 72 and VL CDRs of Ab321. In certain embodiments, the an antibody described herein comprises one or more of the VL FR1 having the amino acid sequence of SEQ ID NO: 69, the VL FR 2 having the amino acid sequence of SEQ ID NO: 70, the VL FR3 having the amino acid sequence of SEQ ID NO: 71, and the VL FR4 having the amino acid sequence of SEQ ID NO: 72 and VL CDRs of Ab321.

In certain embodiments, an antibody described herein comprises one or more VL framework regions (FRs) having the amino acid sequence described herein for Ab322 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 76 and VL CDRs of Ab322. In some embodiments, the VL FR2 has the amino acid sequence of SEQ ID NO: 77 and VL CDRs of Ab322. In some embodiments, the VL FR3 has the amino acid sequence of SEQ ID NO: 78 and VL CDRs of Ab322. In some embodiments, the VL FR4 has the amino acid sequence of SEQ ID NO: 79 and VL CDRs of Ab322. In certain embodiments, the an antibody described herein comprises one or more of the VL FR1 having the amino acid sequence of SEQ ID NO: 76, the VL FR 2 having the amino acid sequence of SEQ ID NO: 77, the VL FR3 having the amino acid sequence of SEQ ID NO: 78, and the VL FR4 having the amino acid sequence of SEQ ID NO: 79 and VL CDRs of Ab322.

In certain embodiments, an antibody described herein comprises one or more VL framework regions (FRs) having the amino acid sequence described herein for Ab323 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 83 and VL CDRs of Ab323. In some embodiments, the VL FR2 has the amino acid sequence of SEQ ID NO: 84 and VL CDRs of Ab323. In some embodiments, the VL FR3 has the amino acid sequence of SEQ ID NO: 85 and VL CDRs of Ab323. In some embodiments, the VL FR4 has the amino acid sequence of SEQ ID NO: 79 and VL CDRs of Ab323. In certain embodiments, the an antibody described herein comprises one or more of the VL FR1 having the amino acid sequence of SEQ ID NO: 83, the VL FR 2 having the amino acid sequence of SEQ ID NO: 84, the VL FR3 having the amino acid sequence of SEQ ID NO: 85, and the VL FR4 having the amino acid sequence of SEQ ID NO: 79 and VL CDRs of Ab323.

In certain embodiments, an antibody described herein comprises one or more VL framework regions (FRs) having the amino acid sequence described herein for Ab324 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 88 and VL CDRs of Ab324. In some embodiments, the VL FR2 has the amino acid sequence of SEQ ID NO: 89 and VL CDRs of Ab324. In some embodiments, the VL FR3 has the amino acid sequence of SEQ ID NO: 90 and VL CDRs of Ab324. In some embodiments, the VL FR4 has the amino acid sequence of SEQ ID NO: 79 and VL CDRs of Ab324. In certain embodiments, the an antibody described herein comprises one or more of the VL FR1 having the amino acid sequence of SEQ ID NO: 88, the VL FR 2 having the amino acid sequence of SEQ ID NO: 89, the VL FR3 having the amino acid sequence of SEQ ID NO: 90, and the VL FR4 having the amino acid sequence of SEQ ID NO: 79 and VL CDRs of Ab324.

In certain embodiments, an antibody described herein comprises one or more VL framework regions (FRs) having the amino acid sequence described herein for Ab325 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 93 and VL CDRs of Ab325. In some embodiments, the VL FR2 has the amino acid sequence of SEQ ID NO: 70 and VL CDRs of Ab325. In some embodiments, the VL FR3 has the amino acid sequence of SEQ ID NO: 94 and VL CDRs of Ab325. In some embodiments, the VL FR4 has the amino acid sequence of SEQ ID NO: 79 and VL CDRs of Ab325. In certain embodiments, the an antibody described herein comprises one or more of the VL FR1 having the amino acid sequence of SEQ ID NO: 93, the VL FR 2 having the amino acid sequence of SEQ ID NO: 70, the VL FR3 having the amino acid sequence of SEQ ID NO: 94, and the VL FR4 having the amino acid sequence of SEQ ID NO: 79 and VL CDRs of Ab325.

In certain embodiments, an antibody described herein comprises one or more VL framework regions (FRs) having the amino acid sequence described herein for Ab326 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 76 and VL CDRs of Ab326. In some embodiments, the VL FR2 has the amino acid sequence of SEQ ID NO: 77 and VL CDRs of Ab326. In some embodiments, the VL FR3 has the amino acid sequence of SEQ ID NO: 96 and VL CDRs of Ab326. In some embodiments, the VL FR4 has the amino acid sequence of SEQ ID NO: 79 and VL CDRs of Ab326. In certain embodiments, the an antibody described herein comprises one or more of the VL FR1 having the amino acid sequence of SEQ ID NO: 76, the VL FR 2 having the amino acid sequence of SEQ ID NO: 77, the VL FR3 having the amino acid sequence of SEQ ID NO: 96, and the VL FR4 having the amino acid sequence of SEQ ID NO: 79 and VL CDRs of Ab326.

In certain embodiments, an antibody described herein comprises one or more VL framework regions (FRs) having the amino acid sequence described herein for Ab327 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 97 and VL CDRs of Ab327. In some embodiments, the VL FR2 has the amino acid sequence of SEQ ID NO: 98 and VL CDRs of Ab327. In some embodiments, the VL FR3 has the amino acid sequence of SEQ ID NO: 99 and VL CDRs of Ab327. In some embodiments, the VL FR4 has the amino acid sequence of SEQ ID NO: 64 and VL CDRs of Ab327. In certain embodiments, the an antibody described herein comprises one or more of the VL FR1 having the amino acid sequence of SEQ ID NO: 97, the VL FR 2 having the amino acid sequence of SEQ ID NO: 98, the VL FR3 having the amino acid sequence of SEQ ID NO: 99, and the VL FR4 having the amino acid sequence of SEQ ID NO: 64 and VL CDRs of Ab327.

In certain embodiments, an antibody described herein comprises one or more VL framework regions (FRs) having the amino acid sequence described herein for Ab328 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 104 and VL CDRs of Ab328. In some embodiments, the VL FR2 has the amino acid sequence of SEQ ID NO: 105 and VL CDRs of Ab328. In some embodiments, the VL FR3 has the amino acid sequence of SEQ ID NO: 96 and VL CDRs of Ab328. In some embodiments, the VL FR4 has the amino acid sequence of SEQ ID NO: 79 and VL CDRs of Ab328. In certain embodiments, the an antibody described herein comprises one or more of the VL FR1 having the amino acid sequence of SEQ ID NO: 104, the VL FR 2 having the amino acid sequence of SEQ ID NO: 105, the VL FR3 having the amino acid sequence of SEQ ID NO: 96, and the VL FR4 having the amino acid sequence of SEQ ID NO: 79 and VL CDRs of Ab328.

In certain embodiments, an antibody described herein comprises one or more VL framework regions (FRs) having the amino acid sequence described herein for Ab329 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 107 and VL CDRs of Ab329. In some embodiments, the VL FR2 has the amino acid sequence of SEQ ID NO: 108 and VL CDRs of Ab329. In some embodiments, the VL FR3 has the amino acid sequence of SEQ ID NO: 109 and VL CDRs of Ab329. In some embodiments, the VL FR4 has the amino acid sequence of SEQ ID NO: 110 and VL CDRs of Ab329. In certain embodiments, the an antibody described herein comprises one or more of the VL FR1 having the amino acid sequence of SEQ ID NO: 107, the VL FR 2 having the amino acid sequence of SEQ ID NO: 108, the VL FR3 having the amino acid sequence of SEQ ID NO: 109, and the VL FR4 having the amino acid sequence of SEQ ID NO: 110 and VL CDRs of Ab329.

In certain embodiments, an antibody described herein comprises one or more VL framework regions (FRs) having the amino acid sequence described herein for Ab330 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 115 and VL CDRs of Ab330. In some embodiments, the VL FR2 has the amino acid sequence of SEQ ID NO: 116 and VL CDRs of Ab330. In some embodiments, the VL FR3 has the amino acid sequence of SEQ ID NO: 117 and VL CDRs of Ab330. In some embodiments, the VL FR4 has the amino acid sequence of SEQ ID NO: 118 and VL CDRs of Ab330. In certain embodiments, the an antibody described herein comprises one or more of the VL FR1 having the amino acid sequence of SEQ ID NO: 115, the VL FR 2 having the amino acid sequence of SEQ ID NO: 116, the VL FR3 having the amino acid sequence of SEQ ID NO: 117, and the VL FR4 having the amino acid sequence of SEQ ID NO: 118 and VL CDRs of Ab330.

In certain embodiments, an antibody described herein comprises one or more VL framework regions (FRs) having the amino acid sequence described herein for Ab331 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 123 and VL CDRs of Ab331. In some embodiments, the VL FR2 has the amino acid sequence of SEQ ID NO: 116 and VL CDRs of Ab331. In some embodiments, the VL FR3 has the amino acid sequence of SEQ ID NO: 117 and VL CDRs of Ab331. In some embodiments, the VL FR4 has the amino acid sequence of SEQ ID NO: 118 and VL CDRs of Ab331. In certain embodiments, the an antibody described herein comprises one or more of the VL FR1 having the amino acid sequence of SEQ ID NO: 123, the VL FR 2 having the amino acid sequence of SEQ ID NO: 116, the VL FR3 having the amino acid sequence of SEQ ID NO: 117, and the VL FR4 having the amino acid sequence of SEQ ID NO: 118 and VL CDRs of Ab331.

In certain embodiments, an antibody described herein comprises one or more VL framework regions (FRs) having the amino acid sequence described herein for Ab332 (e.g., see Table 3), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VL region comprising FR1, CDR1, FR2, CDR2, FR3, CDR3, and FR4. In certain embodiments, the VL FR1 has the amino acid sequence of SEQ ID NO: 88 and VL CDRs of Ab332. In some embodiments, the VL FR2 has the amino acid sequence of SEQ ID NO: 89 and VL CDRs of Ab332. In some embodiments, the VL FR3 has the amino acid sequence of SEQ ID NO: 124 and VL CDRs of Ab332. In some embodiments, the VL FR4 has the amino acid sequence of SEQ ID NO: 125 and VL CDRs of Ab332. In certain embodiments, the an antibody described herein comprises one or more of the VL FR1 having the amino acid sequence of SEQ ID NO: 88, the VL FR 2 having the amino acid sequence of SEQ ID NO: 89, the VL FR3 having the amino acid sequence of SEQ ID NO: 124, and the VL FR4 having the amino acid sequence of SEQ ID NO: 125 and VL CDRs of Ab332.

In certain embodiments, an antibody described herein comprises one or more VH framework regions (FRs) having the amino acid sequence described herein for Ab320 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 65 and VH CDRs of Ab320. In some embodiments, the VH FR2 has the amino acid sequence of SEQ ID NO: 66 and VH CDRs of Ab320. In some embodiments, the VH FR3 has the amino acid sequence of SEQ ID NO: 67 and VH CDRs of Ab320. In some embodiments, the VH FR4 has the amino acid sequence of SEQ ID NO: 68 and VH CDRs of Ab320. In certain embodiments, the an antibody described herein comprises one or more of the VH FR1 having the amino acid sequence of SEQ ID NO: 65, the VH FR 2 having the amino acid sequence of SEQ ID NO: 66, the VH FR3 having the amino acid sequence of SEQ ID NO: 67, and the VH FR4 having the amino acid sequence of SEQ ID NO: 68 and VH CDRs of Ab320.

In certain embodiments, an antibody described herein comprises one or more VH framework regions (FRs) having the amino acid sequence described herein for Ab321 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 73 and VH CDRs of Ab321. In some embodiments, the VH FR2 has the amino acid sequence of SEQ ID NO: 74 and VH CDRs of Ab321. In some embodiments, the VH FR3 has the amino acid sequence of SEQ ID NO: 75 and VH CDRs of Ab321. In some embodiments, the VH FR4 has the amino acid sequence of SEQ ID NO: 68 and VH CDRs of Ab321. In certain embodiments, the an antibody described herein comprises one or more of the VH FR1 having the amino acid sequence of SEQ ID NO: 73, the VH FR 2 having the amino acid sequence of SEQ ID NO: 74, the VH FR3 having the amino acid sequence of SEQ ID NO: 75, and the VH FR4 having the amino acid sequence of SEQ ID NO: 68 and VH CDRs of Ab321.

In certain embodiments, an antibody described herein comprises one or more VH framework regions (FRs) having the amino acid sequence described herein for Ab322 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 80 and VH CDRs of Ab322. In some embodiments, the VH FR2 has the amino acid sequence of SEQ ID NO: 81 and VH CDRs of Ab322. In some embodiments, the VH FR3 has the amino acid sequence of SEQ ID NO: 82 and VH CDRs of Ab322. In some embodiments, the VH FR4 has the amino acid sequence of SEQ ID NO: 68 and VH CDRs of Ab322. In certain embodiments, the an antibody described herein comprises one or more of the VH FR1 having the amino acid sequence of SEQ ID NO: 80, the VH FR 2 having the amino acid sequence of SEQ ID NO: 81, the VH FR3 having the amino acid sequence of SEQ ID NO: 82, and the VH FR4 having the amino acid sequence of SEQ ID NO: 68 and VH CDRs of Ab322.

In certain embodiments, an antibody described herein comprises one or more VH framework regions (FRs) having the amino acid sequence described herein for Ab323 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 86 and VH CDRs of Ab323. In some embodiments, the VH FR2 has the amino acid sequence of SEQ ID NO: 66 and VH CDRs of Ab323. In some embodiments, the VH FR3 has the amino acid sequence of SEQ ID NO: 87 and VH CDRs of Ab323. In some embodiments, the VH FR4 has the amino acid sequence of SEQ ID NO: 68 and VH CDRs of Ab323. In certain embodiments, the an antibody described herein comprises one or more of the VH FR1 having the amino acid sequence of SEQ ID NO: 86, the VH FR 2 having the amino acid sequence of SEQ ID NO: 66, the VH FR3 having the amino acid sequence of SEQ ID NO: 87, and the VH FR4 having the amino acid sequence of SEQ ID NO: 68 and VH CDRs of Ab323.

In certain embodiments, an antibody described herein comprises one or more VH framework regions (FRs) having the amino acid sequence described herein for Ab324 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 65 and VH CDRs of Ab324. In some embodiments, the VH FR2 has the amino acid sequence of SEQ ID NO: 66 and VH CDRs of Ab324. In some embodiments, the VH FR3 has the amino acid sequence of SEQ ID NO: 91 and VH CDRs of Ab324. In some embodiments, the VH FR4 has the amino acid sequence of SEQ ID NO: 92 and VH CDRs of Ab324. In certain embodiments, the an antibody described herein comprises one or more of the VH FR1 having the amino acid sequence of SEQ ID NO: 65, the VH FR 2 having the amino acid sequence of SEQ ID NO: 66, the VH FR3 having the amino acid sequence of SEQ ID NO: 91, and the VH FR4 having the amino acid sequence of SEQ ID NO: 92 and VH CDRs of Ab324.

In certain embodiments, an antibody described herein comprises one or more VH framework regions (FRs) having the amino acid sequence described herein for Ab325 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 65 and VH CDRs of Ab325. In some embodiments, the VH FR2 has the amino acid sequence of SEQ ID NO: 66 and VH CDRs of Ab325. In some embodiments, the VH FR3 has the amino acid sequence of SEQ ID NO: 91 and VH CDRs of Ab325. In some embodiments, the VH FR4 has the amino acid sequence of SEQ ID NO: 95 and VH CDRs of Ab325. In certain embodiments, the an antibody described herein comprises one or more of the VH FR1 having the amino acid sequence of SEQ ID NO: 65, the VH FR 2 having the amino acid sequence of SEQ ID NO: 66, the VH FR3 having the amino acid sequence of SEQ ID NO: 91, and the VH FR4 having the amino acid sequence of SEQ ID NO: 95 and VH CDRs of Ab325.

In certain embodiments, an antibody described herein comprises one or more VH framework regions (FRs) having the amino acid sequence described herein for Ab326 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 80 and VH CDRs of Ab326. In some embodiments, the VH FR2 has the amino acid sequence of SEQ ID NO: 81 and VH CDRs of Ab326. In some embodiments, the VH FR3 has the amino acid sequence of SEQ ID NO: 82 and VH CDRs of Ab326. In some embodiments, the VH FR4 has the amino acid sequence of SEQ ID NO: 68 and VH CDRs of Ab326. In certain embodiments, the an antibody described herein comprises one or more of the VH FR1 having the amino acid sequence of SEQ ID NO: 80, the VH FR 2 having the amino acid sequence of SEQ ID NO: 81, the VH FR3 having the amino acid sequence of SEQ ID NO: 82, and the VH FR4 having the amino acid sequence of SEQ ID NO: 68 and VH CDRs of Ab326.

In certain embodiments, an antibody described herein comprises one or more VH framework regions (FRs) having the amino acid sequence described herein for Ab327 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine, rodent, chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 100 and VH CDRs of Ab327. In some embodiments, the VH FR2 has the amino acid sequence of SEQ ID NO: 101 and VH CDRs of Ab327. In some embodiments, the VH FR3 has the amino acid sequence of SEQ ID NO: 102 and VH CDRs of Ab327. In some embodiments, the VH FR4 has the amino acid sequence of SEQ ID NO: 103 and VH CDRs of Ab327. In certain embodiments, the an antibody described herein comprises one or more of the VH FR1 having the amino acid sequence of SEQ ID NO: 100, the VH FR 2 having the amino acid sequence of SEQ ID NO: 101, the VH FR3 having the amino acid sequence of SEQ ID NO: 102, and the VH FR4 having the amino acid sequence of SEQ ID NO: 103 and VH CDRs of Ab327.

In certain embodiments, an antibody described herein comprises one or more VH framework regions (FRs) having the amino acid sequence described herein for Ab328 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 80 and VH CDRs of Ab328. In some embodiments, the VH FR2 has the amino acid sequence of SEQ ID NO: 81 and VH CDRs of Ab328. In some embodiments, the VH FR3 has the amino acid sequence of SEQ ID NO: 106 and VH CDRs of Ab328. In some embodiments, the VH FR4 has the amino acid sequence of SEQ ID NO: 68 and VH CDRs of Ab328. In certain embodiments, the an antibody described herein comprises one or more of the VH FR1 having the amino acid sequence of SEQ ID NO: 80, the VH FR 2 having the amino acid sequence of SEQ ID NO: 81, the VH FR3 having the amino acid sequence of SEQ ID NO: 106, and the VH FR4 having the amino acid sequence of SEQ ID NO: 68 and VH CDRs of Ab328.

In certain embodiments, an antibody described herein comprises one or more VH framework regions (FRs) having the amino acid sequence described herein for Ab329 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 111 and VH CDRs of Ab329. In some embodiments, the VH FR2 has the amino acid sequence of SEQ ID NO: 112 and VH CDRs of Ab329. In some embodiments, the VH FR3 has the amino acid sequence of SEQ ID NO: 113 and VH CDRs of Ab329. In some embodiments, the VH FR4 has the amino acid sequence of SEQ ID NO: 114 and VH CDRs of Ab329. In certain embodiments, the an antibody described herein comprises one or more of the VH FR1 having the amino acid sequence of SEQ ID NO: 111, the VH FR 2 having the amino acid sequence of SEQ ID NO: 112, the VH FR3 having the amino acid sequence of SEQ ID NO: 113, and the VH FR4 having the amino acid sequence of SEQ ID NO: 114 and VH CDRs of Ab329.

In certain embodiments, an antibody described herein comprises one or more VH framework regions (FRs) having the amino acid sequence described herein for Ab330 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 119 and VH CDRs of Ab330. In some embodiments, the VH FR2 has the amino acid sequence of SEQ ID NO: 120 and VH CDRs of Ab330. In some embodiments, the VH FR3 has the amino acid sequence of SEQ ID NO: 121 and VH CDRs of Ab330. In some embodiments, the VH FR4 has the amino acid sequence of SEQ ID NO: 122 and VH CDRs of Ab330. In certain embodiments, the an antibody described herein comprises one or more of the VH FR1 having the amino acid sequence of SEQ ID NO: 119, the VH FR 2 having the amino acid sequence of SEQ ID NO: 120, the VH FR3 having the amino acid sequence of SEQ ID NO: 121, and the VH FR4 having the amino acid sequence of SEQ ID NO: 122 and VH CDRs of Ab330.

In certain embodiments, an antibody described herein comprises one or more VH framework regions (FRs) having the amino acid sequence described herein for Ab331 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 119 and VH CDRs of Ab331. In some embodiments, the VH FR2 has the amino acid sequence of SEQ ID NO: 120 and VH CDRs of Ab331. In some embodiments, the VH FR3 has the amino acid sequence of SEQ ID NO: 121 and VH CDRs of Ab331. In some embodiments, the VH FR4 has the amino acid sequence of SEQ ID NO: 122 and VH CDRs of Ab331. In certain embodiments, the an antibody described herein comprises one or more of the VH FR1 having the amino acid sequence of SEQ ID NO: 119, the VH FR 2 having the amino acid sequence of SEQ ID NO: 120, the VH FR3 having the amino acid sequence of SEQ ID NO: 121, and the VH FR4 having the amino acid sequence of SEQ ID NO: 122 and VH CDRs of Ab331.

In certain embodiments, an antibody described herein comprises one or more VH framework regions (FRs) having the amino acid sequence described herein for Ab332 (e.g., see Table 4), wherein the antibody immunospecifically binds to ALK (e.g., human ALK ECD, e.g., amino acid residues 21-1038 of SEQ ID NO: 467). In specific embodiments, an antibody (e.g., murine (e.g., rodent), chimeric or humanized antibody) described herein comprises a VH region comprising FR1, CDR1, FR2, CDR2, FR3, CDR3, and FR4. In certain embodiments, the VH FR1 has the amino acid sequence of SEQ ID NO: 126 and VH CDRs of Ab332. In some embodiments, the VH FR2 has the amino acid sequence of SEQ ID NO: 127 and VH CDRs of Ab332. In some embodiments, the VH FR3 has the amino acid sequence of SEQ ID NO: 128 and VH CDRs of Ab332. In some embodiments, the VH FR4 has the amino acid sequence of SEQ ID NO: 92 and VH CDRs of Ab332. In certain embodiments, the an antibody described herein comprises one or more of the VH FR1 having the amino acid sequence of SEQ ID NO: 126, the VH FR 2 having the amino acid sequence of SEQ ID NO: 127, the VH FR3 having the amino acid sequence of SEQ ID NO: 128, and the VH FR4 having the amino acid sequence of SEQ ID NO: 92 and VH CDRs of Ab332.

In specific embodiments, an antibody described herein, which immunospecifically binds to ALK (e.g., human ALK ECD, e.g., amino acid residues 21-1038 of SEQ ID NO: 467), comprises framework regions (e.g., framework regions of the VL domain and/or VH domain) that are human framework regions or derived from human framework regions. Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In certain embodiments, an antibody described herein comprises framework regions (e.g., framework regions of the VL domain and/or VH domain) that are primate (e.g., non-human primate) framework regions or derived from primate (e.g., non-human primate) framework regions.

For example, CDRs from antigen-specific non-human antibodies, typically of rodent origin (e.g., mouse or rat), can be grafted onto homologous human or non-human primate acceptor frameworks. In one embodiment, the non-human primate acceptor frameworks are from Old World apes. In a specific embodiment, the Old World ape acceptor framework is from *Pan troglodytes, Pan paniscus* or *Gorilla gorilla*. In a particular embodiment, the non-human primate acceptor frameworks are from the chimpanzee *Pan troglodytes*. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks is derived from the cynomolgus monkey *Macaca* cynomolgus. Non-human primate framework sequences are described in U.S. Patent Application Publication No. US 2005/0208625.

In specific aspects, a composite human antibody can be generated using, for example, Composite Human Antibody™ technology (Antitope Ltd., Cambridge, United Kingdom). For example, composite human antibodies can be generated by fusing together segments of unrelated human antibody variable regions, which are subsequently evaluated for their avoidance of T cell epitope inclusion (see, e.g., Baker et al., 2010, Self Nonself., 1(4):314-322; and Bryson et al., 2010, BioDrugs, 24(1):1-8), for example, deimmunization (see, e.g., Jones et al., 2009, Methods Mol Biol., 525:405-23).

In certain aspects, antibodies described herein are deimmunized antibodies. Deimmunization is a technology for location and removal of T-cell epitopes through the combined use of immunological and molecular biology techniques (see, e.g., Jones et al., 2009, Methods Mol Biol., 525:405-23; and Perry et al., 2008, Drugs R D., 9(6):385-96). For example, mutations to remove T-cell epitopes can generally be introduced, for example in the constant region, VL and/or VH regions, without significantly reducing the binding affinity of an antibody. In certain embodiments, mutations to remove T-cell epitopes are introduced in one or more VL CDRs and/or VH CDRs without significantly reducing the binding affinity of an antibody. In specific embodiments, mutations to remove T-cell epitopes are not introduced in VL CDRs and/or VH CDRs of an antibody. In certain embodiments, mutations to remove T-cell epitopes are introduced in one or more VL FRs and/or VH FRs without significantly reducing the binding affinity of an antibody.

In certain embodiments, an antibody described herein or an antigen-binding fragment thereof comprises amino acid sequences with certain percent identity relative to any one of Ab320-Ab332 and Ab351-Ab446.

The determination of percent identity between two sequences (e.g., amino acid sequences or nucleic acid sequences) can be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and) (BLAST programs of Altschul et al., 1990, J. Mol. Biol. 215:403. BLAST nucleotide searches can be performed with the NBLAST nucleotide program parameters set, e.g., for score=100, word length=12 to obtain nucleotide sequences homologous to a nucleic acid molecules described herein. BLAST protein searches can be performed with the) (BLAST program parameters set, e.g., to score 50, word length=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of)(BLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 395, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 395, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab320 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 395, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab320 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 396, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 396, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab320 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 396, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab320 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 395, and (ii) a VH domain having at least 80%, at least 85%, at least 90%, at least 95%, or at least 98% sequence identity to the amino acid sequence of SEQ ID NO: 396, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab320 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 397, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 397, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab321 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 397, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab321 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 398, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 398, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab321 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 398, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab321 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 397, and (ii) a VH domain having at least 80%, at least 85%, at least 90%, at least 95%, or at least 98% sequence identity to the amino acid sequence of SEQ ID NO: 398, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab321 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 399, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 399, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab322 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 399, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab322 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 400 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 400, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab322 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 400, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab322 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 399, and (ii) a VH domain having at least 80%, at least 85%, at least 90%, at least 95%, or at least 98% sequence identity to the amino acid sequence of SEQ ID NO: 400, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab322 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 401, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 401, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab323 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 401, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab323 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 402 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 402, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab323 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 402, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab323 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 401, and (ii) a VH domain having at least 80%, at least 85%, at least 90%, at least 95%, or at least 98% sequence identity to the amino acid sequence of SEQ ID NO: 402, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab323 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 403, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 403, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab324 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 403, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab324 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 404 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 404, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab324 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 404, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab324 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 403, and (ii) a VH domain having at least 80%, at least 85%, at least 90%, at least 95%, or at least 98% sequence identity to the amino acid sequence of SEQ ID NO: 404, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab324 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 405, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 405, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab325 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 405, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab325 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 406 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 406, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab325 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 406, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab325 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 405, and (ii) a VH domain having at least 80%, at least 85%, at least 90%, at least 95%, or at least 98% sequence identity to the amino acid sequence of SEQ ID NO: 406, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab325 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 407, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 407, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab326 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 407, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab326 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 408 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 408, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab326 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 408, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab326 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 407, and (ii) a VH domain having at least 80%, at least 85%, at least 90%, at least 95%, or at least 98% sequence identity to the amino acid sequence of SEQ ID NO: 408, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab326 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 409, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 409, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab327 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 409, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab327 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 410 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 410, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab327 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 410, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab327 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 409, and (ii) a VH domain having at least 80%, at least 85%, at least 90%, at least 95%, or at least 98% sequence identity to the amino acid sequence of SEQ ID NO: 410, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab327 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 411, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 411, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab328 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 411, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab328 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 412 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 412, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab328 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 412, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab328 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 411, and (ii) a VH domain having at least 80%, at least 85%, at least 90%, at least 95%, or at least 98% sequence identity to the amino acid sequence of SEQ ID NO: 412, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab328 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 413, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 413, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab329 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 413, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab329 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 414 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 414, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab329 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 414, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab329 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 413, and (ii) a VH domain having at least 80%, at least 85%, at least 90%, at least 95%, or at least 98% sequence identity to the amino acid sequence of SEQ ID NO: 414, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab329 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 415, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 415, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab330 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 415, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab330 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 416 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 416, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab330 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 416, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab330 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 415, and (ii) a VH domain having at least 80%, at least 85%, at least 90%, at least 95%, or at least 98% sequence identity to the amino acid sequence of SEQ ID NO: 416, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab330 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 417, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 417, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab331 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 417, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab331 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 418 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 418, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab331 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 418, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab331 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 417, and (ii) a VH domain having at least 80%, at least 85%, at least 90%, at least 95%, or at least 98% sequence identity to the amino acid sequence of SEQ ID NO: 418, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab331 (e.g., as set forth in Tables 1 and 2, Tables 5 and 6, or Tables 9 and 10).

In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 419, wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VL domain having at least 80%, at least 85%, at least 90%, at least 95%, or at least 98% sequence identity to the amino acid sequence of SEQ ID NO: 419, wherein the antibody immunospecifically binds to ALK (e.g., human ALK ECD, e.g., amino acid residues 21-1038 of SEQ ID NO: 467), and wherein the antibody comprises CDRs (e.g., VL CDRs 1-3) that are identical to the CDRs (e.g., VL CDRs 1-3) of antibody Ab332 (e.g., as set forth in Table 1, Table 5, or Table 9).

In certain embodiments, an antibody described herein or an antigen-binding fragment thereof comprises a VL domain comprising VL framework regions having at least 80%, at least 85%, at least 90%, at least 95%, or at least 98% sequence identity to the amino acid sequence of the framework regions of SEQ ID NO: 419, wherein the antibody immunospecifically binds to ALK (e.g., human ALK ECD, e.g., amino acid residues 21-1038 of SEQ ID NO: 467). In a particular embodiment, the antibody comprises VL CDRs that are identical to the VL CDRs of antibody Ab332 (e.g., as set forth in Table 1, Table 5, or Table 9).

In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 420 wherein the antibody immunospecifically binds to ALK (e.g., human ALK ECD, e.g., amino acid residues 21-1038 of SEQ ID NO: 467). In certain embodiments, an antibody described herein or an antigen-binding fragment thereof comprises a VH domain having at least 80%, at least 85%, at least 90%, at least 95%, or at least 98% sequence identity to the amino acid sequence of SEQ ID NO: 420, wherein the antibody immunospecifically binds to ALK (e.g., human ALK ECD, e.g., amino acid residues 21-1038 of SEQ ID NO: 467), and wherein the antibody comprises CDRs (e.g., VH CDRs 1-3) that are identical to the CDRs (e.g., VH CDRs 1-3) of antibody Ab332 (e.g., as set forth in Table 2, Table 6, or Table 10).

In certain embodiments, an antibody described herein or an antigen-binding fragment thereof comprises a VH domain comprising VH framework regions having at least 80%, at least 85%, at least 90%, at least 95%, or at least 98% sequence identity to the amino acid sequence of the framework regions of SEQ ID NO: 420, wherein the antibody immunospecifically binds to ALK (e.g., human ALK ECD, e.g., amino acid residues 21-1038 of SEQ ID NO: 467). In specific embodiments, such an antibody comprises CDRs (e.g., VH CDRs 1-3) identical to the CDRs (e.g., VH CDRs 1-3) of antibody Ab332 (e.g., as set forth in Table 2, Table 6, or Table 10).

In certain embodiments, an antibody described herein or an antigen-binding fragment thereof comprises (i) a VL domain having at least 80%, at least 85%, at least 90%, at least 95%, or at least 98% sequence identity to the amino acid sequence of SEQ ID NO: 419, and (ii) a VH domain having at least 80%, at least 85%, at least 90%, at least 95%, or at least 98% sequence identity to the amino acid sequence of SEQ ID NO: 420, respectively, wherein the antibody immunospecifically binds to ALK (e.g., human ALK ECD, e.g., amino acid residues 21-1038 of SEQ ID NO: 467). In specific embodiments, such an antibody or an antigen-binding fragment thereof comprises CDRs (e.g., VL CDRs 1-3 and/or VH CDRs 1-3) identical to the CDRs (e.g., VL CDRs 1-3 and/or VH CDRs 1-3) of antibody Ab332 (e.g., as set forth in Tables 1 and 2, Tables 5 and 6, or Tables 9 and 10).

In another embodiment, provided herein are antibodies or fragments thereof that bind to the ECD of human ALK (SEQ ID NO: 467), wherein the antibodies or fragments thereof binds to an ALK epitope comprising at least one, two, three, four, five, six, seven, eight, nine or ten amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 amino acid residues within the C-terminal (T637-S1038) ECD of human ALK (SEQ ID NO: 467). In certain embodiments, the ALK epitope comprises 1, 2, 3, 4, 5, 6, 7, 8, 9, or 10 amino acid residues within the region of human ALK that is flanked by the second MAM domain and the glycine-rich region of the extracellular domain. In certain embodiments, the ALK epitope comprises one, two, three, four, five, six, or each of amino acid residues 648, 664, 666, 721, 723, 768, and 863 within the ECD of human ALK (SEQ ID NO: 467). In certain embodiments, the ALK epitope comprises amino acid residue 648 within the ECD of human ALK (SEQ ID NO: 467). In certain embodiments, the ALK epitope comprises amino acid residues 664 and 666 within the ECD of human ALK (SEQ ID NO: 467). In certain embodiments, the ALK epitope comprises amino acid residues 721 and 723 within the ECD of human ALK (SEQ ID NO: 467). In certain embodiments, the ALK epitope comprises amino acid residue 768 within the ECD of human ALK (SEQ ID NO: 467). In certain embodiments, the ALK epitope comprises amino acid residue 863 within the ECD of human ALK (SEQ ID NO: 467). In a specific embodiment, the ALK epitope is a non-linear epitope.

Also provided herein are antibodies that bind the same or an overlapping epitope of ALK (e.g., an epitope located in an ECD of human ALK, such as in the NTR, MAM1, LDLa, MAM2 or EGF domains of ALK-ECD) as an antibody described herein (e.g., antibody Ab320, Ab321, Ab322, Ab323, Ab324, Ab325, Ab326, Ab327, Ab328, Ab329, Ab330, Ab331, or Ab332), for example, antibodies that compete (e.g., in a dose dependent manner) for binding to ALK (e.g., an ECD of human ALK) with an antibody described herein (e.g., antibody Ab320, Ab321, Ab322, Ab323, Ab324, Ab325, Ab326, Ab327, Ab328, Ab329, Ab330, Ab331, or Ab332), or that competitively inhibit (e.g., in a dose dependent manner) an antibody described herein (e.g., antibody Ab320, Ab321, Ab322, Ab323, Ab324, Ab325, Ab326, Ab327, Ab328, Ab329, Ab330, Ab331, or Ab332) from binding to ALK (e.g., an epitope located on the ECD of human ALK).

In a specific aspect, also provided herein are antibodies that bind the same or an overlapping epitope of ALK (e.g., an epitope located in an ECD of human ALK, such as in in the NTR, MAM1, LDLa, MAM2 or EGF domains of ALK-ECD) as any one of antibodies Ab321, Ab322, Ab326, Ab327, Ab330, and Ab331, and is capable of inhibiting (e.g., partially inhibiting) phosphorylation of ALK and of inhibiting (e.g., partially inhibiting) tumor cell proliferation or tumor growth better.

In a specific aspect, also provided herein are antibodies that bind the same or an overlapping epitope of ALK (e.g., an epitope located in an ECD of human ALK, such as in in the NTR, MAM1, LDLa, MAM2 or EGF domains of ALK-ECD) as any one of antibodies, Ab323, Ab324, Ab325, Ab328, Ab329, and Ab332, and is capable of increasing phosphorylation of ALK and of increasing cell growth or proliferation.

Antibodies that bind to the same or overlapping epitopes of ALK (e.g., an epitope located in an ECD of human ALK such as in the NTR, MAM1, LDLa, MAM2 or EGF domains of ALK-ECD) can be identified using routine techniques such as those utilized in the examples presented herein. An immunoassay, for example, used to demonstrate the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as ALK. Numerous types of competitive binding assays are known, for example: solid phase direct or indirect radioimmunoassay (MA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label RIA using I-125 label (see Morel et al., (1988) Mol. Immunol. 25(1):7); solid phase direct biotin-avidin EIA (Cheung et al., (1990) Virology 176:546); and direct labeled MA. (Moldenhauer et al., (1990) Scand J. Immunol. 32:77). Typically, such an assay involves the use of purified antigen (e.g., ALK, such as an ECD of human ALK) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener et al., J. Immunol., 1983, 130:2308-2315; Wagener et al., J. Immunol. Methods, 1984, 68:269-274; Kuroki et al., Cancer Res., 1990, 50:4872-4879; Kuroki et al., Immunol. Invest., 1992, 21:523-538;

Kuroki et al., Hybridoma, 1992, 11:391-407, and *Using Antibodies: A Laboratory Manual*, Ed Harlow and David Lane editors (Cold Springs Harbor Laboratory Press, Cold Springs Harbor, N.Y., 1999), pp. 386-389.

In certain aspects, competition binding assays can be used to determine whether binding of an antibody is competitively inhibited, e.g., in a dose dependent manner, by another antibody, thereby signaling that the antibodies bind essentially the same epitope, or overlapping epitopes, e.g., sterically overlapping epitopes. Such competition binding assays can include, for example, competition ELISA assays, which can be configured in all number of different formats, using either labeled antigen or labeled antibody. In a particular embodiment, an antibody can be tested in competition binding assays with an antibody described herein, e.g., antibody Ab320, Ab321, Ab322, Ab323, Ab324, Ab325, Ab326, Ab327, Ab328, Ab329, Ab330, Ab331, or Ab332, or a chimeric or Fab antibody thereof, or an antibody comprising VH CDRs and VL CDRs of any of antibodies Ab320-Ab332 and Ab351-Ab446.

In specific aspects, provided herein is an antibody which competitively blocks (e.g., in a dose dependent manner) binding of antibodies comprising the amino acid sequences described herein for specific binding to an ALK polypeptide (e.g., an ECD of ALK, for example human ALK), as determined using assays known to one of skill in the art or described herein (e.g., ELISA competitive assays). In particular embodiments, such a competitively blocking antibody inhibits one or more ALK activities. In specific aspects, provided herein is an antibody which competes (e.g., in a dose dependent manner) for specific binding to an ALK polypeptide (e.g., an ECD of ALK, for example human ALK), with an antibody comprising the amino acid sequences described herein (e.g., VL and/or VH amino acid sequences of antibody Ab320, Ab321, Ab322, Ab323, Ab324, Ab325, Ab326, Ab327, Ab328, Ab329, Ab330, Ab331, or Ab332 (see, e.g., SEQ ID NOS: 395-420), as determined using assays known to one of skill in the art or described herein (e.g., ELISA competitive assays).

In specific aspects, provided herein is an antibody which competes (e.g., in a dose dependent manner) for specific binding to an ALK polypeptide (e.g., an ECD of ALK, for example human ALK), with any one of antibodies Ab320-Ab332 and Ab351-Ab446.

In specific aspects, provided herein is an antibody which competes (e.g., in a dose dependent manner) for specific binding to an ALK polypeptide (e.g., an ECD of ALK, for example human ALK), with an antibody comprising a VL chain region having the amino acid sequence of SEQ ID NO: 395, 397, 399, 401, 403, 405, 407, 409, 411, 413, 415, 417, or 419, and a VH chain region having the amino acid sequence of SEQ ID NO: 396, 398, 400, 402, 404, 406, 408, 410, 412, 414, 416, 418, or 420.

In a specific aspect, also provided herein are antibodies (i) that compete (e.g., in a dose dependent manner) for specific binding to an epitope of an ALK polypeptide (e.g., an epitope of an ECD of human ALK, such as in the NTR, MAM1, LDLa, MAM2 or EGF domains of ALK-ECD), with any one of antibody Ab321, Ab322, Ab326, Ab327, Ab330, or Ab331, and (ii) that are capable of inhibiting (e.g., partially inhibiting) phosphorylation of ALK and of inhibiting (e.g., partially inhibiting) tumor cell proliferation or tumor growth.

In a specific aspect, also provided herein are antibodies (i) that compete (e.g., in a dose dependent manner) for specific binding to an epitope of an ALK polypeptide (e.g., an epitope of an ECD of human ALK, such as in the NTR, MAM1, LDLa, MAM2 or EGF domains of ALK-ECD), with any one of antibody Ab323, Ab324, Ab325, Ab328, Ab329, or Ab332, and (ii) that are capable of increasing phosphorylation of ALK and of increasing cell growth or proliferation.

In a specific embodiment, an antibody described herein is one that is competitively blocked (e.g., in a dose dependent manner) by an antibody that specifically binds ALK and comprises a VL chain region having the amino acid sequence of SEQ ID NO: 395, 397, 399, 401, 403, 405, 407, 409, 411, 413, 415, 417, or 419, and a VH chain region having the amino acid sequence of SEQ ID NO: 396, 398, 400, 402, 404, 406, 408, 410, 412, 414, 416, 418, or 420, for specific binding to an ALK polypeptide (e.g., an ECD of ALK, for example human ALK).

In a specific aspect, also provided herein are antibodies (i) that competitively block (e.g., in a dose dependent manner) any one of antibody Ab321, Ab322, Ab326, Ab327, Ab330, or Ab331, for specific binding to an epitope of an ALK polypeptide (e.g., an epitope of an ECD of human ALK, such as in the NTR, MAM1, LDLa, MAM2 or EGF domains of ALK-ECD), and (ii) that are capable of inhibiting (e.g., partially inhibiting) phosphorylation of ALK and of inhibiting (e.g., partially inhibiting) tumor cell proliferation or tumor growth.

In a specific aspect, also provided herein are antibodies (i) that competitively block (e.g., in a dose dependent manner) any one of antibody Ab323, Ab324, Ab325, Ab328, Ab329, or Ab332, for specific binding to an epitope of an ALK polypeptide (e.g., an epitope of an ECD of human ALK, such as in the NTR, MAM1, LDLa, MAM2 or EGF domains of ALK-ECD), and (ii) that are capable of increasing phosphorylation of ALK and of increasing cell growth or proliferation.

In specific aspects, provided herein is an antibody, or an antigen-binding fragment thereof, which immunospecifically binds to the same epitope as that of an antibody (e.g., any one of antibodies Ab320-Ab332 and Ab351-Ab446) comprising the amino acid sequences described herein (see, e.g., Tables 1-14) for specific binding to an ALK polypeptide (e.g., an ECD of ALK, for example human ALK, such as in the NTR, MAM1, LDLa, MAM2 or EGF domains of ALK-ECD). Assays known to one of skill in the art or described herein (e.g., ELISA assays) can be used to determine if two antibodies bind to the same epitope.

In a specific embodiment, an antibody described herein, or an antigen-binding fragment thereof, immunospecifically binds to the same epitope as that of an antibody that specifically binds ALK (e.g., any one of antibodies Ab320-Ab332 and Ab351-Ab446) and comprises a VL chain region having the amino acid sequence of SEQ ID NO: 395, 397, 399, 401, 403, 405, 407, 409, 411, 413, 415, 417, or 419, and a VH chain region having the amino acid sequence of SEQ ID NO: 396, 398, 400, 402, 404, 406, 408, 410, 412, 414, 416, 418, or 420.

In a specific aspect, also provided herein are antibodies (i) that immunospecifically binds the same epitope of an ALK polypeptide (e.g., an epitope of an ECD of human ALK, such as in the NTR, MAM1, LDLa, MAM2 or EGF domains of ALK-ECD) as that of antibody Ab321, Ab322, Ab326, Ab327, Ab330, or Ab331; and (ii) that are capable of inhibiting (e.g., partially inhibiting) phosphorylation of ALK and of inhibiting (e.g., partially inhibiting) tumor cell proliferation or tumor growth.

In a specific aspect, also provided herein are antibodies (i) that immunospecifically binds the same epitope of an ALK polypeptide (e.g., an epitope of an ECD of human ALK, such as in the NTR, MAM1, LDLa, MAM2 or EGF domains of ALK-ECD) as that of antibody Ab323, Ab324, Ab325, Ab328, Ab329, or Ab332; and (ii) that are capable of increasing phosphorylation of ALK and of increasing cell proliferation or growth.

In one aspect, provided herein are antibodies that immunospecifically bind to ALK (e.g., an ECD of human ALK) and that can modulate ALK activity and/or expression (e.g., inhibit ALK activity and/or expression). In certain embodiments, an ALK antagonist is provided herein that is an antibody described herein that immunospecifically binds to an ECD of human ALK, and that inhibits (e.g., partially inhibits) at least one ALK activity (e.g., ALK phosphorylation or ALK signaling). In certain embodiments, an ALK antagonist provided herein is an antibody described herein that immunospecifically binds to an ECD of human ALK, and that inhibits or decreases/reduces ALK expression. In certain embodiments, provided herein are antibodies that immunospecifically bind to ALK (e.g., an ECD of human ALK) and that (a) inhibit ALK activity in a cell as determined by inhibition of phosphorylation of ALK; (b) induce ALK degradation in a cell; and (c) inhibit tumor cell proliferation or tumor growth. In certain embodiments, provided herein are antibodies that immunospecifically bind to ALK (e.g., an ECD of human ALK) and that (a) inhibit phosphorylation of ALK; (b) induce ALK degradation in a cell; (c) inhibit tumor cell proliferation or tumor growth; and/or (d) inhibit ligand binding to ALK. In certain embodiments, provided herein are antibodies that immunospecifically bind to ALK (e.g., an ECD of human ALK) and that (a) induce ALK degradation in a cell (e.g., cell with ALK amplification or ALK mutation); and (b) inhibit ligand binding to ALK (e.g., in cells expressing wild-type ALK).

In one aspect, provided herein are antibodies that immunospecifically bind to ALK (e.g., an ECD of human ALK) and that can modulate ALK activity and/or expression (e.g., increase ALK activity and/or expression). In certain embodiments, an ALK agonist is provided herein that is an antibody described herein that immunospecifically binds to an ECD of human ALK, and that increases at least one ALK activity (e.g., ALK phosphorylation or ALK signaling). In certain embodiments, an ALK agonist provided herein is an antibody described herein that immunospecifically binds to an ECD of human ALK, and that increases ALK expression. In certain embodiments, provided herein are antibodies that immunospecifically bind to ALK (e.g., an ECD of human ALK) and that (a) increase ALK activity in a cell as determined by an increase in phosphorylation of ALK; (b) reduce ALK degradation in a cell; and (c) increase cell growth or proliferation. In certain embodiments, provided herein are antibodies that immunospecifically bind to ALK (e.g., an ECD of human ALK) and that (a) increase phosphorylation of ALK; (b) reduce ALK degradation in a cell; (c) increase cell growth or proliferation; and/or (d) increase ligand binding to ALK. In certain embodiments, provided herein are antibodies that immunospecifically bind to ALK (e.g., an ECD of human ALK) and that (a) reduce ALK degradation in a cell; and (b) increase ligand binding to ALK. In certain embodiments, provided herein are antibodies that immunospecifically bind to ALK (e.g., an ECD of human ALK) and that (a) increase phosphorylation of ALK; (b) reduce ALK degradation in a cell; (c) increase cell growth or proliferation; and/or (d) increase ligand binding to ALK.

ALK activity can relate to any activity of ALK such as those known or described in the art. Non-limiting examples of ALK activity include: ALK receptor dimerization, ALK receptor phosphorylation (e.g., tyrosine phosphorylation (such as ALK ligand dependent phosphorylation) or autophosphorylation in the cytoplasmic domain), signaling downstream of the ALK receptor (e.g., ERK1/2, STAT1, STAT3, STAT5, or AKT signaling), cell proliferation, including ALK ligand induced enhancement of cell proliferation (e.g., cancer cell proliferation), or cell survival (e.g., cancer cells). ALK activity or ALK function are used interchangeably herein. In certain aspects, ALK activity is induced by ALK ligand binding to ALK receptor. In certain embodiments, an increase in ALK activity or signaling can occur, in the absence of ALK ligand binding ALK receptor, due to high (or overexpression) expression of ALK receptors. High or overexpression of ALK in a cell refers to an expression level which is at least about 10%, 20%, 30%, 40%, 50%, 60%, 70%, 80%, 90%, 100%, 150%, 200%, 250%, 300%, 400%, or 500% more than the expression level of a reference cell known to have normal ALK expression or ALK activity or more than the average expression level of ALK in a population of cells or samples known to have normal ALK expression or ALK activity. Expression levels of ALK can be assessed by methods described herein or known to one of skill in the art (e.g., Western blotting, ELISA, or immunohistochemistry). In certain embodiments, provided herein are antibodies that immunospecifically bind to ALK (e.g., an ECD of human ALK) and decrease ALK expression. In certain embodiments, provided herein are antibodies that immunospecifically bind to ALK (e.g., an ECD of human ALK) and induce ALK degradation or turnover. In certain embodiments, provided herein are antibodies that immunospecifically bind to ALK (e.g., an ECD of human ALK) and block (e.g., partially block) ALK ligand-dependent and ligand-independent ALK signaling.

In certain embodiments, provided herein are antibodies that immunospecifically bind to ALK (e.g., an ECD of human ALK) and increase ALK expression. In certain embodiments, provided herein are antibodies that immunospecifically bind to ALK (e.g., an ECD of human ALK) and reduce ALK degradation or turnover. In certain embodiments, provided herein are antibodies that immunospecifically bind to ALK (e.g., an ECD of human ALK) and increase ALK ligand-dependent and ligand-independent ALK signaling.

In particular embodiments, anti-ALK antibodies provided herein do not have agonist activities. In particular embodiments, anti-ALK antibodies provided herein do not have antagonist activities. In certain embodiments, anti-ALK antibodies provided herein have low agonist activities. Identification of agonist activities is performed by assays known to one of ordinary skill in the art, such as, e.g., cell proliferation assays, ELISA or immunoblot assays to assess phosphorylation of ALK or the activity of downstream ALK signaling components, such as, for example, ERK1/2 and/or AKT.

In specific embodiments, antibodies described herein specifically bind to an ECD of ALK and block or inhibit (e.g., partially inhibit) binding of ALK ligand to ALK by at least about 5%, 10%, 15%, 20%, 25%, 30%, 35%, 40%, 45%, 50%, 55%, 60%, 65%, 70%, 75%, 80%, 85%, 90%, 95%, 98%, or 100% as assessed by methods described herein or known to one of skill in the art, e.g., ELISA assay, flow cytometry, or competition assay.

In specific embodiments, antibodies described herein specifically bind to an ECD of ALK and increase binding of ALK ligand to ALK by at least about 10%, 20%, 30%, 40%, 50%, 60%, 70%, 80%, 90%, 100%, 150%, 200%, 250%, 300%, 400%, or 500% as assessed by methods described herein or known to one of skill in the art, e.g., ELISA assay, flow cytometry, or competition assay.

In certain aspects, inhibition by anti-ALK antibodies described herein (e.g., monoclonal antibody) of ALK ligand binding to ALK can be characterized by $IC_{50}$ values, which reflects the concentration of anti-ALK antibodies achieving 50% inhibition of binding of ALK ligand to ALK. Thus, in specific embodiments, an anti-ALK antibody described herein (e.g., any one of antibodies Ab320-Ab332 and Ab351-Ab446 or an antigen-binding fragment thereof, or an antibody comprising CDRs of any one of antibodies Ab320-Ab332 and Ab351-Ab446) inhibits binding of ALK ligand to ALK with an $IC_{50}$ of at most about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 2 nM, 1 nM, 0.75 nM, 0.5 nM, 0.4 nM, 0.3 nM, 0.2 nM, 0.1 nM, 0.05 nM, 0.01 nM, 0.005 nM, or 0.001 nM, as assessed by methods described herein and/or known to one of skill in the art, (e.g., ELISA assay or flow cytometry). In specific embodiments, an anti-ALK antibody described herein inhibits binding of ALK ligand to ALK with an $IC_{50}$ of at least about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 2 nM, 1 nM, 0.75 nM, 0.5 nM, 0.4 nM, 0.3 nM, 0.2 nM, 0.1 nM, 0.05 nM, 0.01 nM, 0.005 nM, or 0.001 nM, as assessed by methods described herein and/or known to one of skill in the art, (e.g., ELISA assay or flow cytometry). In particular embodiments, an anti-ALK antibody described herein inhibits binding of ALK ligand to ALK with an $IC_{50}$ in the range of about 0.01 nM to 10 nM, 0.1 nM to 20 nM, 0.1 nM to 10 nM, 0.1 nM to 5 nM, or 0.01 nM to 20 nM, as assessed by methods described herein and/or known to one of skill in the art, (e.g., ELISA assay or flow cytometry).

In certain embodiments, an anti-ALK antibody described herein (e.g., any one of antibodies Ab320-Ab332 and Ab351-Ab446 or an antigen-binding fragment thereof, or an antibody comprising CDRs of any one of antibodies Ab320-Ab332 and Ab351-Ab446) does not block or inhibit ALK receptor dimerization. In certain embodiments, an anti-ALK antibody described herein only negligibly (e.g., less than about 2% or 3% or within a standard of error or deviation) inhibits or reduces ALK receptor dimerization. In certain embodiments, an anti-ALK antibody described herein does not induce or enhance ALK receptor dimer dissociation. In certain embodiments, an anti-ALK antibody described herein only negligibly (e.g., less than about 2% or 3% or within a standard of error or deviation) induces or enhances ALK receptor dimer dissociation. In a particular embodiment, an anti-ALK antibody described herein can specifically bind to an ALK receptor dimer and not block or inhibit ALK receptor dimerization. In a particular embodiment, an anti-ALK antibody described herein can specifically bind to an ALK receptor monomer and not block or inhibit ALK receptor dimerization. In certain embodiments, any such antibodies or antigen-binding fragments thereof inhibit ligand binding to ALK.

In certain aspects, as an inhibitor of ALK activity (e.g., ALK antagonist), an antibody described herein (e.g., any one of antibodies Ab321, Ab322, Ab326, Ab327, Ab330, or Ab331, or an antigen-binding fragment thereof, or an antibody comprising CDRs of any one of antibodies Ab321, Ab322, Ab326, Ab327, Ab330, or Ab331) can block or inhibit (e.g., partially inhibit) dimerization of ALK. Generally, ALK receptor dimerization is induced when ALK ligand binds to ALK. Thus, in specific embodiments, antibodies described herein specifically bind to ALK and block or inhibit (e.g., partially inhibit) dimerization of ALK receptors by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoprecipitation assay, relative to dimerization of ALK receptors in the presence of ALK ligand stimulation without any antibody or with an unrelated antibody (e.g., an antibody that does not immunospecifically bind to ALK). In a specific embodiment, antibodies described herein (e.g., any one of antibodies Ab321, Ab322, Ab326, Ab327, Ab330, or Ab331 or an antigen-binding fragment thereof, or an antibody comprising CDRs of any one of antibodies Ab321, Ab322, Ab326, Ab327, Ab330, or Ab331) specifically bind to ALK and partially inhibit dimerization of ALK receptors by about 25% to 75%. Blocking or inhibition (e.g., partial inhibition) of dimerization of ALK receptors by antibodies described herein can be assessed in the presences of ALK ligand stimulation. For example, cells expressing ALK can be contacted with ALK ligand in the presence or absence of anti-ALK antibodies described herein, and the level of ALK receptor dimerization is determined. In certain embodiments, ALK ligand-induced ALK receptor dimerization in the absence of anti-ALK antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than ALK receptor dimerization in the presence of anti-ALK antibody provided herein as assessed by methods described herein or known to one of skill in the art (e.g., immunoprecipitation assays). Tyrosine phosphorylation of one or more residues in the cytoplasmic domain of ALK can be an indicator of ALK receptor dimerization.

In certain aspects, as an activator of ALK activity (e.g., ALK agonist), an antibody described herein (e.g., any one of antibodies Ab323, Ab324, Ab325, Ab328, Ab329, or Ab332, or an antigen-binding fragment thereof, or an antibody comprising CDRs of any one of antibodies Ab323, Ab324, Ab325, Ab328, Ab329, or Ab332) can increase dimerization of ALK. Generally, ALK receptor dimerization is induced when ALK ligand binds to ALK. Thus, in specific embodiments, antibodies described herein specifically bind to ALK and increase dimerization of ALK receptors by at least about 10%, 20%, 30%, 40%, 50%, 60%, 70%, 80%, 90%, 100%, 150%, 200%, 250%, 300%, 400%, or 500% as assessed by methods described herein or known to one of skill in the art, e.g., immunoprecipitation assay, relative to dimerization of ALK receptors in the presence of ALK ligand stimulation without any antibody or with an unrelated antibody (e.g., an antibody that does not immunospecifically bind to ALK). In a specific embodiment, antibodies described herein (e.g., any one of antibodies Ab323, Ab324, Ab325, Ab328, Ab329, or Ab332 or an antigen-binding fragment thereof, or an antibody comprising CDRs of any one of antibodies Ab323, Ab324, Ab325, Ab328, Ab329, or Ab332) specifically bind to ALK and increase dimerization of ALK receptors by about 25% to 75%. Induction of dimerization of ALK receptors by antibodies described herein can be assessed in the presences of ALK ligand stimulation. For example, cells expressing ALK can be contacted with ALK ligand in the presence or absence of anti-ALK antibodies described herein, and the level of ALK receptor dimerization is determined. In certain embodiments, ALK ligand-induced ALK receptor dimerization in the absence of anti-ALK antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold lower than ALK receptor dimerization in the presence of anti-ALK antibody provided herein as assessed by methods described herein or known to one of skill in the art (e.g., immunoprecipitation assays). Tyrosine phosphorylation of one or more residues in the cytoplasmic domain of ALK can be an indicator of ALK receptor dimerization.

In certain embodiments, an anti-ALK antibody described herein can inhibit (e.g., partially inhibit) ALK activity by at least about 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein and/or known to one of skill in the art, relative to ALK activity in the presence of ALK ligand stimulation without any antibody or with an unrelated antibody (e.g., an antibody that does not immunospecifically bind to ALK). In certain embodiments, an anti-ALK antibody described herein can inhibit (e.g., partially inhibit) ALK activity by at least about 25% to about 65% as assessed by methods described herein and/or known to one of skill in the art, relative to ALK activity in the presence of ALK ligand stimulation without any antibody or with an unrelated antibody (e.g., an antibody that does not immunospecifically bind to ALK). Non-limiting examples of ALK activity can include, ALK receptor dimerization, ALK receptor heterodimerization with other receptors, ALK receptor phosphorylation (e.g., tyrosine phosphorylation or autophosphorylation in the cytoplasmic domain), signaling downstream of the ALK receptor (e.g., ERK1/2, STAT1, STAT3, STAT5, or AKT signaling), ALK ligand induced enhancement of cell proliferation, or cell survival, and ALK ligand induced anti-apoptosis.

In certain embodiments, an anti-ALK antibody described herein can increase ALK activity by at least about 10%, 20%, 30%, 40%, 50%, 60%, 70%, 80%, 90%, 100%, 150%, 200%, 250%, 300%, 400%, or 500% as assessed by methods described herein and/or known to one of skill in the art, relative to ALK activity in the presence of ALK ligand stimulation without any antibody or with an unrelated antibody (e.g., an antibody that does not immunospecifically bind to ALK). In certain embodiments, an anti-ALK antibody described herein can increase ALK activity by at least about 25% to about 65% as assessed by methods described herein and/or known to one of skill in the art, relative to ALK activity in the presence of ALK ligand stimulation without any antibody or with an unrelated antibody (e.g., an antibody that does not immunospecifically bind to ALK). Non-limiting examples of ALK activity can include, ALK receptor dimerization, ALK receptor heterodimerization with other receptors, ALK receptor phosphorylation (e.g., tyrosine phosphorylation or autophosphorylation in the cytoplasmic domain), signaling downstream of the ALK receptor (e.g., ERK1/2, STAT1, STAT3, STAT5, or AKT signaling), ALK ligand induced enhancement of cell proliferation, or cell survival, and ALK ligand induced anti-apoptosis.

As an inhibitor of ALK activity (e.g., ALK antagonist), an antibody described herein (e.g., any one of antibodies Ab321, Ab322, Ab326, Ab327, Ab330, or Ab331, or an antigen-binding fragment thereof, or an antibody comprising CDRs of any one of antibodies Ab321, Ab322, Ab326, Ab327, Ab330, or Ab331) can block (e.g., partially block) or inhibit (e.g., partially inhibit) phosphorylation of ALK, specifically tyrosine phosphorylation of one or more residues in the cytoplasmic domain of ALK. Generally, ALK receptor dimerization and phosphorylation is induced when ALK ligand binds to ALK. However, in certain aspects, ALK receptor dimerization and/or phosphorylation can occur independently of ALK ligand binding to ALK receptor. For example ALK receptor dimerization and/or phosphorylation can occur due to gain-of-function mutations or overexpression of ALK.

As an activator of ALK activity (e.g., ALK agonist), an antibody described herein (e.g., any one of antibodies Ab323, Ab324, Ab325, Ab328, Ab329, or Ab332, or an antigen-binding fragment thereof, or an antibody comprising CDRs of any one of antibodies Ab323, Ab324, Ab325, Ab328, Ab329, or Ab332) can induce or increase phosphorylation of ALK, specifically tyrosine phosphorylation of one or more residues in the cytoplasmic domain of ALK. Generally, ALK receptor dimerization and phosphorylation is induced when ALK ligand binds to ALK. However, in certain aspects, ALK receptor dimerization and/or phosphorylation can occur independently of ALK ligand binding to ALK receptor. For example ALK receptor dimerization and/or phosphorylation can occur due to gain-of-function mutations or overexpression of ALK.

Non-limiting examples of tyrosine residues in the cytoplasmic domain of human ALK (e.g., GenBank Accession No. NP_004295.2) that can be phosphorylated, e.g., upon ligand stimulation, include residues 1278 and 1604. In a specific embodiment, an anti-ALK antibody described herein can inhibit receptor phosphorylation at tyrosine residue 1278 and/or 1604 of human ALK.

Thus, in specific embodiments, antibodies described herein (e.g., any one of antibodies Ab321, Ab322, Ab326, Ab327, Ab330, or Ab331, or an antigen-binding fragment thereof, or an antibody comprising CDRs of any one of antibodies Ab321, Ab322, Ab326, Ab327, Ab330, or Ab331) specifically bind to ALK and block, inhibit, or reduce tyrosine phosphorylation in the cytoplasmic domain of ALK by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, e.g., ELISA assay as described in Section 6 or immunoblotting assay, relative to phosphorylation in the presence of ALK ligand stimulation without any antibody or with an unrelated antibody (e.g., an antibody that does not immunospecifically bind to ALK). In particular embodiments, antibodies described herein specifically bind to ALK and block or inhibit tyrosine phosphorylation in the cytoplasmic domain of ALK by at least about 25%, optionally to about 65% or 75%, as assessed by methods described herein or known to one of skill in the art, e.g., ELISA assay as described in Section 6 or immunoblotting assay. In certain embodiments, antibodies described herein specifically bind to ALK and block or inhibit tyrosine phosphorylation of the cytoplasmic domain of ALK by at least about 25% to about 80% as assessed by methods described herein or known to one of skill in the art, e.g., ELISA assay as described in Section 6 or immunoblotting assay. In certain embodiments, antibodies described herein (e.g., any one of antibodies Ab321, Ab322, Ab326, Ab327, Ab330, or Ab331, or an antigen-binding fragment thereof, or an antibody comprising CDRs of any one of antibodies Ab321, Ab322, Ab326, Ab327, Ab330, or Ab331) specifically bind to ALK and block or inhibit tyrosine phosphorylation of the cytoplasmic domain of ALK by at least about 50% to about 80%, 90%, 95% or 100% as assessed by methods described herein or known to one of skill in the art, e.g., ELISA assay as described in Section 6 or immunoblotting assay. In specific embodiments, antibodies described herein specifically bind to ALK and block or inhibit tyrosine phosphorylation of the cytoplasmic domain of ALK with an $IC_{50}$ of less than about 400 pM or less than about 300 pM as assessed by methods described herein (e.g., phosphorylation inhibition assay with NB1 cells expressing ALK as described in Section 6 below) or known to one of skill in the art.

Thus, in specific embodiments, antibodies described herein (e.g., any one of antibodies Ab323, Ab324, Ab325, Ab328, Ab329, or Ab332, or an antigen-binding fragment thereof, or an antibody comprising CDRs of any one of antibodies Ab323, Ab324, Ab325, Ab328, Ab329, or Ab332) specifically bind to ALK and increase tyrosine phosphorylation in the cytoplasmic domain of ALK by at least about 10%, 20%, 30%, 40%, 50%, 60%, 70%, 80%, 90%, 100%, 150%, 200%, 250%, 300%, 400%, or 500% as assessed by methods described herein or known to one of skill in the art, e.g., ELISA assay as described in Section 6 or immunoblotting assay, relative to phosphorylation in the presence of ALK ligand stimulation without any antibody or with an unrelated antibody (e.g., an antibody that does not immunospecifically bind to ALK). In particular embodiments, antibodies described herein specifically bind to ALK and increase tyrosine phosphorylation in the cytoplasmic domain of ALK by at least about 25%, optionally to about 65% or 75%, as assessed by methods described herein or known to one of skill in the art, e.g., ELISA assay as described in Section 6 or immunoblotting assay. In certain embodiments, antibodies described herein specifically bind to ALK and increase tyrosine phosphorylation of the cytoplasmic domain of ALK by at least about 25% to about 80% as assessed by methods described herein or known to one of skill in the art, e.g., ELISA assay as described in Section 6 or immunoblotting assay. In certain embodiments, antibodies described herein (e.g., any one of antibodies Ab323, Ab324, Ab325, Ab328, Ab329, or Ab332, or an antigen-binding fragment thereof, or an antibody comprising CDRs of any one of antibodies Ab323, Ab324, Ab325, Ab328, Ab329, or Ab332) specifically bind to ALK and increase tyrosine phosphorylation of the cytoplasmic domain of ALK by at least about 50% to about 80%, 90%, 95% or 100% as assessed by methods described herein or known to one of skill in the art, e.g., ELISA assay as described in Section 6 or immunoblotting assay.

In specific embodiments, antibodies described herein specifically bind to ALK and block or inhibit tyrosine phosphorylation of the cytoplasmic domain of ALK with an $I_{C50}$ of less than about 200 pM. In specific embodiments, antibodies described herein specifically bind to ALK and block or inhibit tyrosine phosphorylation of the cytoplasmic domain of ALK with an $I_{C50}$ of less than about 150 pM. In specific embodiments, antibodies described herein specifically bind to ALK and block or inhibit tyrosine phosphorylation of the cytoplasmic domain of ALK with an $I_{C50}$ of less than about 50 pM. In specific embodiments, antibodies described herein specifically bind to ALK and block or inhibit tyrosine phosphorylation of the cytoplasmic domain of ALK with an $I_{C50}$ in the range of about 30 pM to about 300 pM, 100 pM to about 500 pM, about 25 pM to about 200 pM, about 40 pM to about 160 pM, about 50 pM to about 125 pM, or about 5 pM to about 100 pM. For example, an $I_{C50}$ for inhibition of tyrosine phosphorylation can be determined by assaying lysates from cells, e.g., NB-1 cells, recombinantly expressing ALK, in ELISA which detects tyrosine phosphorylation, for example, as described in Section 6 below. In certain embodiments, cells, e.g., NB-1 cells, recombinantly expressing ALK, are sorted, e.g., sorted to select for cells highly expressing ALK, prior to use in the phosphorylation inhibition assays. In some embodiments, the cells are not sorted prior to use in the phosphorylation inhibition assays.

In specific embodiments, antibodies described herein (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) specifically bind to ALK and block or inhibit phosphorylation of one or more tyrosine residues in the cytoplasmic domain of ALK by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, e.g., immunoblotting assay, relative to phosphorylation in the presence of ALK ligand stimulation without any antibody or with an unrelated antibody (e.g., an antibody that does not immunospecifically bind to ALK). In specific embodiments, blocking or inhibition (e.g., partial inhibition) of phosphorylation of one or more tyrosine residues of the cytoplasmic domain of ALK by antibodies described herein can be assessed upon ALK ligand stimulation. For example, cells expressing ALK are contacted with ALK ligand in the presence or absence of anti-ALK antibodies described herein, and the level of phosphorylation of one or more tyrosine residues in the cytoplasmic domain of ALK can be determined.

In certain embodiments, ALK ligand induced phosphorylation of one or more tyrosine residues of the cytoplasmic domain of ALK in the absence of anti-ALK antagonist antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than ALK ligand induced phosphorylation of one or more tyrosine residues of the cytoplasmic domain of ALK in the presence of anti-ALK antibody, as assessed by methods described herein or known to one of skill in the art (e.g., immunoblotting assays), relative to phosphorylation in the presence of ALK ligand stimulation without any antibody or with an unrelated antibody (e.g., an antibody that does not immunospecifically bind to ALK).

In specific embodiments, antibodies described herein (e.g., any one of antibodies Ab323, Ab324, Ab325, Ab328, Ab329, or Ab332, or an antigen-binding fragment thereof or an antibody comprising CDRs of any one of antibodies Ab323, Ab324, Ab325, Ab328, Ab329, or Ab332) specifically bind to ALK and increase phosphorylation of one or more tyrosine residues in the cytoplasmic domain of ALK by at least about 10%, 20%, 30%, 40%, 50%, 60%, 70%, 80%, 90%, 100%, 150%, 200%, 250%, 300%, 400%, or 500% as assessed by methods described herein or known to one of skill in the art, e.g., immunoblotting assay, relative to phosphorylation in the presence of ALK ligand stimulation without any antibody or with an unrelated antibody (e.g., an antibody that does not immunospecifically bind to ALK). In specific embodiments, increase in phosphorylation of one or more tyrosine residues of the cytoplasmic domain of ALK by antibodies described herein can be assessed upon ALK ligand stimulation. For example, cells expressing ALK are contacted with ALK ligand in the presence or absence of anti-ALK antibodies described herein, and the level of phosphorylation of one or more tyrosine residues in the cytoplasmic domain of ALK can be determined.

In certain embodiments, ALK ligand induced phosphorylation of one or more tyrosine residues of the cytoplasmic domain of ALK in the absence of anti-ALK agonist antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold lower than ALK ligand induced phosphorylation of one or more tyrosine residues of the cytoplasmic domain of ALK in the presence of anti-ALK antibody, as assessed by methods described herein or known to one of skill in the art (e.g., immunoblotting assays), relative to phosphorylation in the presence of ALK ligand stimulation without any antibody or with an unrelated antibody (e.g., an antibody that does not immunospecifically bind to ALK).

In specific embodiments, antibodies described herein specifically bind to ALK and induce or enhance ALK receptor degradation (e.g., in a cell, such as, for example, an NB-1 cell, or in a tumor cell) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to degradation in the absence of antibody or in the presence of an unrelated antibody (e.g., an antibody that does not immunospecifically bind to ALK). In specific embodiments, antibodies described herein specifically bind to ALK and induce or enhance ALK receptor degradation by at least about 25% or 35%, optionally to about 75%, as assessed by methods described herein or known to one of skill in the art (e.g., pulse-chase assays), relative to degradation in the absence of antibody or in the presence of an unrelated antibody (e.g., an antibody that does not immunospecifically bind to ALK). In specific embodiments, antibodies described herein specifically bind to ALK and induce or enhance ALK receptor degradation (e.g., in a cell, such as, for example, an NB-1 cell, or in a tumor cell) by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to degradation in the absence of antibody or in the presence of an unrelated antibody (e.g., an antibody that does not immunospecifically bind to ALK).

In specific embodiments, antibodies described herein specifically bind to ALK and reduce ALK receptor degradation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to degradation in the absence of antibody or in the presence of an unrelated antibody (e.g., an antibody that does not immunospecifically bind to ALK). In specific embodiments, antibodies described herein specifically bind to ALK and reduce ALK receptor degradation by at least about 25% or 35%, optionally to about 75%, as assessed by methods described herein or known to one of skill in the art (e.g., pulse-chase assays), relative to degradation in the absence of antibody or in the presence of an unrelated antibody (e.g., an antibody that does not immunospecifically bind to ALK). In specific embodiments, antibodies described herein specifically bind to ALK and reduce ALK receptor degradation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to degradation in the absence of antibody or in the presence of an unrelated antibody (e.g., an antibody that does not immunospecifically bind to ALK).

Techniques for quantitating or monitoring degradation (e.g., kinetics or rate of degradation) of cell surface receptors are well known in the art and can involve a variety of fluorescent and radioactive techniques (see, e.g., International Patent Application Publication No. WO 2008/153926 A2). For example, pulse chase experiments or experiments using radiolabeled ligands can be carried out to quantitatively measure degradation of ALK. Alternatively, ALK degradation can be analyzed by western blot or ELISA analysis, see, for example, Section 6.

In specific embodiments, antibodies described herein specifically bind to ALK and induce or enhance ALK receptor internalization (e.g., in a cell, such as, for example, an NB-1 cell, or in a tumor cell) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to internalization in the absence of antibody or in the presence of an unrelated antibody (e.g., an antibody that does not immunospecifically bind to ALK). In specific embodiments, antibodies described herein specifically bind to ALK and induce or enhance ALK receptor internalization by at least about 25% or 35%, optionally to about 75%, as assessed by methods described herein or known to one of skill in the art (e.g., pulse-chase assays), relative to internalization in the presence of an unrelated antibody (e.g., an antibody that does not immunospecifically bind to ALK). In specific embodiments, antibodies described herein specifically bind to ALK and induce or enhance ALK receptor internalization (e.g., in a cell, such as, for example, an NB-1 cell, or in a tumor cell) by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to internalization in the absence of antibody or in the presence of an unrelated antibody (e.g., an antibody that does not immunospecifically bind to ALK).

In specific embodiments, antibodies described herein specifically bind to ALK and reduce ALK receptor internalization by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to internalization in the absence of antibody or in the presence of an unrelated antibody (e.g., an antibody that does not immunospecifically bind to ALK). In specific embodiments, antibodies described herein specifically bind to ALK and reduce ALK receptor internalization by at least about 25% or 35%, optionally to about 75%, as assessed by methods described herein or known to one of skill in the art (e.g., pulse-chase assays), relative to internalization in the presence of an unrelated antibody (e.g., an antibody that does not immunospecifically bind to ALK). In specific embodiments, antibodies described herein specifically bind to ALK and reduce ALK receptor internalization by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to internalization in the absence of antibody or in the presence of an unrelated antibody (e.g., an antibody that does not immunospecifically bind to ALK).

Techniques for quantitating or monitoring receptor internalization (e.g., kinetics or rate of internalization) of cell surface receptors are well known in the art and may involve, for example, a variety of fluorescent and radioactive techniques (see, e.g., International Patent Application Publication No. WO 2008/153926 A2). For example, pulse chase experiments or experiments using radiolabeled ligands can be carried out to quantitatively measure internalization of ALK.

Moreover, signaling events downstream of ALK receptor phosphorylation can serve as indicators of ALK activity. Activated ALK stimulates several distinct signaling pathways, including for example ERK1/2, STAT1, STAT3, STAT5, and AKT.

Thus, in certain aspects, anti-ALK antibodies described herein which act as inhibitors of ALK activity (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) can inhibit signaling of a member of the PI3K-Akt, STAT, or ERK1/2 pathway kinases. In particular embodiments, anti-ALK antibodies described herein which act as inhibitors of ALK activity can inhibit binding (or inhibit interaction) to the cytoplasmic domain of ALK, and/or to one or more members of the PI3K-Akt, STAT, or ERK1/2 pathway kinases. In certain embodiments, anti-ALK antibodies described herein which act as inhibitors of ALK activity can inhibit activation by ALK of one or more members of the PI3K-Akt, STAT, or ERK1/2 pathway kinases. In certain embodiments, anti-ALK antibodies described herein which act as inhibitors of ALK activity can inhibit phosphorylation (e.g., tyrosine phosphorylation in the cytoplasmic domain) of one or more members of the PI3K-Akt, STAT, or ERK1/2 pathway kinases.

Thus, in certain aspects, anti-ALK antibodies described herein which act as activators of ALK activity (e.g., any one of antibodies Ab323, Ab324, Ab325, Ab328, Ab329, or Ab332, or an antigen-binding fragment thereof or an antibody comprising CDRs of any one of antibodies Ab323, Ab324, Ab325, Ab328, Ab329, or Ab332) can induce signaling of a member of the PI3K-Akt, STAT, or ERK1/2 pathway kinases. In particular embodiments, anti-ALK antibodies described herein which act as activators of ALK activity can increase binding to the cytoplasmic domain of ALK, and/or to one or more members of the PI3K-Akt, STAT, or ERK1/2 pathway kinases. In certain embodiments, anti-ALK antibodies described herein which act as activators of ALK activity can increase activation by ALK of one or more members of the PI3K-Akt, STAT, or ERK1/2 pathway kinases. In certain embodiments, anti-ALK antibodies described herein which act as activators of ALK activity can increase phosphorylation (e.g., tyrosine phosphorylation in the cytoplasmic domain) of one or more members of the PI3K-Akt, STAT, or ERK1/2 pathway kinases.

In particular embodiments, anti-ALK antibodies described herein which act as inhibitors of ALK activity (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) can inhibit downstream signaling such as, for example, phosphorylation of ERK1/2, phosphorylation of STAT1, STAT3, or STAT5, or phosphorylation of AKT. Thus, in certain embodiments, an anti-ALK antibody described herein can inhibit or reduce phosphorylation of ERK1/2 by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in Section 6 or immunoblotting assay, relative to phosphorylation without any antibody or with an unrelated antibody (e.g., an antibody that does not immunospecifically bind to ALK). In certain embodiments, an anti-ALK antibody described herein can inhibit or reduce phosphorylation of AKT by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in Section 6 or immunoblotting assay, relative to phosphorylation without any antibody or with an unrelated antibody (e.g., an antibody that does not immunospecifically bind to ALK).

In particular embodiments, anti-ALK antibodies described herein which act as activators of ALK activity (e.g., any one of antibodies Ab323, Ab324, Ab325, Ab328, Ab329, or Ab332, or an antigen-binding fragment thereof or an antibody comprising CDRs of any one of antibodies Ab323, Ab324, Ab325, Ab328, Ab329, or Ab332) can induce downstream signaling such as, for example, phosphorylation of ERK1/2, phosphorylation of STAT1, STAT3, or STAT5, or phosphorylation of AKT. Thus, in certain embodiments, an anti-ALK antibody described herein can increase phosphorylation of ERK1/2 by at least about 10%, 20%, 30%, 40%, 50%, 60%, 70%, 80%, 90%, 100%, 150%, 200%, 250%, 300%, 400%, or 500% as assessed by methods described herein or known to one of skill in the art, e.g., Western blot or ELISA assay as described in Section 6 or immunoblotting assay, relative to phosphorylation without any antibody or with an unrelated antibody (e.g., an antibody that does not immunospecifically bind to ALK). In certain embodiments, an anti-ALK antibody described herein can increase phosphorylation of AKT by at least about 10%, 20%, 30%, 40%, 50%, 60%, 70%, 80%, 90%, 100%, 150%, 200%, 250%, 300%, 400%, or 500% as assessed by methods described herein or known to one of skill in the art, e.g., Western blot or ELISA assay as described in Section 6 or immunoblotting assay, relative to phosphorylation without any antibody or with an unrelated antibody (e.g., an antibody that does not immunospecifically bind to ALK).

In certain aspects, an anti-ALK antibody described herein which can act as an inhibitor of ALK activity (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) or activity can inhibit cellular proliferation of cells (e.g., cancer cells), for example, cells that express ALK and that respond to ALK signaling (e.g., cells that proliferate in response to ALK ligand stimulation and ALK signaling). In certain aspects, an anti-ALK antibody described herein which can act as an inhibitor of ALK activity (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) or activity can inhibit cellular proliferation of cancer cells expressing ALK, such as, for example, NB-1 cells, for example, cells that express ALK and that respond to ALK signaling (e.g., cells that proliferate in response to ALK ligand stimulation and ALK signaling).

Cell proliferation assays are described in the art and can be readily carried out by one of skill in the art. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

In certain aspects, an anti-ALK antibody described herein which can act as an activator of ALK activity (e.g., any one of antibodies Ab323, Ab324, Ab325, Ab328, Ab329, or Ab332, or an antigen-binding fragment thereof or an antibody comprising CDRs of any one of antibodies Ab323, Ab324, Ab325, Ab328, Ab329, or Ab332) or activity can induce cellular proliferation, for example, cells that express ALK and that respond to ALK signaling (e.g., cells that proliferate in response to ALK ligand stimulation and ALK signaling).

In specific embodiments, antibodies described herein (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) specifically bind to ALK and inhibit cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., BrdU incorporation assay).

In specific embodiments, antibodies described herein (e.g., any one of antibodies Ab323, Ab324, Ab325, Ab328, Ab329, or Ab332, or an antigen-binding fragment thereof or an antibody comprising CDRs of any one of antibodies Ab323, Ab324, Ab325, Ab328, Ab329, or Ab332) specifically bind to ALK and increase cell proliferation by at least about 10%, 20%, 30%, 40%, 50%, 60%, 70%, 80%, 90%, 100%, 150%, 200%, 250%, 300%, 400%, or 500% as assessed by methods described herein or known to one of skill in the art (e.g., BrdU incorporation assay).

In specific embodiments, antibodies described herein specifically bind to ALK and block or inhibit cellular proliferation of cells (e.g., cancer cells) with an $IC_{50}$ of less than about 400 pM or less than about 300 pM as assessed by methods described herein (e.g., as described in Section 6 below) or known to one of skill in the art. In specific embodiments, antibodies described herein specifically bind to ALK and block or inhibit cellular proliferation of cells (e.g., cancer cells) with an $IC_{50}$ of less than about 300 nM. In specific embodiments, antibodies described herein specifically bind to ALK and block or inhibit cellular proliferation with an $IC_{50}$ of less than about 150 nM. In specific embodiments, antibodies described herein specifically bind to ALK and block or inhibit cellular proliferation with an $IC_{50}$ of less than about 50 nM. In specific embodiments, antibodies described herein specifically bind to ALK and block or inhibit cellular proliferation with an $IC_{50}$ in the range of about 100 nM to about 500 nM, about 25 nM to about 200 nM, or about 40 nM to about 160 nM, about 50 nM to about 125 nM, or about 5 nM to about 100 nM. In certain embodiments, antibodies described herein specifically bind to ALK and block or inhibit cellular proliferation of NB-1 cells with an $IC_{50}$ in the range of about 1 nM to about 50 nM, about 5 nM to about 30 nM, or about 9 nM to about 25 nM. In certain embodiments, antibodies described herein specifically bind to ALK and block or inhibit cellular proliferation of NB-1 cells with an $IC_{50}$ of less than about 50 nM, less than about 40 nM, less than about 30 nM, less than about 20 nM, less than about 10 nM, or less than about 5 nM.

In certain aspects, an anti-ALK antibody described herein which can act as an inhibitor of ALK activity (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) can reduce or inhibit survival of cells (e.g., cancer cells), for example, cells that express ALK and that respond to ALK signaling (e.g., cells that proliferate in response to ALK ligand stimulation and ALK signaling). Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes are given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration ($IC_{50}$) is determined by regression analysis of these data.

In certain aspects, an anti-ALK antibody described herein which can act as an activator of ALK activity (e.g., any one of antibodies Ab323, Ab324, Ab325, Ab328, Ab329, or Ab332, or an antigen-binding fragment thereof or an antibody comprising CDRs of any one of antibodies Ab323, Ab324, Ab325, Ab328, Ab329, or Ab332) can increase survival of cells, for example, cells that express ALK and that respond to ALK signaling (e.g., cells that proliferate in response to ALK ligand stimulation and ALK signaling).

In specific embodiments, antibodies described herein (e.g., any one of antibodies Ab321, Ab322, Ab326, Ab327, Ab330, or Ab331, or an antigen-binding fragment thereof or an antibody comprising CDRs of any one of antibodies Ab321, Ab322, Ab326, Ab327, Ab330, or Ab331) specifically bind to ALK and inhibit (e.g., partially inhibit) cell survival by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., trypan blue exclusion assay).

In specific embodiments, antibodies described herein (e.g., any one of antibodies Ab323, Ab324, Ab325, Ab328, Ab329, or Ab332, or an antigen-binding fragment thereof or an antibody comprising CDRs of any one of antibodies Ab323, Ab324, Ab325, Ab328, Ab329, or Ab332) specifically bind to ALK and increase cell survival by at least about 10%, 20%, 30%, 40%, 50%, 60%, 70%, 80%, 90%, 100%, 150%, 200%, 250%, 300%, 400%, or 500% as assessed by methods described herein or known to one of skill in the art (e.g., trypan blue exclusion assay).

Cells and cell lines which are appropriate for use in the assays described herein relating to ALK activity are readily available (e.g., ATCC) or can be readily identified using methods known in the art. For example, cells and/or cell lines that express ALK endogenously or that possess ALK signaling or activity are known to one of skill in the art. In certain embodiments, cells or cell lines that are appropriate for use in the assays described herein can express ALK, either endogenously or recombinantly. In particular embodiments, cells or cell lines for use in cell proliferation assays can express ALK, endogenously or recombinantly, and proliferate or increase proliferation in response to ALK ligand stimulation. Cells or cell lines for use in cell viability assays can express ALK, endogenously or recombinantly, and exert changes in cell viability in response to ALK ligand stimulation. Cells or cell lines for use in apoptosis assays can express ALK, endogenously or recombinantly, and exert changes in apoptosis in response to ALK ligand stimulation. Cells or cell lines for use in cell proliferation, cell viability, or other assays can express ALK, endogenously or recombinantly, and exert changes in proliferation or activation of other cell types response to ALK ligand stimulation.

Non-limiting examples of cells that can be used in the methods and assays described herein include NB-1 cells, SKNSH cells, SNKDZ cells, and IMR32 cells. Non-limiting examples of cells that can be used in the methods and assays described herein to assess ligand independent ALK signaling and activity include NB-1 cells, SKNSH cells, SNKDZ cells, and IMR32 cells. In specific embodiments, cells that can be used in the methods and assays described herein to assess ligand-independent ALK activity include ALK amplified cells such as ALK amplified tumor cells or cells expressing mutant ALK, for example a constitutively active mutant ALK. Non-limiting examples of cells that can be used in the methods and assays described herein to assess ligand dependent ALK signaling and activity include NB-1 cells, SKNSH cells, SNKDZ cells, and IMR32 cells. In specific embodiments, cells that can be used in the methods and assays described herein to assess ligand-dependent ALK activity include cells expressing wild-type ALK, for example tumor cells expressing wild-type ALK, or cells (e.g., tumor cells) expressing normal levels of ALK, e.g., cells that do not contain ALK amplification.

Alternatively, cells and cell lines that express ALK, e.g., human ALK, can routinely be generated recombinantly. Non-limiting examples of cells that can be engineered to express ALK recombinantly include COS cells, HEK 293 cells, CHO cells, H1299 cells, fibroblasts (e.g., human fibroblasts) such as NIH3T3 cells, and MEFS. In a specific embodiment, cells for use in the methods described herein are H1299 cells expressing human ALK ECD (e.g., amino acid residues 21-1038 of SEQ ID NO: 467).

In certain aspects, an anti-ALK antibody described herein, which can act as an inhibitor of ALK activity (e.g., any one of antibodies Ab320-Ab332 and Ab351-Ab446, or an antigen-binding fragment thereof or an antibody comprising CDRs of any one of antibodies Ab320-Ab332 and Ab351-Ab446), is capable of inhibiting or reducing metastasis, inhibiting tumor growth or inducing tumor regression in mouse model studies. For example, tumor cell lines can be introduced into nude mice, and the mice can be administered anti-ALK antibodies described herein one or more times, and tumor progression of the injected tumor cells can be monitored over a period of weeks and/or months. In some cases, administration of anti-ALK antibodies to the nude mice can occur prior to introduction of the tumor cell lines. Any appropriate tumor cell line (e.g., tumor cell line expressing ALK) can be used in the mouse xenograft models described herein.

In specific embodiments, antibodies described herein (e.g., any one of antibodies Ab320-Ab332 and Ab351-Ab446, or an antigen-binding fragment thereof or an antibody comprising CDRs of any one of antibodies Ab320-Ab332 and Ab351-Ab446) specifically bind to ALK and inhibit tumor growth or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art. In specific embodiments, antibodies described herein (e.g., any one of antibodies Ab320-Ab332 and Ab351-Ab446 or an antigen-binding fragment thereof, or an antibody comprising CDRs of any one of antibodies Ab320-Ab332 and Ab351-Ab446) specifically bind to ALK and inhibit tumor growth or induce tumor regression in a mouse model by at least about 25% or 35%, optionally to about 75%, as assessed by methods described herein or known to one of skill in the art. In specific embodiments, antibodies described herein specifically bind to ALK and inhibit tumor growth or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art.

Determining tumor growth inhibition or tumor regression can be assessed, for example, by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain aspects, anti-ALK antibodies described herein bind specifically to ALK antigen and can increase survival of animals in tumor xenograft models. In specific embodiments, antibodies described herein (e.g., any one of antibodies Ab320-Ab332 and Ab351-Ab446 or an antigen-binding fragment thereof, or an antibody comprising CDRs of any one of antibodies Ab320-Ab332 and Ab351-Ab446) specifically bind to ALK and increase survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art. In specific embodiments, antibodies described herein (e.g., any one of antibodies Ab320-Ab332 and Ab351-

Ab446 or an antigen-binding fragment thereof, or an antibody comprising CDRs of any one of antibodies Ab320-Ab332 and Ab351-Ab446) specifically bind to ALK and increase survival of mice in tumor xenograft models by at least about 25% or 35%, optionally to about 75%, as assessed by methods described herein or known to one of skill in the art. In specific embodiments, antibodies described herein specifically bind to ALK and increase survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art.

In some embodiments, provided herein are antibodies (e.g., monoclonal antibodies such as chimeric or humanized antibodies), or antigen-binding fragments thereof, which immunospecifically binds to an ECD of human ALK, for example, an antibody comprising CDRs of any one of antibodies Ab320-Ab332 and Ab351-Ab446, for example as set forth in Tables 1, 2, 5, 6, 9, and 10, linked, for example conjugated or fused, to an agent, e.g., a diagnostic, detectable or therapeutic agent, for example, a polypeptide or small molecule. In specific embodiments, the antibody or antigen-binding fragment are conjugated or fused directly to the agent, or are conjugated or fused to the agent via one or more linkers. In particular embodiments, a linker is an enzyme-cleavable linker and/or a disulfide linker.

In particular embodiments, antibodies and antigen-binding fragments thereof can be linked to detectable molecules or substances including, but not limited to, various enzymes, prosthetic groups (such as, but not limited to, streptavidin/biotin and avidin/biotin), fluorescent molecules, bioluminescent molecules, radioactive molecules, such as radioisotopes, quantum dots, or other nanoparticles, and positron emitting metals using various positron emission tomographies, and non-radioactive paramagnetic metal ions. In other particular embodiments, antibodies, or antigen-binding fragments thereof, can be linked to a therapeutic agent, such as a cytotoxin, e.g., a cytostatic or cytocidal agent, or a radioactive metal ion, e.g., alpha-emitters. For example, a cytotoxin or cytotoxic agent includes any agent that is detrimental to cells.

In yet other embodiments, antibodies or antigen-binding fragments described herein can be fused to agents, such as peptides, to facilitate purification. For example, such a peptide can be a hexa-histidine peptide, such as the tag provided in a pQE vector (QIAGEN, Inc.), among others, many of which are commercially available. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating agents, including polypeptides, to antibodies are well known, see, e.g., Arnon et al., in Monoclonal Antibodies And Cancer Therapy, Reisfeld et al. (eds.), pp. 243-56 (Alan R. Liss, Inc. 1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Ashkenazi et al., Proc. Natl. Acad. Sci. USA, 88: 10535-10539, 1991; and Zheng et al., J. Immunol., 154:5590-5600, 1995.

Antibodies and antigen-binding fragments described herein can also be attached to solid supports. Such solid supports can include, but are not limited to, glass, cellulose, polyacrylamide, nylon, polystyrene, polyvinyl chloride or polypropylene. Such attachment can be useful, for example, for immunoassays or purification of the target antigen.

5.2 Antibody Production

Antibodies or an antigen-binding fragments described herein that immunospecifically bind to ALK (e.g., ECD of human ALK) can be produced by any method known in the art, for example, by chemical synthesis or by recombinant expression techniques. Such methods can employ conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Monoclonal antibodies can, for example, be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology. For example, monoclonal antibodies can be produced recombinantly from host cells engineered to express an antibody described herein (e.g., anti-ALK antibody comprising the CDRs of any one of antibodies Ab320-Ab332 and Ab351-Ab446) or a fragment thereof, for example, a light chain and/or heavy chain of such an antibody.

Further, the antibodies described herein or antigen-binding fragments thereof can also be generated using various phage display methods known in the art. In phage display methods, functional antibody domains are displayed on the surface of phage particles which carry the polynucleotide sequences encoding them. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

Antibodies described herein can, for example, include chimeric antibodies. A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

Antibodies or antigen-binding fragments produced using techniques such as those described herein can be isolated using standard, well known techniques. For example, antibodies or antigen-binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography. As used herein, an "isolated" or "purified" antibody is substantially free of cellular material or other proteins from the cell or tissue source from which the antibody is derived, or substantially free of chemical precursors or other chemicals when chemically synthesized.

Antibody fragments which recognize specific ALK antigens (e.g., ECD of ALK) and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region. Alternatively, antibody fragments described herein can routinely be produced via well known recombinant expression techniques. See, e.g., PCT publication No. WO 92/22324; Mullinax et al., 1992, BioTechniques 12(6):864-869; Sawai et al., 1995, AJRI 34:26-34; and Better et al., 1988, Science 240:1041-1043.

Antibodies described herein can, for example, include humanized antibodies, e.g., deimmunized or composite human antibodies. Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8): 1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

A composite human antibody can be generated using, for example, Composite Human Antibody™ technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody. Such antibodies can comprise human constant region sequences, e.g., human light chain and/or heavy chain constant regions.

A deimmunized antibody is an antibody in which T-cell epitopes have been removed. Methods for making deimmunized antibodies have been described. See, e.g., Jones et al., Methods Mol Biol. 2009; 525:405-23, xiv, and De Groot et al., Cell. Immunol. 244:148-153(2006)). Deimmunized antibodies comprise T-cell epitope-depleted variable regions and human constant regions. Briefly, VH and VL of an antibody are cloned and T-cell epitopes are subsequently identified by testing overlapping peptides derived from the VH and VL of the antibody in a T cell proliferation assay. T cell epitopes are identified via in silico methods to identify peptide binding to human MHC class II. Mutations are introduced in the VH and VL to abrogate binding to human MHC lass II. Mutated VH and VL are then utilized to generate the deimmunized antibody.

Antibodies described herein can, for example, be multispecific, e.g., bispecific, antibodies. Methods for making multispecific (e.g, bispecific antibodies) have been described, see, for example, U.S. Pat. Nos. 7,951,917, 7,183,076, 8,227,577, 5,837,242, 5,989,830, 5,869,620, 6,132,992, and 8,586,713.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Human antibodies can be produced using any method known in the art. For example, well known transgenic mice which are incapable of expressing functional endogenous murine immunoglobulins, but which can express human immunoglobulin genes, can be used. Alternatively, for example, phage display techniques, described above, can be utilized. Moreover, in some embodiments, human antibodies can, for example, be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., ECD of human ALK). Such methods are known and are described in the art, see, e.g., Shinmoto et al., Cytotechnology, 2004, 46:19-23; Naganawa et al., Human Antibodies, 2005, 14:27-31.

5.2.1 Polynucleotides, Cells and Vectors

In certain aspects, provided herein are polynucleotides comprising a nucleotide sequence encoding an antibody described herein or an antigen-binding fragment thereof (e.g., a variable light chain region and/or variable heavy chain region) that immunospecifically binds to an ALK antigen, and vectors, e.g., vectors comprising such polynucleotides for recombinant expression in host cells (e.g., *E. coli* and mammalian cells). In certain aspects, provided herein are cells (e.g., host cells) that express such antibodies or antigen-binding fragments. Also provided herein are methods of making the antibodies and antigen-binding fragments described herein.

In certain aspects, provided herein are polynucleotides comprising a nucleotide sequence encoding the light chain or heavy chain of an antibody described herein. In certain embodiments, provided herein are polynucleotides comprising a nucleotide sequence encoding the light chain and heavy chain of an antibody described herein. The polynucleotides can comprise nucleotide sequences encoding a light chain comprising the VL FRs and CDRs of antibodies described herein (see, e.g., Tables 3, 7, and 1, and Tables 1, 5, and 9, respectively). The polynucleotides can comprise nucleotide sequences encoding a heavy chain comprising the VH FRs and CDRs of antibodies described herein (see, e.g., Tables 4, 8, and 12, and Tables 2, 6, and 10, respectively). In specific embodiments, a polynucleotide described herein encodes a VL chain region comprising the amino acid sequence of SEQ ID NO: 395, 397, 399, 401, 403, 405, 407, 409, 411, 413, 415, 417, or 419. In specific embodiments, a polynucleotide described herein encodes a VH chain region comprising the amino acid sequence of any one of SEQ ID NOs: 396, 398, 400, 402, 404, 406, 408, 410, 412, 414, 416, 418, or 420.

In particular embodiments, provided herein are polynucleotides comprising a nucleotide sequence encoding an anti-ALK antibody comprising three VL chain CDRs, e.g., containing VL CDR1, VL CDR2, and VL CDR3 of any one of antibodies Ab320-Ab332 and Ab351-Ab446 (e.g., see Tables 1, 5, and 9). In specific embodiments, provided herein are polynucleotides comprising three VH chain CDRs, e.g., containing VH CDR1, VH CDR2, and VH CDR3 of any one of antibodies Ab320-Ab332 and Ab351-Ab446 (e.g., see Tables 2, 6, and 10). In specific embodiments, provided herein are polynucleotides comprising a nucleotide sequence encoding an anti-ALK antibody comprising three VH chain CDRs, e.g., containing VL CDR1, VL CDR2, and VL CDR3 of any one of antibodies Ab320-Ab332 and Ab351-Ab446 (e.g., see Tables 1, 5, and 9) and three VH chain CDRs, e.g., containing VH CDR1, VH CDR2, and VH CDR3 of any one of antibodies Ab320-Ab332 and Ab351-Ab446 (e.g., see Tables 2, 6, and 10).

In particular embodiments, provided herein are polynucleotides comprising a nucleotide sequence encoding an anti-ALK antibody comprising a VL chain region, e.g., containing FR1-CDR1-FR2-CDR2-FR3-CDR3-FR4, comprising an amino acid sequences described herein (e.g., see Tables 1, 5, and 9, or Table 3, 7, and 11). In specific embodiments, provided herein are polynucleotides comprising a nucleotide sequence encoding an anti-ALK antibody comprising a VH chain region, e.g., containing FR1-CDR1-FR2-CDR2-FR3-CDR3-FR4, comprising an amino acid sequence described herein (e.g., see Tables 2, 6, and 10, or Table 4, 8, and 12).

In certain embodiments, a polynucleotide described herein comprises a nucleotide sequence encoding an antibody provided herein comprising a variable light (VL) chain region comprising an amino acid described herein (e.g., see Table 13), wherein the antibody immunospecifically binds to an ALK polypeptide, e.g., a human ALK polypeptide, for example, an ECD of ALK (e.g., human ALK), for example amino acid residues 21-1038 of SEQ ID NO: 467.

In certain embodiments, a polynucleotide described herein comprises a nucleotide sequence encoding an antibody provided herein comprising a variable heavy (VH) chain region comprising an amino acid sequence described herein (e.g., see Table 14), wherein the antibody immunospecifically binds to an ALK polypeptide, e.g., a human ALK polypeptide, for example, an ECD of ALK (e.g., human ALK), for example amino acid residues 21-1038 of SEQ ID NO: 467.

In certain aspects, a polynucleotide comprises a nucleotide sequence encoding an antibody described herein comprising a VL chain region comprising one or more VL FRs having the amino acid sequence described herein (e.g., see Table 3), wherein the antibody immunospecifically binds to an ALK polypeptide, e.g., a human ALK polypeptide, for example, an ECD of ALK (e.g., human ALK), for example amino acid residues 21-1038 of SEQ ID NO: 467. In certain aspects, a polynucleotide comprises a nucleotide sequence encoding an antibody described herein comprising a VH chain region comprising one or more VH FRs having the amino acid sequence described herein (e.g., see Table 4), wherein the antibody immunospecifically binds to an ALK polypeptide, e.g., a human ALK polypeptide, for example, an ECD of ALK (e.g., human ALK), for example amino acid residues 21-1038 of SEQ ID NO: 467. In certain aspects, a polynucleotide comprises a nucleotide sequence encoding an antibody described herein comprising a VL chain region comprising one or more VL FRs having the amino acid sequence described herein (e.g., see Table 3), and a VH chain region comprising one or more VH FRs having the amino acid sequence described herein (e.g., see Table 4), wherein the antibody immunospecifically binds to an ALK polypeptide, e.g., a human ALK polypeptide, for example, an ECD of ALK (e.g., human ALK), for example amino acid residues 21-1038 of SEQ ID NO: 467.

In specific embodiments, a polynucleotide provided herein comprises a nucleotide sequence encoding an antibody described herein comprising: framework regions (e.g., framework regions of the VL domain and VH domain) that are human framework regions, wherein the antibody immunospecifically binds an ALK polypeptide, e.g., a human ALK polypeptide, for example, an ECD of ALK (e.g., human ALK), for example amino acid residues 21-1038 of SEQ ID NO: 467.

In a certain embodiment, a polynucleotide provided herein comprises a nucleotide sequence as described in Table 16 or 17, encoding a VH or a VL, respectively, of an antibody described herein (e.g., Ab320-Ab332 and Ab351-Ab446), which immunospecifically binds to an ALK polypeptide, e.g., a human ALK polypeptide, for example, an ECD of ALK (e.g., human ALK), for example amino acid residues 21-1038 of SEQ ID NO: 467.

TABLE 16

VL Nucleic Acid Sequences

NUCLEOTIDE SEQUENCES

| | |
|---|---|
| Ab320 VL | GACATCCAGATGACTCAGTCTCCAGCCTCCCTGGCTGCATCTGTGGGAGAAACTGTCACCA TCACATGTCGAGCAAGTGAGAACATTTACTACAGTTTAGCATGGTATCAGCAGAAGCAAG |

TABLE 16-continued

VL Nucleic Acid Sequences

| | NUCLEOTIDE SEQUENCES |
|---|---|
| SEQ ID NO: 441 | GGAAATCTCCTCAGCTCCTGATCTATAATGCAAACAGCTTGGAAGATGGTGTCCCATCGAG GTTCAGTGGCAGTGGATCTGGGACACAGTATTCTATGAAGATCAACAGCATGCAGCCTGA AGATACCGCAACTTATTTCTGTAAACAGGCTTATGACGTTCCATTCACGTTCGGCTCGGGG ACAAAGTTGGAAATAAAACGG |
| Ab321 VL SEQ ID NO: 443 | GCTATCCAGATGACACAGACTACATCCTCCCTGTCTGCCTCTCTGGGAGACAGAGTCACCA TCAGTTGCAGTGTAAGTCAGGGCATTAGCAATTCTTTAAACTGGTATCAGCAGAAACCAGA TGGAACTGTTAAACTCCTGATCTATTACACATCAAGTTTACACTCAGGAGTCCCATCAAGG TTCAGTGGCAGTGGGTCTGGGACAGATTATTCTCACCATCAGCAACCTGGAACCTGAAG ATATTGCCACTTACTATTGTCAGCAGTATAGTAAGCTTCCGCTCACGTTCGGTGCTGGGAC CAAGCTGGAGCTGAAACGG |
| Ab322 VL SEQ ID NO: 445 | GACATTGTGATGACCCAGTCTCAAAGATTCATGTCCACATCAGTAGGAGACAGGGTCAGC GTCACCTGCAAGGCCAGTCAGAATGTGGGTACTAATGTAGCCTGGTATCAACAGAAACCA GGGCAATCTCCTAAAGCACTGATTTACTCGGCATCCTACCGGTACAGTGGAGTCCCTGATC GCTTCACAGGCAGTGGATCTGGGACAGATTTCACTCTCACCGTCAGCAATGTGCAGTCTGA AGACTTGGCAGAGTATTTCTGTCAGCAATATAACAGCTATCCGTACATGTACACGTTCGGA GGGGGGACCAAGCTGGAAATAAAACGG |
| Ab323 VL SEQ ID NO: 447 | GACATTGTGATGACCCAGTCTCACAAATTCATGTCCACATCAGTAGGAGACAGGGTCAGC ATCACCTGCAAGGCCAGTCAGGATGTGAGTACTGCTGTAGCCTGGTATCAACAAAAACCA GGGCAATCTCCCAAACCACTGATTTACTGGGCATCCACCCGGCACACTGGAGTCCCTGATC GCTTCACAGGCAGTGGATCTGGGACAGATTATACTCTCACCATCAGCAGTGTGCAGACTGA AGACCTGGCACTTTATTACTGTCAGCAACATTATAGCACTCCTCGGACGTTCGGTGGAGGC ACCAAGCTGGAAATCAAACGG |
| Ab324 VL SEQ ID NO: 449 | GACATTGTGCTGACCCAATCTCCAGCTTCTTTGGCTGTGTCTCTAGGGCAGAGGGCCACCA TCTCCTGCAGAGCCAGCGAAAGTGTTGATAATTATGGCATTAGTTTTATGAACTGGTTCCA ACAGAAACCAGGACAGCCACCCAAACTCCTCATCTATGCTGCATCCAACCAAGGATCCGG GGTCCCTGCCAGGTTTAGTGGCAGTGGGTCTGGGACAGACTTCAGCCTCAACATCCATCCT ATGGAGGAGGATGATACTGCAATGTATTTCTGTCAGCAAAGTAAGGAGGTTCCGTGGACG TTCGGTGGAGGCACCAAGCTGGAAATCAAACGG |
| Ab325 VL SEQ ID NO: 451 | GATATCCAGATGACACAGACTACATCCTCCCTGTCTGCCTCTCTGGGAGACAGAGTCACCA TCAGTTGCAGGGCAAGTCAGGACATTAGCAATTATTTAAACTGGTATCAGCAGAAACCAG ATGGAACTGTTAAACTCCTGATCTACTACACATCAAGATTACACTCAGGAGTCCCATCAAG GTTCAGTGGCAGTGGGTCTGGAACAGATTATTCTCTCACCATTAGCAACCTGGAGCAAGAA GATATTGCCACTTACTTTTGCCAACAGGGTAATACGCTTCCTCGGACGTTCGGTGGAGGCA CCAAGCTGGAAATCAAACGG |
| Ab326 VL SEQ ID NO: 453 | GACATTGTGATGACCCAGTCTCAAAGATTCATGTCCACATCAGTAGGAGACAGGGTCAGC GTCACCTGCAAGGCCAGTCAGAATGTGGGTACTAATGTAGCCTGGTATCAACAGAAACCA GGGCAATCTCCTAAAGCACTGATTTACTCGGCATCCTACCGGTACAGTGGAGTCCCTGATC GCTTCACAGGCAGTGGATCTGGGACAGATTTCACTCTCACCATCAGCAATGTGCAGTCTGA AGACTTGGCAGAGTATTTCTGTCAACAATATAACAGCTATCCGTACATGTACACGTTCGGA GGGGGGACCAAGCTGGAAATAAAACGG |
| Ab327 VL SEQ ID NO: 455 | GACATTGTGATGACCCAGTCTCAAAAATTCATGTCCACATCAGTAGGAGACAGGGTCAGC ATCACCTGTAAGGCCAGTCAGAATGTGGGTACTGCTGTAGCCTGGTATCAACTGAAACCA GGACAATCTCCTAAACTACTGATTTACTCGGCATCCAATCGGTTCACTGGAGTCCCTGATC GCTTCACAGGCAGTGGATCTGGGACAGATTTCACTCTCACCATCAGCAATATGCAGTCTGA AGACCTGGCAGATTATTTCTGCCAGCAATATAGCAGCTATCCTCTCACGTTCGGCTCGGGG ACAAAGTTGGAAATAAAACGG |
| Ab328 VL SEQ ID NO: 457 | GACATTGTGATGACCCAGTCTCAAAAATTCATGTCCACATCAGTAGGAGACAGGGTCAGC GTCACCTGCAAGGCCAGTCAGAATGTGGGTACTAATGTAGCCTGGTATCAACAGAAACCA GGGCACTCTCCTAAAGCACTGATTTACTCGGCATCCTACCGGTACAGTGGAGTCCCTGATC GCTTCACAGGCAGTGGATCTGGGACAGATTTCACTCTCACCATCAGCAATGTGCAGTCTGA AGACTTGGCAGAGTATTTCTGTCAGCGATATAACAGCTATCCGTACATGTTCACGTTCGGA GGGGGGACCAAGCTGGAAATAAAACGG |
| Ab329 VL SEQ ID NO: 459 | GACATCCAGATGCACAGTCTCCTGCCTCCCTGTCTGCATCTCTGGAAGAAATTGTCACCA TCACATGCCAGGCAAGCCAGGACATTGATAATTACTTATCGGTATCAGCAGAAACCAG GGAAATCTCCTCACCTCCTGATCCACAGTGCAACCAGCTTGGCAGATGGGGTCCCATCAAG GTTCAGCGGCGGTAGATCTGGCACACAGTTTTCTCTTAAGATCAACAGACTACAGGTTGAA GATACTGGGATCTATTACTGTCTACAACATTATAGTGGTTGGACGTTCGGTGGAGGCACCA AGTTGGAGTTGAAACGG |
| Ab330 VL SEQ ID NO: 461 | GACATCCAGATGACCCAGTCTCCATCCTCCATGTCTGCATCTCTGGGAGACAGAGTCACTA TTACTTGCCAGGCAAGTCAGGACATTGGGAATTATTTAATCTGGTTTCAACAGAAACCAGG GAAGTCTCCTAGGCCTCTGATTTATATGCAACCAACTTGGCAAATGGGGTCCCATCAAGG TTCAGTGGCAGTAGGTCTGGCTCAGAATATTCTCTGACCATTACCAGCCTGGAGTCTGAAG ATATGGCAGACTATCACTGTCTACAATATAAACAGCATCTCACGTTCGGCTCAGGGACGAA GTTGGAGATAGAACGG |

TABLE 16-continued

VL Nucleic Acid Sequences

NUCLEOTIDE SEQUENCES

Ab331 VL SEQ ID NO: 463
```
GACATCCAGATGACCCAGTCTCCATCCTCCATGTCTGCATCTCTGGGAGACAGAATCACTA
TTACTTGCCAGGCAAGTCAGGACATTGGGAATTATTTAATCTGGTTTCAACAGAAACCAGG
GAAGTCTCCTAGGCCTCTGATTTATTATGCAACCAACTTGGCAAATGGGGTCCCATCAAGG
TTCAGTGGCAGTAGGTCTGGCTCAGAATATTCTCTGACCATTACCAGCCTGGAGTCTGAAG
ATATGGCAGACTATCACTGTCTACAATATAAACAGCATCTCACGTTCGGCTCAGGGACGAA
GTTGGAGATAGAACGG
```

Ab332 VL SEQ ID NO: 465
```
GAGGTCCAGCTGCAACAATCTGGACCTGAGCTGGTGAAGCCTGGGACTTCAGTGAAGATA
TCCTGTAAGGCTTCTGGATACACGTTCACTGACTACTACATGAACTGGATGAAGCAGAGCC
ATGGAAAGAGCCTTGAGTGGATTGGAGATATTAATCCTAACAATGGTGTTACTAGCTACA
ACCAGAAGTTCAAGGGCAAGGCCACATTGACTGTAGACAAGTCCTCCAGCACAGCCTACA
TGGAGCTCCGCAGCCTGACATCTGAGGACTCTGCAGTCTATTACTGTGCAAGAGAGGACTA
CGGTAGTAACTACTTTGACTACTGGGGCCAAGGCACCACTCTCACAGTCTCCTCAG
```

TABLE 17

VH Nucleic Acid Sequences

NUCLEOTIDE SEQUENCES

Ab320 VH SEQ ID NO: 442
```
CAGGTTCAGCTGCAGCAGTCTGGGGCTGAGCTGGTGAAGCCTGGGGCCTCAGTGAAGATT
TCCTGCAAAGCTTCTGGCTACGCATTCAGTAGCTACTGGATGAACTGGGTGAAGCAGAGG
CCTGGAAAGGGTCTTGAGTGGATTGGACAGATTTATCCTGGAGATGGTGATACTAACTACA
ACGGAAAGTTCAAGGGCAAGGCCACACTGACTGCAGACAAATCCTCCAGCACAGCCTACA
TGCAGCTCAGCAGCCTGACCTCTGAGGACTCTGCGGTCTATTTCTGTGCCTCTTATTACTAC
GGTAGTAAGGCTTACTGGGGCCAAGGGACTCTGGTCACTGTCTCTGCA
```

Ab321 VH SEQ ID NO: 444
```
CAGGTCCAACTGCAGCAGCCTGGGGCTGAGTTTGTGAAGCCTGGGGCTTCAGTGAAGCTG
TCCTGCAAGGCTTCTGGCTACACCTTCACCAGCTACTGGATGCACTGGGTGAAGCAGAGGC
CTGGACGAGGCCTTGAGTGGATTGGAAGGATTGATCCTAATAGTGGTGGTACTAAGTACA
ATGAGAAGTTCAAGAGCAAGGCCACACTGACTGTAGACAAACCCTCCAGCACAGCCTACA
TGCAGCTCAGCAGCCTGACATCTGAGGACTCTGCGGTCTATTATTGTGCAAGAGATTACTA
CGGTAGTAGCTACCGGTTTGCTTACTGGGGCCAAGGGACTCTGGTCACTGTCTCTGCA
```

Ab322 VH SEQ ID NO: 446
```
CAGGTCCAGCTGCAGCAGTCTGGGGCTGAACTGGCAAAACCTGGGGCCTCAGTGAAGCTG
TCCTGCAAGGCTTCTGGCTACACCTTTACTAACTACTGGATGCACTGGGTAAAACAGAGGC
CTGGACAGGGTCTGGAATGGATTGGATACATTAATCCTAGCAGTGGTTATACTAAGTACAA
TCAGAAGTTCAAGGACAAGGCCACATTGACTGCAGACAAATCCTCCAGCACAGCCTACAT
GCAGCTGAGCAGCCTGACATATGAGGACTCTGCAGTCTATTACTGTGCAAGAGATTACTAC
GGTAGTAGCTCCTGGTTTGCTTACTGGGGCCAAGGGACTCTGGTCACTGTCTCTGCA
```

Ab323 VH SEQ ID NO: 448
```
CAGGTTCAGCTGCAGCAGTCTGGGGCTGAGCTGGTGAAGCCTGGGGCCTCAGTGAAGATT
TCCTGCAAAACTTCTGGCTACACATTCAGCAACTACTGGATGAACTGGGTGAAGCAGAGG
CCTGGAAAGGGTCTTGAGTGGATTGGACAGATTTTTCCTGGAGATGCTGATGCTAACTACA
ACGGAAAGTTCAAGGGCAAGGCCACACTGACTGCAGACAAATCCTCCAGCGCAGCCTTCA
TGCAGCTCAGCAGCCTGACCTCTGAGGACTCTGCGGTCTATTTCTGTGCAAGATTAGTTA
CGACGGGGCGTTTGCTTACTGGGGCCAAGGGACTCTGGTCACTGTCTCTGCA
```

Ab324 VH SEQ ID NO: 450
```
CAGGTTCAGCTGCAACAGTCTGGGGCTGAGCTGGTGAAGCCTGGGGCCTCAGTGAAGATT
TCCTGCAAAGCTTCTGGCTACGCATTCAGTAGCTACTGGGTGAACTGGGTGAAGCAGAGG
CCTGGAAAGGGTCTTGAGTGGATTGGACAGATTTATCCTGGAGATGGTGATACTAACTACA
ACGGAAAGTTCAAGGGCAAGGCCACACTGACTGCAGACAAATCCTCCAGCACAGCCTACA
TGCAGCTCAGCAGCCTGACCTCTGAGGACTCTGCGGTCTATTTCTGTGCAAGATCAAGAGG
GTATTTCTACGGTAGTACCTACGACTCCTGGGGCCAAGGCACCACTCTCACAGTCTCCTCA
```

Ab325 VH SEQ ID NO: 452
```
CAGGTTCAGCTGCAGCAGTCTGGGGCTGAGCTGGTGAAGCCTGGGGCCTCAGTGAAGATT
TCCTGCAAAGCTTCTGGCTACGCATTCAGTAGCTACTGGATGAACTGGGTGAAGCAGAGG
CCTGGAAAGGGTCTTGAGTGGATTGGACAGATTTATCCTGGAGATGGTGATACTAACTACA
ACGGAAAGTTCAAGGGCAAGGCCACACTGACTGCAGACAAATCCTCCAGCACAGCCTACA
TGCAGCTCAGCAGCCTGACCTCTGAGGACTCTGCGGTCTATTTCTGTGCAAGATGGTACTA
CGGTAGTTACTATGCTATGGACTACTGGGGTCAAGGAACCTCAGTCACCGTCTCCTCA
```

Ab326 VH SEQ ID NO: 454
```
CAGGTCCAGCTGCAGCAGTCTGGGGCTGAACTGGCAAAACCTGGGGCCTCAGTGAAGCTG
TCCTGCAAGGCTTCTGGCTACACCTTTACTAGCTACTGGATGCACTGGGTAAAACAGAGGC
CTGGACAGGGTCTGGAATGGATTGGATACATTAAGCCTAGCAGTGGTTATACTAAGTACA
ATCAGAAGTTCAAGGACAAGGCCACATTGACTGCAGACAAATCCTCCAGCACAGCCTACA
TGCAGCTGAGCAGCCTGACATATGAGGACTCTGCAGTCTATTACTGTGCAAGAGATTACTA
CGGTAGTAGCTCCTGGTTTGCTTACTGGGGCCAAGGGACTCTGGTCACTGTCTCTGCA
```

TABLE 17-continued

VH Nucleic Acid Sequences

NUCLEOTIDE SEQUENCES

Ab327 VH SEQ ID NO: 456
```
GACGTGAAGCTGGTGGAGTCTGGGGAAGGCTTAGTGAAGCCTGGAGGGTCCCTGAAACTC
TCCTGTGCAGCCTCTGGATTCACTTTCAGTAGCTATGCCATGTCTTGGGTTCGCCAGACTCC
AGAGAAGAGGCTGGAGTGGGTCACATACATTAGTAGTGGTGGTGATTACATCTACTATGC
AGACACTGTGAAGGGCCGATTCACCATCTCCAGAGACAATGCCAGGAACACCCTGTACCT
GCAAATGAGCAGTCTGAAGTCTGAGGACACAGCCATGTATTACTGTACAAGAGAGCGGAT
ATGGTTACGACGGTTCTTCGATGTCTGGGGCACAGGGACCACGGTCACCGTCTCCTCA
```

Ab328 VH SEQ ID NO: 458
```
CAGGTCCAGCTGCAGCAGTCTGGGGCTGAACTGGCAAAACCTGGGGCCTCAGTGAAGCTG
TCCTGCAAGGCTTCTGGCTACACCTTTACTAGCTACTGGATGCACTGGGTAAAACAGAGGC
CTGGACAGGGTCTGGAATGGATTGGATACATTAATCCTAGCAGTGGTTATACTAAGTACAA
TCAGAAGTTCAAGGACAAGGCCACATTGACTGCAGACAAATCCTCCAGCACAGCCTACAT
GCAGCTGAGCAGCCTGACATTTGAGGACTCTGCAGTCTATTACTGTGCAAGAGATTACTAC
GGTAGTAGCTCCTGGTTTGCTTACTGGGGCCAAGGGACTCTGGTCACTGTCTCTGCA
```

Ab329 VH SEQ ID NO: 460
```
CAGGTGCAGCTGAAGGAGTCAGGACCTGGCCTGGTGAAGCCCTCAGCGACCCTGTCTCTC
ACCTGCACTGTCTCTGGGTTCTCATTAACCAGTTATCATGTGTGCTGGATTCGACAGACTCC
AGGAAAGGGTCTGGAGTGGATGGGAGTAATATGGGGTGATGGAAGGACAACATATAATC
CACCTCTCAAATCCCGACTGAGCATCAGCAGGGACACCTCCAAGAGCCAAGTTTTCTTAAA
AATGAGCAGTCTGAAAACTGAAGACACAGCCACCTATTACTGTGCCAGAGCGACTATGAC
GGGCCACGGGGATGCCTGGGGTCAAGGAGCCTCAGTCACTGTCTCCTCA
```

Ab330 VH SEQ ID NO: 462
```
GAGGTACAGGTCGTGGAAACAGGGGGAGGCGTGGTGCAGCCTGGGAAATCTCTTGAAATC
ACCTGTGCCACGTCAGGATTGACCTTCAGTACGGCCTGGATGTACTGGGTTCGCCAGTCTT
CAGATAGGCGACTAGAGTGGATTGCTCGAATTAAAGACAAATCTAACAAGTTTGCATCCG
ACTATGTGGAATCTGTGAGAGGAAGATTCACCATCTCAAGAGATGATTCCAGAAGTTCCGT
TTACTTGCAGATGAACAACTTAAAAGAGGAAGACACTGCCACTTATTACTGTACTACATCT
TATGGATATGCCTGGGGCCAAGGAGTCATGGTCACAGTCTCCTCA
```

Ab331 VH SEQ ID NO: 464
```
GAGGTACAGGTCGTGGAAACAGGGGGAGGCGTGGTGCAGCCTGGGAAATCTCTTGAGATC
ACCTGTGCCACGTCAGGATTGACCTTCAGTACGGCCTGGATGTACTGGGTTCGCCAGTCTT
CAGATAGGCGACTAGAGTGGATTGCTCGAATTAAAGACAAATCTAACAATTTTGCATCCG
ACTATGTGGAATCTGTGAGAGGAAGATTCACCATCTCAAGAGATGATTCCAGAAGTTCCGT
TTACTTACAGATGAACAACTTAAAAGAGGAAGACACTGCCACTTATTACTGTACTACATCT
TATGGATATGCCTGGGGCCAAGGAGTCATGGTCACAGTCTCCTCA
```

Ab332 VH SEQ ID NO: 466
```
GAGGTCCAGCTGCAACAATCTGGACCTGAGCTGGTGAAGCCTGGGACTTCAGTGAAGATA
TCCTGTAAGGCTTCTGGATACACGTTCACTGACTACTACATGAACTGGATGAAGCAGAGCC
ATGGAAAGAGCCTTGAGTGGATTGGAGATATTAATCCTAACAATGGTGTTACTAGCTACA
ACCAGAAGTTCAAGGGCAAGGCCACATTGACTGTAGACAAGTCCTCCAGCACAGCCTACA
TGGAGCTCCGCAGCCTGACATCTGAGGACTCTGCAGTCTATTACTGTGCAAGAGAGGACTA
CGGTAGTAACTACTTTGACTACTGGGGCCAAGGCACCACTCTCACAGTCTCCTCAG
```

In certain embodiments, a polynucleotide provided herein is linked to a promoter and/or other polynucleotide regulatory element for expression of such polynucleotide sequence in a host cell. In certain embodiments, the promoter is derived from the genome of mammalian cells (e.g., metallothionein promoter) or from mammalian viruses (e.g., the adenovirus late promoter, the vaccinia virus 7.5K promoter). In a specific embodiment, the expression of nucleotide sequences encoding antibodies described herein is regulated by a constitutive promoter, inducible promoter or tissue specific promoter.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody described herein, which immunospecifically binds to an ALK polypeptide, e.g., a human ALK polypeptide, for example, an ECD of ALK (e.g., human ALK), for example amino acid residues 21-1038 of SEQ ID NO: 467, wherein the antibody comprises a light chain, and wherein the amino acid sequence of the VL chain region can comprise any amino acid sequence described herein (e.g., SEQ ID NO: 395, 397, 399, 401, 403, 405, 407, 409, 411, 413, 415, 417, or 419), and wherein the constant region of the light chain comprises the amino acid sequence of a human kappa light chain constant region. In another particular embodiment, a polynucleotide provided herein comprises a nucleotide sequence encoding an antibody described herein, which immunospecifically binds to an ALK polypeptide, e.g., a human ALK polypeptide, for example, an ECD of ALK (e.g., human ALK), for example amino acid residues 21-1038 of SEQ ID NO: 467, and comprises a light chain, wherein the amino acid sequence of the VL chain region can comprises any amino acid sequence described herein (e.g., SEQ ID NO: 395, 397, 399, 401, 403, 405, 407, 409, 411, 413, 415, 417, or 419), and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to an ALK polypeptide, e.g., a human ALK polypeptide, for example, an ECD of ALK (e.g., human ALK), for example amino acid residues 21-1038 of SEQ ID NO: 467, wherein the antibody comprises a heavy chain, wherein the amino acid sequence of the VH chain region can comprise any amino acid sequence described herein (e.g., SEQ ID NO: 396, 398, 400, 402, 404, 406, 408, 410, 412, 414, 416, 418, or 420), and wherein the constant region of the heavy chain comprises the amino acid sequence of a human gamma (γ) heavy chain constant region, for example, human gamma (γ) 1 heavy chain constant region, human gamma (γ) 2 heavy chain constant region, human gamma (γ) 3 heavy chain constant region, or human gamma (γ) 4 heavy chain constant region.

In yet another specific embodiment, a polynucleotide provided herein comprises a nucleotide sequence encoding an antibody described herein (or an antigen-binding fragment thereof), which immunospecifically binds an ALK polypeptide, e.g., a human ALK polypeptide, for example, an ECD of ALK (e.g., human ALK), for example amino acid residues 21-1038 of SEQ ID NO: 467, wherein the antibody comprises a VL chain region and a VH chain region comprising any amino acid sequences described herein, and wherein the constant regions comprise the amino acid sequences of the constant regions of a human $IgG_1$ (e.g., isotype a, z, or f), $IgG_2$ (e.g., human $IgG_{2a}$ or human $IgG_{2b}$), or human $IgG_4$.

The polynucleotides described herein can be produced and the nucleotide sequences of the polynucleotides determined, by any method known in the art. Nucleotide sequences encoding antibodies described herein, e.g., antibodies comprising sequences described in Tables 1-14, and, optionally, comprising constant region sequences, for example, human constant region sequences, can be determined using methods well known in the art, e.g., nucleotide codons known to encode particular amino acids can be identified and assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR. Alternatively, a polynucleotide encoding an antibody described herein can be generated from nucleic acid or nucleic acids using methods well known in the art (e.g., PCR and other molecular cloning methods).

In certain aspects, provided herein are cells that express (e.g., recombinantly) antibodies described herein (or an antigen-binding fragment thereof) which specifically bind to an ECD of human ALK. Provided herein are vectors (e.g., expression vectors) comprising polynucleotides comprising nucleotide sequences encoding anti-ALK antibodies or a fragment for recombinant expression in host cells, for example, in mammalian cells. Also provided herein are host cells comprising such vectors for recombinantly expressing anti-ALK antibodies described herein (e.g., human or humanized antibody). In a particular aspect, provided herein are methods for producing an antibody or antigen-binding fragment described herein, comprising expressing such an antibody or fragment from a host cell.

Methods which are well known to those skilled in the art for expressing the antibodies and antigen-binding fragments described herein. For example, methods are well known that can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment described herein, for example, an antibody heavy and/or light chain, heavy and/or light chain variable domain, heavy and/or light chain CDR(s), linked to a promoter for expression of such sequences. Such vectors can, for example, include nucleotide sequences for encoding antibodies and fragments comprising constant regions.

An expression vector can, for example, be transferred to a cell by conventional techniques and the resulting cells can then be cultured by conventional techniques to produce an antibody described herein (e.g., an antibody comprising the CDRs of any one of antibodies Ab320-Ab332 and Ab351-Ab446) or an antigen-binding fragment thereof. Thus, provided herein are host cells containing a polynucleotide encoding an antibody described herein or an antigen-binding fragment thereof linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein (e.g., an antibody comprising the CDRs of any one of antibodies Ab320-Ab332 and Ab351-Ab446), or a fragment thereof. In specific embodiments, a host cell contains two different vectors, a first vector comprising a polynucleotide encoding a heavy chain or a heavy chain variable region of an antibody described herein (e.g., an antibody comprising the CDRs of any one of antibodies Ab320-Ab332 and Ab351-Ab446), or a fragment thereof, and a second vector comprising a polynucleotide encoding a light chain or a light chain variable region of an antibody described herein (e.g., an antibody comprising the CDRs of any one of antibodies Ab320-Ab332 and Ab351-Ab446), or a fragment thereof. In other embodiments, a first host cell comprises a first vector comprising a polynucleotide encoding a heavy chain or a heavy chain variable region of an antibody described herein (e.g., an antibody comprising the CDRs of any one of antibodies Ab320-Ab332 and Ab351-Ab446), or a fragment thereof, and a second host cell comprises a second vector comprising a polynucleotide encoding a light chain or a light chain variable region of an antibody described herein (e.g., an antibody comprising the CDRs of any one of antibodies Ab320-Ab332 and Ab351-Ab446). In specific embodiments, a heavy chain/heavy chain variable region expressed by a first cell associated with a light chain/light chain variable region of a second cell to form an anti-ALK antibody described herein (e.g., antibody comprising the CDRs of any one of antibodies Ab320-Ab332 and Ab351-Ab446) or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-ALK antibody described herein (e.g., antibody comprising the CDRs of any one of antibodies Ab320-Ab332 and Ab351-Ab446), and a second vector comprising a polynucleotide encoding a heavy chain/heavy chain variable region of an anti-ALK antibody described herein (e.g., antibody comprising the CDRs of any one of antibodies Ab320-Ab332 and Ab351-Ab446).

A variety of host-expression vector systems can be utilized to express antibody molecules described herein (e.g., an antibody comprising the CDRs of any one of antibodies Ab320-Ab332 and Ab351-Ab446) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein (e.g., an antibody comprising the CDRs of any one of antibodies Ab320-Ab332 and Ab351-Ab446) or an antigen-binding fragment thereof are CHO cells, for example CHO cells from the CHO GS System™ (Lonza). In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein which immunospecifically bind to an ECD of ALK is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, anti-ALK antibodies described herein (e.g., an antibody comprising the CDRs of any one of antibodies Ab320-Ab332 and Ab351-Ab446) are produced in mammalian cells, such as CHO cells.

For long-term, high-yield production of recombinant proteins, stable expression cells can be generated. For example, cell lines which stably express an anti-ALK antibody described herein (e.g., an antibody comprising the CDRs of any one of antibodies Ab320-Ab332 and Ab351-Ab446) or an antigen-binding fragment thereof can be engineered. In specific embodiments, a cell provided herein stably expresses a light chain/light chain variable domain and a heavy chain/heavy chain variable domain which associate to form an antibody described herein (e.g., an antibody comprising the CDRs of any one of antibodies Ab320-Ab332 and Ab351-Ab446) or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-ALK antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds.), Current Protocols in Human Genetics, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or antigen-binding fragment described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein")

and/or variants of an antibody, for example, different post-translational modified forms of an antibody or other different versions of an antibody (e.g., antibody fragments). When the antibody is recombinantly produced, it is also generally substantially free of culture medium, that is, culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, 5%, or 1% (by dry weight) of chemical precursors or compounds other than the antibody of interest. In a specific embodiment, antibodies described herein are isolated or purified.

5.3 Pharmaceutical Compositions and Kits

Provided herein are compositions, pharmaceutical compositions, and kits comprising one or more antibodies (e.g., anti-ALK antibodies comprising CDRs of any one of antibodies Ab320-Ab332 and Ab351-Ab446) described herein, or antigen-binding fragments thereof. In particular aspects, compositions (e.g., pharmaceutical compositions) described herein are suitable for in vitro, ex vivo, or in vivo uses, for example, use in humans. In specific embodiments, provided herein is a pharmaceutical composition comprising an antibody (e.g., a humanized antibody) described herein (or an antigen-binding fragment thereof) and a pharmaceutically acceptable carrier or excipient.

As used herein, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

Formulations containing one or more antibodies provided herein (e.g., antibodies comprising CDRs of any one of antibodies Ab320-Ab332 and Ab351-Ab446) or an antigen-binding fragment thereof can, for example, be prepared for storage by mixing the antibody or antigen-binding fragment having the desired degree of purity with optional physiologically acceptable carriers, excipients or stabilizers (*Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.). Such formulations can, for example, be in the form of, e.g., lyophilized formulations or aqueous solutions. Pharmaceutical carriers suitable for administration of the antibodies or fragments provided herein can include any such carriers known to those skilled in the art to be suitable for the particular mode of administration. Acceptable carriers, excipients, or stabilizers are nontoxic to recipients at the dosages and concentrations employed, and can include buffers such as phosphate, citrate, and other organic acids; and/or non-ionic surfactants such as TWEEN™, PLURONICS™ or polyethylene glycol (PEG).

Formulations to be used for in vivo administration can be sterile. This can be readily accomplished, for example, by filtration through, e.g., sterile filtration membranes.

In one embodiment, compositions provided herein are formulated for single dosage administration. To formulate a composition, the weight fraction of compound is dissolved, suspended, dispersed or otherwise mixed in a selected carrier at a desired concentration.

In certain aspects, an antibody provided herein (e.g., antibody comprising CDRs of any one of antibodies Ab320-Ab332 and Ab351-Ab446) is included in the pharmaceutically acceptable carrier in an effective amount sufficient to exert a therapeutically useful effect in the absence of, or with minimal or negligible, undesirable side effects on the patient treated.

In certain embodiments, compositions described herein are provided for administration to humans or animals (e.g., mammals) in unit dosage forms, such as sterile parenteral (e.g., intravenous) solutions or suspensions containing suitable quantities of the compounds or pharmaceutically acceptable derivatives thereof. Compositions are also provided for administration to humans and animals in unit dosage form, such as tablets, capsules, pills, powders, granules, and oral or nasal solutions or suspensions, and oil-water emulsions containing suitable quantities of an anti-ALK antibody or antigen-binding fragment. The antibody or antigen-binding fragment is, in one embodiment, formulated and administered in multiple-dosage forms. Unit-dose forms as used herein refers to physically discrete units suitable for human or animal (e.g., mammal) subjects and packaged individually as is known in the art. Each unit-dose contains a predetermined quantity of an anti-ALK antibody sufficient to produce the desired effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles. Hence, in specific aspects, a multiple-dose form is a multiple of unit-doses which are not segregated in packaging.

In certain embodiments, one or more anti-ALK antibodies described herein (e.g., antibodies comprising CDRs of any one of antibodies Ab320-Ab332 and Ab351-Ab446) or an antigen-binding fragment thereof are in a liquid pharmaceutical formulation. Liquid pharmaceutically administrable compositions can, for example, be prepared by dissolving, dispersing, or otherwise mixing an antibody and optional pharmaceutical adjuvants in a carrier, such as, for example, water, saline, aqueous dextrose, glycerol, glycols, and the like, to thereby form a solution or suspension. In certain embodiments, a pharmaceutical composition provided herein to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent, e.g., sterile solutions, ready for injection just prior to use. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

In certain embodiments, intravenous or intraarterial infusion of a sterile aqueous solution containing an anti-ALK antibody or fragment described herein is an effective mode of administration. Another embodiment is a sterile aqueous or oily solution or suspension containing an anti-ALK antibody described herein injected as necessary to produce the desired pharmacological effect.

In specific embodiments, an anti-ALK antibody described herein can be suspended in micronized or other suitable form. The form of the resulting mixture depends upon a number of factors, including the intended mode of administration and the solubility of the compound in the selected carrier or vehicle.

In other embodiments, the pharmaceutical formulations are lyophilized powders, which can be reconstituted for administration as solutions, emulsions and other mixtures. They can also be reconstituted and formulated as solids or gels.

Lyophilized powder can, for example, be prepared by dissolving an anti-ALK antibody provided herein, in a suitable solvent. In some embodiments, the lyophilized powder is sterile. Suitable solvents can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. A suitable solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides an example of a formulation. In one embodiment, the resulting solution will be apportioned into vials for lyophilization. Lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier.

In certain aspects, anti-ALK antibodies provided herein can be formulated for local administration or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

Anti-ALK antibodies and other compositions provided herein can also be formulated to be targeted to a particular tissue, organ, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, anti-ALK antibodies described herein are targeted (or otherwise administered) to the visual organs, bone marrow, gastrointestinal tract, lungs, brain, or joints. In specific embodiments, an anti-ALK antibody described herein is capable of crossing the blood-brain barrier.

Provided herein is a pharmaceutical pack or kit comprising one or more containers filled with one or more of the ingredients of the pharmaceutical compositions described herein, such as one or more anti-ALK antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits comprising one or more of the antibodies or antibody fragments described herein. In one embodiment, a kit comprises an antibody or antibody fragment described herein, in one or more containers. In a specific embodiment, kits described herein contain a substantially isolated ALK antigen (e.g., ECD of human ALK) as a control. In another specific embodiment, the kits described herein further comprise a control antibody which does not react with an ALK antigen. In another specific embodiment, kits described herein contain one or more elements for detecting the binding of a modified antibody to an ALK antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized ALK antigen. The ALK antigen provided in the kit can also be attached to a solid support. In a more specific embodiment, the detecting means of the above described kit includes a solid support to which an ALK antigen is attached. Such a kit can also include a non-attached reporter-labeled anti-human antibody or anti-mouse/rat antibody. In this embodiment, binding of the antibody to the ALK antigen can be detected by binding of the said reporter-labeled antibody.

5.4 Uses and Methods

In particular aspects, provided herein are methods of modulating ALK activity with an anti-ALK antibody (e.g., any one of antibodies Ab320-Ab332 and Ab351-Ab446, or an antigen-binding fragment thereof, or an antibody comprising CDRs of any one of antibodies Ab320-Ab332 and Ab351-Ab446, or an antigen-binding fragment thereof; or an antibody comprising the VL and the VH of any one of Ab320-Ab332 and Ab351-Ab446) or an antigen-binding fragment thereof described herein. In certain embodiments, the anti-ALK antibody is an ALK antagonist.

In specific embodiments, provided herein are methods of inhibiting (e.g., partially inhibiting) ALK activity with an anti-ALK antibody described herein which is an ALK antagonist. In certain embodiments, provided herein are methods of managing or treating a condition or disorder using an anti-ALK antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) which is an ALK antagonist.

In particular embodiments, provided herein are methods for treating, e.g., managing, hyperproliferative disorders, such as cancer (e.g., anaplastic large cell lymphoma, inflammatory myofibroblastic tumors, lung cancer, for example, small cell lung carcinoma or non-small cell lung cancer, e.g., adenocarcinoma, such as bronchioalveolar carcinoma, squamous cell carcinoma or large-cell carcinoma, diffuse large B-cell lymphoma, squamous cell carcinoma, breast carcinoma, melanoma, pancreatic cancer, B-cell non-Hodgkin's lymphoma, thyroid carcinoma, retinoblastoma, Ewing sarcoma, prostate cancer, colon cancer, colorectal cancer, glioblastoma, rhabdomyosarcoma, ovarian cancer, head and neck cancer, e.g., head and neck squamous cell carcinomas, medulloblastoma or neuroblastoma) or neurofibromatosis in a subject (e.g., a human subject, such as a pediatric subject), comprising administering to a subject in need thereof a therapeutically effective amount of an antibody (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or an antigen-binding fragment described herein that binds specifically to an ECD of human ALK. In certain embodiments, provided herein is a method of alleviating, inhibiting or reducing the progression or severity of one or more symptoms associated with hyperproliferative disorders, such as cancer or neurofibromatosis. In certain embodiments, the hyperproliferative disorder comprises cells expressing ALK. In specific aspects, the hyperproliferative disorder comprises cells comprising an ALK mutation.

In certain aspects, the subject being treated is a pediatric subject. For example, in certain aspects, provided herein is a method for treating cancer in a pediatric subject, comprising administering to the pediatric subject a therapeutically effective amount of an antibody or antigen-binding fragment thereof provided herein. In certain aspects, the cancer is glioblastoma, rhabdomyosarcoma, neuroblastoma, or medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises:
(i) a light chain variable region (VL) comprising:
(a) a VL complementarity determining region (CDR) 1 comprising the amino acid sequence of KASQNVGTNVA (SEQ ID NO:13);
(b) a VL CDR2 comprising the amino acid sequence of SASYRYS (SEQ ID NO:14); and
(c) a VL CDR3 comprising the amino acid sequence of QX$_1$YNSYPYMX$_2$T (SEQ ID NO:468), wherein X$_1$ is Q or R and X$_2$ is Y or F; and
(ii) a heavy chain variable region (VH) comprising:
(a) a VH CDR1 comprising the amino acid sequence X$_3$YWMH (SEQ ID NO:469), wherein X$_3$ is N or S;
(b) a VH CDR2 comprising the amino acid sequence of YIX$_4$PSSGYTKYNQKFKD (SEQ ID NO:470), wherein X$_4$ is N or K; and
(c) a VH CDR3 comprising the amino acid sequence of DYYGSSSWFAY (SEQ ID NO:18).

In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises:
(i) a light chain variable region (VL) comprising:
(a) a VL CDR1 comprising the amino acid sequence of KASQNVGTNVA (SEQ ID NO:13);
(b) a VL CDR2 comprising the amino acid sequence of SASYRYS (SEQ ID NO:14); and
(c) a VL CDR3 comprising the amino acid sequence of QQYNSYPYMYT (SEQ ID NO:15); and
(ii) a heavy chain variable region (VH) comprising:
(a) a VH CDR1 comprising the amino acid sequence of SYWMH (SEQ ID NO:10);
(b) a VH CDR2 comprising the amino acid sequence of YIKPSSGYTKYNQKFKD (SEQ ID NO:34); and
(c) a VH CDR3 comprising the amino acid sequence of DYYGSSSWFAY (SEQ ID NO:18).

In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises:
  (i) a light chain variable region (VL) comprising:
    (a) a VL CDR1 comprising the amino acid sequence of KASQNVGTNVA (SEQ ID NO:13);
    (b) a VL CDR2 comprising the amino acid sequence of SASYRYS (SEQ ID NO:14); and
    (c) a VL CDR3 comprising the amino acid sequence of QQYNSYPYMYT (SEQ ID NO:15); and
  (ii) a heavy chain variable region (VH) comprising:
    (a) a VH CDR1 comprising the amino acid sequence of SYWMH (SEQ ID NO:10);
    (b) a VH CDR2 comprising the amino acid sequence of YINPSSGYTKYNQKFKD (SEQ ID NO:17); and
    (c) a VH CDR3 comprising the amino acid sequence of DYYGSSSWFAY (SEQ ID NO:18).

In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises:
  (i) a light chain variable region (VL) comprising:
    (a) a VL CDR1 comprising the amino acid sequence of KASQNVGTNVA (SEQ ID NO:13);
    (b) a VL CDR2 comprising the amino acid sequence of SASYRYS (SEQ ID NO:14); and
    (c) a VL CDR3 comprising the amino acid sequence of QQYNSYPYMYT (SEQ ID NO:15); and
  (ii) a heavy chain variable region (VH) comprising:
    (a) a VH CDR1 comprising the amino acid sequence of NYWMH (SEQ ID NO:16);
    (b) a VH CDR2 comprising the amino acid sequence of YINPSSGYTKYNQKFKD (SEQ ID NO:17); and
    (c) a VH CDR3 comprising the amino acid sequence of DYYGSSSWFAY (SEQ ID NO:18).

In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises:
  (i) a light chain variable region (VL) comprising:
    (a) a VL CDR1 comprising the amino acid sequence of KASQNVGTNVA (SEQ ID NO:13);
    (b) a VL CDR2 comprising the amino acid sequence of SASYRYS (SEQ ID NO:14); and
    (c) a VL CDR3 comprising the amino acid sequence of QRYNSYPYMFT (SEQ ID NO:41); and
  (ii) a heavy chain variable region (VH) comprising:
    (a) a VH CDR1 comprising the amino acid sequence of SYWMH (SEQ ID NO:10);
    (b) a VH CDR2 comprising the amino acid sequence of YINPSSGYTKYNQKFKD (SEQ ID NO:17); and
    (c) a VH CDR3 comprising the amino acid sequence of DYYGSSSWFAY (SEQ ID NO:18).

In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises:
  (i) a light chain variable region (VL) comprising:
    (a) a VL CDR1 comprising the amino acid sequence of KASQNVGTNVA (SEQ ID NO:13);
    (b) a VL CDR2 comprising the amino acid sequence of SASYRYS (SEQ ID NO:14); and
    (c) a VL CDR3 comprising the amino acid sequence of QRYNSYPYMFT (SEQ ID NO:41); and
  (ii) a heavy chain variable region (VH) comprising:
    (a) a VH CDR1 comprising the amino acid sequence of NYWMH (SEQ ID NO:16);
    (b) a VH CDR2 comprising the amino acid sequence of YINPSSGYTKYNQKFKD (SEQ ID NO:17); and
    (c) a VH CDR3 comprising the amino acid sequence of DYYGSSSWFAY (SEQ ID NO:18).

In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises:
  (i) a light chain variable region (VL) comprising:
    (a) a VL CDR1 comprising the amino acid sequence of KASQNVGTNVA (SEQ ID NO:13);
    (b) a VL CDR2 comprising the amino acid sequence of SASYRYS (SEQ ID NO:14); and
    (c) a VL CDR3 comprising the amino acid sequence of QRYNSYPYMFT (SEQ ID NO:41); and
  (ii) a heavy chain variable region (VH) comprising:
    (a) a VH CDR1 comprising the amino acid sequence of SYWMH (SEQ ID NO:10);
    (b) a VH CDR2 comprising the amino acid sequence of YIKPSSGYTKYNQKFKD (SEQ ID NO:34); and
    (c) a VH CDR3 comprising the amino acid sequence of DYYGSSSWFAY (SEQ ID NO:18).
In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises a VL region comprising SEQ ID NO: 421 and a VH region comprising SEQ ID NO: 430. In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises a VL region comprising SEQ ID NO: 421 and a VH region comprising SEQ ID NO: 432. In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises a VL region comprising SEQ ID NO: 421 and a VH region comprising SEQ ID NO: 433. In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises a VL region comprising SEQ ID NO: 425 and a VH region comprising SEQ ID NO: 430. In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises a VL region comprising SEQ ID NO: 425 and a VH region comprising SEQ ID NO: 432. In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain aspects, provided herein is a method for treating cancer in a subject, comprising administering to the pediatric subject a therapeutically effective amount of an antibody or antigen-binding fragment thereof, wherein the antibody or antigen-binding fragment thereof specifically binds to an anaplastic lymphoma kinase (ALK) extracellular domain (ECD), and comprises a VL region comprising SEQ ID NO: 425 and a VH region comprising SEQ ID NO: 433. In certain embodiments, the subject is a pediatric subject. In certain embodiments, the cancer is lung cancer. In certain embodiments, the cancer is small cell lung carcinoma. In certain embodiments, the cancer is non-small cell lung cancer. In certain embodiments, the cancer is a lung adenocarcinoma. In certain embodiments, the cancer is a lung squamous cell carcinoma. In certain embodiments, the cancer is neuroblastoma. In certain embodiments, the cancer is pediatric neuroblastoma. In certain embodiments, the cancer is glioma. In certain embodiments, the cancer is pediatric glioma. In certain embodiments, the cancer is rhabdomyosarcoma. In certain embodiments, the cancer is pediatric rhabdomyosarcoma. In certain embodiments, the cancer is medulloblastoma. In certain embodiments, the cancer is pediatric medulloblastoma.

In certain embodiments, the anti-ALK antibody or antigen-binding fragment thereof for use in the methods provided herein is an antibody, e.g., a monoclonal antibody, such as a humanized monoclonal antibody, comprising CDRs of any one of antibodies Ab321, Ab322, Ab326, Ab327, Ab330, or Ab331, for example, as set forth in Tables 1, 2, 5, 6, 9, or 10. In specific embodiments, the anti-ALK antibody or antigen-binding fragment thereof for use in the methods provided herein is an antibody comprising the VL and VH of any one of Ab321, Ab322, Ab326, Ab327, Ab330, Ab331, or Ab351-Ab446. In particular embodiments, the anti-ALK antibody inhibits an ALK activity (e.g., phosphorylation of ALK, ALK signaling, inhibition of cell proliferation, or inhibition of tumor growth).

As used herein, "administer" or "administration" refers to the act of physically delivering a substance (e.g., a humanized anti-ALK antibody provided herein or an antigen-binding fragment thereof) to a subject or a patient (e.g., human), such as by mucosal, topical, intradermal, parenteral, intravenous, subcutaneous, intramuscular delivery and/or any other method of physical delivery described herein or known in the art.

"Treating" refers to a method sufficient to reduce and/or ameliorate the severity and/or duration of a given condition, disorder or disease described herein and/or a symptom related thereto, and can, for example, include the reduction, slowing, or amelioration of the advancement or progression of a given disease, reduction, slowing, or amelioration of the recurrence, development or onset of a given condition, disorder or disease, and/or improvement or enhancement of the effect(s) of a second therapy (e.g., a therapy other than administration of an anti-ALK antibody provided herein). "Treating" includes methods that manage a given condition, disorder or disease. The terms "manage," "managing," "management" and the like refer to the beneficial effects that a subject derives from a therapy which does not result in a cure of a condition, disorder or disease associated with ALK. An "effective amount" or "therapeutically effective amount" refers to an amount of a therapy, e.g., an anti-ALK antibody or antigen-binding fragment thereof as described herein, sufficient for use in a such a method of treating.

As used herein, the term "side effects" encompasses unwanted and adverse effects of a therapy. Unwanted effects are not necessarily adverse. An adverse effect from a therapy can be harmful or uncomfortable or risky. Examples of side effects can include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (63$^{rd}$ ed., 2009).

As used herein, the terms "subject" and "patient" are used interchangeably. As used herein, a subject is a mammal such as a non-primate (e.g., cows, pigs, horses, cats, dogs, goats, rabbits, rats, mice, etc.) or a primate (e.g., monkey and human), for example a human. In one embodiment, the subject is a mammal, e.g., a human, diagnosed with a condition or disorder provided herein (e.g., hyperproliferative disorders, such as cancer or neurofibromatosis). In another embodiment, the subject is a mammal, e.g., a human, at risk of developing a condition or disorder provided herein (e.g., hyperproliferative disorders, such as cancer or neurofibromatosis).

In certain embodiments, ALK is amplified in the subject, e.g., the human subject, treated in accordance with the methods provided herein. Identification of ALK amplification in a sample from a subject can be performed by assays known to one of ordinary skill in the art, such as, e.g., quantitative reverse transcription PCR, immunoblot assays, DNA fingerprinting, karyotyping (for example, by multicolor fluorescence in situ hybridization (mFISH)), comparative genome hybridization, and gene expression profiling. As a non-limiting example, protein expression of tumor samples can be characterized using immunohistochemical assays to measure the amount of ALK protein present in a sample. In certain embodiments, ALK amplification in a subject results in ligand-independent ALK signaling in cells of the subject. Identification of ligand-independent ALK signaling in the subject can be performed by assays known to one of ordinary skill in the art, such as, e.g., quantitative reverse transcription PCR or immunoblot assays. For example, primary cells from the subject can be extracted and cultured in the presence and absence of ALK ligand, and ALK downstream signaling events, such as, e.g., phosphorylation of ERK1/2 and/or AKT, can be assessed by, e.g., ELISA or immunoblot. In certain embodiments, a subject comprises cells (e.g., tumor cells) that express an ALK mutant, for example a constitutively active ALK mutant. In certain embodiments, a subject expresses an ALK comprising one or more mutations. In certain embodiments, a subject expresses an ALK protein comprising an leucine amino acid substitution at ALK amino acid residue Phe1174. In certain embodiments, a subject expresses an ALK protein comprising an glutamine amino acid substitution at ALK amino acid residue Arg1275. In certain embodiments, a subject expresses an ALK protein comprising a mutation in one or more of the following residues: Pro36, Pro157, Val198, Arg 259, Gly640, Leu684, Gly718, Met770, Asp993, Ile1170, Ala1200, Leu1204, Gly1128, Arg1192, Arg1275, Asp1091, Gly1128, Thr1151, Met1166, Ile1171, Phe1174, Arg1192, Leu1196, Phe1245, Ile1250, Arg1275, Glu1407, Glu1433, Arg1464, Gly1494, and Ala1553. In certain embodiments, a subject has cancer, wherein cancer cells in the subject express mutant ALK, e.g., constitutively active mutant ALK. In certain embodiments, a subject has cancer, wherein cancer cells in the subject express an ALK comprising one or more deletions in the ALK gene. Identification of mutations or deletions in a sample from a subject can be performed by assays known to one of ordinary skill in the art, such as, e.g., DNA extraction, generation of complementary DNA, and cDNA sequencing. The cDNA sequence, for example, can be utilized to obtain the translation product by methods known to one of ordinary skill in the art. Genetic deletions and amino acid substitutions can be identified by, for example, comparing the sequence from the sample from the subject to a wild type and/or consensus sequence.

Provided herein are methods of treating, e.g., managing, a condition (e.g., hyperproliferative disorders, such as cancer or neurofibromatosis) by inhibiting an activity of ALK with an anti-ALK antibody (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) described herein that acts as an ALK antagonist. An example of a condition which can be treated or managed with an ALK antagonist includes cancer (e.g., anaplastic large cell lymphoma, inflammatory myofibroblastic tumors, lung cancer, for example, small cell lung carcinoma or non-small cell lung cancer, e.g., adenocarcinoma, such as bronchioalveolar carcinoma, squamous cell carcinoma or large-cell carcinoma, diffuse large B-cell lymphoma, squamous cell carcinoma, breast carcinoma, melanoma, pancreatic cancer, B-cell non-Hodgkin's lymphoma, thyroid carcinoma, retinoblastoma, Ewing sarcoma, prostate cancer, colon cancer, colorectal cancer, glioblastoma, rhabdomyosarcoma, ovarian cancer, head and neck cancer, e.g., head and neck squamous cell carcinomas, medulloblastoma or neuroblastoma) or neurofibromatosis, described in more detail below.

Provided herein is a method of treating, e.g., managing, cancer (e.g., anaplastic large cell lymphoma, inflammatory myofibroblastic tumors, lung cancer, for example, small cell lung cancer or non-small cell lung cancer, e.g., adenocarcinoma, such as bronchioalveolar carcinoma, squamous cell carcinoma or large-cell carcinoma, diffuse large B-cell lymphoma, squamous cell carcinoma, breast carcinoma, melanoma, pancreatic cancer, B-cell non-Hodgkin's lymphoma, thyroid carcinoma, retinoblastoma, Ewing sarcoma, prostate cancer, colon cancer, colorectal cancer, glioblastoma, rhabdomyosarcoma, ovarian cancer, head and neck cancer, e.g., head and neck squamous cell carcinomas, medulloblastoma or neuroblastoma) or neurofibromatosis in a subject, for example a pediatric subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method treating, e.g., managing, anaplastic large cell lymphoma in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method of treating, e.g., managing, inflammatory myofibroblastic tumors in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method of treating, e.g., managing, lung cancer, for example, small cell lung carcinoma or non-small cell lung cancer, e.g., adenocarcinoma, such as bronchioalveolar carcinoma, squamous cell carcinoma or large-cell carcinoma, in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method of treating, e.g., managing, diffuse large B-cell lymphoma in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method of treating, e.g., managing, squamous cell carcinoma in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method of treating, e.g., managing, rhabdomyosarcoma in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method of treating, e.g., managing, glioblastoma in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method of treating, e.g., managing, neuroblastoma in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Provided herein is a method treating, e.g., managing, neurofibromatosis in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of neurofibroma growth.

Provided herein is a method of treating, e.g., managing, cancer characterized by ligand-independent ALK signaling, such as, for example, a cancer characterized by ALK amplification, in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK. In particular embodiments, the antibody or antigen binding fragment thereof inhibits an ALK activity, inhibits or reduces ALK expression, or reduces the number of ALK-expressing cells. In particular embodiments, such a method involves inhibition of tumor growth and cancer cell proliferation.

Non-limiting examples of cancers which can be treated, e.g., managed, in the methods provided herein include anaplastic large cell lymphoma, inflammatory myofibroblastic tumors, lung cancer, for example, small cell lung carcinoma or non-small cell lung cancer, e.g., adenocarcinoma, such as bronchioalveolar carcinoma, squamous cell carcinoma or large-cell carcinoma, diffuse large B-cell lymphoma, squamous cell carcinoma, breast carcinoma, melanoma, pancreatic cancer, B-cell non-Hodgkin's lymphoma, thyroid carcinoma, retinoblastoma, Ewing sarcoma, prostate cancer, colon cancer, colorectal cancer, glioblastoma, rhabdomyosarcoma, ovarian cancer, head and neck cancer, e.g., head and neck squamous cell carcinomas, medulloblastoma or neuroblastoma. In certain embodiments, the cancer expresses or overexpresses ALK. In certain embodiments, the cancer expresses ALK comprising a mutation. In certain embodiments, the cancer expresses an ALK gene comprising one or more deletions in the ALK gene. In certain embodiments, the cancer expresses ALK comprising an amino acid substitution.

In a particular embodiment, provided herein is a method of inhibiting or reducing tumor growth or cancer (e.g., anaplastic large cell lymphoma, inflammatory myofibroblastic tumors, lung cancer, for example, small cell lung carcinoma or non-small cell lung cancer, e.g., adenocarcinoma, such as bronchioalveolar carcinoma, squamous cell carcinoma or large-cell carcinoma, diffuse large B-cell lymphoma, squamous cell carcinoma, breast carcinoma, melanoma, pancreatic cancer, B-cell non-Hodgkin's lymphoma, thyroid carcinoma, retinoblastoma, Ewing sarcoma, prostate cancer, colon cancer, colorectal cancer, glioblastoma, rhabdomyosarcoma, ovarian cancer, head and neck cancer, e.g., head and neck squamous cell carcinomas, medulloblastoma or neuroblastoma) or neurofibromatosis cell proliferation in a subject, comprising administering to a subject in need thereof a therapeutically effective amount of an antibody described herein (e.g., an antibody comprising CDRs of any one of antibodies Ab321, Ab322, Ab326, Ab327, Ab330, or Ab331 or an antibody comprising the VL and VH of any one of Ab321, Ab322, Ab326, Ab327, Ab330, Ab332, or Ab351-Ab446) or antigen-binding fragment thereof which specifically binds to an ECD of human ALK and inhibits an ALK activity or inhibits or reduces ALK expression, or reduces the number of ALK-expressing cells.

An anti-ALK antibody described herein or an antigen-binding fragment thereof, which is an ALK antagonist for use in the methods provided herein is capable of inhibiting (e.g., partially inhibiting) or decreasing/reducing ALK expression and/or an ALK activity. Activities of ALK are known in the art. In specific embodiments, an anti-ALK antibody described herein which is an ALK antagonist inhibits (e.g., partially inhibits) one or more of the following ALK activities: phosphorylation (e.g., autophosphorylation) of ALK receptor (e.g., ECD of ALK), ALK ligand binding to ALK receptor, cell migration, cell survival, ALK receptor homodimerization, and downstream signaling pathways (e.g., phosphorylation of ERK1/2, AKT, STAT1, STAT3, and STAT5). Methods for measuring these activities are known in the art.

In specific embodiments, an anti-ALK antibody described herein which is an ALK antagonist inhibits (e.g., partially inhibits), by at least about 10%, 20%, 30%, 40%, 50%, 60%, 70%, 80%, 90%, 97%, 98%, 99%, or 100%, one or more such ALK activities.

The anti-ALK antibodies or antigen-binding fragments thereof provided herein, which specifically bind to an ECD of human ALK may also be combined or used in combination with a second therapy, e.g., a second agent, useful in the treatment of the diseases or conditions disclosed herein. In certain embodiments, the compound is in the form of a pharmaceutical composition, as described in the sections above. Accordingly, provided herein are methods of using the compounds and/or pharmaceutical compositions disclosed herein in combination with a second therapy, e.g., a second agent.

As used herein, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

In certain embodiments, the second agent modulates an immune checkpoint molecule. In certain embodiments, the immune checkpoint molecule is selected from the group consisting of CD28, OX40, Glucocorticoid-Induced Tumour-necrosis factor Receptor-related protein (GITR), CD137 (4-1BB), CD27, Herpes Virus Entry Mediator (HVEM), T cell Immunoglobulin and Mucin-domain containing-3 (TIM-3), Lymphocyte-Activation Gene 3 (LAG-3), Cytotoxic T-Lymphocyte-associated Antigen-4 (CTLA-4), V-domain Immunoglobulin Suppressor of T cell Activation (VISTA), B and T Lymphocyte Attenuator (BTLA), PD-1, and PD-L1. In certain embodiments, the second agent is an antibody or antigen-binding fragment thereof.

In certain embodiments, the second agent is an agonist of an immune checkpoint molecule. In certain embodiments, the immune checkpoint molecule is selected from the group consisting of CD28, OX40, Glucocorticoid-Induced Tumour-necrosis factor Receptor-related protein (GITR), CD137 (4-1BB), CD27, and Herpes Virus Entry Mediator (HVEM). In certain embodiments, the second agent is an antibody or antigen-binding fragment thereof.

In certain embodiments, the second agent is an antagonist of an immune checkpoint molecule. In certain embodiments, the immune checkpoint molecule is selected from the group consisting of T cell Immunoglobulin and Mucin-domain containing-3 (TIM-3), Lymphocyte-Activation Gene 3 (LAG-3), Cytotoxic T-Lymphocyte-associated Antigen-4 (CTLA-4), V-domain Immunoglobulin Suppressor of T cell Activation (VISTA), B and T Lymphocyte Attenuator (BTLA), PD-1, and PD-L1. In certain embodiments, the second agent is an antibody or antigen-binding fragment thereof.

In certain embodiments, the second agent is an antibody or antigen-binding fragment thereof. In certain embodiments, the antibody or antibody-binding fragment thereof binds PD-1. In certain embodiments, the antibody or antibody-binding fragment thereof that binds PD-1 is nivolumab (OPDIVO®, BMS-936558, MDX-1106, ONO-4538; Bristol-Myers Squibb, Ono Pharmaceuticals, Inc.), pembrolizumab (KEYTRUDA®, lambrolizumab, MK-3475; Merck), pidilizumab (CT-011; Curetech, Medivation); MEDI0680 (AMP-514; MedImmune, AstraZeneca); PDR-001 (Novartis), SHR1210, or INCSHR1210; Incyte, Hengrui). In certain embodiments, the antibody or antigen-binding fragment thereof binds PD-L1. In certain embodiments, the antibody or antigen-binding fragment thereof that binds PD-L1 is durvalumab (MEDI4736; MedImmune, AstraZeneca), BMS-936559 (MDX-1105; Bristol-Myers Squibb), avelumab (MSB0010718C; Merck Serono, Pfizer), or atezolizumab (MPDL-3280A; Genentech, Roche). In certain embodiments, the antibody or antibody-binding fragment thereof binds LAG-3. In certain embodiments, the antibody or antibody-binding fragment thereof that binds LAG-3 is BMS-986016 (Bristol-Myers Squibb), GSK2831781 (GlaxoSmithKline), or LAG525 (Novartis). In certain embodiments, the antibody or antibody-binding fragment thereof binds CTLA-4. In certain embodiments, the antibody or antibody-binding fragment thereof that binds CTLA-4 is ipilimumab (YERVOY™, BMS-734016, MDX010, MDX-101; Bristol-Myers Squibb), or tremelimumab (CP-675,206; MedImmune, AstraZeneca). In certain embodiments, the antibody or antibody-binding fragment thereof binds OX40. In certain embodiments, the antibody or antibody-binding fragment thereof that binds OX40 is MEDI6469 (MedImmune, AstraZeneca), MEDI0562 (MedImmune, AstraZeneca), or KHK4083 (Kyowa Hakko Kirin). In certain embodiments, the antibody or antibody-binding fragment thereof binds GITR. In certain embodiments, the antibody or antibody-binding fragment thereof that binds GITR is TRX518 (Leap Therapeutics) or MEDI1873 (MedImmune, AstraZeneca). In certain embodiments, the antibody or antibody-binding fragment thereof binds CD137 (4-1BB). In certain embodiments, the antibody or antibody-binding fragment thereof that binds CD137 (4-1BB) is PF-2566 (PF-05082566; Pfizer), or urelumab (BMS-663513; Bristol-Myers Squibb). In certain embodiments, the antibody or antibody-binding fragment thereof binds CD27.

In certain embodiments, the antibody or antibody-binding fragment thereof that binds CD27 is varilumab (CDX-1127; Celldex Therapies).

In particular embodiments, the second therapy is an ALK-targeting tyrosine kinase inhibitor (TKI). In more particular embodiments, the ALK-targeting TKI is crizotinib (XALKORI®, Pfizer). In more particular embodiments, the ALK-targeting TKI is lorlatinib (PF-06463922, Pfizer). In more particular embodiments, the ALK-targeting TKI is entrectinib (Ignyta). In more particular embodiments, the ALK-targeting TKI is ceritinib (ZYKADIA®, Novartis). In particular embodiments, the second therapy is a second ALK-targeting antibody or fragment thereof. In particular embodiments, the ALK-targeting therapy is ALECENSA® (alectinib, CH5424802, R05424802, Genentech). In particular embodiments, the ALK-targeting therapy is brigatinib (AP26113, Ariad Pharmaceuticals). In particular embodiments, the ALK-targeting therapy is X-396 (Xcovery). In certain embodiments, the cancer is lung cancer. In certain embodiments, the cancer is small cell lung carcinoma. In certain embodiments, the cancer is non-small cell lung cancer. In certain embodiments, the cancer is metastatic non-small cell lung cancer. In certain embodiments, the cancer is a lung adenocarcinoma. In certain embodiments, the cancer is a lung squamous cell carcinoma. In certain embodiments, the cancer comprises ALK-expressing cells. In certain embodiments, the cancer comprises cells that express a mutant ALK. In certain embodiments, the ALK-targeting agent is ceritinib and the subject is resistant to crizotinib.

In particular embodiments, the second therapy is a BRAF targeted therapy (e.g., vemurafenib (ZELBORAF®), dabrafenib (TAFINLAR®), encorafenib (LGX818, Novartis), PLX-4720, PLX-3603 (R05212054, Roche/Genentech), PLX-8394 (Daiichi Sankyo), CEP-32496 (Ambit Biosciences), XL281 (BMS-908662, Exelixis), or RAF265 (CHIR-265, Novartis)), an MEK (mitogen-activated protein kinase (MAPK) kinase, also known as MAPKK) inhibitor (e.g., selumetinib (AZD6244, ARRY-142866, AstraZeneca), WX-554 (Wilex), trametinib (MEKINIST®; GlaxoSmithKline), refametinib (Ardea Biosciences), E-6201 (Eisai), MEK-162 (Novartis), cobimetinib (GDC-0973; XL-518; Exelixis, Roche), TAK-733 (Takeda Pharmaceuticals), binimetinib (Array BioPharma), PD-0325901 (Pfizer), pimasertib (MSC1936369; EMD Serono), MSC2015103 (EMD Serono), WX-554 (WILEX), or R048987655 (CH4987655; CIF/RG7167; Chugai Pharmaceuticals)). In particular embodiments, the second therapy is a PI3K, mTOR, AKT, or CDK pathway inhibitor. In particular embodiments, the second therapy is an aurora kinase inhibitor. In particular embodiments, the second therapy is an n-myc inhibitor. In particular embodiments, the second therapy is a chk1 inhibitor e.g., LY2606368 (Array Biopharma) or CCT244747 (Institute of Cancer Research; Sareum Ltd., Cancer ResearchTechnology Ltd.). In particular embodiments, the second therapy is a weel inhibitor. In particular embodiments, the second therapy is a proteasome inhibitor (e.g., bortezomib (PS-341; VELCADE® (Millennium Pharmaceuticals); NEOMIB® (Getwell); BORTECAD® (Cadila Healthcare)).

In particular embodiments, the second therapy is an HDAC inhibitor, such as suberoylanilide hydroxamic acid (SAH A, vorinostat, ZOLINZA®, Merck), belinostat (PXD101; Beleodaq; TopoTarget), entinostat (MS 275; Syndax Pharmaceuticals), panobinostat (LBH589; FARYDAK®; Novartis), valproic acid, romidepsin (FR901228; ISTODAX®; Celgene), valproate, quisinostate (JNJ-26481585), AR-42 (Arno Therapeutics), pracinostate (SB939; S*Bio Pte. Ltd.), or tubacin.

In particular embodiments, the second therapy is ALKS 4230 (RDB1419, RDB1450, Alkermes). In particular embodiments, the second therapy is a CDK4/6 inhibitor, for example, ribociclib (LEE0011, Novartis). In particular embodiments, the second therapy is an HSP90 inhibitor, for example, retaspimycin hydrochloride (IPI-504, Infinity Pharmaceuticals) or ganetespib (STA-9090, Synta Pharmaceuticals). In particular embodiments, the second therapy is ADCETRIS® (brentuximab vedotin, Seattle Genetics).

In particular aspects, provided herein is a method for treating, e.g., managing, neuroblastoma comprising administering to a subject in need thereof therapeutically effective amount of anti-ALK antibody described herein or an antigen-binding fragment thereof, which specifically binds to an ECD of human ALK, in combination with a second therapy, such as a therapy known to one of skill in the art as a standard of care for neuroblastoma. In particular embodiments, the second therapy is a GD2-targeting monoclonal antibody. In more particular embodiments, the GD2-targeting monoclonal antibody is dinutuximab (UNITUXIN®, United Therapeutics) or hu3F8 (Memorial Sloan-Kettering Cancer Center). In particular embodiments, the second therapy is a cytokine. In more particular embodiments, the cytokine is IL-2 or GM-CSF. In particular embodiments, the second therapy is retinoic acid. In particular embodiments, the second therapy is chemotherapy. In more particular embodiments, the chemotherapy is one or more of lenalidomide, etoposide, taxanes, irinotecan, and cyclophosphamide. In certain aspects, the second therapy is a drug therapy. In particular embodiments, the second therapy is a vaccine therapy or immunoadjuvant. In certain aspects, the second therapy is another treatment, such as surgery or radiation therapy. In particular embodiments, the second therapy is radiation or radiotherapy. In more particular embodiments, the radiotherapy is mIBG/I-131.

5.4.1 Diagnostic Uses

In one aspect, anti-ALK antibodies described herein and antigen-binding fragments thereof, which specifically bind to an ECD of human ALK can be used for diagnostic purposes to detect, diagnose, or monitor a condition described herein (e.g., a condition involving ALK and/or abnormal ALK signaling and/or abnormal ALK expression), such as cancer (e.g., anaplastic large cell lymphoma, inflammatory myofibroblastic tumors, non-small cell lung cancer, diffuse large B-cell lymphoma, squamous cell carcinoma, glioblastoma, rhabdomyosarcoma, or neuroblastoma). In specific embodiments, anti-ALK antibodies described herein or an antigen-binding fragment thereof for use in diagnostic purposes are labeled. Methods provided herein for diagnostic purposes to detect, diagnose, or monitor a condition described herein can be in vitro methods, in situ methods, or ex vivo methods. Methods provided herein for diagnostic purposes to detect, diagnose, or monitor a condition described herein can be in vivo methods.

In certain embodiments, provided herein are methods for the detection of a condition described herein, such as cancer, comprising: (a) assaying the expression of ALK in a sample of a subject using one or more antibodies described herein (e.g., any one of antibodies Ab320-Ab332 and Ab351-Ab446, or an antibody comprising CDRs of any one of antibodies Ab320-Ab332 and Ab351-Ab446) or an antigen-binding fragment thereof; and (b) comparing the level of ALK expression with a control level, e.g., levels in normal tissue samples (e.g., from a patient not having a condition described herein, or from the same patient before onset of the condition), whereby an increase or decrease in the assayed level of ALK expression compared to the control level of ALK expression is indicative of a condition described herein.

In certain embodiments, provided herein are methods for the detection of cancer expressing ALK (e.g., overexpressing ALK), comprising: (a) assaying the expression of ALK in a sample of a subject using one or more antibodies described herein (e.g., any one of antibodies Ab320-Ab332 and Ab351-Ab446, or an antibody comprising CDRs of any one of antibodies Ab320-Ab332 and Ab351-Ab446) or an antigen-binding fragment thereof; and (b) comparing the level of ALK expression with a control level, e.g., levels in normal samples (e.g., from a patient not having cancer, a patient having cancer that does not overexpress ALK, or from the same patient before onset of cancer). In specific aspects, an increase or decrease in the assayed level of ALK expression compared to a control level of ALK expression is indicative of cancer expressing ALK.

In a specific embodiment, provided herein is a method of diagnosing an ALK-expressing cancer in a patient, wherein the method comprises the steps of:
(a) contacting a biological sample from the patient with one or more antibodies described herein (e.g., any one of antibodies Ab320-Ab332 and Ab351-Ab446, or an antibody comprising CDRs of any one of antibodies Ab320-Ab332 and Ab351-Ab446) or an antigen-binding fragment thereof;
(b) detecting binding of the antibody or antigen-binding fragment to ALK to determine an ALK protein level in the biological sample from the patient; and
(c) comparing the ALK protein level with a standard ALK protein level.

In a specific embodiment, provided herein is a method of monitoring ALK protein level during treatment of an ALK-expressing cancer in a patient, wherein the method comprises the steps of:
(a) contacting a biological sample from the patient with one or more antibodies described herein (e.g., any one of antibodies Ab320-Ab332 and Ab351-Ab446, or an antibody comprising CDRs of any one of antibodies Ab320-Ab332 and Ab351-Ab446) or an antigen-binding fragment thereof;
(c) detecting binding of the antibody or antigen-binding fragment to ALK to determine an ALK protein level in the biological sample from the patient; and
(d) comparing the ALK protein level with a standard ALK protein level.

Any sample (e.g., bodily fluid or tissue sample) from a subject can be used in diagnostic methods provided herein. Non-limiting examples of samples which can be used in diagnostic methods provided herein include, serum sample, plasma sample, tissue sample, urine sample, tumor sample, and stool sample.

Antibodies described herein can be used to assay ALK levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105: 3087-3096). Other antibody-based methods useful for detecting protein gene expression include immunoassays, such as the enzyme linked immunosorbent assay (ELISA) and the radioimmunoassay (MA). Suitable antibody assay labels are known in the art and include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin.

In one embodiment, monitoring of a condition described herein (e.g., a condition involving ALK and/or abnormal ALK signaling and/or abnormal ALK expression), such as cancer, is carried out by repeating the method for diagnosing for a period of time after initial diagnosis.

Presence of the labeled molecule can be detected in the subject using methods known in the art for in vivo scanning. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

6. EXAMPLES

The examples in this section (i.e., Section 6) are offered by way of illustration, and not by way of limitation.

6.1 Example 1: Generation of Anti-ALK Antibodies

Described herein is the generation of anti-ALK antibodies that immunospecifically bind to human ALK.

Figure 2:
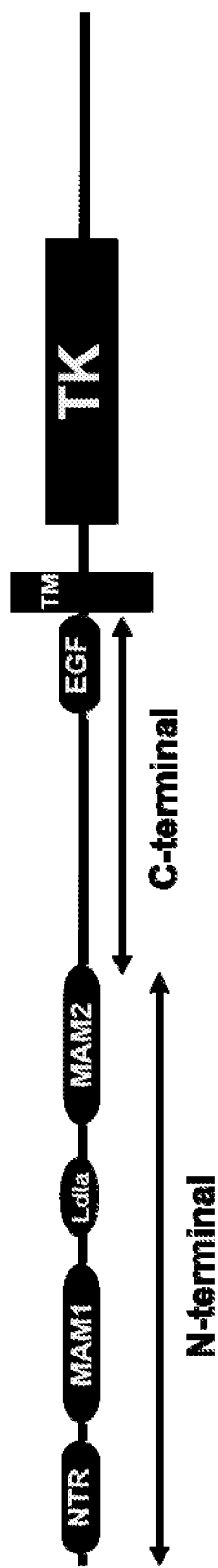
FIG. 2 depicts the ALK domain arrangement and antigens used for animal immunization.

FIG. 1 depicts an exemplary amino acid sequence of human ALK (SEQ ID NO.: 467). The ALK extracellular domain (ECD) contains a positively-charged heparin-binding N-terminal region (NTR), two Meprin A5 protein RPTP mu (MAM) domains flanked by a low-density lipoprotein A domain (LDLa), and a glycine rich region that separates the last MAM domain from an EGF-like domain. Following the transmembrane domain (TM), the intracellular region contains a classic tyrosine kinase domain (TK). FIG. 2 is a schematic diagram of the ALK domain arrangement.

Human ALK ECD was expressed as two independent His-tagged proteins; the N-terminal ECD region (M1-G640; includes signal peptide) and the C-terminal ECD region (T637-S1038). The purified proteins encoding both of these regions were used, separately, as antigens to immunize rodents (mice and rats). Hybridoma fusions from ALK-immunized rodent spleens were screened for binding to their respective antigens. Among the antibodies generated are antibodies Ab320-Ab332, as described herein. Subcloned and protein A-purified monoclonal antibodies were utilized in the studies described below.

Certain of the murine antibody sequences were used to design and generate humanized antibodies. In particular, such antibodies were designed using a homology modeling approach, followed by in silico CDR grafting (MIGS, LLC, Lebanon, N.H.).

6.2 Example 2: Affinity, Murine Cross-Reactivity, and Domain Mapping of Anti-ALK Antibodies $K_D$ Determination by Flow Cytometry:

Flow cytometry was utilized to measure the affinity at steady state ($K_D$) with which different ALK antibodies bind to ALK on the surface of NB1 cells (FIG. 3). Titration of each antibody on NB1 cells for 2-4 hours at 4° C. was followed by incubation with a fluorescently-labeled secondary antibody. The normalized mean fluorescent intensity (MFI) shown as "% Max binding" was plotted as a function of antibody concentration. The data were fit to a one site binding isotherm using GraphPad Prism, from which affinity values were derived.

Anti-ALK monoclonal antibodies generated in Example 1, above, include antibodies that bind to cell-surface expressed ALK with nanomolar to sub-nanomolar affinity, as summarized in Table 18, below.

Mouse ALK Cross-Reactivity:

Purified mAbs were evaluated for their ability to bind murine ALK by solid-state ELISA, or flow cytometry on Neuro-2a cells that express low levels of endogenous murine ALK.

For solid-state ELISA, 100 ng/well of mouse and human purified ALK antigens were coated and the plates were subsequently blocked with BSA. anti-ALK antibodies were titrated, and binding was followed with an HRP-conjugated secondary antibody that recognizes rat or mouse antibodies. Luminescence data were plotted as a function of the log-transformed anti-ALK antibody concentration and fit to a 4-parameter non-linear regression equation.

Alternatively, Neuro-2a cells were incubated with 10-100 nM of anti-ALK antibodies, followed by a fluorescently-labeled secondary antibody. Mean fluorescence intensity (MFI) of live-gated cells treated with anti-ALK antibodies was divided by background, determined using the secondary antibody alone.

As summarized in Table 18, below, certain of the antibodies generated in Example 1 cross-react with murine ALK.

Domain Mapping:

Antibodies that bind to the N-terminal region of human ALK (M1-G640) were further domain mapped by Western blotting. Purified proteins encoding each isolated domain (NTR, MAM1, LdLa, or MAM2), or N-terminal domain truncations were run on SDS-PAGE and transferred to nitrocellulose. Blocked membranes were incubated with each N-terminal region binding anti-ALK antibody, followed by incubation with an HRP-conjugated secondary antibody. Differential binding of each allowed narrowing down an epitope location. The results of the domain mapping are presented in Table 18, below.

Competitive Binding:

Antibodies that bind to the C-terminal region of human ALK ECD (T637-S1038) were further characterized using a competitive binding assay. A pairwise matrix approach was used whereby each antibody was fluorescently labeled and tested for its ability to bind to ALK-expressing cells pre-incubated with an unlabeled antibody. The ability of both antibodies to bind the C-terminal domain simultaneously was tested via flow cytometry. If both antibodies bound simultaneously, they were put into different bins and considered to belong to a separate epitope class. If both antibodies did not bind simultaneously, they were put in the same bin, and assumed to either belong to the same or similar epitope class or to induce an ALK configuration that precludes simultaneous antibody binding. After testing all of the antibodies, the C-terminal ALK ECD binding antibodies were shown to belong to two bins (bin 1 and bin 2). The binning data is presented in Table 18, below.

6.3 Example 3: Anti-ALK Antibodies and ALK Activity and Turnover

ALK antibodies generated in Example 1 were tested for an ability to either stimulate or inhibit basal levels of ALK activity.

Western Blot:

NB1 cells grown in media with reduced serum were treated with 30-100 nM of each antibody generated in Example 1 or with the ALK inhibitor crizotinib for 1-2 hours. Cell lysates were subjected to SDS-PAGE and transferred to nitrocellulose. Immunoblotting was performed with antibodies against total, and phospho-specific ALK, AKT, and MAPK (purchased from Cell Signaling and utilized per manufacturer's instructions). HRP (horse radish peroxidase)-conjugated secondary antibodies (Thermo Scientific, Waltham, Mass.) were used along with Supersignal West Pico Chemiluminescent Substrate (Thermo Scientific, Waltham, Mass.) to image blots.

Phospho-ALK ELISA:

NB1 cells grown in media with reduced serum were treated with 30-100 nM of an antibody generated in Example 1 for 1-2 hours. Cell lysates were incubated on ELISA plates with an anti-ALK antibody (Cell Signaling Technology, Danvers, Mass.), followed by incubation with a pan-phosphotyrosine antibody coupled to HRP (R&D, Minneapolis, Minn.). Luminescent data were obtained using a plate reader. Control-normalized data (wherein the control was a IgG1 antibody), are shown.

Results:

Anti-ALK monoclonal antibodies generated in Example 1 were evaluated via Western blotting for their ability to activate or inhibit basal levels of ALK phosphorylation in NB1 cells (FIG. 4A). A subset of ALK antibodies stimulated ALK tyrosine phosphorylation and a different subset of antibodies inhibited basal levels of ALK phosphorylation. See also Table 18, below. A similar effect was seen with ALK-mediated downstream signaling. That is, ALK antibodies that stimulated ALK tyrosine phosphorylation increased MAPK and AKT phosphorylation, whereas ALK antibodies that inhibited ALK tyrosine phosphorylation decreased basal levels of MAPK and AKT phosphorylation (FIG. 4A). Similar results were obtained in ELISA-based ALK phosphorylation assays from lysates of NB1 cells treated with ALK antibodies (FIG. 4B).

Furthermore, 24 hour treatment of NB1 cells with 100 nM of anti-ALK mAbs resulted in differences in ALK turnover (as measured by total protein levels), as shown in FIG. 5. See also Table 18, below.

6.4 Example 4: Anti-ALK Antibodies NB1 Cell Proliferation and Morphology

As shown herein, ALK antibodies generated in Example 1 show cell proliferation effects consistent with their effects on ALK activity. The results presented herein also demonstrate that the anti-proliferative effects of crizotinib can be enhanced with an ALK antagonist antibody described herein, and rescued with an ALK agonist antibody described herein.

Phospho-ALK ELISA:

NB1 cells grown in media with reduced serum were treated with 30-100 nM of each anti-ALK antibody generated in Example 1 for 1-2 hours. Cell lysates were incubated on ELISA plates with an anti-ALK antibody (Cell Signaling Technology, Danvers, Mass.), followed by incubation with a pan-phosphotyrosine antibody coupled to HRP (Thermo Scientific, Waltham, Mass.). Luminescent data were obtained using a plate reader. Control-normalized data (control was an IgG1 antibody) were plotted as a function of the log-transformed drug concentration and were fit to a 4-parameter non-linear regression equation using GraphPad Prism.

Results:

The effect of ALK antibodies generated in Example 1 on the proliferation of NB1 cells was consistent with their effect on phosphorylation of ALK and downstream signaling (FIG. 6). Inhibitory antibodies exhibited anti-proliferative effects while agonistic antibodies stimulated NB1 cell growth.

Treatment of NB1 cells with an inhibitory ALK antibody (Ab326) caused the cells to adopt a rounded morphology. By contrast, treatment with Ab324, an ALK agonist, caused the cells to spread out.

Titration of crizotinib, a small molecule ALK tyrosine kinase inhibitor, resulted in dose-dependent killing of NB1 cells (FIG. 7A-B). Co-titration of crizotinib with ALK inhibitory antibodies (Ab326 or Ab327) enhanced the anti-proliferative effect of crizotinib. By contrast, addition of a constant amount of ALK agonistic antibodies (Ab323 and Ab324) partially rescued NB1 cell death. This effect could be determined visually on slides in similarly treated NB1 cells.

Table 18 summarizes antibody characteristics for the anti-ALK antibodies generated in Example 1 that bind to the ALK ECD, as presented in the foregoing Examples.

TABLE 18

Summary of the biochemical properties of monoclonal antibodies against the ALK ECD

| Ab | $K_D$ [nM] | mouse ALK binding | ALK turnover | ALK phosphorylation | ALK ECD Region | Bin/ Domain |
|---|---|---|---|---|---|---|
| Ab320 | 0.35 | ++ | − | no effect | C-terminal | 1 |
| Ab321 | 0.2 | +++ | − | inhibitor | C-terminal | 2 |
| Ab322 | 0.5 | − | − | inhibitor | C-terminal | 2 |
| Ab323 | 0.08 | +++ | ++ | weak agonist | C-terminal | 1 |
| Ab324 | 0.4 | + | +++ | strong agonist | C-terminal | 1 |
| Ab325 | 0.1 | + | ++ | moderate agonist | C-terminal | 1 |
| Ab326 | 0.35 | +++ | − | inhibitor | C-terminal | 2 |
| Ab327 | 0.4 | +++ | ++ | inhibitor | C-terminal | 2 |
| Ab328 | 0.5 | +++ | +++ | weak agonist | C-terminal | 2 |
| Ab329 | 0.34 | +++ | ND | weak agonist | N-terminal | MAM1 |
| Ab330 | 3.13 | + | ND | inhibitor | N-terminal | LDLa or MAM2 |
| Ab331 | 2.50 | − | ND | inhibitor | N-terminal | MAM1 |
| Ab332 | 1.55 | + | ND | weak agonist | N-terminal | NTR |
| Ab333 | 0.4 | − | ++ | no effect | C-terminal | 1 |
| Ab334 | 0.5 | + | +++ | weak agonist | C-terminal | 2 |
| Ab335 | 1 | ++ | − | inhibitor | C-terminal | 2 |
| Ab336 | 0.1 | +++ | − | inhibitor | C-terminal | 2 |
| Ab337 | 0.16 | − | ND | weak agonist | N-terminal | MAM1 |
| Ab338 | 28.68 | +++ | ND | weak agonist | N-terminal | ND |
| Ab339 | 0.27 | − | ND | weak agonist | N-terminal | ND |
| Ab340 | 3.92 | + | ND | weak agonist | N-terminal | ND |
| Ab341 | 1.62 | − | ND | weak agonist | N-terminal | ND |
| Ab342 | 9.12 | ++ | ND | weak agonist | N-terminal | ND |
| Ab343 | 4.86 | ND | ND | weak agonist | N-terminal | ND |
| Ab344 | 1.40 | ++ | ND | weak agonist | N-terminal | ND |
| Ab345 | 7.97 | ++ | ND | weak agonist | N-terminal | MAM1 |
| Ab346 | 0.28 | + | ND | weak agonist | N-terminal | LDLa or MAM2 |
| Ab347 | 0.21 | − | ND | weak agonist | N-terminal | ND |
| Ab348 | 1.71 | − | ND | weak agonist | N-terminal | ND |
| Ab349 | 0.48 | − | ND | weak agonist | N-terminal | ND |
| Ab350 | 0.19 | − | ND | weak agonist | N-terminal | MAM1 |

− none
+ weak
++ moderate
+++ strong
ND not determined

6.5 Example 5: Anti-ALK Antibodies NB Mouse Model

As shown herein, anti-ALK Ab326, generated in Example 1 shows in vivo antitumor activity in a patient-derived (PDX) neuroblastoma tumor model.

Protocol:

Patient-derived (PDX) neuroblastoma tumor model mice were produced. The patient-derived tumor had an F1174L mutation. Mice received two weekly intraperitoneal doses of Ab326 or a control IgG1 at 10 mg/kg. See FIG. 8A.

Results:

The effect of Ab326, generated in Example 1, on the patient-derived NB tumor mouse model was consistent with its inhibitory effect on phosphorylation of ALK and downstream signaling (FIG. 8A). Tumor volume was reduced over a two-week period in comparison with a control IgG1 antibody. Western blot analysis of homogenates of tumors harvested 72 hours after the second dose showed a reduction in both total ALK and phosphorylated ALK in tumors treated with Ab326 (FIG. 8B).

6.6 Example 6: Humanized Anti-ALK Antibodies

The humanized ALK antibodies designed in Example 1 were tested for monovalent affinity, wherein the kinetic data are fit to a single binding site equation to obtain relative affinity values.

Protocol:

Kinetic measurements of the monovalent affinity of the 96 humanized ALK antibody variants (Ab351-Ab446) were collected. Affinity ranking was performed using a BLitz® System (ForteBio, Menlo Park, Calif.). Humanized anti-ALK antibodies were immobilized at 0.5 mg/mL using Protein A tips. Once baseline stability was ensured, purified ALK proteins at 70 µg/mL were added. The resulting kinetic data were fit to a single binding site equation, from which the quoted monovalent $K_D$ values were derived.

Results:

The 96 antibodies and the monovalent affinity for all 96 antibodies are shown below in Tables 19 and 20.

TABLE 19

The 96 humanized ALK Antibodies.

| | 1 | 2 | 3 | 4 | 5 | 6 | 7 | 8 | 9 | 10 | 11 | 12 |
|---|---|---|---|---|---|---|---|---|---|---|---|---|
| A | Ab351 | Ab352 | Ab353 | Ab354 | Ab355 | Ab356 | Ab357 | Ab358 | Ab359 | Ab360 | Ab361 | Ab362 |
| B | Ab399 | Ab400 | Ab401 | Ab402 | Ab403 | Ab404 | Ab405 | Ab406 | Ab407 | Ab408 | Ab409 | Ab410 |
| C | Ab363 | Ab364 | Ab365 | Ab366 | Ab367 | Ab368 | Ab369 | Ab370 | Ab371 | Ab372 | Ab373 | Ab374 |
| D | Ab411 | Ab412 | Ab413 | Ab414 | Ab415 | Ab416 | Ab417 | Ab418 | Ab419 | Ab420 | Ab421 | Ab422 |
| E | Ab375 | Ab376 | Ab377 | Ab378 | Ab379 | Ab380 | Ab381 | Ab382 | Ab383 | Ab384 | Ab385 | Ab386 |
| F | Ab423 | Ab424 | Ab425 | Ab426 | Ab427 | Ab428 | Ab429 | Ab430 | Ab431 | Ab432 | Ab433 | Ab434 |
| G | Ab387 | Ab388 | Ab389 | Ab390 | Ab391 | Ab392 | Ab393 | Ab394 | Ab395 | Ab396 | Ab397 | Ab398 |
| H | Ab435 | Ab436 | Ab437 | Ab438 | Ab439 | Ab440 | Ab441 | Ab442 | Ab443 | Ab444 | Ab445 | Ab446 |

TABLE 20

The monovalent affinity for each of the corresponding 96 ALK antibodies in Table 19, above.

| | KD (M) | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 1.20E−07 | 7.72E−08 | 3.84E−07 | 1.33E−07 | 8.65E−08 | 1.28E−07 | 1.47E−07 | 1.18E−07 | 1.00E−07 | 1.37E−07 | 1.53E−07 | 1.49E−07 |
| B | 1.07E−07 | 8.15E−08 | 1.06E−06 | 8.76E−08 | 9.42E−08 | 1.32E−07 | 1.95E−07 | 1.10E−07 | 1.09E−07 | 1.44E−07 | 2.08E−07 | 1.44E−07 |
| C | 1.19E−07 | 1.28E−07 | 1.49E−06 | 2.19E−07 | 1.14E−07 | 1.98E−07 | 2.10E−07 | 2.53E−06 | 1.30E−07 | 1.88E−07 | 2.80E−07 | 2.53E−07 |
| D | 1.43E−07 | 1.11E−07 | 1.66E−06 | 1.42E−07 | 1.28E−07 | 1.80E−07 | 1.70E−07 | 1.31E−07 | 1.07E−07 | 2.33E−07 | 2.80E−07 | 1.73E−07 |
| E | 1.4E−07 | 1.03E−07 | 9.27E−07 | 1.67E−07 | 1.18E−07 | 1.41E−07 | 1.8E−07 | 1.41E−07 | 1.32E−07 | 2.01E−07 | 6.26E−07 | 2.57E−07 |
| F | 2.66E−07 | 2.47E−07 | 2.29E−06 | 8.68E−07 | 1.62E−07 | 2.53E−07 | 3.26E−07 | 2.11E−07 | 2.52E−07 | 3.37E−07 | 1.97E−07 | 3.29E−07 |
| G | 1.58E−07 | 1.08E−07 | 1.55E−06 | 2.88E−07 | 1.75E−07 | 1.79E−07 | 1.86E−07 | 1.57E−07 | 1.32E−07 | 1.76E−07 | 3.78E−07 | 2.21E−07 |
| H | 3.17E−07 | 1.2E−07 | 0.006078 | 3.1E−07 | 1.38E−07 | 1.38E−07 | 1.67E−07 | 2.19E−07 | 1.45E−07 | 2.36E−07 | 5.21E−07 | 3.93E−07 |

Humanized antibodies tested, as above, for affinity to rat ALK (rALK; SEQ ID NO: 518), human ALK (hALK, SEQ ID NO: 519), and mouse ALK (mALK; SEQ ID NO: 517) demonstrated binding to rALK with greater affinity than hALK or mALK (Table 21). An alignment of hALK, rALK, and mALK is shown in FIG. 9. Amino acid residues that differ between rat ALK and mouse ALK are boxed. $K_D$ values for both NB1 (human) cells and Neuro2a (mouse) cells were also determined. The better binding to cell surface hALK than cell surface mALK was shown to be a result of a decreased dissociation rate in binding to hALK.

TABLE 21

Binding of humanized ALK antibodies to ALK species orthologs.

| | Estimated Monovalent Affinity (single dose kinetics) | | | $K_D$ for Cells (FACS) | | | |
|---|---|---|---|---|---|---|---|
| | human ALK | mouse ALK | rat ALK | NB1 (human) | | Neuro2a (mouse) | |
| Antibody | (nM) | (nM) | (nM) | Mean | SEM | Mean | SEM |
| Ab352 | 105 | 205 | 24 | 1.4 | 0.26 | 7.7 | 3.1 |
| Ab355 | 103 | 150 | 31 | 1.26 | 0.22 | 5.1 | 2.3 |
| Ab400 | 59 | 103 | 18 | 1.3 | 0.23 | 7.4 | 4.3 |
| Ab402 | 71 | 147 | 24 | 1.5 | 0.18 | 2.8 | 0.85 |

TABLE 21-continued

Binding of humanized ALK antibodies to ALK species orthologs.

| | Estimated Monovalent Affinity (single dose kinetics) | | | $K_D$ for Cells (FACS) | | | |
|---|---|---|---|---|---|---|---|
| | human ALK | mouse ALK | rat ALK | NB1 (human) | | Neuro2a (mouse) | |
| Antibody | (nM) | (nM) | (nM) | Mean | SEM | Mean | SEM |
| Ab403 | 80 | 120 | 22 | 0.73 | 0.072 | 4.15 | 2.4 |
| Ab326 | 69 | 120 | 35 | 0.94 | 0.21 | 0.58 | 0.02 |

All references (e.g., publications or patents or patent applications) cited herein are incorporated herein by reference in their entirety as if each individual reference (e.g., publication or patent or patent application) was specifically and individually indicated to be incorporated by reference in its entirety. In the case of any conflict, this specification will control.

As used herein, the singular forms "a", "and," and "the" include plural referents unless the context clearly indicates otherwise. Thus, for example, reference to "a peptide sequence" includes a plurality of such sequences and so forth.

Other embodiments are within the following claims.

What is claimed:

1. An antibody or an antigen-binding fragment thereof, which specifically binds to an anaplastic lymphoma kinase (ALK) extracellular domain (ECD), comprising:
   (i) a light chain variable region (VL) comprising:
       (a) a VL complementarity determining region (CDR) 1 comprising the amino acid sequence of KASQNVGTNVA (SEQ ID NO: 13);
       (b) a VL CDR2 comprising the amino acid sequence of SASYRYS (SEQ ID NO: 14); and
       (c) a VL CDR3 comprising the amino acid sequence of QX$_1$YNSYPYMX$_2$T (SEQ ID NO: 468), wherein X$_1$ is Q or R and X$_2$ is Y or F; and
   (ii) a heavy chain variable region (VH) comprising:
       (a) a VH CDR1 comprising the amino acid sequence X$_3$YWMH (SEQ ID NO: 469), wherein X$_3$ is N or S;
       (b) a VH CDR2 comprising the amino acid sequence of YIX$_4$PSSGYTKYNQKFKD (SEQ ID NO: 470), wherein X$_4$ is N or K; and
       (c) a VH CDR3 comprising the amino acid sequence of DYYGSSSWFAY (SEQ ID NO: 18).

2. The antibody or antigen-binding fragment thereof of claim 1, wherein the VL comprises:
   (a) a VL CDR1 comprising the amino acid sequence of KASQNVGTNVA (SEQ ID NO: 13);
   (b) a VL CDR2 comprising the amino acid sequence of SASYRYS (SEQ ID NO: 14); and
   (c) a VL CDR3 comprising the amino acid sequence of QQYNSYPYMYT (SEQ ID NO: 15);
   and wherein the VH comprises:
   (d) a VH CDR1 comprising the amino acid sequence of NYWMH (SEQ ID NO: 16);
   (e) a VH CDR2 comprising the amino acid sequence of YINPSSGYTKYNQKFKD (SEQ ID NO: 17); and
   (f) a VH CDR3 comprising the amino acid sequence of DYYGSSSWFAY (SEQ ID NO: 18).

3. The antibody or antigen-binding fragment thereof of claim 1, wherein the VL comprises the amino acid sequence of SEQ ID NO: 399 and the VH comprises the amino acid sequence of SEQ ID NO: 400.

4. The antibody or antigen-binding fragment thereof of claim 1, which comprises a heavy chain constant region.

5. The antibody or antigen-binding fragment thereof of claim 4, wherein the heavy chain constant region is a human IgG constant region.

6. The antibody or antigen-binding fragment thereof of claim 1, which comprises a light chain constant region selected from the group consisting of a human kappa constant region and a human lambda constant region.

7. The antibody or antigen-binding fragment thereof of claim 1, wherein the antibody is a human antibody, a humanized antibody, a chimeric antibody, a recombinant antibody, a multispecific antibody, or an antigen-binding fragment thereof; wherein the antigen-binding fragment is an Fv, Fab, F(ab')2, Fab', dsFv, scFv, or sc(Fv)2.

8. The antibody or antigen-binding fragment thereof of claim 1, wherein the antibody is a monoclonal antibody.

9. A composition comprising the antibody or antigen-binding fragment thereof of claim 1, and a pharmaceutically acceptable carrier.

10. A method of inhibiting the proliferation of a cell expressing ALK, said method comprising contacting the cell with the antibody or antigen-binding fragment thereof of claim 1.

\* \* \* \* \*